US012187735B2

United States Patent
Ling et al.

(10) Patent No.: US 12,187,735 B2
(45) Date of Patent: Jan. 7, 2025

(54) MATTER OF COMPOSITION, SYNTHESIS, FORMULATION AND APPLICATION OF FL118 PLATFORM POSITIONS 7 AND 9-DERIVED ANALOGUES FOR TREATMENT OF HUMAN DISEASE

(71) Applicant: Canget BioTekpharma LLC, Buffalo, NY (US)

(72) Inventors: Xiang Ling, Amherst, NY (US); Qingyong Li, Hangzhou (CN); Fengzhi Li, Buffalo, NY (US)

(73) Assignee: Canget BioTekpharma LLC, Buffalo, NY (US)

( * ) Notice: Subject to any disclaimer, the term of this patent is extended or adjusted under 35 U.S.C. 154(b) by 0 days.

(21) Appl. No.: 16/818,343

(22) Filed: Mar. 13, 2020

(65) Prior Publication Data
US 2020/0231596 A1    Jul. 23, 2020

Related U.S. Application Data

(63) Continuation of application No. PCT/US2019/051595, filed on Sep. 17, 2019.
(Continued)

(51) Int. Cl.
C07D 491/22    (2006.01)
A61K 9/20    (2006.01)
(Continued)

(52) U.S. Cl.
CPC ............ *C07D 491/22* (2013.01); *A61K 47/40* (2013.01); *A61K 9/0053* (2013.01); *A61K 9/20* (2013.01); *A61K 45/06* (2013.01)

(58) Field of Classification Search
CPC ........ A61K 47/40; A61K 9/0053; A61K 9/20; A61K 45/06; A61K 9/2018; A61K 9/0095;
(Continued)

(56) References Cited

U.S. PATENT DOCUMENTS 5,342,947 A    7/1994 Lackey
2004/0266803 A1*   12/2004 Wani .................... C07D 491/22
514/279
(Continued)

FOREIGN PATENT DOCUMENTS

CN    109810114 A    5/2019
EP    3808751 A1    4/2021
(Continued)

OTHER PUBLICATIONS

Jaxel, Structure-Activity Study of the Actions of Camptothecin Derivatives on Mammalian Topoisomerase I: Evidence for a Specific Receptor Site and a Relation to Antitumor Activity, Cancer Research, 1989, 49, pp. 1465-1469 (Year: 1989).*
(Continued)

*Primary Examiner* — Savitha M Rao
*Assistant Examiner* — Andrew P Lee
(74) *Attorney, Agent, or Firm* — McAndrews, Held & Malloy, Ltd.

(57) ABSTRACT

Described herein, are the chemical synthesis, matter of compositions, formulation, function, methods and uses of the FL118 platform Positions 7 and/or 9-derived analogues for treating cancer or other human diseases. Compounds derived from chemical modifications of the FL118 platform are employed alone or in combination with other anti-cancer agents to preclude, eliminate or reverse cancer phenotypes. This invention intends to realize unique personalized cancer treatment (personalized precision medicine) through application of a series of structural relevant individual FL118 platform-derived analogues, which target multiple cellular human disease-relevant proteins and their signaling pathways.

14 Claims, 34 Drawing Sheets

Related U.S. Application Data

(60) Provisional application No. 62/732,553, filed on Sep. 17, 2018.

(51) Int. Cl.
  *A61K 45/06* (2006.01)
  *A61K 47/40* (2006.01)
  *A61K 9/00* (2006.01)

(58) Field of Classification Search
  CPC ... A61K 47/38; A61K 9/2054; A61K 31/4745
  See application file for complete search history.

(56) References Cited

U.S. PATENT DOCUMENTS

| | | | |
|---|---|---|---|
| 2009/0202540 A1* | 8/2009 | Gant | A61P 35/00 424/133.1 |
| 2014/0066470 A1 | 3/2014 | Li et al. | |
| 2016/0375042 A1 | 12/2016 | Zhou | |
| 2018/0170944 A1 | 6/2018 | Li et al. | |

FOREIGN PATENT DOCUMENTS

| | | | | |
|---|---|---|---|---|
| WO | WO-9725332 A1 * | 7/1997 | ........... | C07D 491/22 |
| WO | 20070095389 A2 | 8/2007 | | |
| WO | 2015148415 | 10/2015 | | |
| WO | 2019238046 | 12/2019 | | |

OTHER PUBLICATIONS

Zhou, Uptake and efflux of FL118 and two FL118 derivatives in 3D cell model, Jul. 12, 2019, Cytotechnology, 71, pp. 785-795. (Year: 2019).*

Gharib et al., Liposomes incorporating cyclodextrin-drug inclusion complexes: Current state of knowledge, 2015, 129, pp. 175-186 ( Year: 2015).*

Kang, Cyclodextrin complexation: influence on the solubility, stability, and cytotoxicity of camptothecin, an antineoplastic agent, European Journal of Pharmaceutical Sciences, 2002, 15, pp. 163-170. (Year: 2002).*

WIPO, Written Opinion of the International Searching Authority for PCT/US2019/051595, 4 pages, Jan. 15, 2020.

WIPO, International Search Report for PCT/US2019/051595, 5 pages, Jan. 15, 2020.

Applicant, Revised Article 19 amendment for PCT/US19/51595, 23 pages, Dec. 16, 2019.

European Patent Office, Search Report regarding Application No., 19862812.5, 9 pages, dated Apr. 22, 2022.

Intellectual Property Office of India, First Examination Report regarding Serial No. 202117010607, 6 pages, Sep. 29, 2022.

Japanese Office Action for JP Appl No. 2021-539490, dated Sep. 13, 2023 (141 pages).

* cited by examiner

MATTER OF COMPOSITION, SYNTHESIS, FORMULATION AND APPLICATION OF FL118 PLATFORM POSITIONS 7 AND 9-DERIVED ANALOGUES FOR TREATMENT OF HUMAN DISEASE

CROSS-REFERENCE TO RELATED APPLICATIONS

This application is the national stage application of international PCT application number PCT/US19/51595/, filed Sep. 17, 2019, which claimed benefit of U.S. provisional application No. 62/732,553, filed Sep. 17, 2018, the subject matter of each of the above referenced disclosures is expressly incorporated by reference herein. The subject matter of the PCT international patent application number PCT/US2015/022095 entitled "USE OF THE FL118 CORE CHEMICAL STRUCTURE PLATFORM TO GENERATE FL118 DERIVATIVES FOR TREATMENT OF HUMAN DISEASE" filed on Mar. 24, 2015 is expressly incorporated by reference herein.

STATEMENT OF GOVERNMENT-SPONSORED RESEARCH

This invention was made in part with United States government support under Grant Number R44CA176937 awarded by the National Cancer Institute (NCI) to Canget BioTekpharma LLC. The United States government has certain rights in the invention.

FIELD OF THE INVENTION

The present disclosure relates to the matter of composition, synthesis, formulation, demonstration and protection of the FL118 Positions 7 and 9-derived analogues for treatment and/or prevention of human disease including human cancer and neoplasm that are associated with treatment-resistant and survival pathways, cancer targets and cancer biomarkers.

BACKGROUND

The FL118 compound chemical structure has been shown to be effective in treatment of different human disease including cancer.

SUMMARY OF THE INVENTION

We have provided a lot of evidence in our previously filed PCT international patent application (PCT/US2015/022095) mentioned above that the FL118 compound chemical structure appears to be a great platform for chemical generation of a series of FL118 analogues for treatment of different human disease including cancer. Our follow-up studies further indicated the novelty of FL118 platform. For example, we demonstrated that while the FL118 chemical structure is similar to camptothecin (CPT) and the FDA-approved CPT analogues irinotecan, SN-38 (active metabolite of irinotecan) and topotecan, which are known to use the topoisomerase I (Top1) as their therapeutic target, the antitumor activity/efficacy of FL118 is irrelevant to Top1 expression (Li F, et al. Top1: a major target of FL118 for its antitumor efficacy or mainly involved in its side effects of hematopoietic toxicity? Am J Cancer Res 2017; 7: 370-82). Specifically, we demonstrated that in human colorectal cancer animal models FL118 can exhibit high antitumor efficacy to regress tumors with no or very low Top1 expression, while tumors with high Top1 expression can show high resistance or show much less sensitivity to FL118 treatment.

We have thoroughly reviewed all the CPT analogues that were moved into clinical trials in the past 6+ decades, we found that the entire academic and industrial field has largely used Top1 inhibition intensity to predict the antitumor potential of a CPT analogue. However, accumulating evidence supports our notion that certain CPT analogues can exert significant non-Top1-mediated antitumor activity; in fact, Top1 activity inhibition by such analogues appears to be involved in the drug side effects (e.g. hematopoietic toxicity), since normal tissue and cell renewal requires Top1 for DNA replication. The fact is that while most (if not all) of the CPT analogues in clinical development that exhibited stronger inhibition of Top1 activity than either irinotecan and/or topotecan; yet, extensive clinical trials with these analogues did not show a significant advantage over irinotecan or topotecan in antitumor activity and/or high side-effect toxicities (Li F, Jiang T, Li Q, Ling X: CPT and its derivatives are known to target Top1 as their mechanism of action: did we miss something in CPT analogue molecular targets for treating human disease such as cancer? Am J Cancer Res 2017, 7:2350-94). We predict that if further focusing on finding CPT analogues with strong inhibition of Top1 function/activity as the primary criterion for preclinical and clinical development of CPT analogues, we may continuously be unable to make a breakthrough in the development of next generation of novel CPT analogues with high efficacy and low toxicities for human disease (e.g. cancer) treatment.

We propose to develop CPT derivatives that exhibits low inhibitory effects on Top1 function/activity, while targeting multiple key disease-associated genes and/or gene products. Such molecules should possess high efficacy and low toxicity for fighting cancer and other human diseases.

In this invention, we provide examples of various FL118 platform-derive compounds synthesized in our research team to demonstrate that FL118 platform-derived compounds are a rich resource to discover great compounds that exhibit high anticancer efficacy with low toxicity to treat various types of cancer.

The present disclosure provides a composition comprising Formula 1 having the following formula:

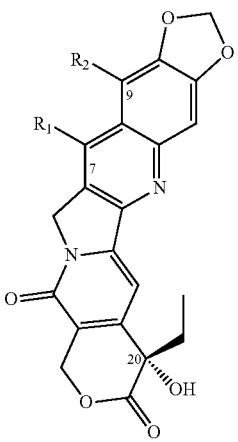

Formula 1

In one situation, wherein the "R2" on Position 9 of Formula 1 is "H", and the "R1" on the Position 7 of Formula 1 is independently selected from, but is not limited to, the Group I-a, Group II-a, Group III-a and Group IV-a below:
Group I-a:
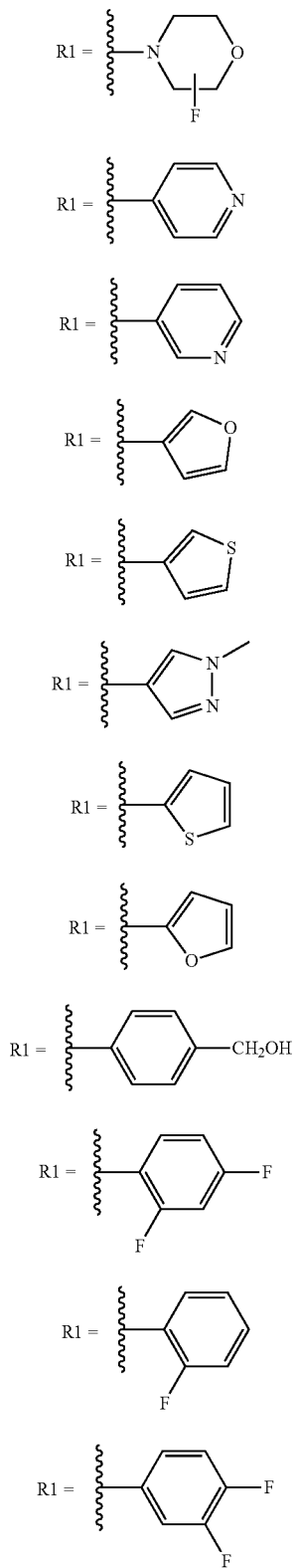
WF-5
W-b1
W-b2
W-b3
W-b4
W-b5
W-b6
W-b7
W-b9
Hx4
Hx5
Hx6
-continued
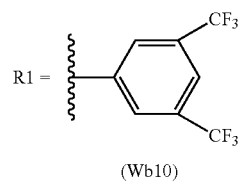
(Wb10)
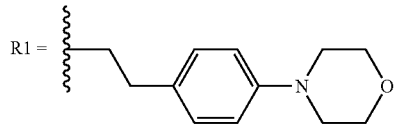
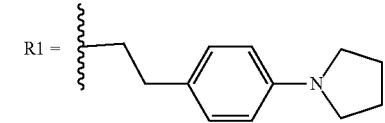
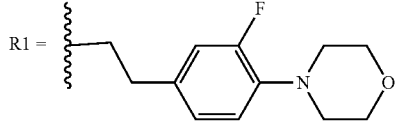
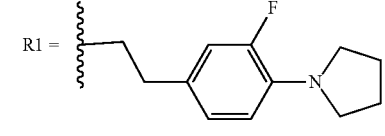
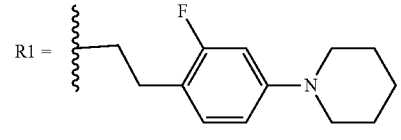
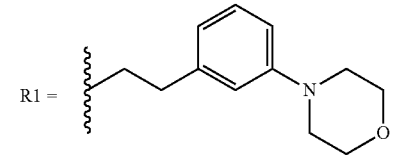
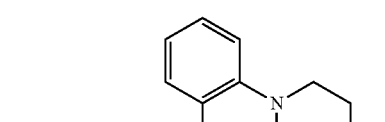
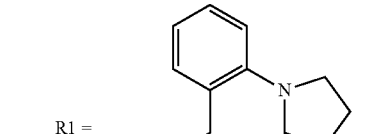
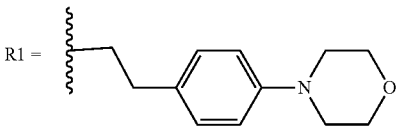
Hx7
Wgz1D
Wgz1E
Wgz1G
Wgz1H
Wgz1I
Wgz1J
Wgz1K
Wgz1L
Wgz1M

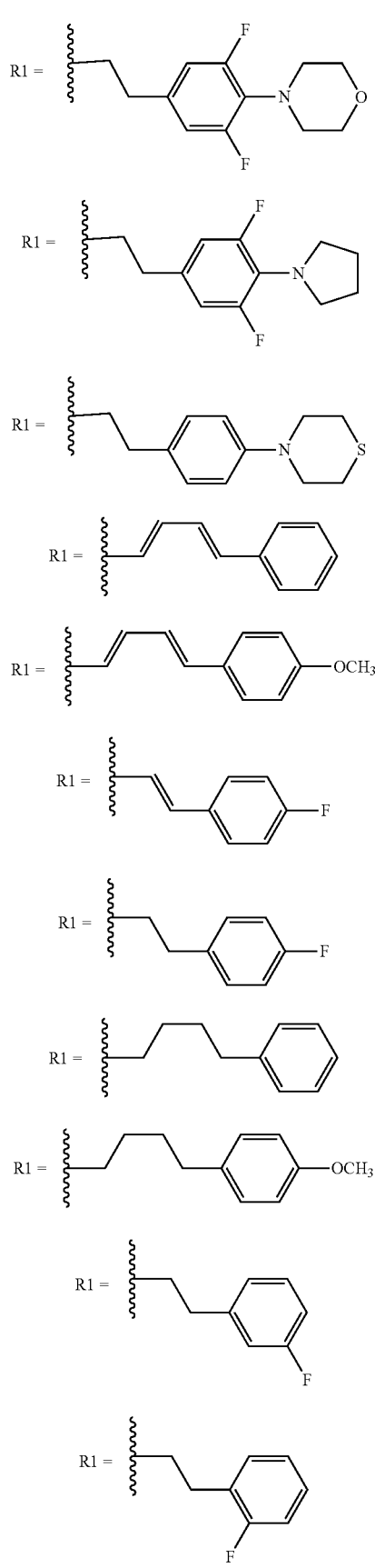
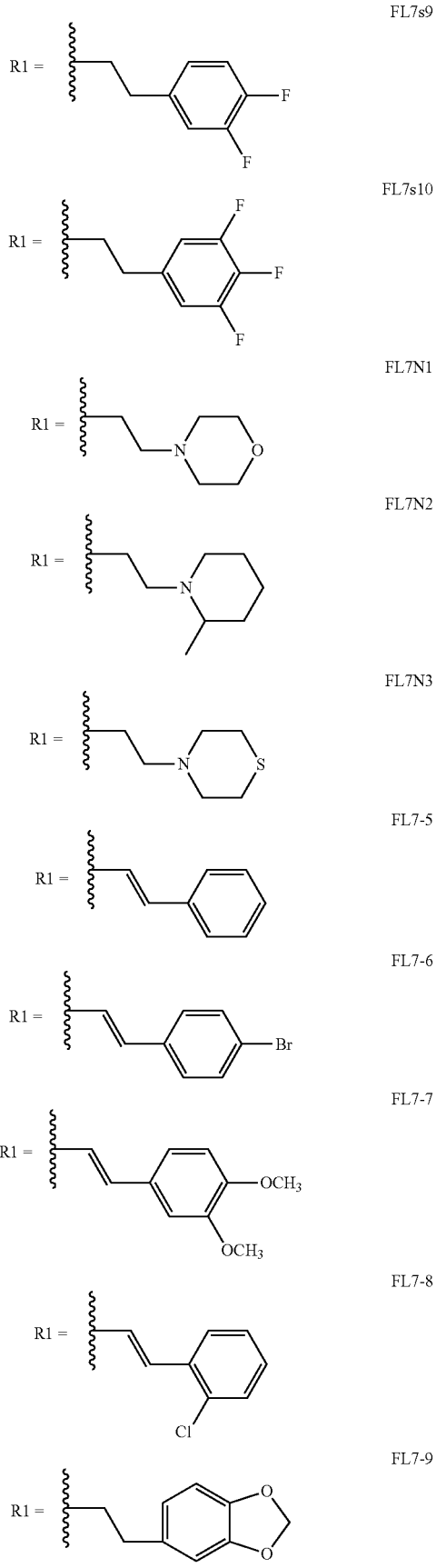

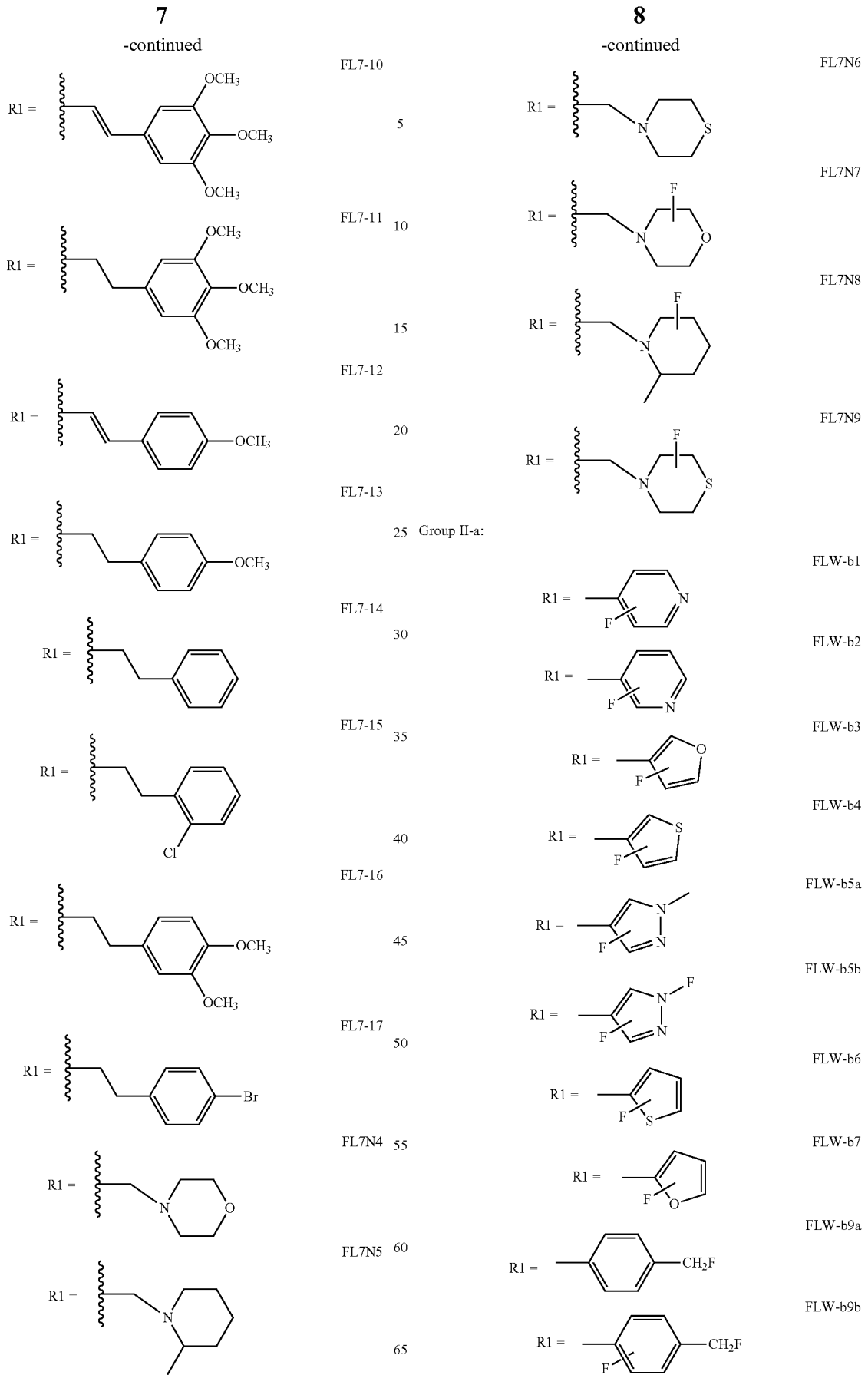

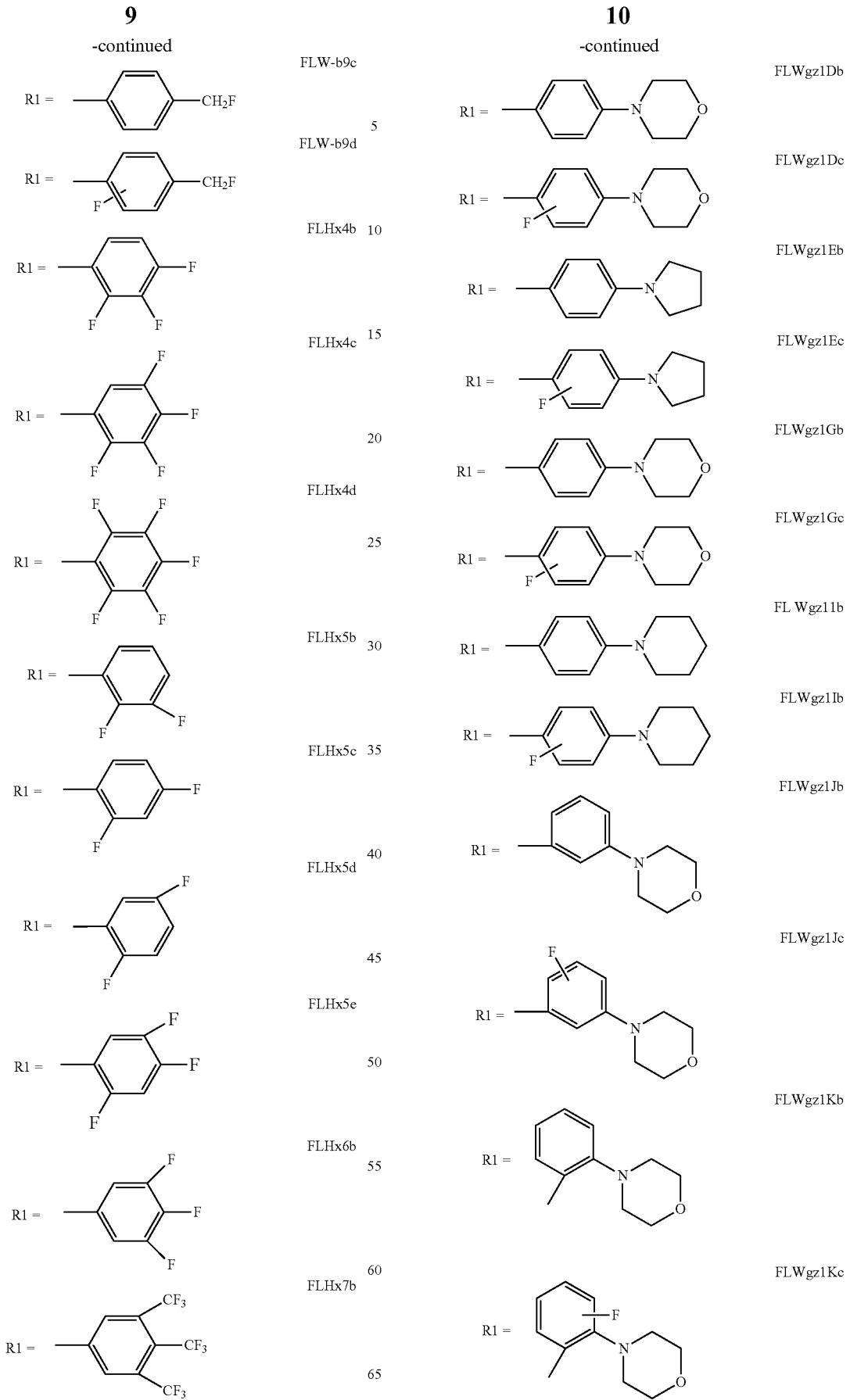

-continued
R1 = 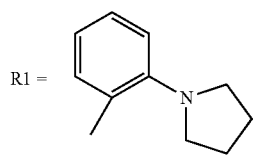
FLWgz1Lb
R1 = 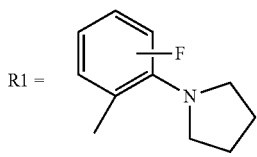
FLWgz1Lc
R1 = 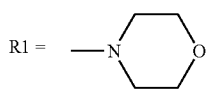
FL7N1b
R1 = 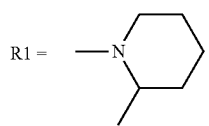
FL7N2b
R1 = 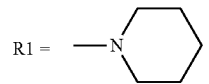
FL7N2c
R1 = 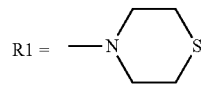
FL7N3b
R1 = 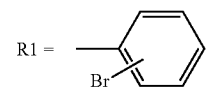
FL7-6b
R1 = 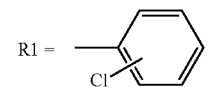
FL7-8b
R1 = 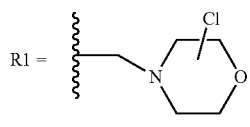
FL7N4a
R1 = 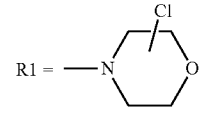
FL7N1c
R1 = 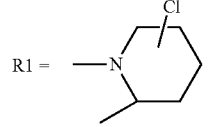
FL7N2d
R1 = 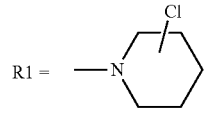
FL7N2e
R1 = 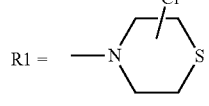
FL7N3c
-continued
R1 = 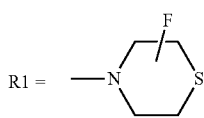
FL7N3d
R1 = 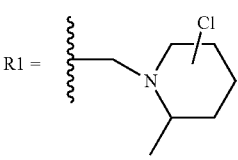
FL7N5a
R1 = 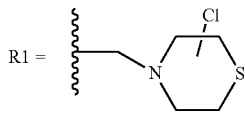
FL7N6a
R1 = 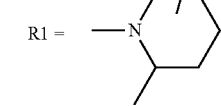
FL7N2f
R1 = 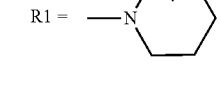
FL7N2g
Group III-a:
R1 = 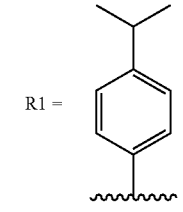
7Q1
R1 = 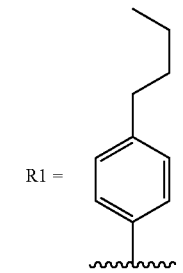
7Q2
R1 = 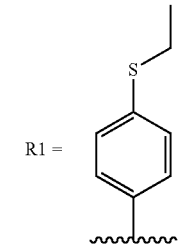
7Q3

-continued
R1 = 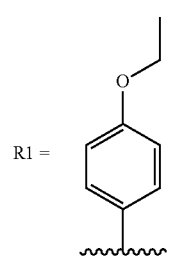
7Q4
R1 = 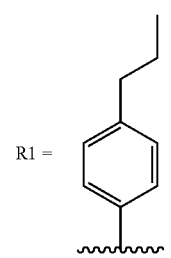
7Q5
R1 = 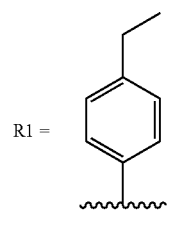
7Q6
R1 = 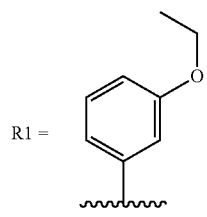
7Q7
R1 = 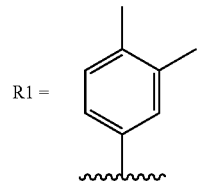
7Q8
R1 = 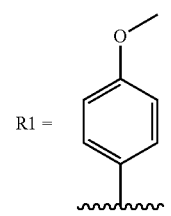
7Q9
R1 = 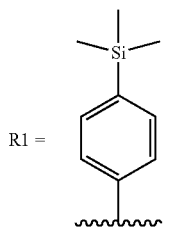
7Q10
-continued
R1 = 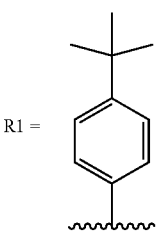
7Q11
R1 = 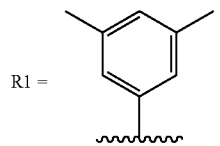
7Q12
R1 = 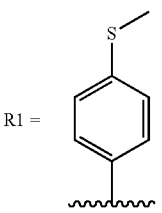
7Q13
R1 = 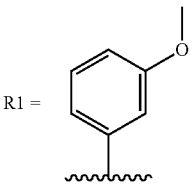
7Q14
R1 = 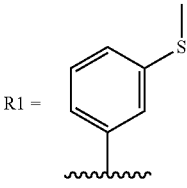
7Q15
R1 = 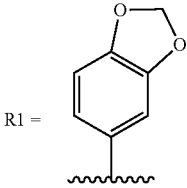
7Q16
R1 = 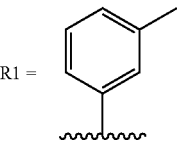
7Q17
R1 = 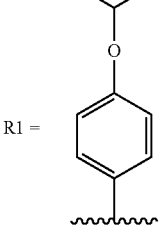
7Q18

| | |
|---|---|
| R1 = 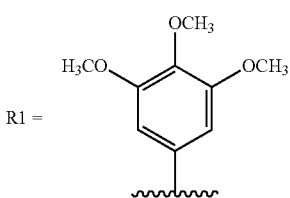 | 7Q19 |
| R1 = 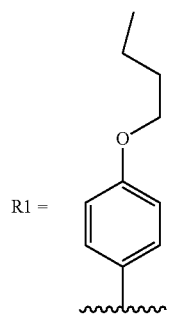 | 7Q21 |
| R1 = 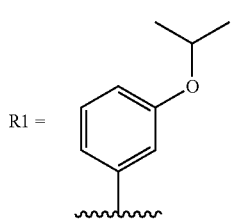 | 7Q22 |
| R1 = 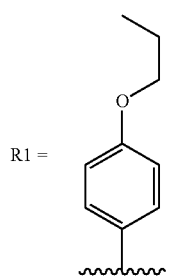 | 7Q23 |
| R1 = 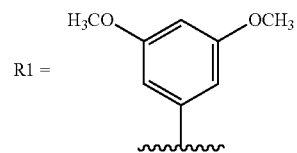 | 7Q24 |
| R1 = 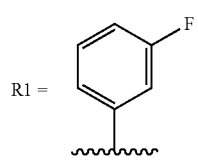 | 7Q25 |
| R1 = 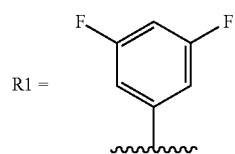 | 7Q27 |
| | |
|---|---|
| R1 = 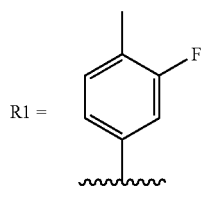 | 7Q28 |
| R1 = 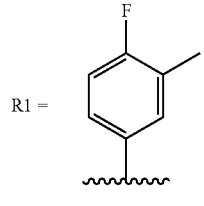 | 7Q29 |
| R1 = 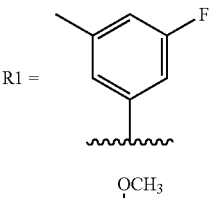 | 7Q30 |
| R1 = 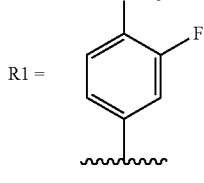 | 7Q31 |
| R1 = 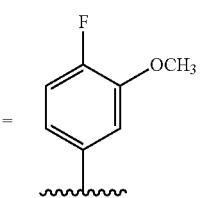 | 7Q32 |
| R1 = 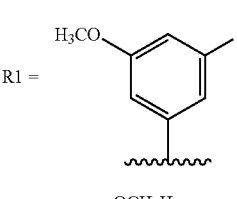 | 7Q33 |
| R1 = 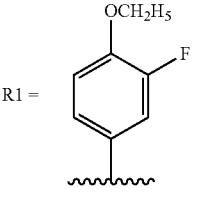 | 7Q34 |
| R1 = 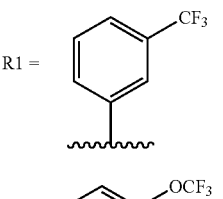 | 7Q35 |
| R1 = 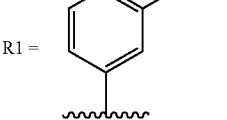 | 7Q36 |

-continued
R1 = 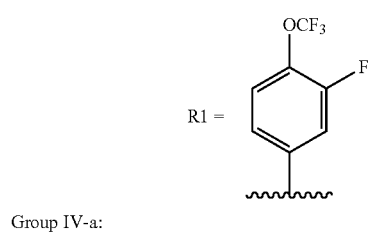 7Q37
Group IV-a:
R1 = 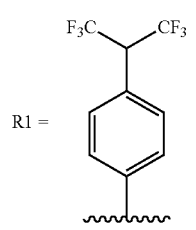 7FL1a
R1 = 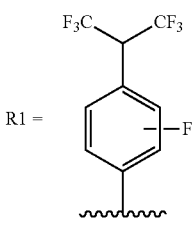 7FL1b
R1 = 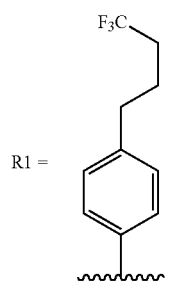 7FL2
R1 = 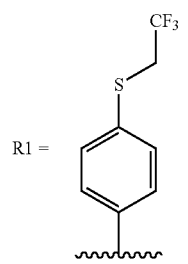 7FL3
R1 = 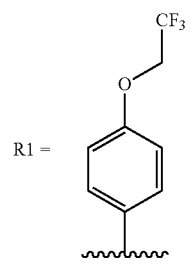 7FL4a
-continued
R1 = 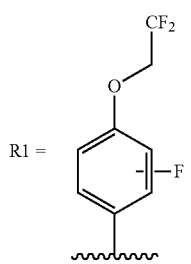 7FL4b
R1 = 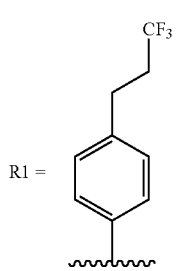 7FL5a
R1 = 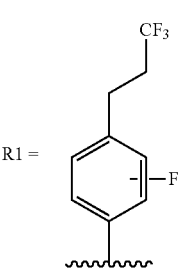 7FL5b
R1 = 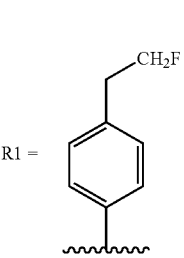 7FL6a
R1 = 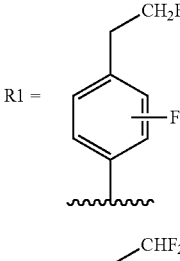 7FL6b
R1 = 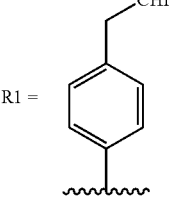 7FL6c -continued
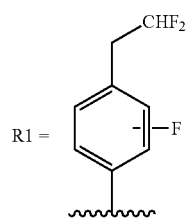
7FL6d
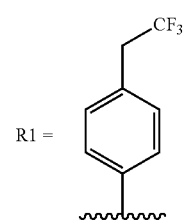
7FL6e
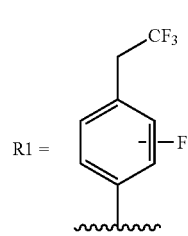
7FL6f
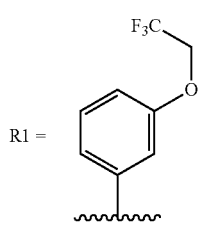
7FL7
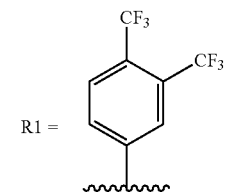
7FL8a
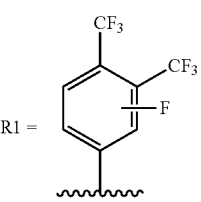
7FL8b
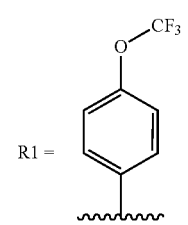
7FL9a
-continued
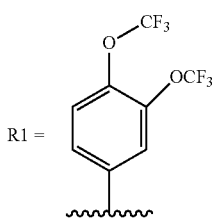
7FL9b
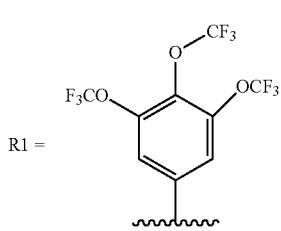
7FL9c
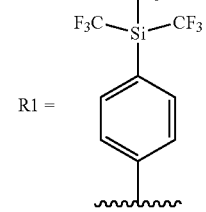
7FL10
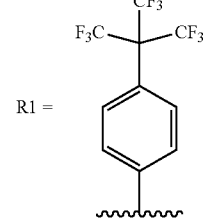
7FL11
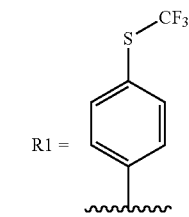
7FL13
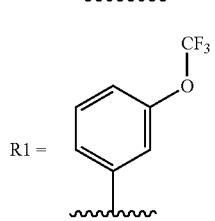
7FL14
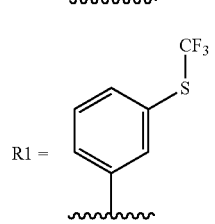
7FL15

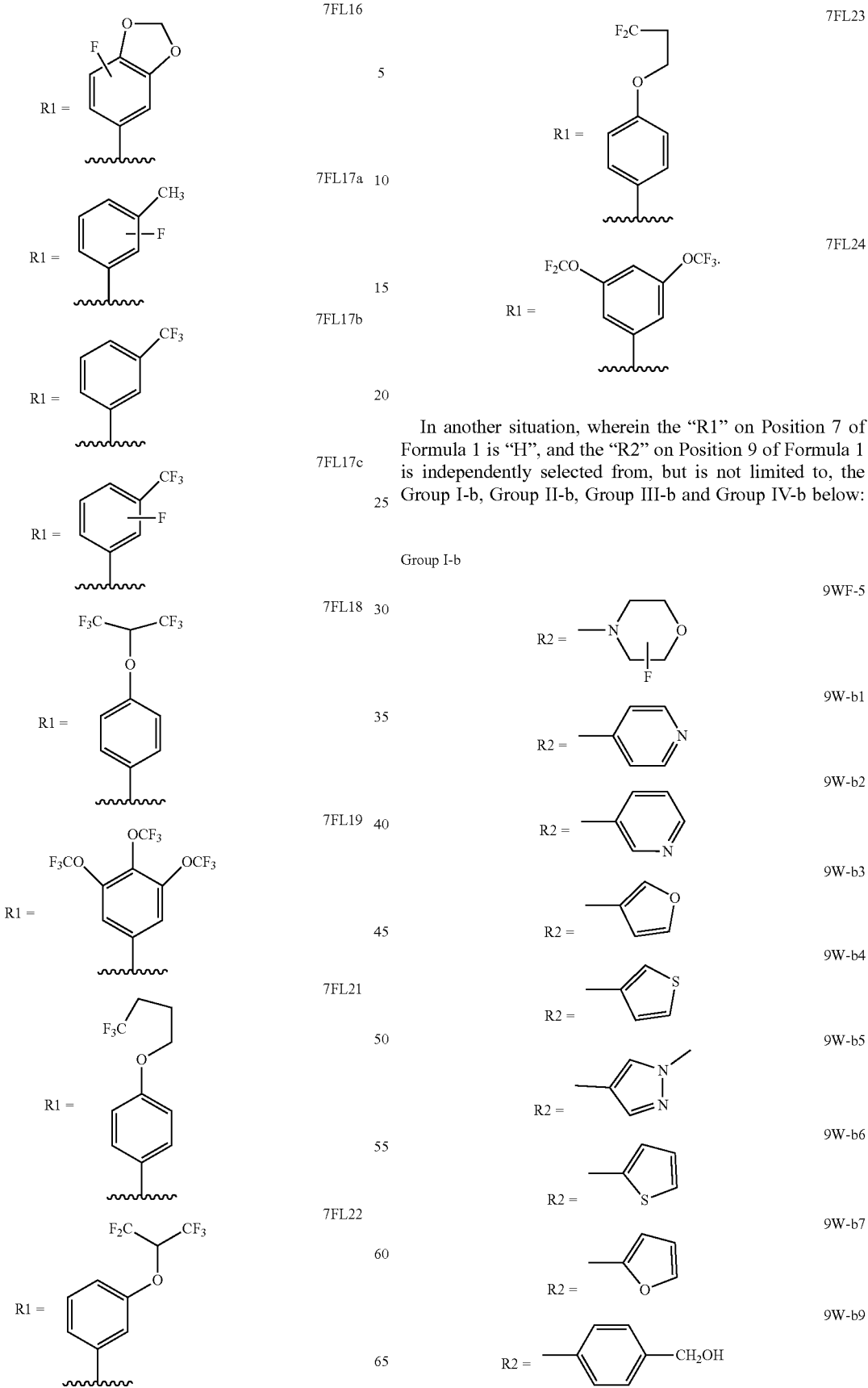
In another situation, wherein the "R1" on Position 7 of Formula 1 is "H", and the "R2" on Position 9 of Formula 1 is independently selected from, but is not limited to, the Group I-b, Group II-b, Group III-b and Group IV-b below:
Group I-b

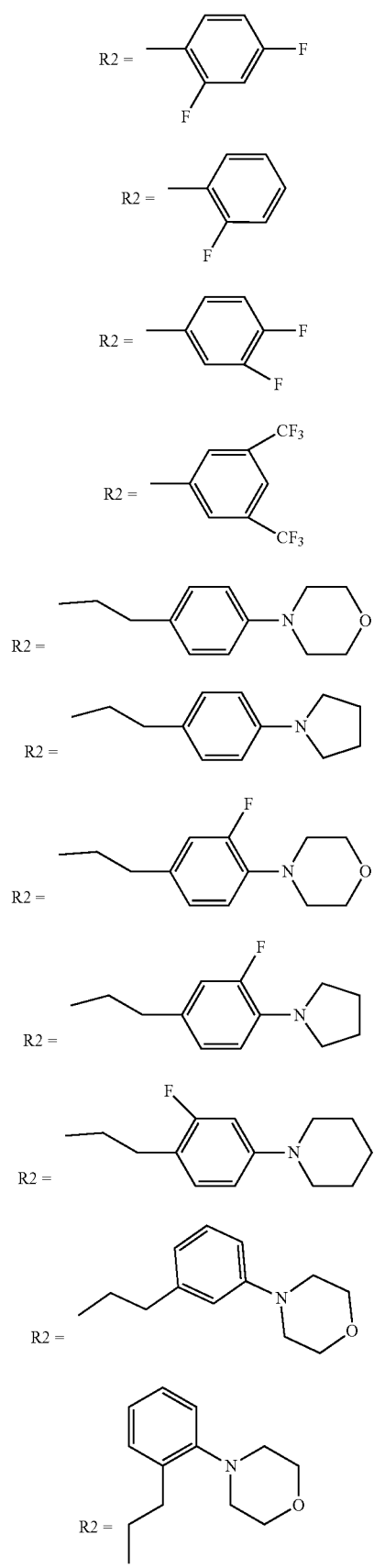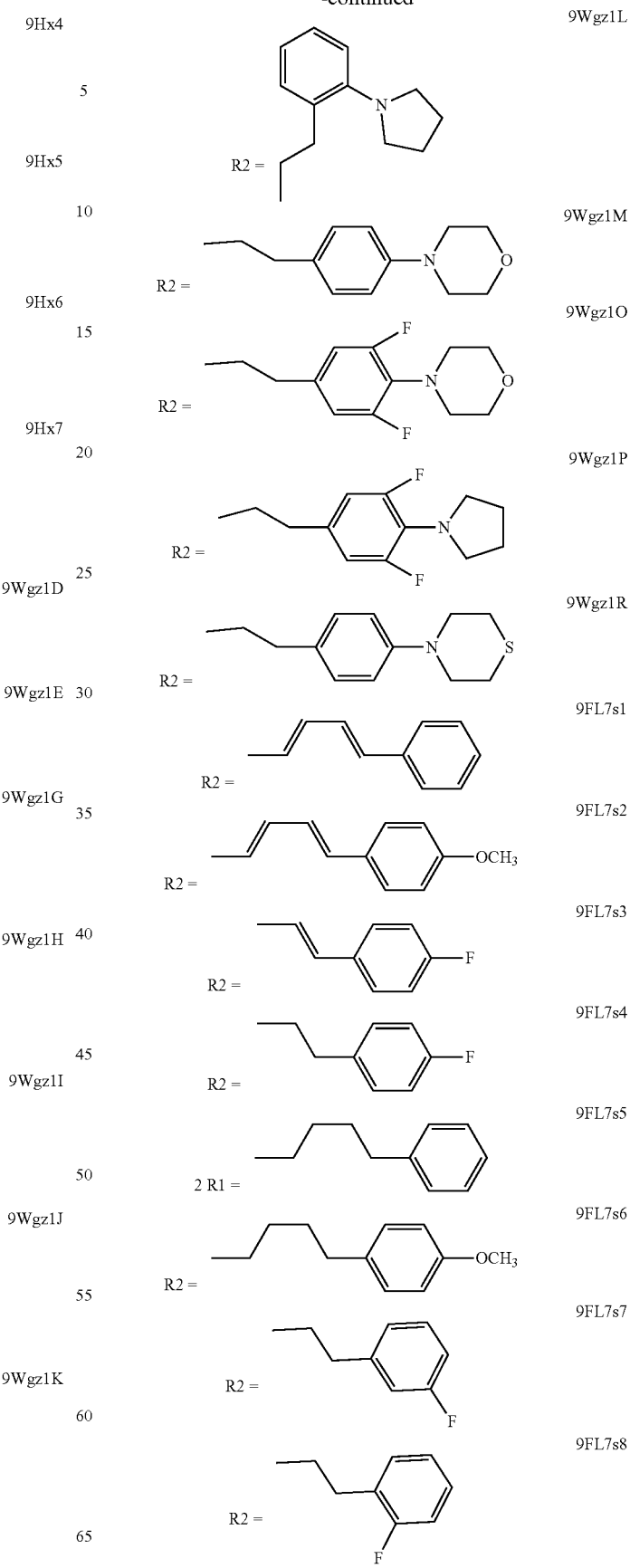

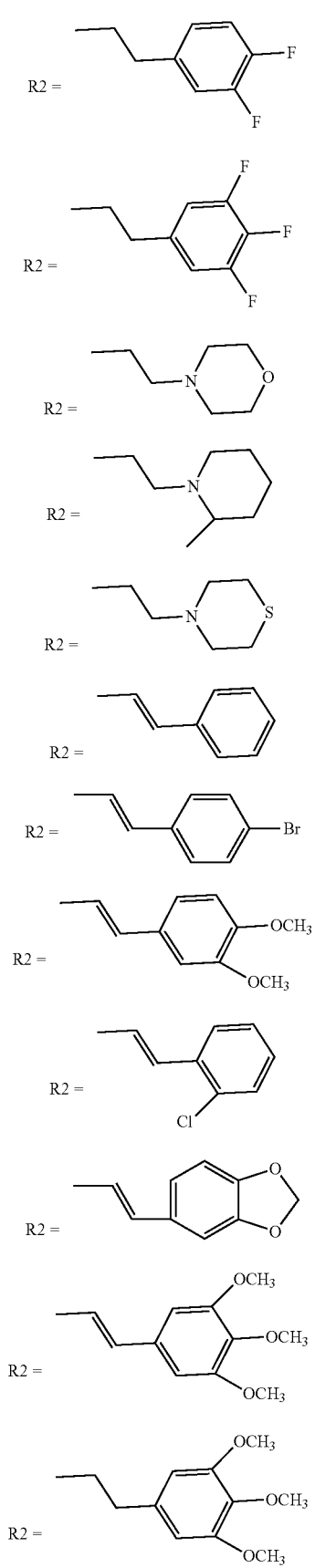
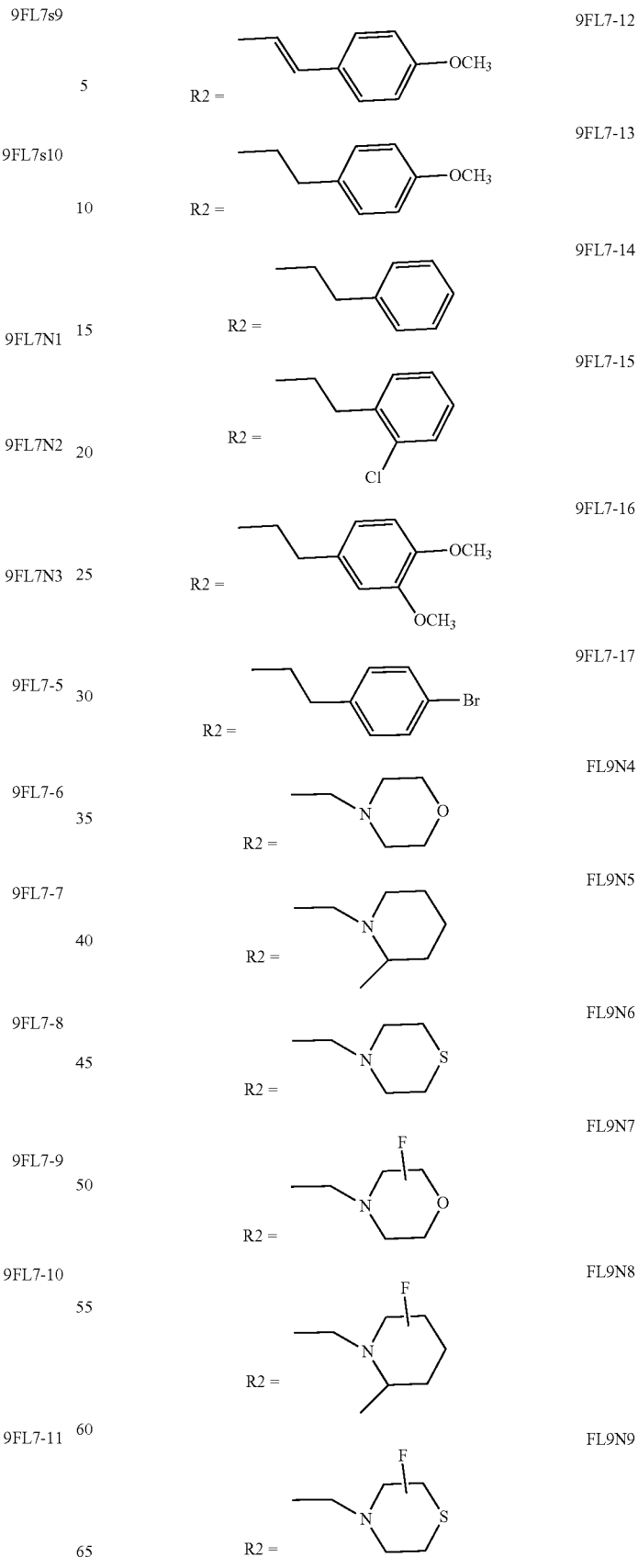

-continued
Group II-b
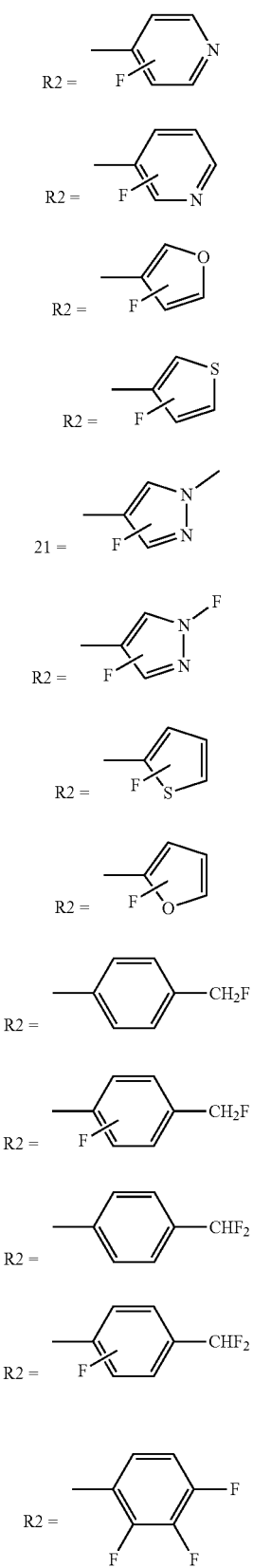
9FLW-b1
9FLW-b2
9FLW-b3
9W-b4
9FLW-b5a
9FLW-b5b
9FLW-b6
9FLW-b7
9FLW-b9a
9FLW-b9b
9FLW-b9c
9FLW-b9d
9FLHx4b
-continued
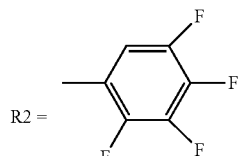 9FLHx4c
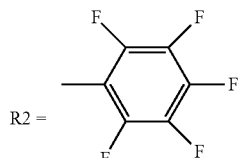 9FLHx4d
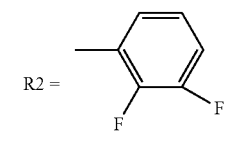 9FLHx5b
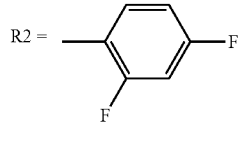 9FLHx5c
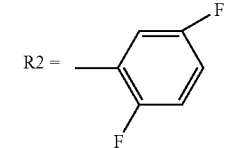 9FLHx5d
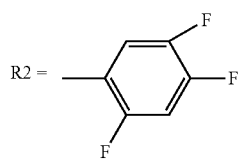 9FLHx5e
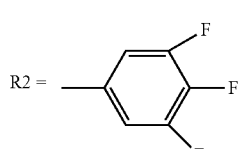 9FLHx6b
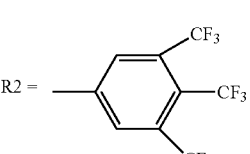 9FLHx7b
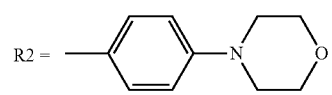 9FLWgz1Db
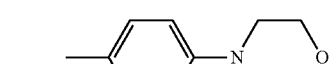 9FLWgz1Dc
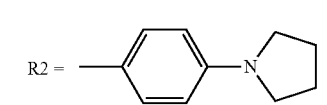 9FLWgz1Eb

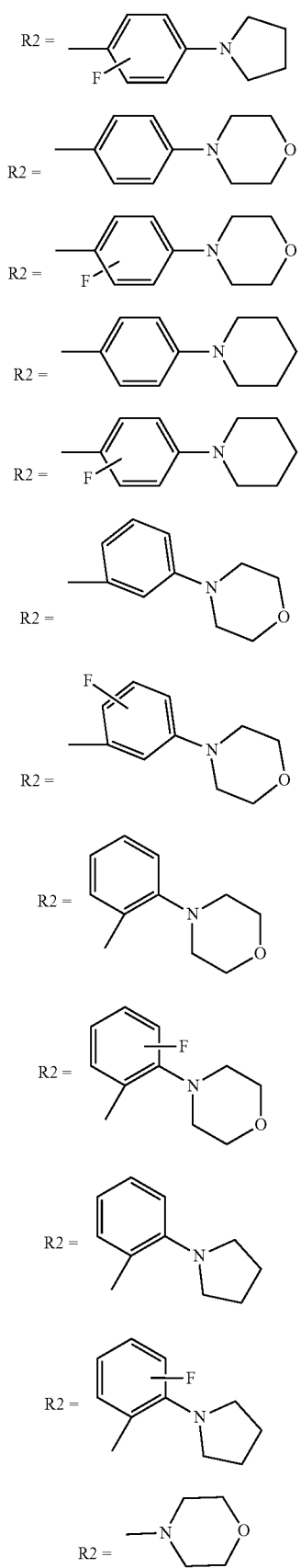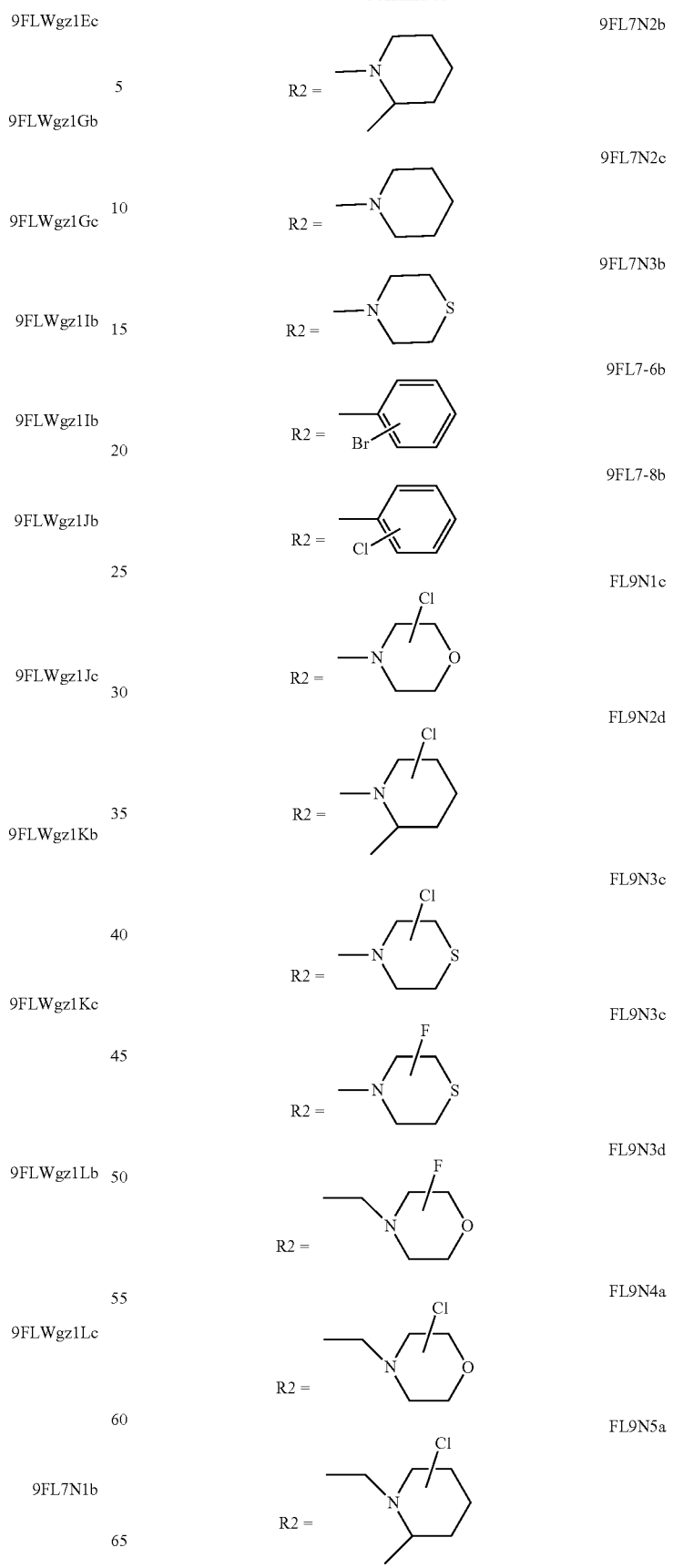

-continued
R2 = 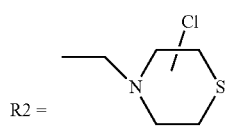 FL9N6a
R2 = 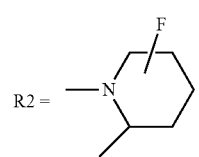 FL9N2f
R2 = 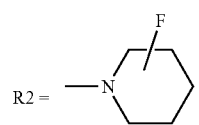 FL9N2g
Group III-b
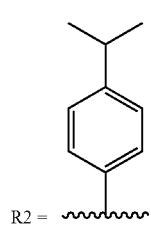 9Q1
R2 =
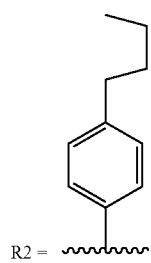 9Q2
R2 =
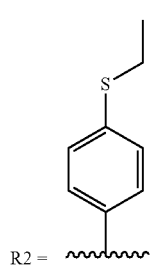 9Q3
R2 =
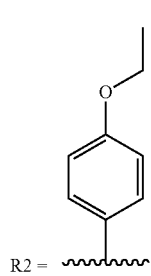 9Q4
R2 =
-continued
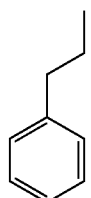 9Q5
R2 =
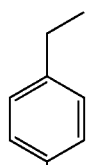 9Q6
R2 =
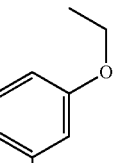 9Q7
R2 =
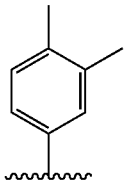 9Q8
R2 =
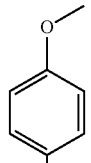 9Q9
R2 =
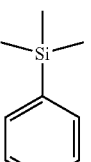 9Q10
R2 =
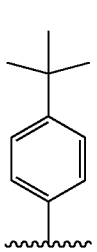 9Q11
R2 =

33
-continued
9Q12
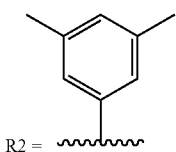
R2 =
9Q13
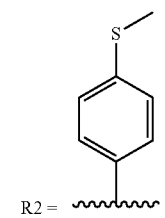
R2 =
9Q14
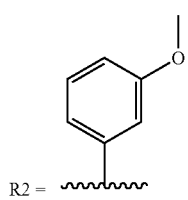
R2 =
9Q15
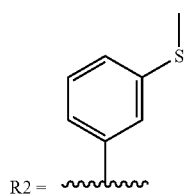
R2 =
9Q16
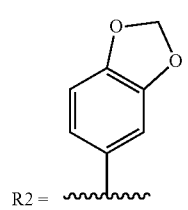
R2 =
9Q17
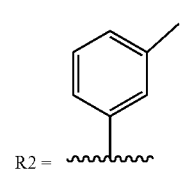
R2 =
9Q18
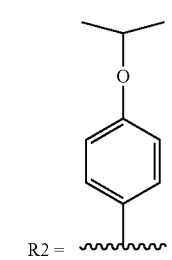
R2 =
34
-continued
9Q19
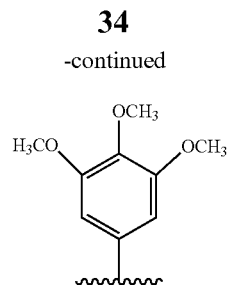
R2 =
9Q21
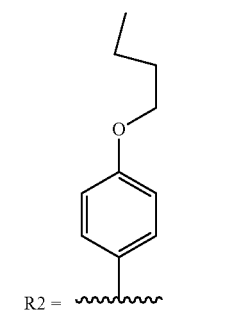
R2 =
9Q22
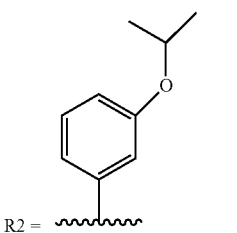
R2 =
9Q23
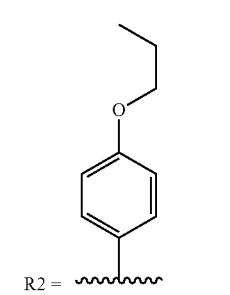
R2 =
9Q24
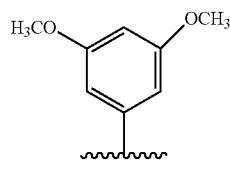
R2 =
9Q25
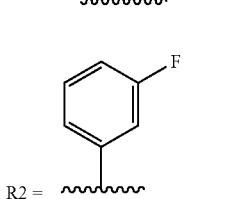
R2 =
9Q27
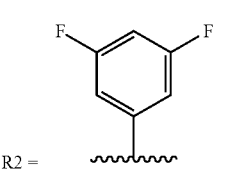
R2 =

9Q28 R2 = 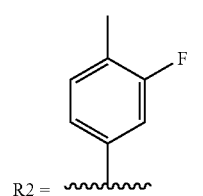
9Q29 R2 = 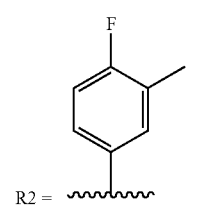
9Q30 R2 = 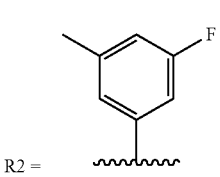
9Q31 R2 = 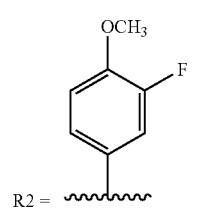
9Q32 R2 = 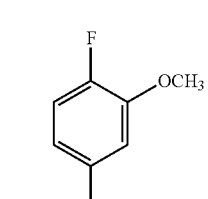
9Q33 R2 = 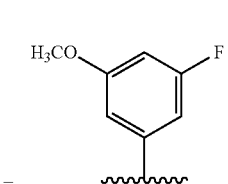
9Q34 R2 = 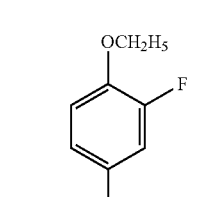
9Q35 R2 = 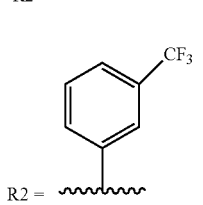
9Q36 R2 = 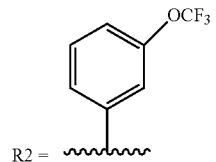
9Q37 R2 = 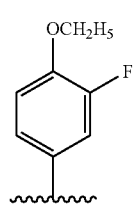
Group IV-b
9FL1a R2 = 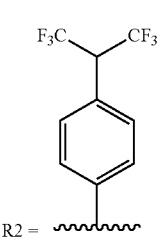
9FL1b R2 = 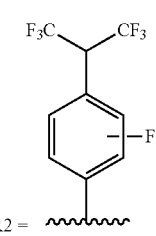
9FL2 R2 = 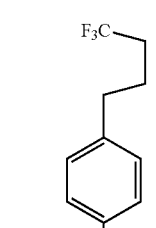
9FL3 R2 = 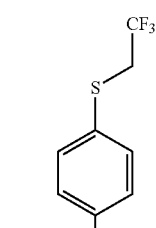

| | |
|---|---|
| 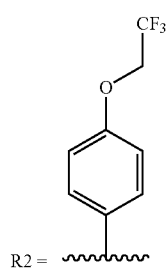 R2 = | 9FL4a |
| 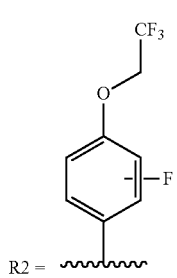 R2 = | 9FL4b |
| 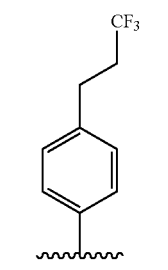 | 9FL5a |
| 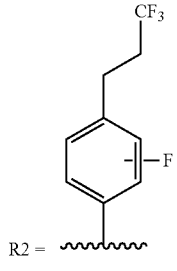 R2 = | 9FL5b |
| 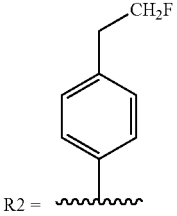 R2 = | 9FL6a |
| 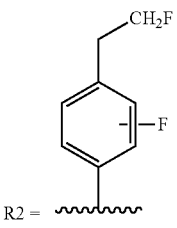 R2 = | 9FL6b |
| | |
|---|---|
| 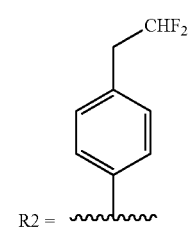 R2 = | 9FL6c |
| 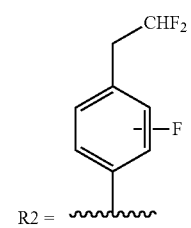 R2 = | 9FL6d |
| 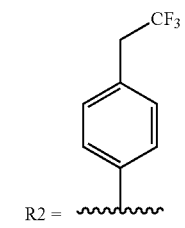 R2 = | 9FL6e |
| 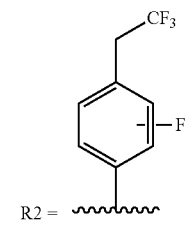 R2 = | 9FL6f |
| 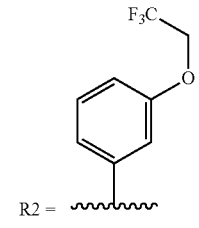 R2 = | 9FL7 |
| 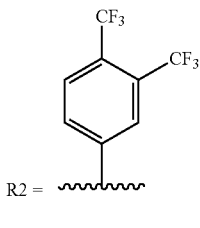 R2 = | 9FL8a |
| 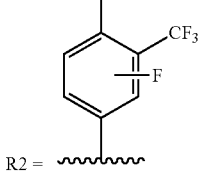 R2 = | 9FL8b |

39
-continued
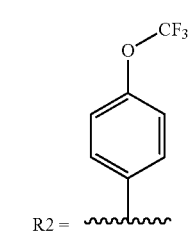
R2 = 
9FL9a
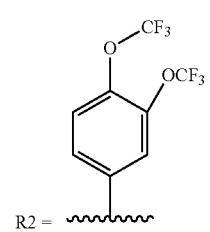
R2 = 
9FL9b
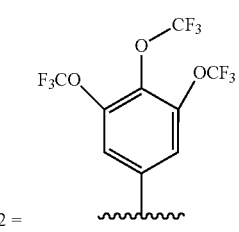
R2 = 
9FL9c
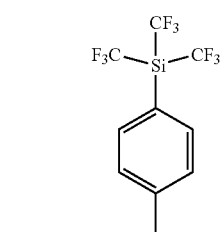
R2 = 
9FL10
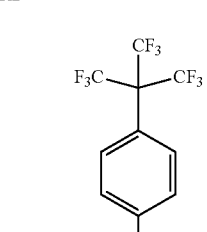
R2 = 
9FL11
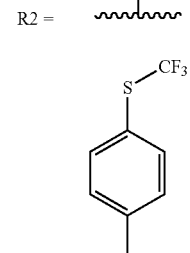
R2 = 
9FL13
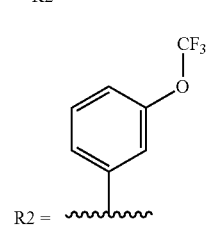
R2 = 
9FL14
40
-continued
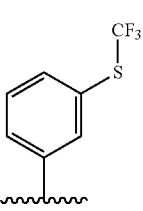
R2 = 
9Q15
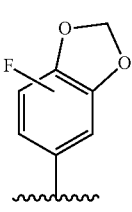
R2 = 
9FL16
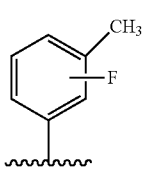
R2 = 
9FL17a
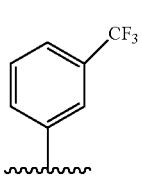
R2 = 
9FL17b
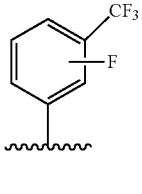
R2 = 
9FL17c
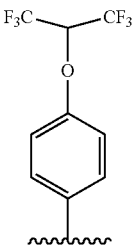
R2 = 
9FL18
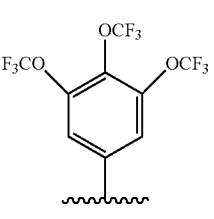
R2 = 
9FL19

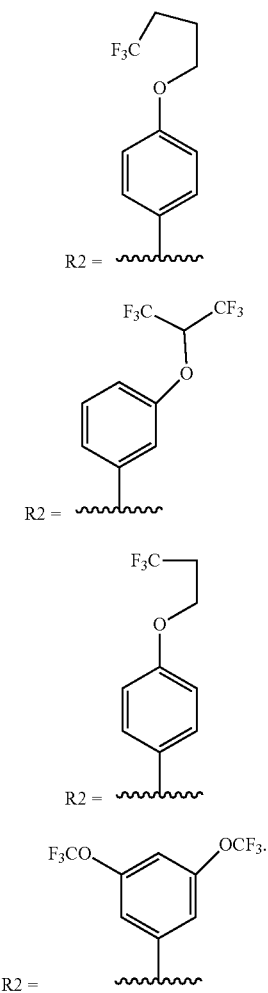

9FL21

R2 =

9FL22

R2 =

9FL23

R2 =

9FL24

R2 =

In the third situation, wherein the "R2" on Position 9 of Formula 1 is one of the following chemical groups: F—, Cl—, Br—, I—, FCH$_2$—, F$_2$CH—, F$_3$C—, ClCH$_2$—, Cl$_2$CH—, Cl$_3$C—, BrCH$_2$—, Br$_2$CH—, Br$_3$C—, ICH$_2$—, I$_2$CH—, I$_3$C—, HO—, HONH—, CH$_3$O—, FCH$_2$O—, F$_2$CHO—, ClCH$_2$O—, Cl$_2$CHO—, NH$_2$—, NH$_2$CH$_2$—, NH$_2$CFH—, CH$_3$NH—, FCH$_2$NH—, F$_2$CHNH—, ClCH$_2$NH—, Cl$_2$CHNH—, (CH$_3$)$_2$N—, (FCH$_2$)$_2$N—, (F$_2$CH)$_2$N—, (ClCH$_2$)$_2$N—, (Cl$_2$CH)$_2$N—, —NHC(O)NH$_2$, —C(O)CH$_3$, —C(O)CH$_2$F, —C(O)CHF$_2$, —C(O)CH$_2$Cl, —C(O)CHCl$_2$, —CO$_2$CH$_3$, —CO$_2$CH$_2$F, —CO$_2$CHF$_2$, CO$_2$CH$_2$Cl, —CO$_2$CHCl$_2$, and —C(O)N(CH$_2$)$_2$, and the "R1" on Position 7 of Formula 1 is independently selected from, but is not limited to, the Group I-a, Group II-a, Group III-a and Group IV-a.

In the fourth situation, wherein the "R1" on Position 7 of Formula 1 is one of the following chemical groups: F—, Cl—, Br—, I—, FCH$_2$—, F$_2$CH—, F$_3$C—, ClCH$_2$—, Cl$_2$CH—, Cl$_3$C—, BrCH$_2$—, Br$_2$CH—, Br$_3$C—, ICH$_2$—, I$_2$CH—, I$_3$C—, HO—, HONH—, CH$_3$O—, FCH$_2$O—, F$_2$CHO—, ClCH$_2$O—, Cl$_2$CHO—, NH$_2$—, NH$_2$CH$_2$—, NH$_2$CFH—, CH$_3$NH—, FCH$_2$NH—, F$_2$CHNH—, ClCH$_2$NH—, Cl$_2$CHNH—, (CH$_3$)$_2$N—, (FCH$_2$)$_2$N—, (F$_2$CH)$_2$N—, (ClCH$_2$)$_2$N—, (Cl$_2$CH)$_2$N—, —NHC(O)NH$_2$, —C(O)CH$_3$, —C(O)CH$_2$F, —C(O)CHF$_2$, —C(O)CH$_2$Cl, —C(O)CHCl$_2$, —CO$_2$CH$_3$, —CO$_2$CH$_2$F, —CO$_2$CHF$_2$, CO$_2$CH$_2$Cl, —CO$_2$CHCl$_2$, and —C(O)N(CH$_2$)$_2$, and the "R2" on Position 9 of Formula 1 is independently selected from, but is not limited to, the Group I-b, Group II-b, Group III-b and Group IV-b.

In illustrative embodiments, the compounds of Formula 1 also include their Position 20 ester corresponding compounds derived from various esterifying chemical groups, and all of the compounds of Formula 1 are administered orally, intravenously, subcutaneously, transdermally, intraperitoneally, or by inhalation. In illustrative embodiments, the disease is selected from the group consisting of a neoplastic disease, an autoimmune disease, restenosis, and any other human disease relevant to abnormal cell proliferation such as Tuberous Sclerosis Complex (TSC) and cancer.

In some embodiments, the disease is one or more cancers selected from the group consisting of solid tumors, blood cancers, fibrosarcoma, myxosarcoma, liposarcoma, chondrosarcoma, osteogenic sarcoma, chordoma, angiosarcoma, endotheliosarcoma, lymphangiosarcoma, pseudomyxoma peritonei, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, head and neck cancer, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, glioblastoma, glioblastoma multiforme, astrocytoma, medulloblastoma, craniopharyngioma, ependymoma, pinealoma, hemangioblastoma, acoustic neuroma, oliodendroglioma, Schwannoma, meningioma, melanoma, neuroblastoma, retinoblastoma, leukemia, acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia, lymphoma, Hodgkin's disease, non-Hodgkin's disease, multiple myeloma and thymoma or any combination thereof.

In suitable embodiments, the one or more cancers are one or more metastatic cancers, primary tumors, refractory cancers, progressive cancers, invasive cancers, solid tumors, disseminated tumors or hematological cancers. In illustrative embodiments, the one or more cancers are refractory to one or more therapeutic indications. In illustrative embodiments, the refractory cancer phenotype comprises expression of one or more resistance markers selected from the group reported in our previous invention (PCT/US2015/022095) that consists of, but not limited to, survivin, Mcl-1, XIAP, cIAP2, ABC transporter proteins, hypoxia inducing factor 1α (HIF-1α), Hdm2, HdmX, p53, mutant APC, and/or mutant Kras. In illustrative embodiments, the ABC transporter proteins are selected from the group consisting of ABCG2, ABCC4, MDR1, MRP1, heat shock protein 60 (HSP60), stress-70 protein (GRP75), ATP-dependent RNA helicase DDX5 (p68), nucleolar RNA helicase 2 (DDX21), elongation factor 2(EF2), pre-mRNA-splicing factor ATP-dependent RNA helicase (DHX15), Transitional endoplasmic reticulum ATPase (TERA), Transferrin receptor protein (TFR1), MAP kinase-activated protein kinase 2 (MAPK2), Catenin beta-1 (CTNB1), Early endosome antigen 1 (EEA1), Guanine nucleotide-binding protein subunit beta- 2-like 1 (GBLP), Electron transfer flavoprotein subunit alpha (ETFA), Proteasome activator complex subunit 3 (PSME3), UPF0368 protein Cxorf26 (CX026), Peroxiredoxin-2 (PRDX2), Peroxiredoxin-1 (PRDX1), Thioredoxin-dependent peroxide reductase (PRDX3), Serine/arginine-rich splicing factor 3 (SRSF3), Proteasome subunit beta type-2 (PSB2), Glutathione S-transferase P (GSTP1), MAP/microtubule affinity-regulating kinase 3 (MARK3), DNA-damage inducible 1 (DDI1), tumor protein D52-like 2 (TPD52L2), calcium channel, voltage-dependent, beta 1 subunit (CACNB1), Probable G-protein coupled receptor 1 (PGPCR1), ubiquitin specific peptidase 2 (USP2), melanocortin 2 receptor (MC2R), Fibroblast growth factor 18 (FGF18), tumor protein p53 inducible protein 3 (TP53I3), CCHC-type zinc finger, nucleic acid binding protein (CNBP), WD repeat domain 22 (WDR22), Potassium voltage-gated channel subfamily E member 1 (PVGCSE-M1), ubiquitin-conjugating enzyme E2T (putative) (UBE2T), Ubiquitin-like protein 7 (ULP7), RNA binding motif, single stranded interacting protein 2 (RBMS2), Cytoplasmic tyrosine-protein kinase (BMX), and cyclin B1 interacting protein 1 (CCNB1IP1). In illustrative embodiments, the p53 is wild type, null or a p53 mutant, or wherein there is an aberration in a canonical p53 pathway, or any combination thereof.

In illustrative embodiments, the compound of Formula 1 includes acute treatment resistance. In some embodiments, the compound of Formula 1, and their pharmaceutically acceptable salt of the compound of Formula 1 for overcoming acute and chronic acquired and/or inherent treatment resistance is administered to the subject separately, sequentially or simultaneously with one or more agents selected from the group consisting of chemotherapeutic agents, chemopreventive agents, are derived from natural plants, are derived from non-plants, curcumin, resveratrol, vitamin D3, vintain A, vitamin E, vitamin C, isothiocyanates (ITCs), allyl isothiocyanate (AITC), silibinin (silybin), Sulindac, selenium-containing compounds, Methylseleninic acid, *Amoora rohituka*-derived AMR analogs, AMR-Me, AMR-MeOAc, terameprocol, celecoxib, imatinib, quercetin, Epigallocatechin-3-gallate (EGCG), Deguelin, 3,3'-Diindolylmethane (DIM), Emodin, Genistein, Tolfenamic acid, Simvastatin, Gambogic acid, Docosahexaenoic acid, Ursolic acid, Oleanolic acid, Bufalin, Sulforaphane, Noscapine, Indomethacin (indomethacin), Lupeol, Decursin, Avicin D, Ciglitazone, Bevacizumab (Avastin), crolibulin, Baicalein, Paxilline, Purvalanol A, NU6140, Ardisianone, NVP-BGT226, HDAC inhibitors, MS-275/Entinostat, SAHA, Anacardic acid, Diterpenes, Bufotalin, Withaferin A, Plumbagin, Flavokawain A, Flavokawain B, Ponicidin, Escin, Kuguacin J, LQB-118, Crotepoxide, Kuguaglycoside C, Destruxin B, Evodiamine, Sesamin, prostanoids, endothelin antagonists, cytoplasmic kinase inhibitors, receptor kinase inhibitors, endothelin receptor antagonists, ambrisentan, bosentan, and sitaxsentan, PDE5 (PDE-V) inhibitors, sildenafil, tadalafil, and vardenafil, calcium channel blockers, amlodipine, felodipine, varepamil, diltiazem, menthol, prostacyclin, treprostinil, iloprost, beraprost, nitric oxide, oxygen, heparin, warfarin, diuretics, digoxin, cyclosporins, cyclosporin A, CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, antibodies to CD40, antibodies to gp39, CD154, CD40 fusion proteins, gp39 fusion proteins, CD401g, CD8gp39, nuclear translocation inhibitors of NF-kappa B function, deoxyspergualin (DSG), cholesterol biosynthesis inhibitors, HMG CoA reductase inhibitors, lovastatin, simvastatin, non-steroidal anti-inflammatory drugs (NSAIDs), ibuprofen, aspirin, acetaminophen, leflunomide, deoxyspergualin, cyclooxygenase inhibitors, celecoxib, steroids, prednisolone, dexamethasone, gold compounds, beta-agonists, salbutamol, LABAs, salmeterol, leukotriene antagonists, montelukast, antiproliferative agents, methotrexate, FK506, tacrolimus, Prograf, mycophenolate mofetil, cytotoxic drugs, azathioprine, VP-16, etoposide, fludarabine, doxorubin, adriamycin, amsacrine, camptothecin, cytarabine, gemcitabine, fluorodeoxyuridine, melphalan, cyclophosphamide, antimetabolites, methotrexate, topoisomerase inhibitors, camptothecin, DNA alkylators, cisplatin, kinase inhibitors, sorafenib, microtubule poisons, paclitaxel, TNF-α inhibitors, tenidap, anti-TNF antibodies, soluble TNF receptors, hydroxy urea, rapamycin, sirolimus, and Rapamune, or any combination thereof.

In illustrative embodiments, the compound of Formula 1 is formulated into various forms of aqueous suspension, nanoparticles or solid status such as tablet, capsules, etc. In illustrative embodiments, the salt is a chloride, phosphate, mesylate, bismesylate, tosylate, lactate, tartrate, malate, bisacetate, or citrate salt. In illustrative embodiments, the compound of Formula 1, the pharmaceutically acceptable salt of the compound of Formula 1, the pharmaceutically acceptable salt of the tautomer, is administered in a total daily dosage from about 0.01 mg/kg to about 10 mg/kg. In illustrative embodiments, the compound of Formula 1, the pharmaceutically acceptable salt of the compound, is administered from one to five times weekly.

In illustrative embodiments, the compound of Formula 1, the pharmaceutically acceptable salt of the compound, is administered in unit dosage form, wherein the unit dose comprises from about 0.01 mg/kg to about 10 mg/kg of the compound, tautomer, and/or salts based on the subject's body weight, or from about 0.01 mg/kg to about 20 mg/kg of the compound, tautomer, and/or salts.

In illustrative embodiments, the unit dose is sufficient to provide: (a) a $C_{max}$ of about 10 to 400 ng/mL of the compound in a subject's plasma or a $C_{max}$ of about 10 to 400 ng/mL of the compound in the subject's blood when it is administered to the subject; and/or (b) about 1 to 50 ng/mL of the compound in a subject's plasma 12 hours after administration or about 1 to 50 ng/mL of the compound in the subject's blood 12 hours after administration to the subject; and/or (c) about 0 to 5 ng/mL of the compound in a subject's plasma 24 hours after administration or about 0 to 5 ng/mL of the compound in the subject's blood 24 hours after administration to the subject; and/or (d) active gradients of Formula 1 sustain 1-25 ng/mL (gram) in tumor within 48 hours after administration to the subject. In illustrative embodiments, the subject is a human subject.

In illustrative embodiments, the compound of Formula 1 is a compound of any of the embodiments described herein.

In illustrative embodiments, a pharmaceutical composition is provided herein, which comprises the compound of Formula 1, the pharmaceutically acceptable salt of the compound, which further includes a pharmaceutically acceptable carrier. In illustrative embodiments, the present disclosure provides for the use of an active ingredient for the preparation of pharmaceutical compositions for treating a neoplastic disease in a subject or a biological condition associated with the neoplastic disease in the subject, wherein the active ingredient is a compound of Formula 1.

In illustrative embodiments, the compound of Formula 1 is a compound of any of the embodiments described herein.

In one aspect, the present invention entails a method for chemically synthesizing the individual compounds of Formula 1.

In one aspect, the present invention provides for an aqueous suspension formulation of the foregoing compound of Formula 1, where the formulation comprises in saline and a type of cyclodextrin such as hydroxypropyl-β-cyclodextrin from about 0.1 to about 10% (w/v) in saline. In some embodiments, the formulation finally reaches a status of ethanol-containing suspension up to 40 mg/mL of a compound of Formula 1 containing 40% (w/v) of a type of cyclodextrin such as hydroxypropyl-β-cyclodextrin; in some embodiments before saline dilution. In some illustrative embodiments, the formulation finally reaches a status of organic solvent-free. In illustrative embodiments, the formulation entails hydroxypropyl-β-cyclodextrin from 0.1 to 10% in saline (w/v) and propylene glycol (PG) from 1 to 5% (PG) (w/v or w/w) with or without a polyethylene glycol 400 from 0 to 4% (w/v), where the combination of the propylene glycol and polyethylene glycol in total is from 1 to 5% total (w/v).

In one aspect, the present invention entails a method of producing an ethanol-containing or organic solvent-free formulation containing a compound of Formula 1, or a pharmaceutically acceptable salt of the compound of Formula 1.

In illustrative embodiments, the cyclodextrin is hydroxypropyl-β-cyclodextrin. In illustrative embodiments, the hydroxypropyl-β-cyclodextrin (HPPCD) is present in the aqueous suspension formulation at a final concentration of about from 0.1 to about 10% (w/v) in saline. In illustrative embodiments, the other solvent is selected from one or more of propylene glycol (PG), polyethylene glycol (PEG) 300, and PEG400. In illustrative embodiments, the one or more of PG, PEG300 and PEG400 is present in the formulation at a concentration of about from 1 to about 5% of total in saline (w/v) in the suspension status or 0-5% in a powder/tablet status (w/w). In illustrative embodiments, the emulsifier is hydroxypropyl methylcellulose (HPMC). In some embodiment, the HPMC with viscosity of 40-60 cps is present in the formulation at a final concentration of about from 2% to about 5% (w/v). In illustrative embodiments, the formulation at a final concentration from 0.1 to 10 mg/mL of a Formula 1 compound as final concentration after dilution.

In one aspect, the present invention entails a method of producing an organic solvent-free powder/tablet formulation containing a compound of Formula 1, or a pharmaceutically acceptable salt of the compound of Formula 1.

In another aspect, the present invention provides an organic solvent-free powder capsule/tablet formulation of the foregoing compounds from Formula 1, where the formulation comprises Fillers/Binders/Diluents (celluloses/cellulose derivatives, starches/starch derivatives, lactose), Disintegrant (colloidal silicone dioxide, croscarmellose sodium, crosspovidone), Glidant (dibasic calcium phosphate, colloidal silicone dioxide), Lubricants (magnesium stearate, stearic acid, polyethylene glycol, Talc), Antimicrobials/Preservative (propylene glycol/PG, propylene paraben, methyl paraben, glycerin).

In the next aspect, the present invention provides an organic solvent-free powder capsule/tablet formulation of the foregoing compounds selected from Formula 1, where the formulation comprises microcrystalline cellulose (MCC, 30%-80%), corn starch (0%-40%), lactose (10%-25%), colloidal silicone dioxide (1%-3%), dibasic calcium phosphate (1%-10%), magnesium stearate (0.2%-3%), propylene glycol (1%-5%).

In another aspect, the present invention provides an organic solvent-free powder of HPβCD-formulated FL118 complex powders that are directly dissolved in an aqueous solution such as saline with 0-5% propylene glycol (PG) to make the powder into a suspension for intraperitoneal (i.p./IP/ip), intravenous (i.v./iv/IV) or oral (p.o./po) administration for treatment of cancer.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

FIG. 21-1 shows the antitumor efficacy and toxicity (body weight changes) of the FL118 platform-derived analogue 7Q6 in pancreatic cancer (14244) and colorectal cancer (27454) patient-derived xenograft (PDX) tumor in animal models. PDX tumor establishment, drug formulation for oral administration, vehicle composition and experimental SCID mice of PDX tumors preparation were the same as described in FIGS. 7 and 13. PDX tumor SCID mice treatment with vehicle and 7Q6, respectively, was initiated 7-14 days after the transplanted tumors reached 100-200 mm$^3$ (designated day 0). The animal model of PDX tumors was orally treated weekly for 4 times as shown with black arrows (one course/cycle). A. Pancreatic cancer PDX14244 tumor curve profile obtained after with vehicle or with 7Q6 treatment. B. Colorectal cancer PDX27454 tumor curve profile obtained after with vehicle or with 7Q6 treatment. C. The animal body weight change profile after with vehicle or with 7Q6 treatment was shown over the experimental period.

FIG. 21-2 shows the antitumor efficacy and toxicity (body weight changes) of the FL118 platform-derived analogue 7Q6 in colorectal cancer (27454) patient-derived xenograft (PDX) tumor in animal models. PDX tumor establishment, drug formulation for intra-peritoneal (i.p.) administration, vehicle composition and experimental SCID mice of PDX tumors preparation were the same as described in FIGS. 7 and 13. PDX tumor SCID mice treatment with vehicle and 7Q6 via i.p. for only one time as shown (arrowed), respectively, was initiated 7-14 days after the transplanted tumors reached 100-200 mm$^3$ (designated day 0). A. Colorectal cancer PDX27454 tumor curve profile obtained after with vehicle or with 7Q6 treatment. B. The animal body weight change profile after with vehicle or with 7Q6 treatment was shown.

Figure 1:
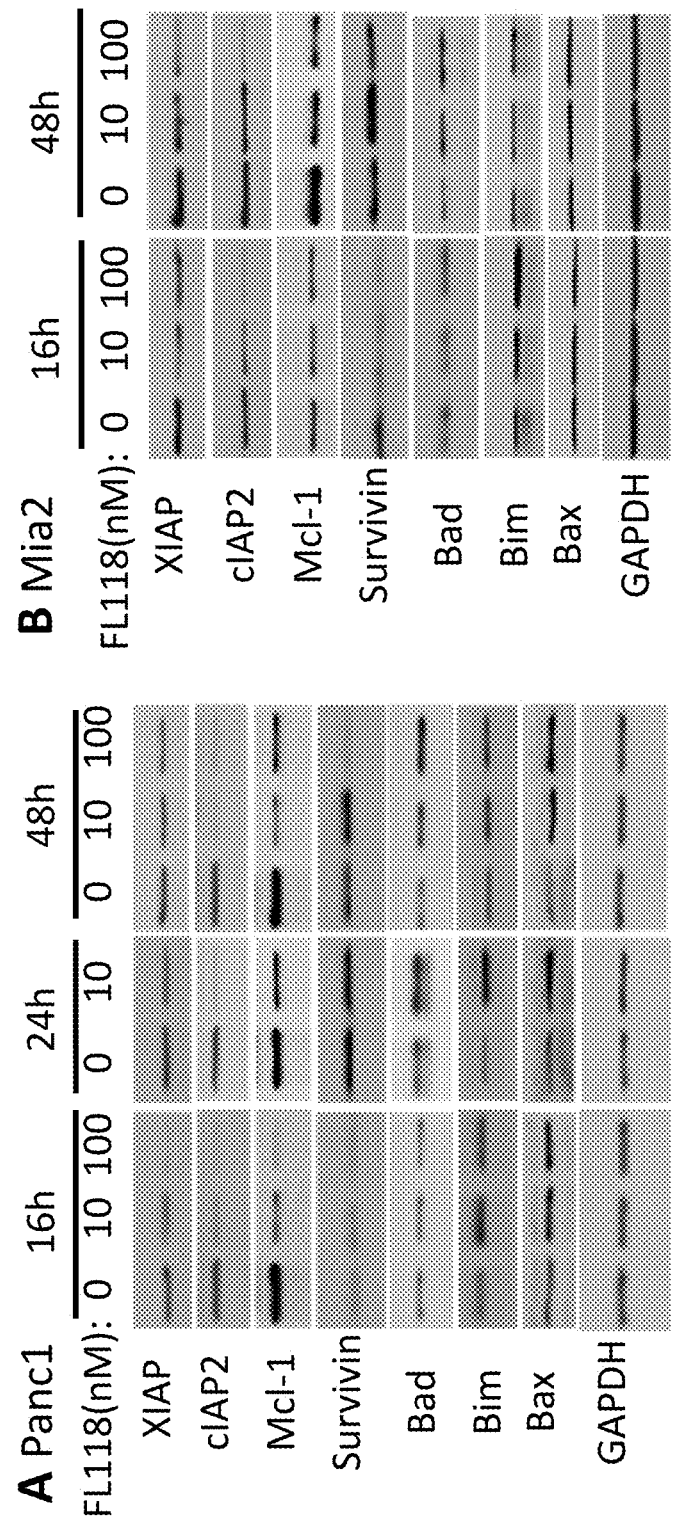
FIG. 1 shows that FL118 platform downregulates the expression of multiple antiapoptotic proteins and upregulates certain proapoptotic proteins in pancreatic cancer cells: Subconfluent pancreatic cancer cells were treated with FL118 as shown, and the expression of antiapoptotic proteins survivin, Mcl-1, XIAP, and cIAP2 as well as proapoptotic proteins Bad, Bim and Bax was detected by western blots using corresponding antibodies for each protein. GAPDH is an internal control for protein loading. The result from PANC1 pancreatic cancer cell line is shown in A, and the result from MIA PaCa2 (Mia2) pancreatic cancer cell line is shown in B.

- Table 1: Effects of FL118 on BALB/cj mouse hematological parameters.
- Table 2: Effects of FL118 on BALB/cj mouse serum biochemical parameters.
- Table 3: Effects of FL118 on beagle dogs' hematological parameters.
- Table 4: Effects of FL118 on beagle dogs' serum biochemical parameters.
- Table 5: In vitro antitumor activity of FL118 7Q-series derivatives ($IC_{50}/EC_{50}$ in μM).
- Table 6: In vitro antitumor activity of FL118 9Q-series derivatives ($IC_{50}/EC_{50}$ in μM).
- Table 7: FL7s- and FL7-series $IC_{50}/EC_{50}$ in cancer cells in nM.
- Table 8: FL7N-series $IC_{50}/EC_{50}$ in cancer cells in nM.
- Table 9: Wb-series $IC_{50}/EC_{50}$ in cancer cells in nM.
- Table 10: Hx-series $IC_{50}/EC_{50}$ in cancer cells in nM.
- Table 11: Experimental design of the beagle dogs for FL118 toxicity and MTD studies.
- Table 12: Potential biochemical biomarkers and targets identified using ligands (FL118 and FL118 analogue) through ligand affinity purification and tritium ($^3$H)-labeled ligand screening of protein ProtoArray.

DETAILED DESCRIPTION OF THE INVENTION

The present disclosure relates to, inter alia, a novel class of compounds which function as anti-cancer agents. Likewise, methods for synthesis and utility of such compounds in the treatment and/or prevention of human disease conditions are disclosed herein. The present disclosure further relates to pharmaceutical formulations of the compounds, which possess therapeutic and/or prophylactic indications for subjects in need of treatment.

The definitions of certain terms as used in this specification are provided below. Unless defined otherwise, all technical and scientific terms used herein generally have the same meaning as commonly understood by one of ordinary skill in the art to which this invention belongs. As used in this specification and the appended claims, the singular forms "a", "an" and "the" include plural referents unless the content clearly dictates otherwise. For example, reference to "a compound" includes a combination of two or more compounds, and the like.

Terminology

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the enumerated value.

As used herein, the "administration" of an agent or drug, e.g., one or more antiapoptotic protein and/or signaling inhibitor compounds, to a subject or subjects includes any route of introducing or delivering to a subject a compound to perform its intended function. Administration can be carried out by any suitable route, including orally, intranasally, by inhalation, parenterally (intravenously, intramuscularly, intraperitoneally, or subcutaneously), rectally, or topically. Administration includes self-administration and the administration by another. It is also to be appreciated that the various modes of treatment or prevention of medical conditions as described are intended to mean "substantial", which includes total but also less than total treatment/prevention, and wherein some biologically or medically relevant result is achieved.

As used herein, the terms "assessing," "assaying," "determining," and "measuring" are used interchangeably and include both quantitative and qualitative determinations. These terms refer to any form of measurement, and include determining if a characteristic, trait, or feature is present or not. Assessing may be relative or absolute. "Assessing the presence of" includes determining the amount of something present and/or absent.

As used herein, the term "clinical factors" refers to any data that a medical practitioner may consider in determining a diagnosis, prognosis, or therapeutic regimen for treating or preventing a disease or diseases. Such factors include, but are not limited to, the patient's medical history, a physical examination of the patient, complete blood count, examination of blood cells or bone marrow cells, cytogenetics, pulmonary health, vascular indications of disease, and immunophenotyping of cells.

As used herein, the terms "comparable" or "corresponding" in the context of comparing two or more samples, responses to treatment, or drugs, refer to the same type of sample, response, treatment, and drug respectively used in the comparison. In some embodiments, comparable samples may be obtained from the same individual at different times. In other embodiments, comparable samples may be obtained from different individuals, e.g., a patient and a healthy individual. In general, comparable samples are normalized by a common factor for control purposes.

As used herein, the term "composition" refers to a product with specified ingredients in the specified amounts, as well as any product which results, directly or indirectly, from combination of the specified ingredients in the specified amounts.

As used herein, the term "diagnosis" means detecting a disease or disorder or determining the stage or degree of a disease or disorder. Typically, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease, i.e., there may be differential diagnoses that can be inferred from a diagnostic factor or symptom. Likewise, there may be instances where a factor or symptom that is indicative of a particular disease is present in an individual that does not have the particular disease. The term "diagnosis" also encompasses determining the therapeutic effect of a drug therapy, or predicting the pattern of response to a drug therapy. The diagnostic methods may be used independently, or in combination with other diagnosing and/or staging methods known in the medical art for a particular disease or disorder.

As used herein, the terms "drug," "compound," "active agent," "agent," "actives," "pharmaceutical composition," "pharmaceutical formulation," and "pharmacologically active agent" are used interchangeably and refer to any chemical compound, complex or composition, charged or uncharged, that is suitable for administration and that has a beneficial biological effect, suitably a therapeutic effect in the treatment of a disease or abnormal physiological condition, although the effect may also be prophylactic in nature. The terms also encompass pharmaceutically acceptable, pharmacologically active derivatives of those active agents specifically mentioned herein, including, but not limited to, salts, esters, amides, prodrugs, active metabolites, analogs, and the like. When the terms "active agent," "pharmacologically active agent," and "API" (active pharmaceutical ingredient) are used, then, or when a particular active agent is specifically identified, it is to be understood that applicants intend to include the active agent per se as well as pharmaceutically acceptable, pharmacologically active salts, esters, amides, prodrugs, conjugates, metabolites, analogs, etc.

As used herein, the terms "effective amount" or "pharmaceutically effective amount" or "therapeutically effective amount" of a composition, is a quantity sufficient to achieve a desired therapeutic and/or prophylactic effect, e.g., an amount which results in the prevention of, or a decrease in, the symptoms associated with a disease that is being treated. The amount of a composition of the invention administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present invention can also be administered in combination with one or more additional therapeutic compounds.

As used herein, the term "neoplastic disease" refers to cancers of any kind and origin and precursor stages thereof. Accordingly, the term "neoplastic disease" includes the subject matter identified by the terms "neoplasia", "neoplasm", "cancer", "pre-cancer" or "tumor." A neoplastic disease is generally manifest by abnormal cell division resulting in an abnormal level of a particular cell population. Likewise, the monoclonal expansion of endothelial cells may refer to a "neoplasm" of the pulmonary arteriolar endothelial cells. The abnormal cell division underlying a neoplastic disease, moreover, is typically inherent in the cells and not a normal physiological response to infection or inflammation. In some embodiments, neoplastic diseases for diagnosis using methods provided herein include carcinoma. By "carcinoma," it is meant a benign or malignant epithelial tumor.

As used herein, the term "pharmaceutically acceptable salt" includes a salt with an inorganic base, organic base, inorganic acid, organic acid, or basic or acidic amino acid. As salts of inorganic bases, the invention includes, for example, alkali metals such as sodium or potassium; alkaline earth metals such as calcium and magnesium or aluminum; and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, maleic acid, lactic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

As used herein, the term "prognosis" refers to a prediction of the probable course and outcome of a clinical condition or disease. A prognosis is usually made by evaluating factors or symptoms of a disease that are indicative of a favorable or unfavorable course or outcome of the disease. The phrase "determining the prognosis" as used herein refers to the process by which the skilled artisan can predict the course or outcome of a condition in a patient. The term "prognosis" does not refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition. The terms "favorable prognosis" and "positive prognosis," or "unfavorable prognosis" and "negative prognosis" as used herein are relative terms for the prediction of the probable course and/or likely outcome of a condition or a disease. A favorable or positive prognosis predicts a better outcome for a condition than an unfavorable or negative prognosis. In a general sense, a "favorable prognosis" is an outcome that is relatively better than many other possible prognoses that could be associated with a particular condition, whereas an unfavorable prognosis predicts an outcome that is relatively worse than many other possible prognoses that could be associated with a particular condition. Typical examples of a favorable or positive prognosis include a better than average cure rate, a lower propensity for metastasis, a longer than expected life expectancy, differentiation of a benign process from a cancerous process, and the like. For example, a positive prognosis is one where a patient has a 50% probability of being cured of a particular cancer after treatment, while the average patient with the same cancer has only a 25% probability of being cured.

As used herein, the term "reference level" refers to a level of a substance which may be of interest for comparative purposes. In some embodiments, a reference level may be a specified composition dosage as an average of the dose level from samples taken from a control subject. In other embodiments, the reference level may be the level in the same subject at a different time, e.g., a time course of administering the composition, such as the level determined at 2, 4, 6, 8, and 10 minutes (min), etc.

As used herein, the terms "sample" or "test sample" refer to any liquid or solid material containing collected from a subject. In suitable embodiments, a test sample is obtained from a biological source, i.e., a "biological sample," such as cells in culture or a tissue sample from an animal, most preferably, a murine subject, mammal or human subject.

As used herein, the terms "subject" or "individual," refer to a mammal, such as a mouse, rat, or human, but can also be another animal such as a domestic animal, e.g., a dog, cat, or the like, a farm animal, e.g., a cow, a sheep, a pig, a horse, or the like, or a laboratory animal, e.g., a monkey, a rat, a mouse, a rabbit, a guinea pig, or the like. The term "patient" refers to a "subject" who is, or is suspected to be, afflicted with a disease.

As used herein, the terms "treating" or "treatment" or "alleviation" refer to both therapeutic treatment and prophylactic or preventative measures, wherein the objective is to prevent or slow down (lessen) the targeted pathologic condition or disorder. A subject is successfully "treated" for a disorder if, after receiving a therapeutic agent according to the methods of the present invention, the subject shows observable and/or measurable reduction in or absence of one or more signs and symptoms of a particular disease or condition.

As used herein, reference to a certain element such as "hydrogen" or "H" is meant to include all isotopes of that element. For example, if an R group is defined to include hydrogen or H, it also includes deuterium and tritium.

Overview

Control of human disease to extend life span and quality of life is the goal in clinical practice. In the field of human cancer control, the challenge is the treatment (e.g., chemotherapy and radiation) resistance, which results in untreatable disease or a high rate of metastasis and/or recurrence after treatment. Therefore, cancer treatment resistance, metastasis and recurrence are the primary causes of cancer death and continue to challenge the entire field.

Critical analysis of the peer-reviewed literature indicates that the challenge for overcoming treatment resistance is that the inherent or acquired (induced) resistance to treatment is through diverse mechanisms, often resulting from the fact that cancer cells usually possess diverse genetic and epigenetic alternations and abnormal expression of cancer-associated proteins. To address the challenge in treatment resistance, the fact that treatment resistance results from diverse mechanisms must be addressed. The prior art is devoid of efficacious strategies to this end.

Using one molecularly targeted agent in concert with one or two traditional cytotoxic drugs as a combination regimen has been previously employed. However, this approach is only able to alleviate the treatment resistance related to toxicity and efficacy for some of cancer patients with particular cancer types and/or favorable genetic background. Another challenging problem of treatment resistance is that cancer is a highly heterogeneous disease (Swanton C: Intra-tumor heterogeneity: evolution through space and time, Cancer research 2012, 72:4875-4882); gene-expression signatures of favorable versus unfavorable prognosis can be detected in different regions of the same tumor, and a significant percentage of somatic mutations may not be detected across every tumor region of the same tumor (Gerlinger M, et al.: Intratumor heterogeneity and branched evolution revealed by multiregion sequencing, The New England journal of medicine 2012, 366:883-892). This extensive intra-tumor heterogeneity presents difficult challenges with respect to personalized cancer treatment (personalized medicine) and biomarker development. Therefore, new strategies to resolve such challenges are needed.

One aspect of the present invention involves the invention of some particular anticancer compounds with specific spectrum of activity demonstrated in examples, which were created by the present inventors, but where such compounds nevertheless possess defined multiple targeting mechanisms, quantitatively and/or qualitatively, to combat cancer cell treatment resistance. Among the novel compounds disclosed herein, while each compound can target or bypass multiple resistant factors, individual compounds show distinct selectivity (quantitatively and/or qualitatively) with broad-spectrum overlap. Such a group of compounds impart therapeutic indications, which overcome treatment resistance resulted from diverse genetic and/or epigenetic alternations and abnormal cancer-associated gene expression. Thus, individual compounds target a particular cancer type or the same type of cancer with overlapped but distinct genetic backgrounds. In turn, this imparts novel strategies of personalized precision medicine to resolve the treatment resistance challenge. Likewise, from a cost-effective point of view since each anticancer compound has a defined particular target set (quantitatively or qualitatively), in order to save biomarker testing costs for some cancer patients for diagnostic and/or prognostic indications, these individual drugs can be also used for cancer treatment in general without a pre-biomarker testing procedure. For these patients a particular drug selection would be based on general knowledge related to the cancer and the drugs, but not based on biomarker or genetic determinations (since in most cases if not all, the relationship is usually not so clearly defined), although this would compromise the maximal value of these types of drugs. This unprecedented strategy to overcome treatment resistance at a manner of personalized precision medicine comes out of our unexpected results recently obtained. See Examples.

The anti-cancer drug, camptothecin (CPT) was initially identified and isolated from plant extracts by Dr. Mansukh Wani and Dr. Monroe Wall in collaboration with National Cancer Institute (NCI) of the United States. While a variety of camptothecin structure-based compounds (camptothecin derivatives) have been synthesized, only two camptothecin analogs, irinotecan and topotecan (both are camptothecin structure-based derivatives), were commercialized in clinical practice for cancer treatment. Currently, irinotecan and topotecan represent the best two compounds identified among camptothecin structure-based analogs in terms of their antitumor activity versus their toxicity. However, cancer resistance to irinotecan or topotecan treatment is a common issue in clinical practice, which seriously challenges the scope of their application. In our previous patent (PCT/US15/22095), we demonstrated that some of our unique compounds protected in the previous invention would effectively overcome irinotecan- and topotecan-resistant tumors (see our recent publication after filing the patent for detail: Ling X, et al: FL118, a novel camptothecin analogue, overcomes irinotecan and topotecan resistance in human tumor xenograft models, Am J of Transl Res 2015, 7:1765-1781).

A unique camptothecin analogue, FL118, targets and bypasses multiple treatment resistant factors and functions to eliminate many types of human tumor xenografts in animal models. See Ling X, et al.: A Novel Small Molecule FL118 That Selectively Inhibits Survivin, Mcl-1, XIAP and cIAP2 in a p53-Independent Manner, Shows Superior Antitumor Activity, PLOS ONE 2012, 7:e45571. Studies also revealed that the antitumor activity of FL118 is highly dependent on its primary structure and steric configuration (Zhao J, et al.: Antitumor activity of FL118, a survivin, Mcl-1, XIAP, cIAP2 selective inhibitor, is highly dependent on its primary structure and steric configuration, Molecular Pharmaceutics 2014; 11: 457-467). Results from the previous patent (PCT/US15/22095) reveal that FL118 effectively overcomes irinotecan and topotecan-induced treatment resistance (Ling, et al., Am J of Transl Res 2015, 7:1765-1781). FL118 effectively bypasses the refractory phenotypes emanated from the ATP-binding cassette (ABC) transporters such as ABCG2, while SN-38 (active metabolite of irinotecan) and topotecan were substrates of ABCG2 and unable to bypass ABCG2-induced treatment resistance. Now these findings from the previous invention (PCT/US15/22095) were published in Westover D, et al: FL118, a novel camptothecin derivative, is insensitive to ABCG2 expression and shows improved efficacy in comparison with irinotecan in colon and lung cancer models with ABCG2-induced resistance, Molecular Cancer 2015, 14:92. Furthermore, our recent studies indicated that the known therapeutic target of camptothecin, irinotecan/SN-38 (active metabolite of irinotecan) and topotecan is topoisomerase I (Top1), and Top1 expression is required for them to show antitumor activity. In contrast, the antitumor efficacy of the FL118 platform is irrelevant to the expression of Top1, human tumors without the expression of Top1 exhibited high sensitivity to FL118 treatment (Li F, et al: Topoisomerase I (Top1): a major target of FL118 for its antitumor efficacy or mainly involved in its side effects of hematopoietic toxicity? Am J Cancer Res. 2017; 7: 370-82).

In this invention, we demonstrated that individual compounds derived from the FL118 platform show distinct anti-cancer activity and toxicity among different cancer types or in the same cancer types with different individual drugs. This invention has also described in various embodiments of the further development of the ethanol-containing formulation and organic solvent-free formulation of water-insoluble FL118 and/or FL118 analogues in aqueous suspension format, powder capsule format or tablet format for oral (per oral, po/p.o.), intra-peritoneal (ip/IP/i.p.) or intravenous (iv/IV/i.v.) administration.

In illustrative embodiments, the present invention provides the matter of compositions and chemical synthesis of a group of compounds that were derived from the Positions 7 or Position 9 of the FL118 platform as well as the use of these novel compounds of Formula 1 for human disease such as cancer treatment. Examples for detailed synthesis of individual FL118 core structure platform-derived analogues are described below.

Synthesis of Exemplary FL118 (10,11-Methylenedioxy-Camptothecin) Platform Position 7-Derived Compounds
Preparation of FL118 Platform Derivatives at the 7th Position with Cinnamenyl (Exemplar):

Step 1: Preparation of
6'-amino-3',4'-methylenedioxy chalcone 3,4-methylenedioxy acetophenone was dissolved in nitromethane (80 mL), and concentrated nitric acid (20.7 mL) was added dropwise to it. The mixture reacted for 2 hr and saturated sodium bicarbonate solution was added dropwise to it to get the pH to about 7. The mixture was extracted with dichloromethane for 3 times. The organic layer was combined, washed with brine, dried by anhydrous $MgSO_4$ and concentrated. The yellow oil resultant was purified by column chromatography (ethyl acetate:petroleum ether-1:8) and resulted in 7.8 g light yellow solid (76%). mp 110-112° C.

6-nitro-3,4-methylenedioxy acetophenone (7.8g, 37.3 mmol) was dissolved in ethyl acetate (70 mL) and catalytic amount Pd/C was added. The mixture reacted under hydrogen balloon for 12 hr. The catalyst was filtered out and the filtrate was concentrated. The resultant was 5.5g light yellow solid (83%). mp 123-124° C.

6-amino-3,4-methylenedioxy acetophenone (0.2g, 1.1 mmol) was dissolved in anhydrous alcohol (10 ml), sodium hydroxide (0.4g, 11 mmol) and benzaldehyde (0.14g, 1.3 mmol) were added in sequence. The mixture reacted for 12 hr and solution was concentrated. The mixture was purified by column chromatography (ethyl acetate:petroleum ether=1:4) and resulted in 0.21 g yellow solid (71%). mp 130-132° C.
$^1$H NMR ($CDCl_3$, 600 MHz) δ: 8.08 (s, 1H, ArH), 7.81 (d, J=15.2 Hz, 1H, =CHAr), 7.53 (d, J=15.2 Hz, 1H, ArCOCH=), 6.79 (d, J=7.7 Hz, 2H, ArH), 6.67 (d, J=7.7 Hz, 2H, ArH), 6.60 (t, J=7.7 Hz, 1H, ArH), 6.54 (s, 1H, ArH), 6.20 (brs, 2H, $NH_2$), 6.02 (s, 2H, $OCH_2O$).

The preparing process of 6'-amino-3',4'-methylenedioxy-4-bromo-chalcone was the same as that of 6'-amino-3',4'-methylenedioxy chalcone, except that the reagents were 6-amino-3,4-methylenedioxy acetophenone and 4-bromo-benzaldehyde; The preparing process of 6'-amino-3',4'-methylenedioxy-3,4-dimethoxy-chalcone was the same as that of 6'-amino-3',4'-methylenedioxy chalcone, except that the reagents were 6-amino-3,4-methylenedioxy acetophenone and 3,4-dimethoxy-benzaldehyde; The preparing process of 6'-amino-3',4'-methylenedioxy-2-chloro-chalcone was the same as that of 6'-amino-3',4'-methylenedioxy chalcone, except that the reagents were 6-amino-3,4-methylenedioxy acetophenone and 2-chloro-benzaldehyde; The preparing process of 6'-amino-3',4'-methylenedioxy-3,4-methylenedioxy-chalcone was the same as that of 6'-amino-3',4'-methylenedioxy chalcone, except that the reagents were 6-amino-3,4-methylenedioxy acetophenone and 3,4-methylenedioxy benzaldehyde; The preparing process of 6'-amino-3',4'-methylenedioxy-3,4,5-trimethoxy-chalcone was the same as that of 6'-amino-3',4'-methylenedioxy chalcone, except that the reagents were 6-amino-3,4-methylenedioxy acetophenone and 3,4,5-trimethoxy-benzaldehyde; The preparing process of 6-amino-3,4'-methylenedioxy-4-methoxy-chalcone was the same as that of 6-amino-3,4-methylene-dioxy chalcone, except that the reagents were 6-amino-3,4-methylenedioxy acetophenone and 4-methoxy-benzaldehyde;

Step 2: Preparing the FL118
(10,11-methylenedioxy-camptothecin) Derivatives at the 7th Position with Cinnamenyl FL7-5: 20 (S)-7-cinnamenyl-10,11-methylenedioxy-camptothecin (4S)-4-Ethyl-7,8-dihydro-4-hydroxy-1H-pyrano[3,4-f]indolizine-3,6,10(4H)-trione (200 mg, 0.76 mmol) was dissolved in anhydrous toluene (70 mL). 6'-amino-3',4'-methylenedioxy chalcone (0.37g, 1.37 mmol) and para-toluenesulfonic (26.2 mg, 0.15 mmol) were added. The mixture reacted at 110° C. under nitron for 24 hr. The mixture was cooled and the solvent was removed under reduced pressure. The compounds were purified by column chromatography (dichloromethane:methanol=97:3) and resulted in 270 mg light yellow solid (72%). mp 220-222° C.

$^1$H NMR (CF$_3$COOD, 600 MHz) δ: 8.19 (s, 1H), 7.98 (s, 1H), 7.91 (s, 1H), 7.87 (d, J=4.4 Hz, 2H), 7.81 (d, J=16.5 Hz, 1H), 7.69 (s, 1H), 7.60 (s, 3H), 6.48 (s, 2H), 6.00 (d, J=16.5 Hz, 1H), 5.95 (s, 2H), 5.66 (d, J=17.04 Hz, 1H), 2.21 (m, 2H), 1.20 (t, J=7.2 Hz, 3H). $^{13}$C NMR (CF$_3$COOD, 150 MHz) δ: 178.6, 160.4, 159.7, 154.9, 153.7, 151.4, 148.8, 142.4, 142.2, 141.2, 136.5, 133.9, 131.3, 130.2, 128.5, 128.4, 123.9, 120.1, 107.3, 105.7, 103.5, 99.6, 76.2, 68.6, 54.8, 33.4, 8.1.

FL7-6: 20 (S)-7-(4-bromo-cinnamenyl)-10,11-methylenedioxy-camptothecin: 7-6 was prepared and purified as described for the synthesis and purifying of 7-5 using (4S)-4-Ethyl-7,8-dihydro-4-hydroxy-1H-pyrano[3,4-f]indolizine-3,6,10(4H)-trione and 6'-amino-3',4'-methylenedioxy-4-bromo-chalcone. The resultant was 300 mg light yellow solid (70%). mp 238° C.

$^1$H NMR (CF$_3$COOD, 600 MHz) δ: 7.46 (s, 1H), 7.31 (s, 1H), 7.07 (d, J=7.4 Hz, 2H), 6.81 (d, J=6.3 Hz, 1H), 6.69 (s, 1H), 6.41 (s, 3H), 6.18 (s, 2H), 5.65 (s, 2H), 5.23 (d, J=7.04 Hz, 2H), 2.11 (m, 2H), 0.92 (t, J=7.2 Hz, 3H). $^{13}$C NMR (CF$_3$COOD, 150 MHz) δ: 177.2, 161.3, 159.7, 153.9, 152.7, 151.4, 148.9, 142.6, 142.2, 141.2, 136.6, 132.9, 131.8, 130.1, 129.4, 128.2, 126.4, 124.9, 123.9, 120.5, 107.7, 105.5, 103.9, 99.6, 76.3, 68.7, 54.3, 33.2, 8.5

FL7-7: 20(S)-7-(3,4-dimethoxy cinnamenyl)-10,11-methylenedioxy-camptothecin: 7-7 was prepared and purified as described for the synthesis and purifying of 7-5 using (4S)-4-Ethyl-7,8-dihydro-4-hydroxy-1H-pyrano[3,4-f]indolizine-3,6,10(4H)-trione and 6'-amino-3',4'-methylenedioxy-3,4-dimethoxy-chalcone. The resultant was 230 mg light yellow solid (53%). mp 192° C.

$^1$H NMR (DMSO-d$_6$, 600 MHz) δ: 7.50 (d, J=7.68 Hz, 2H), 7.40 (d, J=13.2 Hz, 2H), 7.28 (s, 1H), 7.14 (d, J=8.22 Hz, 2H), 6.37 (s, 1H), 6.15 (s, 2H), 5.39 (s, 2H), 4.76 (s, 2H), 3.88 (s, 3H), 3.84 (s, 3H), 2.29 (m, 2H), 1.23 (t, J=7.2 Hz, 3H). $^{13}$C NMR (DMSO-d$_6$, 150 MHz) δ:175.2, 162.9, 159.3, 157.7, 152.4, 150.8, 150.2, 148.6, 145.1, 144.9, 137.5, 135.3, 134.9, 130.9, 127.8, 125.2, 122.8, 121.4, 119.6, 111.5, 110.3, 106.5, 101.7, 97.3, 77.4, 68.2, 55.4, 55.2, 54.8, 20.5, 10.6.

FL7-8: 20 (S)-7-(2-chloro-cinnamenyl)-10,11-methylenedioxy-camptothecin: 7-8 was prepared and purified as described for the synthesis and purifying of 7-5 using (4S)-4-Ethyl-7,8-dihydro-4-hydroxy-1H-pyrano[3,4-f]indolizine-3,6,10(4H)-trione and 6'-amino-3',4'-methylenedioxy-2-chloro-chalcone. The resultant was 250 mg light yellow solid (62%). mp 209-212° C.

$^1$H NMR (CF$_3$COOD, 600 MHz) δ: 7.58 (s, 1H), 7.51 (s, 1H), 7.34 (d, J=7.2 Hz, 2H), 7.11 (d, J=6.8 Hz, 1H), 7.02 (s, 1H), 6.73 (s, 3H), 6.27 (s, 2H), 5.95 (s, 2H), 5.66 (d, J=8.4 Hz, 2H), 2.01 (m, 2H), 0.90 (t, J=7.2 Hz, 3H). $^{13}$C NMR (CF$_3$COOD, 150 MHz) δ: 176.6, 161.4, 159.7, 154.3, 153.5, 151.4, 148.9, 144.4, 142.7, 141.2, 136.5, 133.1, 131.3, 130.2, 128.6, 128.4, 123.9, 120.1, 107.5, 106.7, 104.5, 99.2, 77.2, 68.1, 54.8, 33.4, 8.4.

FL7-9: 20(S)-7-(3,4-methylenedioxy-cinnamenyl)-10,11-methylenedioxy-camptothecin: 7-9 was prepared and purified as described for the synthesis and purifying of 7-5 using (4S)-4-Ethyl-7,8-dihydro-4-hydroxy-1H-pyrano[3,4-f]indolizine-3,6,10(4H)-trione and 6'-amino-3',4'-methylenedioxy-3,4-methylenedioxy-chalcone. The resultant was 150 mg light yellow solid (36%). mp 177° C.

$^1$H NMR (DMSO-d$_6$, 600 MHz) δ: 7.53 (d, J=4.38 Hz, 2H), 7.50 (d, J=7.68 Hz, 3H), 7.21 (d, J=2.76 Hz, 1H), 7.13 (d, J=7.68 Hz, 2H), 6.36 (t, J=8.28 Hz, 2H), 6.21 (s, 2H), 5.39 (s, 2H), 4.76 (s, 2H), 2.29 (m, 2H), 1.08 (t, J=7.38 Hz, 3H). $^{13}$C NMR (DMSO-d$_6$, 150 MHz) δ: 167.7, 154.6, 152.2, 151.1, 149.0, 148.8, 145.7, 139.0, 138.6, 128.7, 126.0, 125.8, 124.1, 115.9, 109.6, 108.6, 104.2, 103.7, 102.9, 99.1, 98.1, 76.2, 68.6, 54.8, 21.3, 8.3

FL7-10: 20(S)-7-(3,4,5-trimethoxy-cinnamenyl)-10,11-methylenedioxy-camptothecin: 7-10 was prepared and purified as described for the synthesis and purifying of 7-5 using (4S)-4-Ethyl-7,8-dihydro-4-hydroxy-1H-pyrano[3,4-f]indolizine-3,6,10(4H)-trione and 6'-amino-3',4'-methylenedioxy-3,4,5-trimethoxy-chalcone. The resultant was 200 mg light yellow solid (45%). mp 167° C.

$^1$H NMR (DMSO-d$_6$, 600 MHz) δ: 7.44 (s, 1H), 7.40 (s, 1H), 7.15 (s, 2H), 6.64 (s, 1H), 6.37 (t, J=8.21 Hz, 2H), 6.21 (s, 2H), 5.39 (s, 2H), 4.76 (s, 2H), 3.91 (s, 6H), 3.74 (s, 3H), 1.85 (m, 2H), 0.89 (t, J=7.38 Hz, 3H). $^{13}$C NMR (DMSO-d$_6$, 150 MHz) δ: 172.3, 159.3, 158.9, 158.4, 156.2, 152.9, 151.5, 149.5, 145.8, 141.3, 140.6, 139.1, 135.9, 133.1, 128.8, 122.3, 121.6, 118.6, 105.9, 105.3, 104.9, 102.1, 100.1, 97.4, 77.3, 68.6, 59.9, 56.2, 56.0, 50.3, 30.4, 7.5

FL7-12: 20(S)-7-(4-methoxy-cinnamenyl)-10,11-methylenedioxy-camptothecin: 7-12 was prepared and purified as described for the synthesis and purifying of 7-5 using (4S)-4-Ethyl-7,8-dihydro-4-hydroxy-1H-pyrano[3,4-f]indolizine-3,6,10(4H)-trione and 6'-amino-3',4'-methylenedioxy-4-methoxy-chalcone. The resultant was 250 mg light yellow solid (62%). mp 203-205° C.

$^1$H NMR (DMSO-d$_6$, 600 MHz) δ: 7.88 (d, J=8.82 Hz, 2H), 7.52 (s, 1H), 7.49 (s, 1H), 7.21 (d, J=8.22 Hz, 2H), 7.12 (d, J=6.9 Hz, 2H), 7.08 (s, 1H), 6.33 (s, 2H), 5.39 (s, 2H), 4.76 (s, 2H), 3.88 (s, 3H), 2.28 (m, 2H), 0.93 (t, J=7.68 Hz, 3H). $^{13}$C NMR (DMSO-d$_6$, 150 MHz) δ:174.5, 162.7, 160.5, 159.3, 154.2, 151.9, 148.5, 139.0, 138.3, 135.8, 131.2, 130.9, 130.4, 128.7, 126.0, 124.4, 116.5, 115.4, 103.9, 103.7, 99.5, 98.1, 76.8, 67.7, 56.2, 54.3, 21.3, 7.9

Preparation of FL118 Platform Derivative at the 7th Position with Phenethyl (Exemplar):

Step 1: Preparation of 6'-amino-3',4'-methylenedioxy dihydrochalcone 6-amino-3,4-methylenedioxy chalcone (0.30g, 1.1 mmol) was dissolved in ethyl acetate (25 mL) and catalytic amount Pd/C was added. The mixture reacted under hydrogen balloon for 10 hr. the catalyst was filtered out and the filtrate was concentrated. The resultant was 0.26g light yellow solid (87%). mp 103-104° C.

$^1$H NMR (CDCl$_3$, 600 MHz) δ: 7.45 (s, 1H, ArH), 6.62 (d, J=6.4 Hz, 2H, ArH), 6.35 (d, J=6.4 Hz, 2H, ArH), 6.31 (s, 1H, ArH), 6.28 (s, 1H, ArH), 6.20 (brs, 2H, NH$_2$), 6.07 (s, 2H, OCH$_2$O), 2.69 (t, J=4.7 Hz, 2H, ArCOCH$_2$), 2.67 (t, J=4.7 Hz, 2H, CH$_2$Ar).

The preparing process of 6'-amino-3',4'-methylenedioxy-4-bromo dihydrochalcone was the same as that of 6'-amino-3',4'-methylenedioxy dihydrochalcone, except that the reagents were 6'-amino-3',4'-methylenedioxy-4-bromo-chalcone; The preparing process of 6'-amino-3',4'-methylenedioxy-3,4-dimethoxy-dihydrochalcone was the same as that of 6'-amino-3',4'-methylenedioxy dihydrochalcone, except that the reagents were 6'-amino-3',4'-methylenedioxy-3,4-dimethoxy-chalcone; The preparing process of 6'-amino-3',4'-methylenedioxy-2-chloro-dihydrochalcone was the same as that of 6'-amino-3',4'-methylenedioxy dihydrochalcone, except that the reagents were 6'-amino-3',4'- methylenedioxy-2-chloro-chalcone; The preparing process of 6'-amino-3',4'-methylenedioxy-3,4-methylenedioxy-dihydrochalcone was the same as that of 6'-amino-3',4'-methylenedioxy dihydrochalcone, except that the reagents were the preparing process of 6'-amino-3',4'-methylenedioxy-3,4-methylenedioxy-chalcone; The preparing process of 6'-amino-3',4'-methylenedioxy-3,4,5-trimethoxy dihydrochalcone was the same as that of 6'-amino-3',4'-methylenedioxy dihydrochalcone, except that the reagents were 6'-amino-3',4'-methylenedioxy-3,4,5-trimethoxy chalcone; The preparing process of 6'-amino-3',4'-methylenedioxy-4-methoxy dihydrochalcone was the same as that of 6'-amino-3',4'-methylenedioxy dihydrochalcone, except that the reagents were 6'-amino-3',4'-methylenedioxy-4-methoxy chalcone.

Step 2: Preparing the FL118 Platform Derivatives at the 7th Position with Phenethyl FL7-14: 20 (S)-7-phenethyl-10,11-methylenedioxy-camptothecin: (4S)-4-Ethyl-7,8-dihydro-4-hydroxy-1H-pyrano[3,4-f]indolizine-3,6,10(4H)-trione (200 mg, 0.76 mmol) was dissolved in anhydrous toluene (70 mL). 6'-amino-3',4'-methylenedioxy dihydrochalcone (0.37g, 1.37 mmol) and para-toluenesulfonic (26.2 mg, 0.15 mmol) were added. The mixture reacted at 110° C. under nitron for 24 hr. The mixture was cooled and the solvent was removed under reduced pressure. The compounds were purified by column chromatography (dichloromethane:methanol=97:3) and resulted in 280 mg light yellow solid (75%). mp 220-223° C.

$^1$H NMR (CF$_3$COOD, 600 MHz) δ: 7.93 (s, 1H), 7.58 (s, 1H), 7.53 (s, 1H), 7.09 (s, 3H), 6.89 (s, 2H), 6.31 (s, 2H), 5.76 (d, J=17.1 Hz, 1H), 5.42 (d, J=17.04 Hz, 1H), 4.75 (dd, J=19.2 Hz, J=18.66 Hz, 2H), 3.58 (d, J=20.34 Hz, 2H), 3.18 (s, 2H), 1.99 (m, 2H), 0.99 (t, J=7.68 Hz, 3H). $^{13}$C NMR (CF$_3$COOD, 150 MHz) δ: 176.2, 157.8, 157.6, 154.9, 152.9, 151.3, 149.7, 139.6, 139.3, 138.6, 129.7, 128.8, 128.5, 128.1, 127.7, 127.2, 121.7, 105.1, 103.8, 100.2, 97.5, 73.8, 66.2, 51.2, 35.1, 33.7, 31.0, 5.8.

FL7-17: 20 (S)-7-(4-bromo-phenethyl)-10,11-methylenedioxy-camptothecin: 7-17 was prepared and purified as described for the synthesis and purifying of 7-14 using (4S)-4-Ethyl-7,8-dihydro-4-hydroxy-1H-pyrano[3,4-f]indolizine-3,6,10(4H)-trione and 6'-amino-3',4'-methylenedioxy-4-bromo-dihydrochalcone. The resultant was 300 mg light yellow solid (68%). mp 240-243° C.

$^1$H NMR (DMSO-d$_6$, 600 MHz) δ: 7.59 (s, 1H), 7.46 (s, 2H), 7.23 (m, 3H), 7.12 (s, 1H), 6.28 (s, 2H), 5.39 (s, 2H), 4.82 (dd, J=18.66 Hz, J=10.98 Hz, 2H), 2.94 (s, 2H), 2.28 (s, 2H), 1.86 (m, 2H), 0.87 (t, J=7.2 Hz, 3H). $^{13}$C NMR (DMSO-d$_6$, 150 MHz) δ: 173.1, 157.2, 151.5, 150.6, 149.6, 147.4, 146.6, 146.1, 142.5, 141.4, 138.3, 129.2, 128.8, 128.7, 126.8, 126.1, 124.7, 118.6, 105.8, 103.2, 100.0, 96.6, 72.9, 65.7, 49.9, 35.2, 30.8, 21.4, 8.3

FL7-16: 20(S)-7-(3,4-dimethoxy phenethyl)-10,11-methylenedioxy-camptothecin: 7-16 was prepared and purified as described for the synthesis and purifying of 7-14 using (4S)-4-Ethyl-7,8-dihydro-4-hydroxy-1H-pyrano[3,4-f]indolizine-3,6,10(4H)-trione and 6'-amino-3',4'-methylenedioxy-3,4-dimethoxy-dihydrochalcone. The resultant was 270 mg light yellow solid (64%). mp 165-168° C.

$^1$H NMR (DMSO-d$_6$, 600 MHz) δ: 7.66 (s, 1H), 7.53 (s, 1H), 7.26 (s, 1H), 6.77 (s, 2H), 6.55 (s, 1H), 6.48 (s, 1H), 6.12 (s, 2H), 5.44 (s, 2H), 4.95 (s, 2H), 3.68 (s, 6H), 3.58 (t, J=7.14 Hz, 2H), 2.93 (t, J=7.14 Hz, 2H), 1.91 (m, 2H), 0.93 (t, J=7.68 Hz, 3H). $^{13}$C NMR (DMSO-d$_6$, 150 MHz) δ:173.1, 157.3, 153.2, 153.1, 151.4, 150.6, 149.7, 149.4, 147.7, 146.8, 142.2, 136.9, 136.6, 128.4, 124.9, 118.5, 106.7, 105.9, 105.5, 103.1, 100.2, 96.4, 72.9, 65.7, 56.3, 56.1, 50.1, 35.6, 31.8, 30.8, 8.3

FL7-15: 20 (S)-7-(2-chloro-phenethyl)-10,11-methylenedioxy-camptothecin: 7-15 was prepared and purified as described for the synthesis and purifying of 7-14 using (4S)-4-Ethyl-7,8-dihydro-4-hydroxy-1H-pyrano[3,4-f]indolizine-3,6,10(4H)-trione and 6'-amino-3',4'-methylenedioxy-2-chloro-dihydrochalcone. The resultant was 270 mg light yellow solid (67%). mp 183-186° C.

$^1$H NMR (DMSO-d$_6$, 600 MHz) δ: 7.48 (d, J=8.28 Hz, 3H), 7.28 (s, 1H), 7.22 (s, 1H), 7.12 (d, J=7.68 Hz, 2H), 6.39 (s, 1H), 6.29 (s, 1H), 5.40 (s, 2H), 4.98 (d, J=10.98 Hz, 2H), 2.28 (s, 4H), 1.82 (m, 2H), 0.86 (t, J=7.14 Hz, 3H). $^{13}$C NMR (DMSO-d$_6$, 150 MHz) δ:175.2, 157.2, 151.5, 150.3, 148.2, 147.1, 146.6, 146.4, 142.5, 140.7, 138.3, 129.3, 128.8, 128.6, 126.8, 126.2, 124.7, 118.6, 105.8, 102.5, 100.1, 97.6, 72.9, 65.7, 49.9, 35.2, 30.7, 22.4, 8.3.

FL7-11: 20(S)-7-(3,4-methylenedioxy-phenethyl)-10,11-methylenedioxy-camptothecin: 7-11 was prepared and purified as described for the synthesis and purifying of 7-14 using (4S)-4-Ethyl-7,8-dihydro-4-hydroxy-1H-pyrano[3,4-f]indolizine-3,6,10(4H)-trione and 6'-amino-3',4'-methylenedioxy-3,4-methylenedioxy-dihydrochalcone. The resultant was 140 mg light yellow solid (31%). mp 155-157° C.

$^1$H NMR (DMSO-d$_6$, 600 MHz) δ: 7.66 (s, 1H), 7.53 (s, 1H), 7.26 (s, 1H), 6.55 (s, 1H), 6.48 (s, 1H), 6.32 (s, 2H), 5.44 (s, 2H), 4.95 (s, 2H), 3.68 (s, 9H), 3.58 (t, J=7.14 Hz, 2H), 2.93 (t, J=7.14 Hz, 2H), 1.91 (m, 2H), 0.93 (t, J=7.68 Hz, 3H). $^{13}$C NMR (DMSO-d$_6$, 150 MHz) δ:173.1, 157.3, 153.2, 153.1, 151.4, 150.6, 149.7, 149.4, 147.7, 146.8, 142.2, 136.9, 136.6, 128.4, 124.9, 118.5, 106.7, 105.9, 105.5, 103.1, 100.2, 96.4, 72.9, 65.7, 60.5, 56.3, 56.1, 50.1, 35.6, 31.8, 30.8, 8.3

FL7-13: 20(S)-7-(4-methoxy-phenethyl)-10,11-methylenedioxy-camptothecin: 7-13 was prepared and purified as described for the synthesis and purifying of 7-14 using (4S)-4-Ethyl-7,8-dihydro-4-hydroxy-1H-pyrano[3,4-f]indolizine-3,6,10(4H)-trione and 6'-amino-3',4'-methylenedioxy-4-methoxy-dihydrochalcone. The resultant was 160 mg light yellow solid (41%). mp 172-175° C.

$^1$H NMR (DMSO-d$_6$, 600 MHz) δ: 7.49 (d, J=7.74 Hz, 2H), 7.41 (s, 1H), 7.21 (s, 1H), 7.13 (d, J=7.14 Hz, 2H), 6.81 (d, J=7.68 Hz, 1H), 6.27 (s, 2H), 5.39 (s, 2H), 4.76 (s, 2H), 3.68 (s, 3H), 2.83 (s, 2H), 2.28 (s, 2H), 1.86 (m, 2H), 0.89 (t, J=6.06 Hz, 3H). $^{13}$C NMR (DMSO-d$_6$, 150 MHz) δ:173.0, 158.3, 157.2, 151.6, 150.5, 149.1, 146.9, 145.8, 142.8, 138.4, 133.2, 130.1, 128.6, 128.0, 126.0, 124.6, 118.7, 114.2, 105.4, 103.3, 99.9, 96.8, 72.9, 65.8, 55.5, 49.9, 34.3, 30.8, 21.3, 8.3

Preparation of FL118 Platform Derivatives at the 7th Position with a Heterocyclic Ethyl Group (Exemplar):

Step 1: Preparation of 6'-amino-3',4'-methylenedioxy-morpholinylethyl benzophenone 3,4-methylenedioxy acetophenone (8.1 g, 49.3 mmol) was dissolved in nitromethane (80 mL, and concentrated nitric acid (20.7 mL) was added dropwise to it. The mixture reacted for 2 hr and saturated sodium bicarbonate solution was added dropwise to it to get the pH to about 7. The mixture was extracted with dichloromethane for 3 times. The organic layer was combined, washed with brine, dried by anhydrous MgSO$_4$ and concentrated. The yellow oil resultant was purified by column chromatography (ethyl acetate:petroleum ether=1:8) and resulted in 7.8 g light yellow solid (76%). mp 110-112° C.;

6-nitro-3,4-methylenedioxy acetophenone (7.8g, 37.3 mmol) was dissolved in DMF-DMA, the mixture reacted at 110° C. for 2 hr and then was cooled to room temperature. Hexane was added and yellow solid precipitated. We filtered and got 9.4g filter cake (95%).

The solid obtained (9.4g, 35.6 mmol) was dissolved in dioxane (60 mL) and morpholine (3.6 mL, 36 mmol). The mixture was heated to reflux for 6 hr. The solvent was removed under reduced pressure and resulted in yellow oil. The compounds were purified by column chromatography (petroleum ether:ethyl acetate=1:2) and resulted in 8.7g light yellow solid (80%).

The resultant compound (8.0g, 26.1 mmol) was dissolved in acetic acid (20 mL) and the mixture was cooled to 0° C. Sodium borohydride (493.1 mg, 13.1 mmol) was added. The solvent was removed under reduced pressure and the compounds were purified by column chromatography (petroleum ether:ethyl acetate=1:2). The result was 5.6 g light yellow solid (70%)

The resultant compound (5.6g, 18.19 mmol) was dissolved in ethyl acetate (70 mL) and catalytic amount Pd/C was added. The mixture reacted under hydrogen balloon for 12 hr. The catalyst was filtered out and the filtrate was concentrated. The result was 4.3g light yellow solid (90%).

$^1$H NMR (500 MHz, DMSO) δ 7.34 (s, 2H), 7.24 (s, 1H), 6.29 (s, 1H), 5.92 (s, 2H), 3.57-3.50 (m, 2H), 2.94 (t, J=7.4 Hz, 2H), 2.57 (t, J=7.3 Hz, 2H), 2.37 (s, 4H).

Preparation of 6'-amino-3',4'-methylenedioxy-thiomorpholinylethyl benzophenone was the same as that of preparation of 6'-amino-3',4'-methylenedioxy-morpholinylethyl benzophenone, except that the reagent was thiomorpholine; preparation of 6'-amino-3',4'-methylenedioxy-(2-methyl)piperidylethyl benzophenone was the same as that of preparation of 6'-amino-3',4'-methylenedioxy-morpholinylethyl benzophenone, except that the reagent was 2-methylpiperidine.

Step 2: Preparing the FL118 Platform Derivatives at the 7th Position with a Heterocyclic Ethyl Group FL7N-1: 20 (S)-7-morpholinylethyl-10,11-methylenedioxy-camptothecin: (4S)-4-Ethyl-7,8-dihydro-4-hydroxy-1H-pyrano[3,4-f]indolizine-3,6,10(4H)-trione (200 mg, 0.76 mmol) was dissolved in anhydrous toluene (70 mL), 6'-amino-3',4'-methylenedioxy-morpholinylethyl benzophenone (0.38g, 1.37 mmol) and para-toluenesulfonic (26.2 mg, 0.15 mmol) were added. The mixture reacted at 110° C. under nitron for 24 hr. The mixture was cooled and the solvent was removed under reduced pressure. The compounds were purified by column chromatography (dichloromethane:methanol=97:3) and resulted in 150 mg light yellow solid (40%). mp>250° C.

$^1$H NMR (CF$_3$COOD, 600 MHz) δ: 7.26 (s, 1H), 6.98 (s, 1H), 6.74 (s, 1H), 5.9 (s, 2H), 4.76 (d, 1H), 4.74 (d, 1H), 4.22 (s, 2H), 3.67 (m, 4H), 2.69 (d, 2H), 2.65 (d, 2H), 2.37 (d, 4H), 1.87 (m, 2H), 0.96 (t, 3H). $^{13}$C NMR (CF$_3$COOD, 150 MHz) δ:178.6, 159.4, 157.7, 156.9, 151.7, 149.4, 145.8, 141.4, 139.2, 126.2, 123.5, 120.9, 108.3, 102.2, 101.5, 101.4, 73.0, 66.8, 58.1, 55.5, 53.7, 45.6, 30.2, 28.5, 28.4, 26.2, 5.6.

FL7N-3: 20 (S)-7-thiomorpholinylethyl-10,11-methylenedioxy-camptothecin: 7N-3 was prepared and purified as described for the synthesis and purifying of 7-28 using (4S)-4-Ethyl-7,8-dihydro-4-hydroxy-1H-pyrano[3,4-f]indolizine-3,6,10(4H)-trione and 6'-amino-3',4'-methylenedioxy-thiomorpholinylethyl benzophenone, resulted in 170 mg light yellow solid (45%). mp>250° C.

$^1$H NMR (CF$_3$COOD, 600 MHz) δ: 7.26 (s, 1H), 6.98 (s, 1H), 6.74 (s, 1H), 5.9 (s, 2H), 4.76 (d, 1H), 4.74 (d, 1H), 4.22 (s, 2H), 2.73 (m, 4H), 2.69 (d, 2H), 2.65 (d, 2H), 2.54 (d, 4H), 1.87 (m, 2H), 0.96 (t, 3H). $^{13}$C NMR (CF$_3$COOD, 150 MHz) δ: 172.6, 159.4, 157.7, 156.9, 151.7, 149.4, 145.8, 141.4, 139.2, 126.2, 123.5, 120.9, 108.3, 102.2, 101.5, 101.4, 73.0, 65.1, 58.3, 58.1, 55.5, 45.6, 30.2, 28.5, 28.4, 26.2, 5.6.

Preparation of FL118 Platform Derivatives at the 7th Position with Aryl or Heteroaryl (Exemplar):

Step 1: 20 (S)-O-acetyl-FL118 (10,11-methylenedioxy-camptothecin): 10,11-methylenedioxy-camptothecin (0.23g, 0.58 mmol) was added into anhydride acetic (6 mL) and pyridine (4 mL), and the mixture reacted for 48 hr. The mixture was poured into 25 mL hexane and solid precipitated. The mixture was filtered and the filter cake was washed by hexane. The result was 240 mg yellow solid (95%). mp>250° C.

Step 2: 20 (S)-O-acetyl-7-chloro-FL118 (10,11-methylenedioxy-camptothecin)

30% hydrogen peroxide solution (3.2 mL, 28 mmol) was added to the mixture of 20 (S)-O-acetyl-10,11-methylenedioxy-camptothecin (0.24g, 0.55 mmol) and acetic acid (20 mL). The mixture reacted at 75° C. for 3 hr. The mixture was cooled and the solvent was removed under reduced pressure. resulted in 210 mg yellow solid (85%). Oxalyl chloride (0.1 mL, 1.1 mmol) was added to the mixture of the compound resulted in (0.21g, 0.47 mmol) in DMF (20 mL) at 0° C. The mixture reacted at 15° C. for 3 h. The mixture was poured into ice water (50 ml) and extracted with dichloromethane for 3 times. The organic layer was combined, dried by anhydrous MgSO$_4$ and concentrated. Then it was purified by column chromatography (dichloromethane:methanol=100:1) and resulted in 0.16 g yellow solid (75%). mp>250° C.

$^1$H NMR (CF$_3$COOD, 600 MHz) δ: 7.42 (s, 1H), 7.36 (s, 1H), 6.74 (s, 1H), 5.9 (s, 2H), 4.76 (d, 1H), 4.74 (d, 1H), 4.22 (s, 2H), 2.01 (s, 3H), 1.96 (m, 2H), 0.96 (t, 3H). $^{13}$C NMR (CF$_3$COOD, 150 MHz) δ: 172.5, 170.6, 162.8, 158.1, 157.0, 150.9, 149.9, 145.5, 142.4, 136.9, 125.7, 122.7, 108.3, 102.7, 101.6, 101.2, 76.0, 65.5, 42.1, 27.0, 21.1, 21.1.

Step 3: 20 (S)-O-acetyl-7-(pyridyl-4-)-FL118 (10,11-methylenedioxy-camptothecin)

In a 10 mL Microwave reaction tube, 20(S)-O-acetyl-7-chloro-10,11-methylenedioxy-camptothecin (0.47g, 1 mmol), pyridyl-4-boric acid (0.18g, 1.5 mmol), cesium fluoride (0.30g, 2.0 mmol), Pd(PPh$_3$)$_4$(0.11g, 0.1 mmol) and dioxane (5 mL) were added in sequence. The mixture reacted under microwave at 120° C. for 30 min. The mixture was cooled and the solvent was removed under reduced pressure. Then it was purified by column chromatography (dichloromethane:acetone=30:1) and resulted in 0.43 g yellow solid (85%). mp>250° C.

W-b1: 20 (S)-7-(pyridyl-4-)-FL118 (10,11-methylenedioxy-camptothecin): 20(S)-O-acetyl-7-(pyridyl-4-)-10,11-methylenedioxy-camptothecin (0.43g, 0.84 mol was dissolved in methanol (20 mL), and sodium methoxide (0.09g, 1.68 mmol) was added. The mixture reacted at room temperature for 12 hr. the pH was adjusted to pH=7.0, and the solvent was removed under reduced pressure. Then it was purified by column chromatography (dichloromethane:acetone=30:1) and resulted in 0.39 g yellow solid (83%). mp>250° C.

$^1$H NMR (CF$_3$COOD, 600 MHz) δ: 8.91 (d, J=5.8 Hz, 2H), 8.32 (d, J=8.6 Hz, 1H), 7.87 (t, J=7.7 Hz, 1H), 7.79-7.70 (m, 2H), 7.63 (t, J=7.7 Hz, 1H), 7.41 (d, J=5.7 Hz,

2H), 6.11 (s, 2H), 5.73 (d, J=16.4 Hz, 1H), 5.30 (d, J=16.4 Hz, 1H), 5.11 (s, 2H), 3.72 (s, 1H), 2.02-1.80 (m, 2H), 1.06 (t, J=7.4 Hz, 3H). $^{13}$C NMR (CF$_3$COOD, 150 MHz) δ: 172.5, 159.7, 157.3, 157.0, 151.6, 149.9, 149.8, 149.6, 145.5, 144.5, 142.7, 141.9, 123.9, 121.6, 121.2, 120.0, 108.1, 106.3, 101.6, 101.2, 73.0, 65.8, 44.6, 30.3, 5.6.

Preparation of FL118 Platform Derivative at the 7th Position with Phenyl (Exemplar):

Step 1: Preparation of 1-(3,5-dimethylbenzoyl)-3,4-methylenedioxy-6-nitrobenzene A mixture of 6-nitro-piperonal (194.3 mg, 1 mmol), palladium chloride (8.87 mg, 0.05 mmol), Tri(1-naphthyl) phosphine (20.6 mg, 0.05 mmol), (3,5-dimethylphenyl) boronic acid (2.0 mmol), K$_2$CO$_3$ (414 mg, 3 mmol) and THF (5 ml) was heated to reflux at 65° C. for 24 h. After the reaction, the mixture was concentrated to dry, dichloromethane was added, then filtrated. Pyridinium dichromate (564.3 mg, 1.5 mmol) was added to the filtrate at r.t. (25° C.). The mixture was stirred at r.t. for 24 h. Filtrated and the filtrate was concentrated to dry. The black solid obtained was purified by column chromatography (ethyl acetate:petroleum ether=1:9) and 278 mg yellow solid (75%) was obtained.

$^1$H NMR (500 MHz, CDCl$_3$) δ: 7.70 (s, 1H), 7.59 (m, 2H), 7.50 (s, 1H), 7.05 (s, 1H), 6.26 (s, 2H), 2.45 (s, 6H).

The preparing process of 1-(4-isopropylbenzoyl)-3,4-methylenedioxy-6-nitrobenzene was the same as that of 1-(3,5-di methylbenzoyl)-3,4-methylenedioxy-6-nitrobenzene, except that the reagents were 2-bromine-6-nitro-piperona and 4-isopropylphenyl boronic acid; The preparing process of 1-(4-butylbenzoyl)-3,4-methylenedioxy-6-nitrobenzene was the same as that of 1-(3,5-di methylbenzoyl)-3,4-methylenedioxy-6-nitrobenzene, except that the reagents were 2-bromine-6-nitro-piperona and 4-butylphenyl boronic acid; The preparing process of 1-(4-ethoxyl benzoyl)-3,4-methylenedioxy-6-nitrobenzene was the same as that of 1-(3,5-dimethylbenzoyl)-3,4-methylenedioxy-6-nitrobenzene, except that the reagents were 2-bromine-6-nitro-piperona and 4-ethoxylphenyl boronic acid;

Step 2: Preparation of 1-(3,5-dimethylbenzoyl)-3,4-methylenedioxy-6-aminobenzene 1-(3,5-di methylbenzoyl)-3,4-methylenedioxy-6-nitrobenzene (224 mg, 0.75 mmol) was dissolved in methanol (50 mL) and catalytic amount Pd/C was added. The mixture reacted under hydrogen balloon for 24 h. The catalyst was filtered out and the filtrate was concentrated. The result was 190 mg light yellow solid (85%).

$^1$H NMR (500 MHz, CDCl$_3$) δ: 7.41 (m, 2H), 7.38 (m, 1H), 6.94 (m, 1H), 6.49 (s, 2H), 6.24 (s, 1H), 5.93 (s, 2H), 2.44 (s, 6H).

The preparing process of 1-(4-isopropylbenzoyl)-3,4-methylenedioxy-6-aminobenzene was the same as that of 1-(3,5-di methylbenzoyl)-3,4-methylenedioxy-6-aminobenzene, except that the reagent was 1-(4-isopropylbenzoyl)-3,4-methylenedioxy-6-nitrobenzene; The preparing process of 1-(4-butylbenzoyl)-3,4-methylenedioxy-6-aminobenzene was the same as that of 1-(3,5-dimethylbenzoyl)-3,4-methylenedioxy-6-aminobenzene, except that the reagent was 1-(4-butylbenzoyl)-3,4-methylenedioxy-6-nitrobenzene; The preparing process of 1-(4-ethoxyl benzoyl)-3,4-methylenedioxy-6-aminobenzene was the same as that of 1-(3,5-dimethylbenzoyl)-3,4-methylenedioxy-6-aminobenzene, except that the reagent was 1-(4-ethoxyl benzoyl)-3,4-methylenedioxy-6-nitrobenzene;

Step 3: Preparing FL118 (10,11-methylenedioxy-camptothecin) Derivatives with the 7th Position being Phenyl FL7Q-12: (20s)-7-(3,5-dimethylphenyl)-10,11-methylenedioxy camptothecin: (4S)-4-Ethyl-7,8-dihydro-4-hydroxy-1H-pyrano[3,4-f]indolizine-3,6,10(4H)-trione (100 mg, 0.38 mmol) was dissolved in anhydrous toluene (40 mL). 1-(3,5-di methylbenzoyl)-3,4-methylenedioxy-6-nitrobenzene (135 mg, 0.5 mmol) and para-toluenesulfonic (13 mg, 0.075 mmol) were added. The mixture reacted at 110° C. under nitron for 24 h. The mixture was cooled and the solvent was removed under reduced pressure. The compounds were purified by column chromatography (dichloromethane:methanol=97:3) and resulted in 38 mg light yellow solid (25%).

$^1$H NMR (600 MHz,) δ: 7.65 (s, 1H), 7.57 (s, 1H), 7.20 (s, 1H), 7.09 (s, 1H), 7.04 (s, 1H), 7.01 (s, 1H), 6.17 (q, J=1.2 Hz, 2H), 5.73 (d, J=16.1 Hz, 1H), 5.30 (d, J=16.1 Hz, 1H), 5.03 (m, 2H), 3.79 (s, 1H), 2.45 (d, J=1.4 Hz, 6H), 1.90 (m, 2H), 1.06 (t, J=7.4 Hz, 3H). $^{13}$C NMR (151 MHz, CDCl$_3$) δ: 174.01, 157.59, 151.35, 150.12, 149.51, 149.14, 148.17, 147.26, 143.35, 138.92, 134.77, 130.80, 126.37, 126.26, 124.81, 117.61, 105.83, 102.29, 101.44, 97.30, 72.79, 66.38, 50.23, 31.54, 21.45, 7.85.

FL7Q-1: (20s)-7-(4-isopropylphenyl)-10,11-methylenedioxy camptothecin: 7Q-1 was prepared and purified as described for the synthesis and purifying of 7Q-20 using (4S)-4-Ethyl-7,8-dihydro-4-hydroxy-1H-pyrano[3,4-f]indolizine-3,6,10(4H)-trioneana and 1-(4-isopropylbenzoyl)-3,4-methylenedioxy-6-aminobenzene. The result was 58 mg light yellow solid (30%).

$^1$H NMR (600 MHz) δ:7.64 (s, 1H), 7.56 (s, 1H), 7.45 (m, 2H), 7.40 (s, 1H), 7.34 (d, J=7.7 Hz, 1H), 7.09 (s, 1H), 6.16 (d, J=2.2 Hz, 2H), 5.72 (d, J=16.1 Hz, 1H), 5.29 (d, J=16.1 Hz, 1H), 5.04 (m, 2H), 3.81 (s, 1H), 2.82 (q, J=7.6 Hz, 2H), 1.90 (m, 2H), 1.39 (t, J=7.6 Hz, 3H), 1.05 (t, J=7.3 Hz, 3H). $^{13}$C NMR (151 MHz, CDCl$_3$) δ: 173.91, 157.52, 151.33, 150.13, 149.49, 149.16, 148.15, 147.17, 145.50, 143.07, 132.06, 128.89, 128.75, 126.51, 124.79, 117.67, 105.83, 102.34, 101.33, 97.30, 72.76, 66.35, 50.26, 31.56, 28.78, 15.47, 7.87.

FL7Q-2: (20s)-7-(4-butylphenyl)-10,11-methylenedioxy camptothecin: 7Q-2 was prepared and purified as described for the synthesis and purifying of 7Q-20 using (4S)-4-Ethyl-7,8-dihydro-4-hydroxy-1H-pyrano[3,4-f]indolizine-3,6,10(4H)-trioneana and 1-(4-butylbenzoyl)-3,4-methylenedioxy-6-aminobenzene. The result was 70 mg light yellow solid (35%).

$^1$H NMR (600 MHz,) δ: 7.58 (s, 1H), 7.51 (s, 1H), 7.41 (m, 3H), 7.33 (d, J=7.8 Hz, 1H), 7.07 (s, 1H), 6.15 (s, 2H), 5.72 (d, J=16.1 Hz, 1H), 5.28 (d, J=16.1 Hz, 1H), 5.02 (m, 2H), 3.83 (s, 1H), 2.77 (t, J=7.8 Hz, 2H), 1.88 (m, 2H), 1.74 (m, 2H), 1.47 (m, 2H), 1.04 (m, 6H). $^{13}$C NMR (151 MHz, CDCl$_3$) δ: 173.91, 157.52, 151.30, 150.12, 149.49, 149.14, 148.17, 147.19, 144.24, 143.05, 132.02, 129.41, 128.60, 126.47, 124.77, 117.64, 105.83, 102.30, 101.33, 97.25, 72.76, 66.34, 50.21, 35.55, 33.52, 31.55, 22.47, 14.01, 7.86.

FL7Q-4: (20s)-7-(4-ethoxylphenyl)-10,11-methylenedioxy camptothecin: 7Q-4 was prepared and purified as described for the synthesis and purifying of 7Q-20 using (4S)-4-Ethyl-7,8-dihydro-4-hydroxy-1H-pyrano[3,4-f]indolizine-3,6,10(4H)-trioneana and 1-(4-ethoxyl benzoyl)-3,4-methylenedioxy-6-aminobenzene. The result was 67 mg light yellow solid (34%).

$^1$H NMR (600 MHz) δ: 7.65 (s, 1H), 7.57 (s, 1H), 7.37 (m, 2H), 7.13 (d, J=7.7 Hz, 3H), 6.17 (d, J=1.6 Hz, 2H), 5.73 (d, J=16.1 Hz, 1H), 5.30 (d, J=16.1 Hz, 1H), 5.05 (m, 2H), 4.18 (q, J=7.0 Hz, 2H), 3.79 (s, 1H), 2.12 (s, 2H), 1.90 (m, 2H), 1.53 (t, J=7.0 Hz, 3H), 1.06 (t, J=7.3 Hz, 3H). $^{13}$C NMR (151 MHz, CDCl$_3$) δ: 173.85, 159.66, 157.49, 151.24, 150.22, 149.36, 149.08, 148.11, 147.12, 142.74, 130.09, 126.64, 126.49, 124.83, 117.59, 115.28, 105.73, 102.31, 101.24, 97.31, 72.75, 66.29, 63.75, 50.23, 31.52, 14.87, 7.83.

Synthesis of Exemplary FL118
(10,11-methylenedioxy-camptothecin) Platform
Position 9-Derived Compounds Preparation of FL118 Platform Derivative at the 9th Position with Phenyl (Exemplar):

Step 1: Preparation of 2-bromine-6-nitro-piperona

NBS (8 mmol, 1.42 g) was added to the stirring solution of 6-nitropiperonal (5 mmol, 1.03g) in concentrated sulfuric acid (8 mL), then the resulting mixture was heated at 45° C. for 45 min. Then ice (100g) was put in. The mixture was extracted with ethyl acetate for 3 times. The organic layer was combined, washed with brine, dried by anhydrous MgSO$_4$ and concentrated. the yellow solid obtained was purified by column chromatography (ethyl acetate:petroleum ether=1:9) and resulted in 1.23 g yellow solid (90%).

$^1$H NMR (500 MHz, DMSO-d6) δ:10.13 (s, 1H), 6.36 (s, 1H), 6.30 (s, 2H).

Step 2: Preparation of 2-(4-ethylphenyl)-6-nitro piperonal

A mixture of 2-bromine-6-nitro-piperona (1 mmol, 274 mg), 4-ethylphenyl boronic acid (1.2 mmol), Pd(dppf)Cl$_2$, (0.1 mmol, 40 mg), K$_2$CO$_3$ (2 mmol, 276 mg), toluene (5 ml) was heated to reflux at 120° C. for 8 h. Then water (25 ml) was added. The mixture was extracted with dichloromethane for 3 times.

The organic layer was combined, washed with brine, dried by anhydrous MgSO$_4$ and concentrated. the yellow solid obtained was purified by column chromatography (ethyl acetate:petroleum ether=1:9) and resulted in 195 mg yellow solid (65%).

$^1$H NMR (500 MHz, Chloroform-d) δ: 10.11 (s, 1H), 7.46 (s, 1H), 7.29 (m, 3H), 6.19 (s, 2H), 2.73 (m, 2H), 1.28 (m, 3H).

The preparing process of 2-(4-isopropylphenyl)-6-nitro piperonal was the same as that of 2-(4-ethylphenyl)-6-nitro piperonal, except that the reagents were 2-bromine-6-nitro-piperona and 4-isopropylphenyl boronic acid; The preparing process of 2-(4-butylphenyl)-6-nitro piperonal was the same as that of 2-(4-ethylphenyl)-6-nitro piperonal, except that the reagents were 2-bromine-6-nitro-piperona and 4-butylphenyl boronic acid; The preparing process of 2-(4-ethoxylphenyl)-6-nitro piperonal was the same as that of 2-(4-ethylphenyl)-6-nitro piperonal, except that the reagents were 2-bromine-6-nitro-piperona and 4-ethoxylphenyl boronic acid; The preparing process of 2-(4-propylphenyl)-6-nitro piperonal was the same as that of 2-(4-ethylphenyl)-6-nitro piperonal, except that the reagents were 2-bromine-6-nitro-piperona and 4-propylphenyl boronic acid; The preparing process of 2-(3-ethoxylphenyl)-6-nitro piperonal was the same as that of 2-(4-ethylphenyl)-6-nitro piperonal, except that the reagents were 2-bromine-6-nitro-piperona and 3-ethoxylphenyl boronic acid;

Step 3: Preparation of 2-(4-ethylphenyl)-6-amino piperonal 2-(4-ethylphenyl)-6-nitro piperonal (195 mg, 0.65 mmol) was dissolved in methanol (70 mL) and catalytic amount Pd/C was added. The mixture reacted under hydrogen balloon for 24 hr. The catalyst was filtered out and the filtrate was concentrated. The resultant was 146 mg light yellow solid (83%).

$^1$H NMR (500 MHz, Chloroform-d) δ: 9.38 (s, 1H), 7.62 (s, 2H), 7.30 (s, 4H), 6.36 (s, 1H), 5.94 (s, 2H), 2.66 (m, 2H), 1.22 (m, 3H).

The preparing process of 2-(4-isopropylphenyl)-6-amino piperonal was the same as that of 2-(4-ethylphenyl)-6-amino piperonal, except that the reagent was 2-(4-isopropylphenyl)-6-nitro piperonal; The preparing process of 2-(4-butylphenyl)-6-amino piperonal was the same as that of 2-(4-ethylphenyl)-6-amino piperonal, except that the reagent was 2-(4-butylphenyl)-6-nitro piperonal; The preparing process of 2-(4-ethoxylphenyl)-6-amino piperonal was the same as that of 2-(4-ethylphenyl)-6-amino piperonal, except that the reagent was 2-(4-ethoxylphenyl)-6-nitro piperonal; The preparing process of 2-(4-propylphenyl)-6-amino piperonal was the same as that of 2-(4-ethylphenyl)-6-amino piperonal, except that the reagent was 2-(4-propylphenyl)-6-nitro piperonal; The preparing process of 2-(3-ethoxylphenyl)-6-amino piperonal was the same as that of 2-(4-ethylphenyl)-6-amino piperonal, except that the reagent was 2-(3-ethoxylphenyl)-6-nitro piperonal;

Step 4: Preparing the FL118
(10,11-methylenedioxy-camptothecin) Derivatives
with the 9th Position being Phenyl FL9Q6: (20s)-9-(4-ethylphenyl)-FL118 (10,11-methylenedioxy camptothecin): (4S)-4-Ethyl-7,8-dihydro-4-hydroxy-1H-pyrano[3,4-f]indolizine-3,6,10(4H)-trione (100 mg, 0.38 mmol) was dissolved in anhydrous toluene (40 mL). 2-(4-ethylphenyl)-6-amino piperonal (146 mg, 0.54 mmol) and para-toluenesulfonic (13.1 mg, 0.075 mmol) were added. The mixture reacted at 110° C. under nitron for 24 hr. The mixture was cooled and the solvent was removed under reduced pressure. The compounds were purified by column chromatography (dichloromethane:methanol=97:3) and resulted in 42 mg light yellow solid (21%).

$^1$H NMR (500 MHz, Chloroform-d) δ: 8.27 (s, 1H), 7.75 (s, 1H), 7.65 (s, 1H), 7.44 (d, J=2.7 Hz, 4H), 6.20 (s, 2H), 5.74 (d, J=16.2 Hz, 1H), 5.31 (d, J=16.3 Hz, 1H), 5.17 (s, 2H), 3.76 (s, 1H), 2.80 (q, J=7.7 Hz, 2H), 1.91 (m, 2H), 1.36 (t, J=7.6 Hz, 3H), 1.06 (t, J=7.3 Hz, 3H). $^{13}$C NMR (151 MHz, CDCl3) δ: 173.99, 157.69, 150.99, 150.17, 149.99, 147.98, 146.88, 146.31, 144.85, 130.30, 129.49, 128.52, 127.84, 127.33, 125.45, 117.78, 116.90, 105.20, 102.15, 97.36, 72.81, 66.36, 50.20, 31.61, 28.75, 15.40, 7.86.

FL9Q1: (20s)-9-(4-isopropylphenyl)-FL118 (10,11-methylenedioxy camptothecin): 9Q1 was prepared and purified as described for the synthesis and purifying of 9Q6 using (4S)-4-Ethyl-7,8-dihydro-4-hydroxy-1H-pyrano[3,4-f]indolizine-3,6,10(4H)-trioneana and 2-(4-isopropylphenyl)-6-amino piperonal. The resultant was 58 mg light yellow solid (30%).

¹H NMR (500 MHz, Chloroform-d) δ: 8.24 (s, 1H), 7.61 (s, 1H), 7.52 (s, 1H), 7.45 (m, 4H), 6.18 (s, 2H), 5.74 (d, J=16.1 Hz, 1H), 5.30 (d, J=16.1 Hz, 1H), 5.16 (s, 2H), 3.79 (s, 1H), 3.06 (p, J=7.0 Hz, 1H), 1.89 (m, 2H), 1.37 (d, J=7.0 Hz, 6H), 1.06 (t, J=7.4 Hz, 3H). ¹³C NMR (151 MHz, CDCl₃) δ: 173.90, 157.65, 150.93, 150.19, 149.93, 149.39, 147.93, 146.82, 146.25, 130.29, 129.58, 127.86, 127.31, 127.08, 125.42, 117.79, 116.90, 105.18, 102.11, 97.36, 72.81, 66.30, 50.20, 34.03, 31.63, 23.96, 7.84.

FL9Q2: (20s)-9-(4-butylphenyl)-FL118 (10,11-methylenedioxy camptothecin): 9Q2 was prepared and purified as described for the synthesis and purifying of 9Q6 using (4S)-4-Ethyl-7,8-dihydro-4-hydroxy-1H-pyrano[3,4-f]indolizine-3,6,10(4H)-trioneana and 2-(4-butylphenyl)-6-amino piperonal. The resultant was 40 mg light yellow solid (20%).

¹H NMR (500 MHz, Chloroform-d) δ: 8.23 (s, 1H), 7.65 (s, 1H), 7.55 (s, 1H), 7.42 (s, 4H), 6.18 (s, 2H), 5.74 (d, J=16.3 Hz, 1H), 5.30 (d, J=16.2 Hz, 1H), 5.16 (s, 2H), 3.79 (s, 1H), 2.75 (m, 2H), 1.91 (m, 2H), 1.71 (m, 2H), 1.46 (q, J=7.4 Hz, 2H), 1.06 (t, J=7.3 Hz, 3H), 1.00 (t, J=7.3 Hz, 3H). ¹³C NMR (151 MHz, CDCl₃) δ: 173.99, 157.68, 150.98, 150.16, 149.98, 147.97, 146.87, 146.29, 143.59, 130.23, 129.44, 129.04, 127.86, 127.32, 125.43, 117.78, 116.92, 105.20, 102.15, 97.36, 72.81, 66.36, 50.22, 35.56, 33.54, 31.61, 22.52, 14.02, 7.87.

FL9Q4: (20s)-9-(4-ethoxylphenyl)-10,11-methylenedioxy camptothecin: 9Q4 was prepared and purified as described for the synthesis and purifying of 9Q6 using (4S)-4-Ethyl-7,8-dihydro-4-hydroxy-1H-pyrano[3,4-f]indolizine-3,6,10(4H)-trioneana and 2-(4-ethoxylphenyl)-6-nitro piperonal. The resultant was 49 mg light yellow solid (25%).

¹H NMR (500 MHz, Chloroform-d) δ: 8.24 (s, 1H), 7.69 (s, 1H), 7.58 (s, 1H), 7.42 (d, J=8.2 Hz, 2H), 7.12 (d, J=7.6 Hz, 2H), 6.19 (s, 2H), 5.75 (d, J=16.2 Hz, 1H), 5.31 (d, J=16.1 Hz, 1H), 5.17 (s, 2H), 4.15 (m, 2H), 3.75 (s, 1H), 1.91 (m, 2H), 1.50 (t, J=6.9 Hz, 3H), 1.06 (t, J=7.4 Hz, 3H). ¹³C NMR (151 MHz, CDCl₃) δ: 173.99, 159.20, 157.68, 150.97, 150.15, 149.96, 147.99, 146.88, 146.34, 131.56, 127.80, 127.30, 125.58, 124.10, 117.78, 116.66, 114.95, 105.09, 102.11, 97.34, 72.81, 66.36, 63.65, 50.20, 31.61, 14.89, 7.86.

FL9Q5: (20s)-9-(4-propylphenyl)-FL118 (10,11-methylenedioxy camptothecin): 9Q5 was prepared and purified as described for the synthesis and purifying of 9Q6 using (4S)-4-Ethyl-7,8-dihydro-4-hydroxy-1H-pyrano[3,4-f]indolizine-3,6,10(4H)-trioneana and 2-(4-propylphenyl)-6-amino piperonal. The resultant was 41 mg light yellow solid (21%).

¹H NMR (500 MHz, Chloroform-d) δ: 8.22 (s, 1H), 7.62 (s, 1H), 7.53 (s, 1H), 7.42 (s, 4H), 6.18 (s, 2H), 5.74 (d, J=16.2 Hz, 1H), 5.30 (d, J=16.2 Hz, 1H), 5.16 (s, 2H), 3.79 (s, 1H), 2.73 (m, 2H), 1.91 (m, 2H), 1.77 (m, 2H), 1.05 (t, J=7.4 Hz, 6H). ¹³C NMR (151 MHz, CDCl3) δ: 174.01, 157.68, 151.02, 150.14, 149.99, 147.98, 146.88, 146.32, 143.37, 130.22, 129.50, 129.08, 127.87, 127.33, 125.45, 117.80, 116.93, 105.19, 102.14, 97.35, 72.80, 66.38, 50.21, 37.95, 31.61, 24.46, 14.02, 7.86.

FL9Q7: (20s)-9-(3-ethoxylphenyl)-10,11-methylenedioxy camptothecin: 9Q7 was prepared and purified as described for the synthesis and purifying of 9Q6 using (4S)-4-Ethyl-7,8-dihydro-4-hydroxy-1H-pyrano[3,4-f]indolizine-3,6,10(4H)-trioneana and 2-(3-ethoxylphenyl)-6-amino piperonal. The resultant was 58 mg light yellow solid (30%).

¹H NMR (500 MHz, Chloroform-d) δ: 8.21 (s, 1H), 7.61 (s, 1H), 7.51 (m, 2H), 7.05 (m, 3H), 6.18 (s, 2H), 5.75 (d, J=16.1 Hz, 1H), 5.31 (d, J=16.1 Hz, 1H), 5.16 (s, 2H), 4.12 (q, J=7.0 Hz, 2H), 3.77 (s, 1H), 1.90 (m, 2H), 1.47 (t, J=6.9 Hz, 3H), 1.06 (t, J=7.4 Hz, 3H). ¹³C NMR (151 MHz, CDCl₃) δ 174.04, 159.34, 157.70, 151.02, 150.13, 150.08, 147.92, 146.89, 146.27, 133.61, 130.03, 127.85, 127.39, 125.33, 122.53, 117.81, 116.84, 116.73, 114.37, 105.38, 102.21, 97.34, 72.80, 66.40, 63.65, 50.21, 31.60, 14.85, 7.86.

Pharmaceutical Compositions

Pharmaceutical compositions were covered by the previous invention (PCT/US15/22095). Here we added new inventions. In one aspect, the present disclosure provides pharmaceutical compositions which include at least one compound of Formula 1 and one or more pharmaceutically acceptable carriers. The compositions of the present invention may contain other therapeutic agents for combination as described above, and may be formulated, for example, by employing conventional or specialized solid or liquid vehicles or diluents, as well as pharmaceutical additives of a type appropriate to the mode of desired administration. Specifically, in the suspension pharmaceutical format, (i) the suspension of a compound of Formula 1 contain ethanol-hydroxypropyl-β-cyclodextrin (HPβCD)-compound complex with saline in the presence or absence of up to 5% propylene glycol (PG) to dilute before oral administration; (ii) the ethanol-HPβCD solution-formulated a compound of Formula 1 complex can directly go into the spray-dry process to get a compound of Formula 1-HPβCD powder complex. Then this powder is jet-milled and the jet milled Formula 1-HPβCD powder can be directly diluted in saline containing up to 5% PG before oral administration; and (iii) the compound of Formula 1-HPβCD complex powder in the tablet format formulation, the pharmaceutical composition contains fillers/binders/diluents (e.g. celluloses/cellulose derivatives, starches/starch derivatives, lactose), disintegrant (e.g. colloidal silicone dioxide, croscarmellose sodium, crosspovidone), glidant (e.g. dibasic calcium phosphate, colloidal silicone dioxide), lubricants (e.g. magnesium stearate, stearic acid, polyethylene glycol, Talc), antimicrobials/preservative (propylene glycol, propylene paraben, methyl paraben, glycerin), etc., according to our techniques plus other well known in the art of pharmaceutical formulation. For example, see, Remington: The Science and Practice of Pharmacy, 21st Ed., Lippincott Williams & Wilkins (2005).

Pharmaceutical compositions are typically formulated to be compatible with its intended route of administration. While this invention focuses on oral administration of FL118 and FL118 core structure platform-derived analogues in an aqueous suspension, such formulation can also be used for ip and iv administration. The tablet formats should be only used for po.

The aqueous suspension format for oral administration includes different recipes. In one recipe, the aqueous suspension contains the complex format of ethanol-HPβCD-a compound of Formula 1 complex formulation, which will be further diluted with saline in the presence or absence of up to 5% PG before oral administration. In another recipe, the ethanol-HPβCD-a compound of Formula 1 complex will directly go into the spray-dry process to get the HPβCD-a compound of Formula 1 complex powder, followed by a jet-milling to get the powder particle size at ≤37 microns. Then the jet-milled HPβCD-a compound of Formula 1 complex powder can be dissolved in saline with up to 5% PG before administration. In the third recipe, the suspension contains an organic solvent-free foregoing compound of Formula 1 formulated with a type of cyclodextrin (e.g. hydroxypropyl-β-cyclodextrin, but not limited to), propylene glycol (PG, 1-5%) with or without polyethylene glycol (PEG) 300 (or PEG400) (0-5%) and hydroxypropyl methylcellulose (HPMC, 2-5%) in saline, which is ready to use.

The powder or tablet format for oral administration includes an organic solvent-free powder/tablet formulation of a foregoing compound of Formula 1 formulated with a type of cyclodextrin (e.g. hydroxypropyl-β-cyclodextrin, but not limited to), where the formulation further comprises microcrystalline cellulose (MCC, 30%-80%), corn starch (0%-40%), lactose (10%-25%), colloidal silicone dioxide (1%-3%), dibasic calcium phosphate (1%-10%), magnesium stearate (0.2%-3%), propylene glycol (1%-10%).

For application to the eye for treatment of retinoblastoma or other human diseases, the active compound may be in the form of a solution or suspension in a suitable sterile aqueous or non-aqueous vehicle in the presence of a low percentage (1-5%) of a cyclodextrin such as β cyclodextrin, hydroxypropyl-β-cyclodextrin, sulfobutylether-β-cyclodextrin but not limited to, which are incorporated into the solvent formulation with or without a thicken agent such as HPMC (hydroxypropyl methylcellulose). Additives, for instance buffers, preservatives including bactericidal and fungicidal agents, such as propylene glycol (PG), phenyl mercuric acetate or nitrate, benzalkonium chloride, or chlorohexidine and thickening agents such as hypromellose may also be included.

The pharmaceutical composition and method of the present disclosure may further include additional therapeutically active compounds (second agents), as noted herein and/or known in the art, which are typically employed for treating one or more pathological conditions in concert with the compositions comprising compounds of Formula 1 of the present disclosure. The combination of therapeutic agents acts synergistically to effect the treatment or prevention of the various diseases, disorders, and/or conditions described herein. Such second agents, include, but are not limited to, chemotherapeutic and/or chemopreventive agents from plants or non-plants such as curcumin, resveratrol, vitamin D3, isothiocyanates (ITCs), e.g., allyl isothiocyanate (AITC), prostanoids, endothelin antagonists, cytoplasmic kinase inhibitors, receptor kinase inhibitors, endothelin receptor antagonists, e.g., ambrisentan, bosentan, and sitaxsentan, PDE5 (PDE-V) inhibitors, e.g., sildenafil, tadalafil, and vardenafil, calcium channel blockers, e.g., amlodipine, felodipine, varepamil, diltiazem, and menthol, prostacyclin, treprostinil, iloprost, beraprost, nitric oxide, oxygen, heparin, warfarin, diuretics, digoxin, cyclosporins, e.g., cyclosporin A, CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39, i.e., CD 154, fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal anti-inflammatory drugs (NSAIDs) such as ibuprofen, aspirin, acetaminophen, leflunomide, deoxyspergualin, cyclooxygenase inhibitors such as celecoxib, steroids such as prednisolone or dexamethasone, gold compounds, beta-agonists such as salbutamol, LABAs such as salmeterol, leukotriene antagonists such as montelukast, antiproliferative agents such as methotrexate, FK506 (tacrolimus, Prograf), mycophenolate mofetil, cytotoxic drugs such as azathioprine, VP-16, etoposide, fludarabine, doxorubin, adriamycin, amsacrine, camptothecin, cytarabine, gemcitabine, fluorodeoxyuridine, melphalan and cyclophosphamide, antimetabolites such as methotrexate, topoisomerase inhibitors such as camptothecin, DNA alkylators such as cisplatin, kinase inhibitors such as sorafenib, microtubule poisons such as paclitaxel, TNF-α inhibitors such as tenidap, anti-TNF antibodies or soluble TNF receptor, hydroxy urea and rapamycin (sirolimus or Rapamune) or derivatives thereof.

The compounds from Formula 1 of the invention may also be prepared as salts which are pharmaceutically acceptable, but it will be appreciated that non-pharmaceutically acceptable salts also fall within the scope of the present disclosure at least to the extent that such salts are useful as intermediates in the preparation of pharmaceutically acceptable salts. Examples of pharmaceutically acceptable salts include, but are not limited to, sulfates, phosphates, mesylates, bismesylates, tosylates, lactates, tartrates, malates, bis-acetates, citrates, bishydrochloride salts, salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulfuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulfonic, trihalomethanesulfonic, toluenesulfonic, benzenesulfonic, isethionic, salicylic, sulphanilic, aspartic, glutamic, edetic, stearic, palmitic, oleic, lauric, pantothenic, tannic, ascorbic, valeric and orotic acids. Salts of amine groups may also comprise quaternary ammonium salts in which the amino nitrogen atom carries a suitable organic group such as an alkyl, alkenyl, alkynyl or aralkyl moiety. The salts may be formed by conventional means, such as by reacting the free base form of the compound with one or more equivalents of the appropriate acid in a solvent or medium in which the salt is insoluble, or in a solvent such as water which is removed in vacuum or by freeze drying or by exchanging the anions of an existing salt for another anion on a suitable ion exchange resin. In some embodiments, the salt is a chloride, sulfate, phosphate, mesylate, bismesylate, tosylate, lactate, tartrate, malate, bis-acetate, citrate, or bishydrochloride salt.

In some embodiments, the compounds of Formula 1 of the present disclosure are administered in a therapeutically effective amount. Such an administration imparts that a compound of Formula 1 will elicit a response associated with, e.g., cells, tissues, fluids, of a subject being sought by the clinician. In some embodiments, from about 0.01 to 5 mg/kg of subject body weight from per day to per week is administered. Suitable dosage levels include, for example, from 0.01 to 5 mg/kg per day to per week, from 0.05 to 1 mg/kg per day to per week, or from 0.1 to 0.5 mg/kg per day to per week or every two weeks. Within this range, in some embodiments, the dosage is from 0.05 to 0.2, 0.2 to 1 or 1 to 5 mg/kg per day or weekly or every two weeks. The dosage may be selected, for example, to any dose within any of these ranges, for therapeutic efficacy and/or symptomatic adjustment of the dosage to the subject being treated.

It will be understood that the specific dose level and frequency of dosage for any particular subject may be varied and will depend upon a variety of factors including the activity of the specific compound of Formula 1 employed, the metabolic stability and length of action of that compound, the age, body weight, general health, sex, diet, mode and time of administration, rate of excretion, drug combination, the severity of the particular condition, and the host undergoing therapy.

Methods and Uses

The present invention identified unique therapeutic indications with respect to treatment (chemotherapy, radiation) resistance factors, which are targeted for overcoming cancer resistance through the use of a compound of Formula 1 to target or bypass two or more of the defined set of treatment resistant factors for cancer control. This set of treatment resistant factors includes aberrant expression of survivin, Mcl-1, XIAP, cIAP2, ATP-binding cassette (ABC) transporter proteins (such as ABCG2, ABCC4, MDR1, MRP1), hypoxia inducing factor 1α (HIF-1α), HdmX and HdmX in the Hdm2/HdmX complex, ERCC6, wild-type, null or mutation of p53 as well as p53 related pathways. Use of alternative study approaches including drug affinity column purification and tritium-labeled compound of Formula 1 probe protein microarray global search of drug-protein interaction, additional biomarkers are revealed. This includes, but not limited to, survivin, Mcl-1, XIAP, cIAP2, ABC transporter proteins, hypoxia inducing factor 1α (HIF-1α), Hdm2, HdmX, p53, mutant APC, and/or mutant Kras. In illustrative embodiments, the ABC transporter proteins are selected from the group consisting of ABCG2, ABCC4, MDR1, MRP1, heat shock protein 60 (HSP60), stress-70 protein (GRP75), ATP-dependent RNA helicase DDX5 (p68), nucleolar RNA helicase 2 (DDX21), elongation factor 2(EF2), pre-mRNA-splicing factor ATP-dependent RNA helicase (DHX15), Transitional endoplasmic reticulum ATPase (TERA), Transferrin receptor protein (TFR1), MAP kinase-activated protein kinase 2 (MAPK2), Catenin beta-1 (CTNB1), Early endosome antigen 1 (EEA1), Guanine nucleotide-binding protein subunit beta-2-like 1 (GBLP), Electron transfer flavoprotein subunit alpha (ETFA), Proteasome activator complex subunit 3 (PSME3), UPF0368 protein Cxorf26 (CX026), Peroxiredoxin-2 (PRDX2), Peroxiredoxin-1 (PRDX1), Thioredoxin-dependent peroxide reductase (PRDX3), Serine/arginine-rich splicing factor 3 (SRSF3), Proteasome subunit beta type-2 (PSB2), Glutathione S-transferase P (GSTP1), MAP/microtubule affinity-regulating kinase 3 (MARK3), DNA-damage inducible 1 (DDI1), tumor protein D52-like 2 (TPD52L2), calcium channel, voltage-dependent, beta 1 subunit (CACNB1), Probable G-protein coupled receptor 1 (PGPCR1), ubiquitin specific peptidase 2 (USP2), melanocortin 2 receptor (MC2R), Fibroblast growth factor 18 (FGF18), tumor protein p53 inducible protein 3 (TP53I3), CCHC-type zinc finger, nucleic acid binding protein (CNBP), WD repeat domain 22 (WDR22), Potassium voltage-gated channel subfamily E member 1 (PVGCSE-M1), ubiquitin-conjugating enzyme E2T (putative) (UBE2T), Ubiquitin-like protein 7 (ULP7), RNA binding motif, single stranded interacting protein 2 (RBMS2), Cytoplasmic tyrosine-protein kinase (BMX), and cyclin B1 interacting protein 1 (CCNB1IP1). In illustrative embodiments, the p53 is wild type, null or a p53 mutant, or wherein there is an aberration in a canonical p53 pathway, or any combination thereof.

The present invention is further illustrated by many examples presented below, which should not be construed as limiting in any way. The following is a description of the materials and methods used throughout the examples.

Cell lines, cell culture and reagents. The human colorectal cancer cell lines (SW620, HT29), the retinoblastoma cell line HT-3, the human pancreatic ductal adenocarcinoma cell lines, PANC1, MIA PaCa2 (Mia2), BxPC3 and ovarian cancer cell line SKVO3 were originally obtained from ATCC. PANC1 that expresses luciferase (lucPANC1) was generated in this study with the parental PANC1 cell lines. Human ovarian cancer cell lines A2780 and its cisplatin-resistant counterpart A2780CP were gifts from Dr. Steven Howell [92]. All these cell lines were maintained in either DMEM or RPMI 1640 medium supplied with 10% fetal bovine serum (FBS, Atlanta Biologicals, Lawrenceville, GA), penicillin (100 units/ml) and streptomycin (0.1 µg/ml) (Invitrogen, Grand Island, NY). Cells were routinely subcultured twice a week and maintained in a humidified incubator with 5% CO2 at 37° C. Cisplatin (Fresenius Kabi USA, LLC), gemcitabine (Pfizer) and Abraxane (Celgene) were from Roswell Park Cancer Institute Hospital Pharmacy. Monoclonal anti-tubulin antibody, polyclonal anti-actin antibody and goat peroxidase-conjugated anti-rabbit IgG antibody were purchased from Sigma (St. Louis, MO). Antibodies for survivin (FL-142), ERCC1, ERCC6, γ-H2AX, ChK1, ChK2, ATM, ATR, RAD51, DNA Pol β and GAPDH were from Santa Cruz (Santa Cruz, CA). Antibodies for Mcl-1, XIAP, cIAP2, Bad, Bim, Bax, cleaved/activated caspase-3 and (cleaved and full length) PARP were from Cell Signaling (Beverly, MA, USA). MTT (3-[4,5-dimethylthiazol-2-yl]-2,5,-diphenyltetrazolium bromide) and leupeptin were purchased from USB (Cleveland, OH). MG132 was purchased from Medchemexpress (Princeton, NJ). D-luciferin potassium salt was purchased from Gold Biotechnology (St. Louis, MO). FL118 was synthesized in house with a purity≥95%. FL118 in the formulated suspension for in vivo animal oral administration is highly stable for more than 12 months and has no observable changes in its antitumor efficacy in comparison with the freshly prepared when tested in human tumor animal models.

Formulation of Formula 1 compounds for in vitro and in vivo studies. For in vitro studies, Formula 1 compounds are initially dissolved in DMSO at 1 mM as a stock solution. Prior to addition of the drug to the cells, the stock solution is further diluted with DMSO to a concentration of a 1000× of the final concentration used for the experiment. The 1000× working stock solution is directly diluted into experiment-relevant buffers/solution or cancer cell type-relevant medium. For in vivo studies, the compounds of Formula 1 are formulated using a know-how method and unique processes described above and below.

Western blotting/Immunoblotting. Cancer cells treated with and without FL118 (in some experiments in the presence of MG132) were lysed in RIPA buffer containing 150 mM NaCl, 1.0% IGEPAL CA-630, 0.5% sodium deoxycholate, 0.1% SDS, and 50 mM Tris, pH 8.0. Fifty µg total protein from each sample were heated at 95° C. for 5 minutes after mixing with equal volume of 2×SDS loading buffer. Samples were separated on 12-15% SDS-polyacrylamide gel electrophoresis (SDS-PAGE) gels and electrotransferred to Pure Nitrocellulose Membranes (Bio-Rad, Hercules, CA). The membrane was then blocked in 5% skim milk in TBS-T buffer (20 mM Tris/HCl pH 7.5, 0.137 M NaCl, and 0.1% Tween 20) at room temperature for 2-3 hours. Next, the membrane was incubated with different primary antibodies in TBS-T containing 5% BSA overnight at 4° C. in the range of dilutions from 1:500 to 1:2000. After washing with TBS-T, the membrane was incubated in TBS-T buffer containing 5% skim milk and corresponding secondary antibody (1:5000) for 45-60 minutes at room temperature with shaking. Protein of interest was detected using Western Lightning Plus—ECL (Perkin Elmer, Waltham, MA) and visualized by various times (3-120 seconds) of exposure. Actin was detected as the internal control to normalize total protein loading for each sample.

DNA sub-G1 flow cytometry analyses. PANC1 and MIA PaCa-2 pancreatic cancer cells were treated with or without FL118 for 48 hours, then harvested by trypsinization and washed with PBS. Cells (~1×10$^6$) were resuspended in 5 ml 70% ethanol. After the initial fixation, cells were suspended in 0.5 ml PBS containing 25 µg/ml PI, 0.2% Triton X-100 and 40 µg/ml RNase A. After 30 minutes incubation at 4° C., the cells were analyzed by flow cytometry. Data from flow cytometry was analyzed using WinList software (Verity Software House Inc., Topsham, ME) and presented as a relative fold sub-G1 DNA content increase in comparison with vehicle-treated controls. Triplicate assays were performed. The experimental results were expressed as the mean±SD. The statistical significance of differences was determined by Student's t-test between two groups.

MTT assays. Cell growth/viability inhibitory effect of drug (FL118, gemcitabine, Abraxane, cisplatin) alone and in combination, respectively, on cell growth was determined by MTT cell viability assay. Viable cells (2500 cells per well) were plated in each well in 96-well plates. After an overnight incubation, cells were treated with and without relevant drugs alone and in combination, respectively, at various concentrations and incubated for 72 hours. MTT, a colorimetric substrate, was added to a final concentration of 0.4 mg/ml to each well. Cells in 96-well plates were further incubated in a 5% $CO_2$ incubator at 37° C. for 4 hours, and then the medium was aspirated. The MTT metabolic product formazan was solubilized by adding 200 µl of DMSO to each well. Absorbance in the relevant wells was measured at 570 nm using an Ultra Microplate Reader (Bio-Tek Instruments). Each experiment was performed at least in triplicate. $IC_{50}/EC_{50}$ values were calculated from a series of drug dose ranges for each analyzed compound, using GraphPad Prism 6 (GraphPad Software, Inc., La Jolla, CA).

Generation of A2780-GFPcODC, A2780CP-GFPcODC and PANC1GFPcODC cells and fluorescence microscopy to detect stem-like and drug resistant green cells. The retroviral expression vector pQCXIN-ZsGreen-cODC (ornithine decarboxylase), containing a green fluorescence marker, was kindly provided by Dr. Frank Pajonk (Vlashi E, et al., In vivo imaging, tracking, and targeting of cancer stem cells. J Natl Cancer Inst. 2009; 101: 350-9). The retroviral particles collected from packaging cells that transfected with the above vector were infected into A2780, A2780CP and PANC1 cells, respectively. The transfected cell pool was used for experiments. The transfected cells were treated with and without cisplatin or FL118 alone or in combination for defined times. Cell images were acquired digitally using the Olympus IX73 Inverted Score s (Olympus). Percentages of living cells were obtained from the average of the total cells counted from 10 microscopic fields.

Matrigel stem cell cultural assay. The sphere formation assay was performed with PANC1 cells by treatment in the presence of vehicle and FL118 at 1, 10 and 100 nM. Spheres were maintained in Improved MEM containing 20 ng/ml epidermal growth factor, 10 ng/ml basic fibroblast growth factor, 5 g/ml insulin and 0.4% Bovine Serum Albumin. PANC1 cells were plated at a density of 1000 cells/well in 24-well ultralow attachment plates (Sigma-Aldrich). Briefly, 1000 PANC1 cells were suspended in 40 µL medium and mixed thoroughly with 60 µL BD Matrigel™ (BD Bioscience, San Jose, CA, USA). The mixture was plated onto the edge of the well, and the plates were incubated in a 5% $CO_2$ incubator at 37° C. for 45 minutes to allow the BD Matrigel™ to solidify. Upon solidification, FL118 treatment was administered. Spheres in each well were set in the plate to grow for 20 days and then quantitated visually under a microscope at the magnification of 10×.

CD44 positive cell sorting and CD44-positive cell colony formation. CD44 positive (CD44+) cells were purified (sorted out) using fluorescence activated cell sorting (FACS). FITC-conjugated mouse anti-human CD44 was used in FACS purification of CD44+ PANC1 cells. Briefly, PANC1 cells were harvested by using 0.25% trypsin/0.02% EDTA. After re-suspension of the cells in cell-culture media, the cells were counted and washed in PBS with 2% FBS and collected by centrifugation. Add 10 µL FITC-CD44 antibody to 1 ml PBS containing 1 million cells and 2% of FBS for 30 minutes on ice. Following the antibody labeling, PANC1 cells were washed in PBS with 2% BSA before flow cytometric analysis was carried out on a BD FACSAria™ III cell sorter (BD Science, USA). PANC1 CD44+ cells were plated in 6-well plates at the density of 300 cells/well, the cells were treated with vehicle or with FL118 at 1, 10 and 100 nM 24 h after seeding. Vehicle and FL118 were washed out with PBS after 72 h treatment; the cells were continuously cultured in complete medium with 10% serum in an incubator at 37° C., 5% $CO_2$ for 12 days. Colonies were fixed, stained with crystal violet solution and images were taken before counting colonies on day 12. The experimental results were expressed as the mean±SD. The statistical significance of differences was determined by Student's t-test between two groups.

Animal model study approval. All in vivo experimental studies were performed following the IACUC-approved mouse protocol, which was approved by the Institutional Animal Care and Use Committee (IACUC) at Roswell Park Comprehensive Cancer Center. All SCID mice used are 6-12 weeks of age.

Human xenograft tumors used. In this invention disclose, human SW620 (colorectal), HT29 (colorectal) and HT-3 (retinoblastoma) cancer cell line-established xenograft tumors were used. Human tumor cell line-derived xenograft tumors are initially established by subcutaneously injecting 2-5×10$^6$ cultured cancer cells in a volume of 100-150 µL medium into the flank area of severe combined immunodeficiency (SCID) mice. The derived tumors are then passed a couple of generations in mice by transplanting 30-50 mg non-necrotic tumor mass via a trocar for experiments or maintenance. In this invention disclose, we also used two types of cancer patient-derived xenograft (PDX) tumors: human colorectal cancer PDX (27454) and human pancreatic cancer PDX (14244). PDX tumors were originally established on severe Combined Immunodeficiency (SCID) mice from pancreatic and colorectal cancer patient tumor tissues obtained from metastatic sites of the disease in the clinic.

Human pancreatic ductal adenocarcinoma (PDAC) orthotopic tumor mouse model and treatment. PANC1 cells (LucPANC1) grown in culture medium were harvested by trypsinization, washed twice in ice-cold PBS, and adjusted to 5×10$^7$ viable cells/ml. Twenty-µL volumes containing 1 million LucPANC1 cells were injected into a SCID mouse pancreas. Specifically, for intra-pancreatic implantation of LucPANC1 cells, SCID mice were anesthetized with isoflurane using the rodent anesthesia machine provided and maintained by the Animal Center. The surgical plane of anesthesia was monitored with pedal withdrawal reflex. Eye ointment was placed in the eyes. The abdomen was shaved and prepared using an iodine scrub and alcohol. An up to one cm incision was made using scissors, one third of the spleen was pulled out and LucPANC1 cells were injected in 20 μL volume (1 million cells) into the tail of the pancreas using a 29 gauge needle. The pancreas was returned to the abdomen and the abdominal wall musculature and the peritoneum were sutured using 5.0 absorbable surgical suture. The skin was closed with wet bond, which was removed 7 days after surgery. Postoperative analgesia was 0.05 mg/kg of buprenorphine subcutaneously q8-12 hours postoperatively as needed. The mice were allowed to recover alone in a cage that was placed on a circulating warm water-heating pad. This reduces post-surgical shock. Once the mice were fully recovered from the surgical procedure and were freely moving around the cage with normal eating and drinking, the mice were returned to their cage. If any mice display signs of a moribund condition during the course of the study, they were euthanized. Healthy orthotopic mice were randomly divided into 2 groups (3 mice per group): a control/vehicle group and an FL118-cisplatin treatment group (of note, LucPANC1 cells are drug resistant and in order to keep the amount of surgical mice to a minimum, the drug alone group was not included in the study). Treatments with vehicle and FL118 plus cisplatin were started 7 days after cell orthotopic implantation. The treatment schedule was that cisplatin at 5 mg/kg (half maximum tolerated dose, ~½MTD) and FL118 at 0.75 mg/kg (~⅙MTD via ip in our studies) were given on days 7, 14, 21 and 28 (q7d×4) via intraperitoneal routes (ip). Bioluminescence imaging (BLI) was taken every 1-3 week (week 1 is the baseline).

Mouse whole body in vivo imaging. SCID mouse whole body imaging was performed to detect luciferase reporter activity using the Xenogen IVIS® in vivo Imaging System (Caliper Life Science, Hopkinton, MA) in the Translational Imaging Shared Resource at Roswell Park Cancer Institute (RPCI). Prior to imaging, tumor-bearing mice were anesthetized with isoflurane (Patterson Logistics Services Inc., Mount Joy, PA) at 2.5% mixed with oxygen in a separate induction chamber. After induction anesthesia, mice were intraperitoneally injected with D-luciferin potassium salt dissolved in PBS at a dose of 75 mg/kg and transferred into the in vivo imaging chamber. Animals were provided 2.5% maintenance anesthesia within the imaging chamber, and ten minutes after D-luciferin injection BLI was performed for detection of luciferase activity. Following imaging, animals were returned to cages and monitored to ensure full recovery. Reported measurements of total flux, representative of BLI signal intensity, were obtained by tracing a region of interest over the entire tumor. All measurements and displayed pseudocolorized BLI radiance images were obtained using the Living Image (PerkinElmer, Waltham, MA) software.

Human pancreatic cancer patient-derived xenograft (PDX) tumor mouse model and treatment. Experiments followed the IACUC-approved mouse protocol. Briefly, human PDAC PDX tumors maintained on SCID mice were isolated, and a piece of non-necrotic tumor tissues (30-40 mg) were subcutaneously transplanted into the flank area of female SCID mice. Seven to 14 days after tumor transplantation at which PDAC PDX tumors were grown to 150-250 mm$^3$ (defined as day 0), mice were randomly divided into the required groups (5 mice per group) for FL118 alone or in combination testing. In this study, we used the timesaving intraperitoneal (ip) route for drug administration. The schedule for FL118 and gemcitabine is weekly for 4-time drug administration either alone or in combination. FL118 in the current study used a basic formulation recipe, which contains FL118 (0.1-0.25 mg/ml), DMSO (5%), and hydroxypropyl-β-cyclodextrin (0.05-0.125%, w/v) in saline. The formulation process was described in detail in our previous patent (PCT/US2011/058558). The vehicle solution contains DMSO (5%), and hydroxypropyl-β-cyclodextrin (0.05-0.125%, w/v) in saline without FL118. Tumor length (L) and width (W) were measured using digital vernier calipers 1-3 times per week until the end of experimental studies. The tumor volume (v) was calculated using the formula: $v=0.5 (L \times W^2)$. Then the tumor size was divided by the day 0 tumor size as percentage tumor size versus day 0. The mean tumor volume±standard deviation (SD) at each time point was derived from 5 mice in each group. The tumor curves were made using Sigma Plot software.

Use of immune-competent BALB/cj mice for FL118 toxicity and MTD studies. Female BALB/cj mice at the age of six weeks were purchased from Jackson Laboratory. Mice were randomly divided into 4 groups with six mice per groups. Mice were then treated with vehicle, FL118 at 10 mg/kg (this is the FL118 MTD in SCID mice), 12.5 mg/kg and 15 mg/kg via oral administration with the schedule qw×4. MTD was defined as the highest dose that results in no drug-related moribund state or death, with a temporary body weight loss of no more than 20%, no significant clinical pathology changes including hematology and biochemistry parameters. Other signs of toxicity documented during the experiment included mouse behavior, fur status, movement and diarrhea. Mouse hematology and chemistry studies were performed in Roswell Park Animal Center in-house service using ProCyte Dx® Hematology Analyzer (IDEXX BioResearch) and Catalyst Dx® Chemistry Analyzer (IDEXX BioResearch). These results are shown in Table 1 and Table 2.

TABLE 1

Effects of FL118 on BALB/cj mouse hematological parameters

|  | RBC (M/μL) | HGB (g/dL) | HCT (%) | MCV (fL) | MCH (pg) | MCHC (g/dL) | RDW-SD (fL) | RET (K/μL) |
|---|---|---|---|---|---|---|---|---|
| Normal range | 3.75-15.2 | 6.1-21.7 | 16.7-69.8 | 39-90.8 | 12.6-31 | 27-37.6 | 24.2-63.1 | 3.6-15.2 |
| Vehicle | 7.51-9.06 | 11.1-13.7 | 33.5-40.6 | 44.6-44.2 | 14.8-15.1 | 33.1-34 | 26.4-28.9 | 5.13-6.4 |
| FL118 (MTD) | 6.01-7.04 | 8.9-10.8 | 26.1-30.9 | 41.9-43.9 | 14.8-15.3 | 33.7-36 | 23-24.8 | 0.67-4.49 |

TABLE 1-continued

Effects of FL118 on BALB/cj mouse hematological parameters

|  | PLT (K/µL) | PDW (fL) | MPV (fL) | WBC (K/µL) | NEUT (K/µL) | LYM (K/µL) | MONO (K/µL) | EOS (K/µL) | BASO (K/µL) |
|---|---|---|---|---|---|---|---|---|---|
| Normal range | 59-2633 | 5.7-23.9 | 5.2-13.1 | 1.1-56.1 | 0.03-32.1 | 0.12-23.5 | 0-5.1 | 0-2.1 | 0-2.3 |
| Vehicle | 179-290 | 7-11.2 | 5.5-7.6 | 4.0-8.5 | 3.6-5.7 | 0.31-1.73 | 0.26-0.95 | 0.01-0.12 | 0-0.01 |
| FL118 (MTD) | 487-1004 | 13.8-14.4 | 8.1-8.6 | 0.33-0.6 | 0.03-0.5 | 0.06-0.17 | 0.03-0.12 | 0.01-0.1 | 0 |

RBC, red blood cell; HGB, hemoglobin; HCT, hematocrit; MCV, RBC mean cell volume; MCH, mean corpuscular/cell hemoglobin; MCHC, mean corpuscular/cell hemoglobin concentration; RDW-SD, red cell distribution width-standard deviation; RET, reticulocyte; PLT, platelet; PDW, platelet distribution width; MPV, mean platelet volume; WBC, white blood cell; NEUT, neutrophil; LYM, lymphocyte; MONO, monocyte; EOS, eosinophil; BASO, basophil.
M, million; K, 1000/thousand.

TABLE 2

Effects of FL118 on BALB/cj mouse serum biochemical parameters

|  | GLU (mg/dL) | BUN (mg/dL) | CREA (mg/dL) | PHOS (mg/dL) | Ca (mg/dL) | TP (g/dL) |
|---|---|---|---|---|---|---|
| Normal range | 90-192 | 18-29 | 0.2-0.8 | 6.1-10.1 | 5.9-9.4 | 3.6-6.6 |
| Vehicle | 89-140 | 8-15 | ≤0.1 | 4.6-5.5 | 9-10.8 | 3.9-4.6 |
| FL118 (MTD) | 87-185 | 16-19 | ≤0.1 | 10-13.3 | 8.1-9.4 | 3.4-4.1 |

|  | ALB (g/dL) | ALT (U/L) | ALP (U/L) | TBIL (mg/dL) | CHOL (mg/dL) | AMYL (U/L) |
|---|---|---|---|---|---|---|
| Normal range | 2.5-4.8 | 28-132 | 62-209 | 0.1-0.9 | 36-96 | 1691-3615 |
| Vehicle | 1.9-2.1 | 76-124 | 42-82 | ≤0.1 | 112-114 | 1266-1272 |
| FL118 (MTD) | 1.7-2.2 | 33-58 | 52-105 | ≤0.1-0.3 | 91-109 | 1483-1982 |

GLU, glucose; BUN/UN, (blood) urea nitrogen; CREA, creatinine; PHOS, phosphorus; Ca, calcium; TP, total protein; ALB, albumin; ALT, alanine transaminase/aminotransferase; ALP/ALKP, alkalinephosphatase; TBIL, total bilirubin; CHOL, cholesterol; AMYL, amylase.

Use of immune-competent beagle dogs for FL118 toxicity and MTD studies. The Contrast Research Organization (CRO) Covance has performed the studies. The experiment method in brief is below:

The FL118 MTD was estimated to be 12 mg/kg/dose for two doses in SCID mice. The calculated FL118 MTD for dogs is 2 mg/kg. Therefore, doses were set as 0.55, 1.1, and 2.2 mg/kg. Nine male and nine female purebred beagle dogs at the age of 5 months with a body weight range of 7.9-10.1 kg for male and 7.2 to 8.3 kg for females were received from Covance Research Products, Inc. (Cumberland, Virginia). Animals were acclimated to the test facility (Greenfield, Indiana) for 15 days prior to initiation. Animals were socially housed by sex. Animals were assigned to the study using a computerized procedure designed to achieve body weight balance with respect to group assignment with the experimental design shown in Table 11.

TABLE 11

Experimental design of the beagle dogs for FL118 toxicity and MTD studies

|  | No. of Animals | | Dose Level | Dose Concentration |
|---|---|---|---|---|
| Group | Male | Female | (mg/kg/dose) | (mg/mL) |
| 1 (Vehicle control) | 2 | 2 | 0 | 0 |
| 2 (Low dose) | 2 | 2 | 0.55 | 0.11 |

TABLE 11-continued

Experimental design of the beagle dogs for FL118 toxicity and MTD studies

|  | No. of Animals | | Dose Level | Dose Concentration |
|---|---|---|---|---|
| Group | Male | Female | (mg/kg/dose) | (mg/mL) |
| 3 (Mid dose) | 2 | 2 | 1.1 | 0.22 |
| 4 (High dose) | 2 | 2 | 2.2 | 0.44 |

Group 1 received vehicle control article only.

The formulation of FL118 in this study are FL118 at 0.11, 0.22 and 0.44 mg/ml in 0.44% (2-hydroxypropyl)-β-cyclo-dextrin (HPβCD), 2% hydroxypropyl methylcellulose (HPMC) and 1% propylene glycol (PG) in sterile saline (0.85% NaCl). This oral administration solution without FL118 was the vehicle control. Dose formulations were administered by oral gavage once on Days 1 and 8 of the dosing phase at a dose volume of 5 mL/kg. Doses were based on the most recently recorded scheduled body weight. Animals were checked twice daily (a.m. and p.m.) for mortality, abnormalities, and signs of pain or distress. Abnormal findings were recorded. Cageside observations were conducted for each animal once daily during the dosing phase, except on days when detailed observations were conducted. Abnormal findings were recorded. Detailed observations were conducted for each animal once during the predose phase and on Days 1, 4, and 8 (prior to dosing, as applicable) of the dosing phase. Detailed observations were also collected for each animal on the day of scheduled sacrifice. Abnormal findings or an indication of normal was recorded. On each day of dosing, cageside observations were conducted for each animal approximately 1, 4, and 24 hours postdose. Abnormal findings were recorded. Postdose observation start times were based on the time dosing was completed for each group/sex. Body weights were recorded twice during the predose phase and on Days 1, 4, and 8 (prior to dosing, as applicable) of the dosing phase. Quantitative food consumption was recorded from Days 1 to 4, 4 to 8, and 8 to 9 of the dosing phase. Blood samples for hematology, coagulation, and clinical chemistry were collected from fasted animals via a jugular vein. Blood samples were collected once during the predose phase and on the day of scheduled sacrifice. The anticoagulants were sodium citrate for coagulation tests and potassium EDTA for hematology tests. Samples for clinical chemistry were collected without anticoagulant.

On Day 10 of the dosing phase, all animals, having been fasted overnight, were anesthetized with sodium pentobarbital, exsanguinated, and necropsied. Terminal body weights were recorded for sacrificed animals. A macroscopic examination of the external features of the carcass; external body orifices; abdominal, thoracic, and cranial cavities; organs; and tissues were performed. A Pathologist was available for consultation during necropsies. Organ weights were recorded at the scheduled sacrifice. Paired organs were weighed together. The statistical data analyses include means and standard deviations (SD) with the parameters of absolute body weight, body weight change, quantitative food consumption, continuous clinical pathology values, and terminal body weights and organ weights Specimen preparation for Pharmacokinetics (PK) studies in tumor bearing mice. Drug PK studies were performed as follows: SCID mice were first inoculated with human SW620 and HT29 tumors (of note, for PK data comparison, both tumors on individual mice at both left and right flank sites), when tumor size grew to approximate 800-1000 mm$^3$, a single oral administration of FL118 was given at a dose of 1.5 mg/kg to six groups of SCID mice (3 mice per group) bearing human SW620 and HT29 xenograft tumors. Of note, 1.5 mg/kg for oral administration of FL118 is close to the FL118 MTD (maximum tolerated dose) for the schedules of daily for five times (q1d×5) and every other day for five times (q2d×5). Tumor tissues and blood samples were collected at a series of time points of 30 minutes, 1 hour, 4 hours, 12 hours and 24 hours. Each tumor tissue was collected in a tube and immediately frozen with liquid nitrogen; each blood sample was collected in a Li-Heparin LH/1.3 tube (SARSTEDT), and plasma was recovered by centrifugation (1500 rpm×2 minutes). The collected plasma from each blood sample was transferred into a new tube and immediately frozen in liquid nitrogen. Liquid nitrogen-frozen specimens were then transferred to an −80° C. freezer for analysis.

Pharmacokinetics analysis of compound after oral administration. Drug in plasma is extracted with acidified methanol. An 800 μL aliquot of ice-cold acidified methanol is added to 200 μL plasma and vortexed for 15 sec. In parallel, FL118 in mouse tissue or human xenograft tumor tissue is first homogenized in 1×PBS (W/V=1 g tissue/3 ml 1×PBS) and then extracted with acidified methanol. An 800 μL aliquot of ice-cold acidified methanol is added to 200 μL homogenized tissue and then vortexed for 1 min. The samples are then centrifuged at 13,000 rpm for 5 min. and the supernatant is transferred to a clean 13×100 mm glass tube. Samples are dried under vacuum and stored at −20° C. until analysis. Dried samples were then reconstituted in 200 μL of mobile phase (80% 3% TEA and 20% acetonitrile pH 5.5) and 15 μL is injected. Analysis is carried out using an Acquity UPLC system with Fluorescence detection interfaced with Empower software. Separation is carried out on an Acquity BEH Shield RP18 1.7 μm, 2.1 mm×100 mm column (Waters). The fluorescence detector is set at the following Excitation (Ex) and Emissions (Em) wavelengths: Ex 370 nm Em 510 nm. The calibration standards are prepared by spiking plasma with FL118; the calibration curve range is 5 ng/mL-500 ng/mL. To ensure quality assurance, quality control samples are prepared in plasma at 25 and 250 ng/mL aliquoted and stored at −20° C. The QC's are injected in duplicate at the beginning and end of the assay. Assay has been validated. Validation consists of running twelve standard curves over the course of 5 days. QC samples are analyzed with each curve. The overall precision (% CV=6.4) and overall accuracy (101%) of the assay calibrators is shown to be excellent. QC precision measured as % CV is equal to 7.5% and overall QC accuracy is 96%.

Use of Tritium ($^3$H)-Labeled FL118 or FL118 Analogue as Probes to Search Biochemical Targets/Biomarker Through Screening of the Invitrogen ProtoArray®.

The $^3$H labeling of a small molecule/ligand (FL118 or an analogue): A 50 ml round bottom flask is charged with 0.8-1 mg FL-2, 120 mg PdBaSO4 5%, 90 Ci T2 Gas, Immersed in silicone oil bath at 180° C.-190° C. for 24 hours. Dissolved in 1 ml of DMSO and back-exchanged 10× with 50% ETOH. Injected directly to CapCeLL Pak C-18 column, mobile phase 30% CH3CN1 0.1% TFA, flow 6 ml/min, U.V.=200 nm, r.t.=40 min. After purification, a probe with a specificity of 16.5 mCi/mml were obtained for screening >9,000 human proteins on the Invitrogen ProtoArray.

ProtoArray® screening with $^3$H-labeled probe (FL-2): 1. Blocking the ProtoArray: a) Immediately place the mailer containing the Human Protein Microarray v5.0 at 4 □ C upon removal from storage at −20 □ C and equilibrate the mailer at 4 □ C for at least 15 minutes prior to use. b) Place Human Protein Microarrays with the barcode facing up in the bottom of a 4-chamber incubation tray such that the barcode end of the microarray is near the tray end containing an indented numeral. c) Using a sterile pipette, add 5 mL FL-2 Assay Buffer into each chamber. Avoid pipetting buffer directly onto the array surface. d) Incubate the tray for 1 hour at 4.C on a shaker set at 50 rpm (circular shaking). e) After incubation, remove Protein Microarrays from FL-2 Assay Buffer. To remove array from the 4-chamber incubation tray, insert the tip of forceps into the indented numeral end and gently pry the array upward. Using a gloved hand, pick up the microarray by holding the array by its edges only. Tap to remove excess liquid from slide surface. f) Proceed immediately to Probing the Array. 2. Probing the ProtoArray: a) Place each ProtoArray horizontally in a separate sterile 50 mL conical tube with about ⅓ of the array extended outside of the tube as shown in the figure below. The barcoded end of the array should protrude from the tube (face up). b) For each ProtoArray, add 100 μL of probing mixture including FL-2 and the positional mapping reagent $^3$H-estradiol and pipet the mixture gently onto the surface of the ProtoArray. c) Gently place a coverslip over the surface of the ProtoArray using forceps to avoid capturing bubbles. d) Position the ProtoArray with coverslip within the conical tube with the printed side of the array facing up. Cap the tube. Place the tube on a flat surface such that the printed side of the array is facing up and the tube is as level as possible. If needed, tape the conical tube on the flat surface to avoid any accidental disturbances. e) Incubate the array at 4 □ C for 90 minutes without shaking. f) Remove conical tube containing ProtoArray from incubator and add 40 mL Tritium SMI Assay Buffer to the tube. g) Incubate the array in buffer for 30 seconds at room temperature. The glass coverslip will float off. Do not remove the coverslip with forceps if it is not dislodged from the array. h) Using forceps, carefully remove the dislodged coverslip without touching the array surface. Discard the coverslip appropriately as radioactive waste. i) Decant the Tritium SMI Assay Buffer. Be sure to dispose of the radioactive waste properly. j) Add 40 mL of fresh Tritium SMI Assay Buffer to the tube. Incubate the array for 30 seconds at room temperature. Decant buffer. Repeat wash step one more time. Be sure to dispose of the radioactive waste properly. k) If Tritium SMI Assay Buffer with NaCl is used, complete one additional wash with Tritium SMI buffer lacking NaCl. 3. Drying and exposing the ProtoArray: a) Remove the array from the chamber at the end of the probing procedure. Tap one edge of the array gently on a laboratory wipe for a few seconds to drain any buffer. b) Place each array in a slide holder (or a sterile 50 mL conical tube, if you do not have a slide holder). Ensure the array is properly placed and is secure in the holder to prevent any damage to the array during centrifugation. c) Centrifuge the array in the slide holder or 50 mL conical tube at 200 Å~g for 1 minute in a centrifuge (equipped with a plate rotor, if you are using the slide holder) at room temperature. Verify the array is completely dry. d) Using transparent tape, adhere the slides to an 8λ10 Exeter Conservation Board (or thick filter paper of similar size). Only tape the top and bottom edges of the slide without covering any array area. The adhesion helps to prevent unwanted movement during the long exposure time and also helps to prevent the tritium from transferring on to the screen. Place ProtoArray in X-ray film cassette and directly overlay with a tritium-sensitive phosphor screen. e) Expose ProtoArray to the phosphor screen for 16 days. 4. Image acquisition and analysis: GenePix Pro v7 (Molecular Devices Corporation) and/or ScanArray. Acquisition Software (PerkinElmer, Inc.) was used for image acquisition and analysis.

FL118 or FL118 analogue affinity column purification of biochemical targets/biomarkers. 1. Ligand (FL118 or an analogue) coupling: a) Equilibrate 2 columns of DADPA UltraLink Support (ThermoFisher) and the bottle of Wash Buffer to room temperature. b) Remove top cap and twist off bottom tab from the column (Use supplied white tips to recap column bottom) (Note: When uncapping column throughout procedure, always remove the top cap before the bottom cap to prevent air bubbles from being drawn into the resin bed. c) Place 2 columns onto a home-made rack to allow storage solution to drain from column. d) Equilibrate column by adding 2 ml of coupling buffer (CB) and allowing it to flow through resin bed and drain from column. Then, gradually equilibrate the resin with 3 ml (column volume is 2 ml) of each of the following solutions with gradual increased DMSO to 80% from 10% before adding FL118 in 80% DMSO:20% CB. Replace bottom cap (a supplied white tip). Discard flow-through from the collection test tube. e) Add 5 ml control solution (4.5 ml DMSO+0.5 ml CB) to the column 1 (see A2 above); Add 5 ml FL118 solution [2.5 ml FL118 (1 mg/ml in DMSO)+2 ml DMSO+0.5 ml CB] to the column 2. f) Resuspend the resin in the control or FL118 solution by gentle reverse up and down. g) Transfer the resin slurry to a 15 ml conical tube labeled with 1 and 2. h) Add 200 µl PharmaLink Coupling Reagent (37% formaldehyde solution) in each 15 ml tube: 200 µl per 2-4 ml FL118 binding solution). i) Cap the tube and incubate the FL118 slurry at 54° C. in swirling for ~ 24 hours. j) Then add 1000 µl BC plus 50 µl Formaldehyde to each column swirling at 55° C. for 48 hours. 2. Transfer Resin Slurry to New Column, Column Washing, and Storage for affinity purification: a) Prepare 4 room temperature empty columns. Open top cap and apply the bottom cap to each column with pure ddH2O to full and then open the bottom cap to let it drain out but not dry. b) Add 1-2 ml CBD3/4 (~50-55% aqueous) to each column and let it drain out but not dry. c) Cap the bottom cap when the solution flow almost out from the column (not let column dry). d) Swirl the two 15 ml reaction tubes to resuspend the control slurry or FL118/resin slurry. Then use 1 ml pipet to 1) transfer control slurry into the column 1 (C1: control-cyto) and 2 (C2: FL118-cyto), and 2) transfer FL118 slurry into the columns 3 (C3: control-nucl) and 4 (C4: FL118-nucl). Of note, a) DMSO/BC=4.5 ml/5.5 ml; and b) column volume is 1 ml now. e) Allow resin to settle and then open the bottom cap to allow the solution to flow out of the upright column to drain all the reaction solution. f) Washing the column with 2 ml CBD3 then 2 ml CBD3, and then with 2 ml ultrapure water/DMSO solution (75:25) to prevent buffer precipitation. Then washing with 1.5 ml 100% DMSO to help remove non-reacted FL118. g) Continuously washing the column with 1 ml CBD6 to each column, and then in turn: with 1 ml CBD5, CBD4, CBD3, CBD2 and CBD1, and finally with 4 ml tris washing buffer (0.1 M Tris, pH 8.0); and then continue to wash column with tris wishing buffer by adding 9×4 ml tris washing buffer (0.1 M Tris, pH 8.0) to quench the active site that were not sealed by FL118. Up on the Wash9 drained to 2 ml, recap column and put columns at oven at 32-37 C for 45 min to facilitate quenching the active site that were not sealed by FL118. Then additional 3×4 ml wash with tris washing buffer (0.1 M Tris, pH 8.0). At the last additional wash with 8 ml tris washing buffer with 0.04% NaN3 (column full), recap the bottom column cap to maintain the Tris buffer for inserting the Disk by merging the whole wet disk into tris washing buffer and pushing disk down to a 1 mm gap using a Pasteur pipet. Then let the solution drain to 2 ml above resin and then capped the column, and store column upright at 4° C. (cold room). 3. Affinity column purification of ligand (FL118 or an analogue)-binding proteins: Cancer cell lysates were passed through affinity column and control column in parallel. After extensive wishing with washing buffer, the proteins binding on the column were eluted with 8M urea buffers. 4. Protein identification: After the eluted protein solution de-urea and concentration through 3K OMEGA Nanosep 1.5 ml tube device. The resulted protein mixtures with control column-resulted mixtures in parallel were analyzed by proteomics described below.

Protein identification from protein mixture using a robust proteomics technology: The obtained protein mixtures were analyzed using the Qu Lab-developed IonStar/MS1-based proteomics technology (Shen X, Shen S, Li J, Hu Q, Nie L, Tu C, Wang X, Orsburn B, Wang J, Qu J: An IonStar Experimental Strategy for MS1 Ion Current-Based Quantification Using Ultrahigh-Field Orbitrap: Reproducible, In-Depth, and Accurate Protein Measurement in Large Cohorts. J Proteome Res 2017, 16:2445-56). Briefly, through a process of protein extraction, reduction, alkylation and organic solvent precipitation and digestion of the obtained protein pellets with trypsin, 4 µg peptide samples in 4 µl will go through the process of Nano LC/UHF-Orbitrap LUMOS MS analyses, as described. Then a stringent set of criteria will be employed for protein identification. The IonStar processing pipeline will be used for MS1 quantification of the identified proteins from our samples. Gene Ontology (GO) annotation (quantified proteins) will be analyzed using online tools of DAVID Bioinformatics Resources v6.7 (http://david.abcc.ncifcrf.gov/) and Ingenuity Pathway Analysis (IPA, Ingenuity Systems). For GO enrichment analysis, all quantified proteins will be used as background. Protein function, upstream regulator, and pathway analysis were carried out using IPA for a Core analysis. Biological and functional annotations assigned by the software will be manually examined and regrouped into respective categories. Hierarchical cluster analysis (uncentered Pearson correlation distance and centroid-linkage) will be analyzed using Cluster 3.0 and displayed by TreeView supporting tree-based and image-based browsing of hierarchical trees (http://www.eisenlab.org), when needed. We will analyze the changes of protein network pathways in UOK262 cells with and without Hx6 treatment using GSEA analysis tools. Based on our proteomics technology, >7000 proteins can be quantified without missing data from a cell lysate sample.

Analysis of API (active pharmaceutical ingredient)-HPβCD powder complex diffraction with X-ray powder diffractometer (XRPD): The crystal or amorphous status of each prepared compound of Formula 1-HPβCD complex powder will be determined using XRPD. Specifically, about 5 mg samples of each powder will be spread onto the center of Si-substrate (samples area will be 1 cm in diameter) for XRPD testing. Laboratory XRPD patterns for samples will be collected at 25° C. The diffraction data will be collected over the angular range of 2θ=3-40° with a step size of 2θ=0.020 and accounting time of 0.12 s/step.

Analysis of miscibility of the API (i.e. a compound of Formula 1)-HPβCD powder complex with Modulated differential scanning calorimetry (mDSC): The miscibility status of API in the API-HPβCD complex powder will be determined using mDSC. Specifically, mDSC analyses will be carried out on a Q2000 differential scanning calorimeter (TA, USA) at a 2° C./min heating rate over the temperature range from room temperature to 300° C. in a dynamic nitrogen atmosphere. Each API-HPβCD complex powder will be weighed into a Tzero aluminum sample pan covered by a pinhole lid; an empty pan served as the reference control for testing. Additionally, the glass transition temperature (Tg) of the API-HPβCD complexes from each of the API compound of Formula 1 powder.

Analysis of the API (i.e. a compound of Formula 1) loading in HPβCD with High performance liquid chromatography (HPLC): The weight percentage of API loading in HPβCD will be determined by HPLC. Specifically, HPLC will be carried out to determine the weight percentage of the API (a compound of Formula 1) load in HPβCD. This will use the Waters XSelect CSH C18 column (3.5 μm, 4.6×150 mm, Waters, Ireland) in the testing. The mobile phase will be a gradient program of 0.05% aqueous trifluoroacetic acid (Mobile phase A) and acetonitrile with 0.05% trifluoroacetic acid (Mobile phase B), which will be pumped at a total flow rate of 1 mL per min. The gradient will be as follows: initial conditions 10% B in A, then linear gradient of 10 to 60% B in A over 15 min, then linear gradient of 60 to 90% B in A over 10 min, 90% B in A hold for 5 min, return to initial conditions for 0.01 min and hold for 10 min. The temperature of the column will be maintained at 30° C. and the eluent will be monitored at a wavelength of 220 nm. The injection volume will be 5.0 μL. The diluent will be DMSO.

Examples

The present invention is further illustrated by the following examples, which should not be construed as limiting in any way. The following is a description of the examples.

FL118 platform inhibits multiple antiapoptotic proteins in drug-resistant pancreatic cancer-stem like cells. Since our invention indicated that FL118 is a great platform for the generation of novel drugs (PCT/US2015/022095) as well as the well-known treatment (drug, radiation) resistance of pancreatic cancer, we therefore determined whether FL118 inhibits multiple antiapoptotic proteins (survivin, Mcl-1, XIAP, cIAP2) in treatment-resistant pancreatic ductal adenocarcinoma (PDAC) cell lines. Pancreatic cancer cell lines Mia-Paca2 (Mia2) and PANC1 were reported to be very aggressive and resistant to all first-line drugs (Legoffic A et al., Identification of genomic alterations associated with the aggressiveness of pancreatic cancer using an ultra-high-resolution CGH array. Pancreatology. 2009; 9: 267-72), because of this we selected to use these cell lines to determine the effect of FL118 on the expression of various antiapoptotic proteins as well as some pro-apoptotic proteins using western blots. Our data showed that FL118 treatment in the range of 16 h (hours) to 48 h differentially modulates the expression of antiapoptotic proteins (XIAP, cIAP2, Mcl-1 or survivin) in both PANC1 and Mia2 cells in a dose-dependent manner (FIGS. 1A and 1B), while such treatment induced the expression of pro-apoptotic proteins (Bad, Bim or Bax) in different degrees (FIGS. 1A and 1B).

Figure 2:
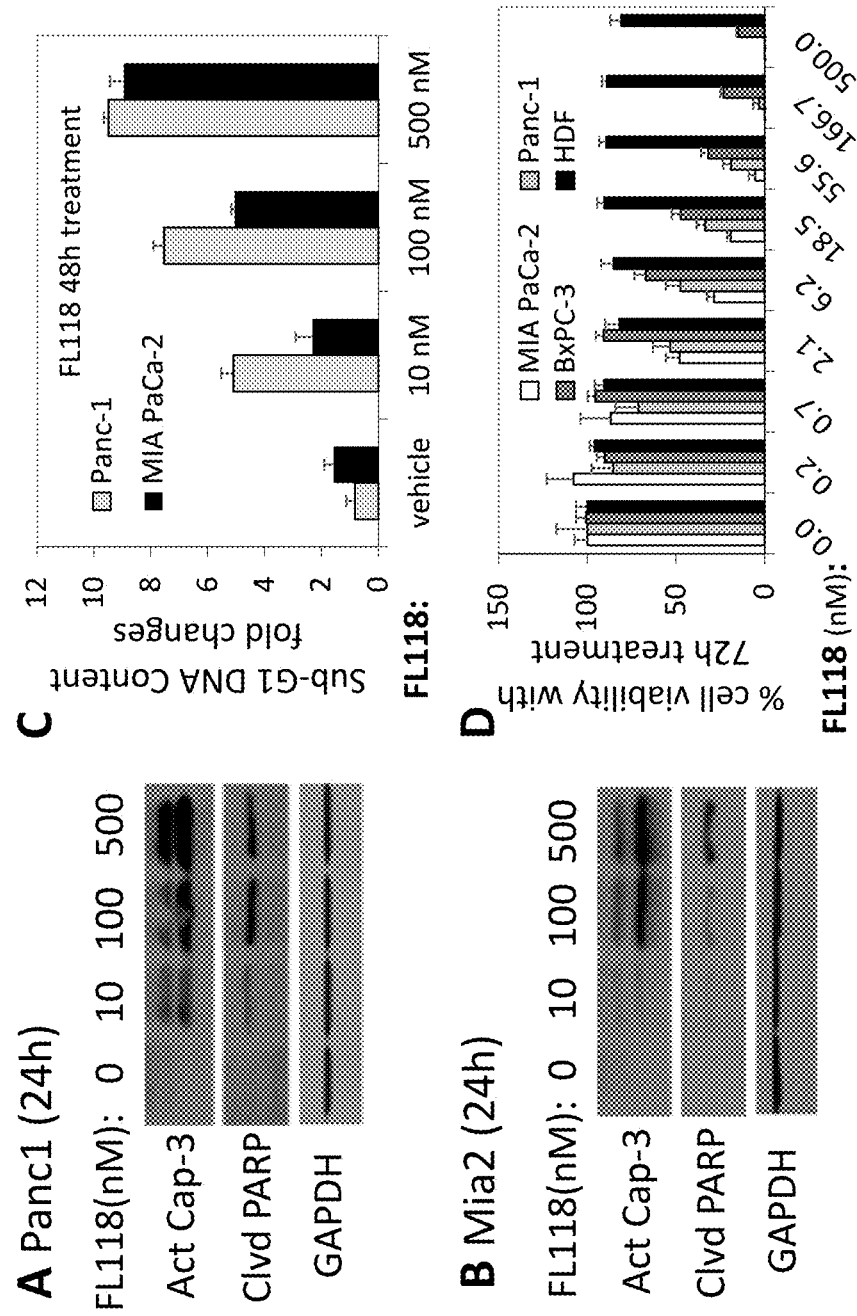
FIG. 2 shows the induction of apoptosis, pancreatic cancer cell killing and cell viability inhibition by FL118 platform: A and B, FL118 treatment results in activation of caspase-3 and cleavage of PARP. Subconfluent pancreatic cancer cells (A, PANC1; B, MIA PaCa2) were treated with FL118 as shown, and the activation of casepase-3 and cleavage of PARP were detected by western blots. GAPDG is the internal control for total protein loading. C, FL118 induces pancreatic cancer cell death. Subconfluent PANC1 and Mia2 pancreatic cancer cells were treated with vehicle or with FL118 at 10, 10 and 500 nM for 48 h. Then the sub-G1 DNA content (later apoptotic dead cells) was determined by flow cytometry. Relative sub-G1 DNA production levels were analyzed and the data were derived from 3 independent testing and shown as histogram as mean±SD. D, FL118 inhibits pancreatic cancer cell viability. Subconfluent Mia2, PANC1 and BxPC3 pancreatic cancer cells as well as normal human dermal fibroblast cells were treated with vehicle (no FL118) or with a series of FL118 concentrations as shown for 72 h. Then the cell viability was determined using MTT assay. The data were shown as histogram with mean±SD derived from 3 independent testing assays.

Next, we determined whether FL118-mediated inhibition of antiapoptotic proteins and induction of pro-apoptotic proteins shown in FIG. 1 would be accompanied by induction of apoptosis and cell killing. Our studies indicated that as short as 24 h treatment with FL118 platform (10-500 nM) strongly induces caspase-3 activation and PARP cleavage (hallmarks of apoptosis, FIG. 2AB) in PANC1 and Mia2 cells. Furthermore, the activation of these apoptotic markers was accompanied with a significant increase of sub-G1 DNA content in PANC1 and Mia2 cells, indicating the cell killing effect of FL118 (FIG. 2C).

Consistent with these findings, we also determined the effect of FL118 on cell viability for PANC1, Mia2, as well as the gemcitabine-sensitive BxPC-3 pancreatic cancer cell lines. Our data revealed that FL118 at low concentrations (nM level) effectively inhibited pancreatic cancer cell viability (FIG. 2D). Based on the published status of gemcitabine resistance and sensitivity of PANC1, Mia2 and BxPC-3 (Legoffic A et al., Pancreatology. 2009; 9: 267-72), FL118 appeared to be more effective in inhibiting the viability of gemcitabine-resistant PANC1 and Mia2 cells in comparison with FL118's effect on the viability of the gemcitabine-sensitive BxPC-3 cells (FIG. 2D). This observation suggests that FL118 platform prefer to kill drug resistant pancreatic cancer cells.

Figure 3:
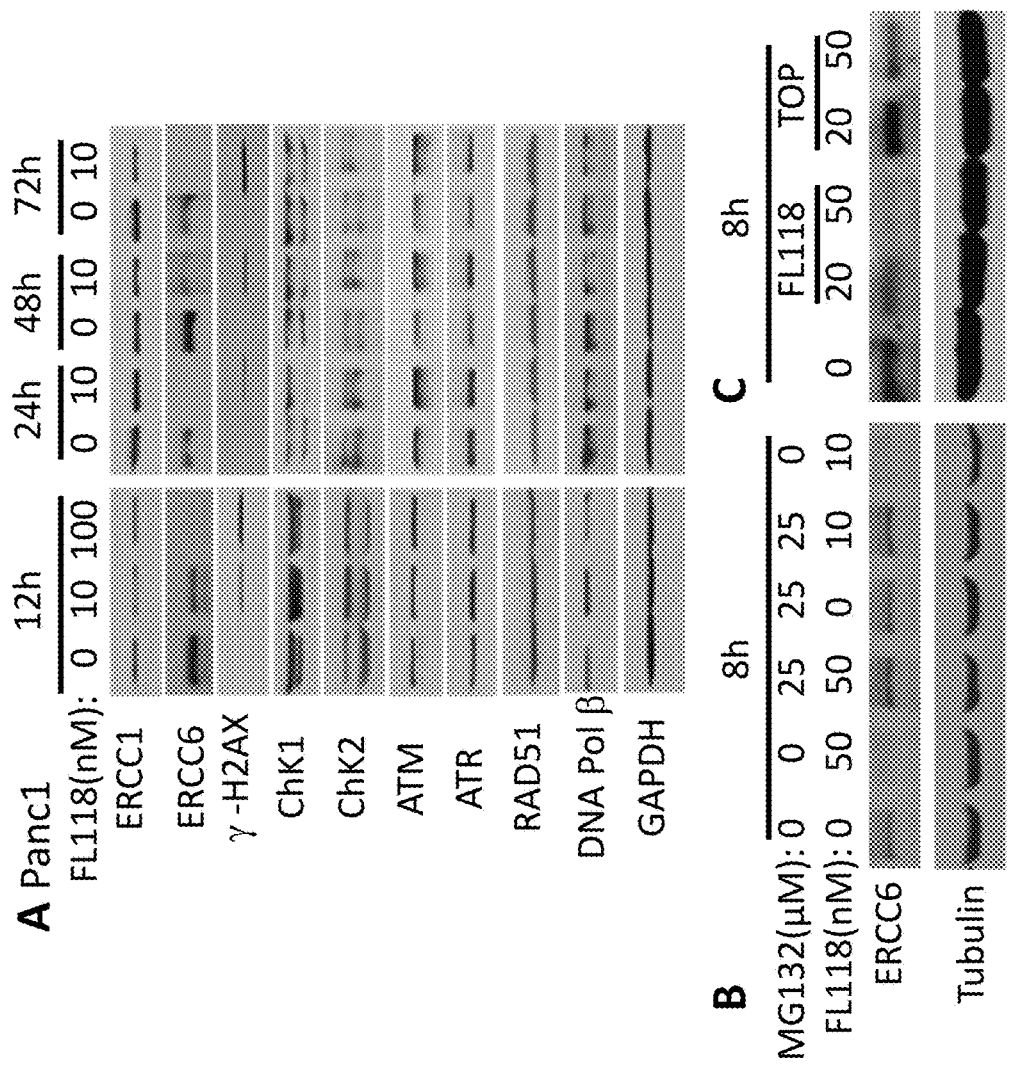
FIG. 3 shows the effects of FL118 platform on the expression of proteins that are involved the pancreatic cancer cell DNA damage and repair: A, Subconfluent PANC1 pancreatic cancer cells were treated with FL118 as shown, and the expression of ERCC1, ERCC6, γ-H2AX, ChK1, ChK2, ATM, ATR, RAD51 and DNA Pol II was detected by western blots using corresponding antibodies for each protein. GAPDH is an internal control for protein loading. B, Decrease of ERCC6 expression can be rescued with proteasome inhibitor MG132. Subconfluent SKOV3 cells were treated with FL118 and MG132 alone or in combination as shown for 8 h, followed by western blot analyses with ERCC6 antibody. Tubulin is the internal control for protein loading. C, Comparison of FL118 and topotecan (TOP) effects on ERCC6 expression. Subconfluent SKOV3 cells were treated with FL118 or TOP as shown for 8 h, followed by western blot analyses with ERCC6 antibody. Tubulin is the internal control for protein loading.

FL118 platform exhibits sustained inhibition of ERCC6 and induction of 2H2AX in drug-resistant pancreatic cancer cells. It is well known that drug/radiation-induced DNA damage can activate ATM signaling, which in turn results in the accumulation and activation of p53 and induces apoptosis. In order to have a deeper insight into the relationship of FL118 platform treatment with potential cellular DNA damage, we determined the effect of FL118 platform on the expression of a panel of DNA damage and repair genes in the treatment-resistance pancreatic cancer cell line PANC1. We found that among the panel of proteins tested that are relevant to DNA damage/repair process (ERCC1, ERCC6, γ-H2AX, ChK1, ChK2, ATM, ATR, RAD51, DNA Pol β), FL118 strongly decreased the expression of ERCC6 and induced γ-H2AX (FIG. 3A). ERCC6 is a critical regulator for preferential repair of active genes. It has also been documented that elevated expression of ERCC6 confers resistance to 5-Fu treatment and is associated with poor survival in CRC patients. Our additional studies indicated that inhibition of ERCC6 expression by FL118 platform appeared to be mediated by the proteasome degradation pathway since the FL118 platform-mediated downregulation of ERCC6 was rescued in the presence of the proteasome inhibitor MG132 (FIG. 3B). Additionally, the FL118 platform had a much stronger effect than topotecan on the inhibition of ERCC6 expression (FIG. 3C).

Figure 4:
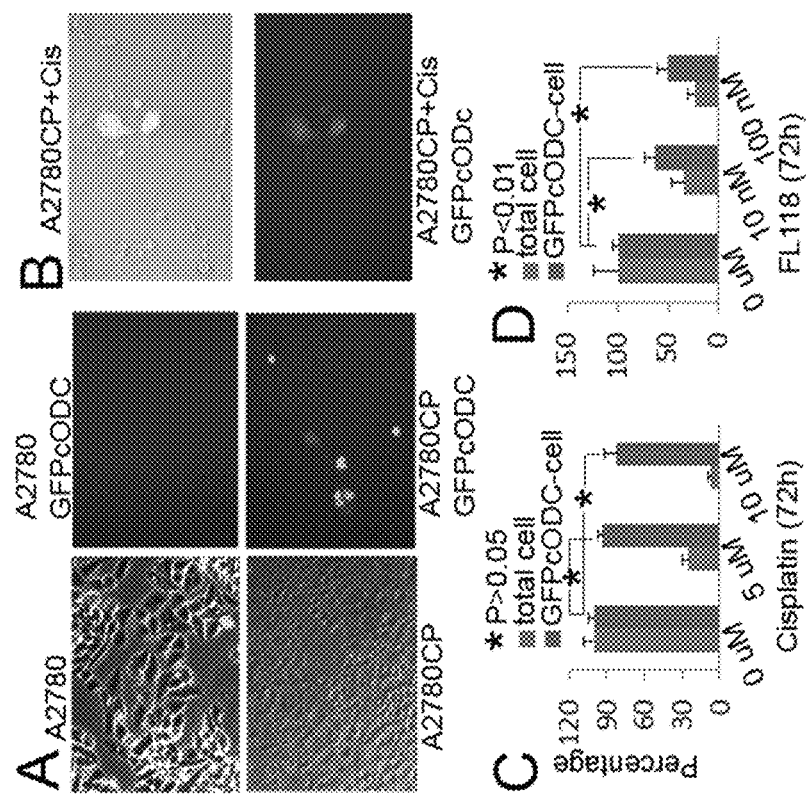
FIG. 4 shows the FL118 platform but not cisplatin is able to eliminate drug-resistant GFPcODC-positive A2780CP cells: A and B, Subconfluent cells were treated with and without cisplatin (Cis) for 72 h. Phase-contrast and GFP imaging of cells were digitally taken. C and D, Quantitative effects of cisplatin (C) and FL118 (D) treatment, respectively, on the percentage changes of drug-resistant GFP-cODC positive A2780CP cells.

The FL118 platform reduces the stem-like cancer cell population in drug-resistant ovarian and pancreatic cancer cells, suggesting its great platform nature. Based on the fact that the FL118 platform could eliminate colorectal cancer without relapse in many cased, we hypothesized that FL118 should effectively reduce drug-resistant cancer cells including cancer stem cells (CSC) because the antiapoptotic proteins survivin and Mcl-1 are known to play important roles in CSC drug resistance. To test this, we used a novel approach developed in Dr. Pajonk's lab for the live tracking of drug resistant cells (Vlashi E, et al., In vivo imaging, tracking, and targeting of cancer stem cells. J Natl Cancer Inst. 2009; 101: 350-9). This approach takes advantage of reduced 26S proteasome activity of drug resistant cells. In the cell line that stably expresses the 26S activity reporter (GFPcODC fusion protein), only drug-resistant cancer cells will remain GFP-positive due to the reduced 26S activity. Here, we used both multidrug-resistant ovarian cancer cell line A2780CP and drug-resistant PDAC cell line PANC1 to test the above hypothesis. We found that in the established GFPcODC-expressing cells, there are significantly more GFPcODC positive cells in the drug-resistant A2780CP70-GFPcODC cells than in the parental drug-sensitive A2780-GFPcODC line (FIG. 4A). As shown, cisplatin treatment of A2780CP70-GFPcODC cells at 10 µM for 72 h killed 90% of the total cell population, but GFPcODC-positive cells survived (FIG. 4B, 4C). In contrast, treatment with the FL118 platform at 10 nM and 100 nM decreased more than 50% of the GFPcODC-positive drug-resistant A2780CP cell population (FIG. 4D).

Figure 5:
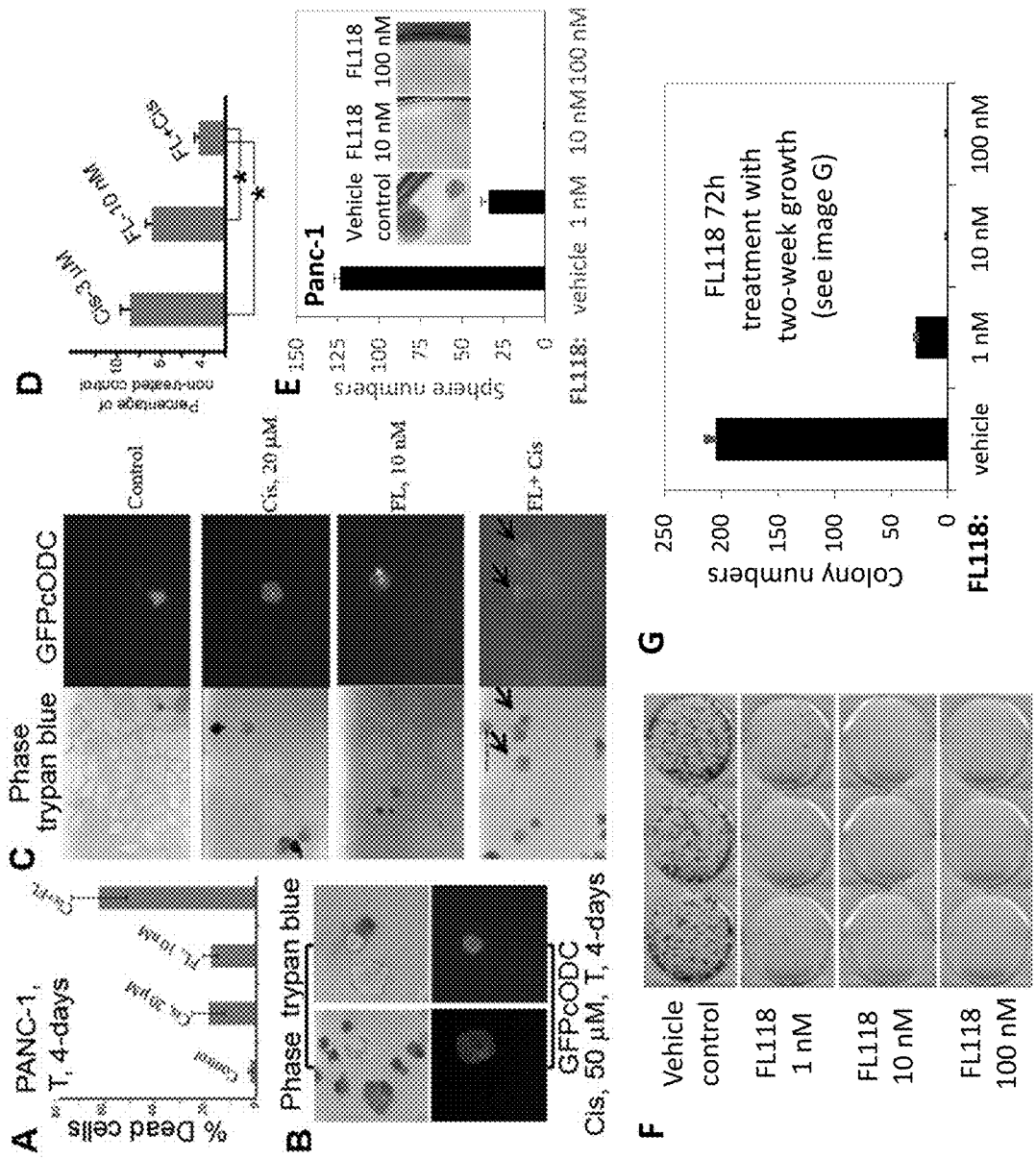
FIG. 5 shows that the FL118 platform targets both proliferative cancer cells and latent stem cell-like cancer cells: A, FL118-cisplatin combination enhances killing of PANC1 cells. Dead cells were determined by trypan blue exclusion. B, GFPcODC-positive cells survive 50-DM cisplatin for 4 days, evaluated with trypan blue exclusion assay. C, FL118-cisplatin kills GFPcODC positive (drug-resistant) cells (arrows). Phase-contrast and GFP imaging of cells were digitally taken. D, FL118-cisplatin combination reduces PANC1 spheroid cell number. *, $P<0.001$. FL, FL118; T, time. E, Effects of FL118 on pancreatic cancer stem cell sphere formation. See detail in the method section. F, Colony formation of CD44 stem cell marker-positive pancreatic cancer cells. G, Quantitative data derived from the data shown in the FIG. 5F.

Next, we applied the same system to generate pancreatic cancer PANC1-GFPcODC cells. We tested FL118-cisplatin combination regimens for drug-resistant cancer cell killing measured by trypan blue exclusion assay. A 4-day single agent treatment with 20 µM cisplatin or 10 nM FL118 induced a similar degree of cell death (~18%), while combination treatment with FL118-cisplatin induced 62% cell death, indicating a 3-fold higher cell killing compared to the single agent treatment (FIG. 5A). GFPcODC-positive PANC1 cells were low (~0.5%) in PANC1-GFPcODC cell line but were extremely drug-resistant, which is consistent with the CSC feature in a typical cancer cell line. GFPcODC-positive (drug resistant) cells could survive 50 µM of cisplatin for a 4-day treatment, while the same treatment killed 92% of GFP-negative (drug sensitive) PANC1 cells (FIG. 5B). Interestingly, in this particular condition, single treatment with cisplatin at 20 µM, or with FL118 at 10 nM appeared unable to kill GFPcODC-positive (drug resistant) cells (FIG. 5C, Cis, 20 µM, FL, 10 nM), while the FL118-cisplatin combination killed the extremely drug resistant GFPcODC-positive PANC1 cells (FIG. 5C, FL+Cis, arrows). However, in our pancreatic CSC spheroid formation experiment, we found that most of the alive drug-resistant, stem cell-like cells were unable to form spheres (FIG. 5D). Specifically, in the spheroid formation for the 10-day pancreatic spheroid culture experiment, 10 nM FL118, 3 µM cisplatin, or their combinations were able to significantly inhibit spheroid formation, especially in the combination situation in comparison with no drug control (100, $p<0.001$, FIG. 5D).

To further confirm these findings, we alternatively used the typical matrigel-based CSC sphere formation assay which is know to more closely mimic in vivo situations. In this assay only drug resistant stem-like cancer cells are able to form spheres. The FL118 platform exhibited high efficacy in inhibiting sphere formation (FIG. 5E). To further demonstrate the effect of FL118 on stem-like, drug-resistant cancer cells, we isolated the CD44 stem cell marker-positive pancreatic cancer cell population from the drug-resistant PANC1 cells. We performed colony formation of CD44 stem cell marker-positive cells using the stem-cell culture condition. Consistent with the data from FIG. 5E, the FL118 platform significantly inhibited colony formation at even 1 nM, while FL118 at 10 and 100 nM was able to completely eliminate colony formation of CD44 stem cell marker-positive PANC1 cell (FIG. 5F-G). These results (FIG. 5E-G) indicate that the drug-resistant, stem-like cancer cells in the CD44 stem cell marker-positive PANC1 cells are much more sensitive to FL118 treatment than the artificially-generated GFPcODC-positive PANC1 cells (FIG. 5C-D). Thus, the GFPcODC-positive cell model may be an extremely drug resistant cell model or a less actual cell mimic system after transfection of the GFPcODC-expressing vector and selection process for obtaining GFPcODC-expressing cells, which may not fully mimic the CD44 stem cell marker-positive drug resistant cells. Alternatively, the discrepancy may also result from the further enrichment of the highly drug-resistant population after selection of GFP-cODC-expressing cells. Together, our collective studies strongly suggest that the FL118 platform alone and FL118 in combination with cytotoxic drugs are novel therapeutic options, which can effectively reduce drug-resistant, stem-like pancreatic cancer cell populations.

Figure 6:
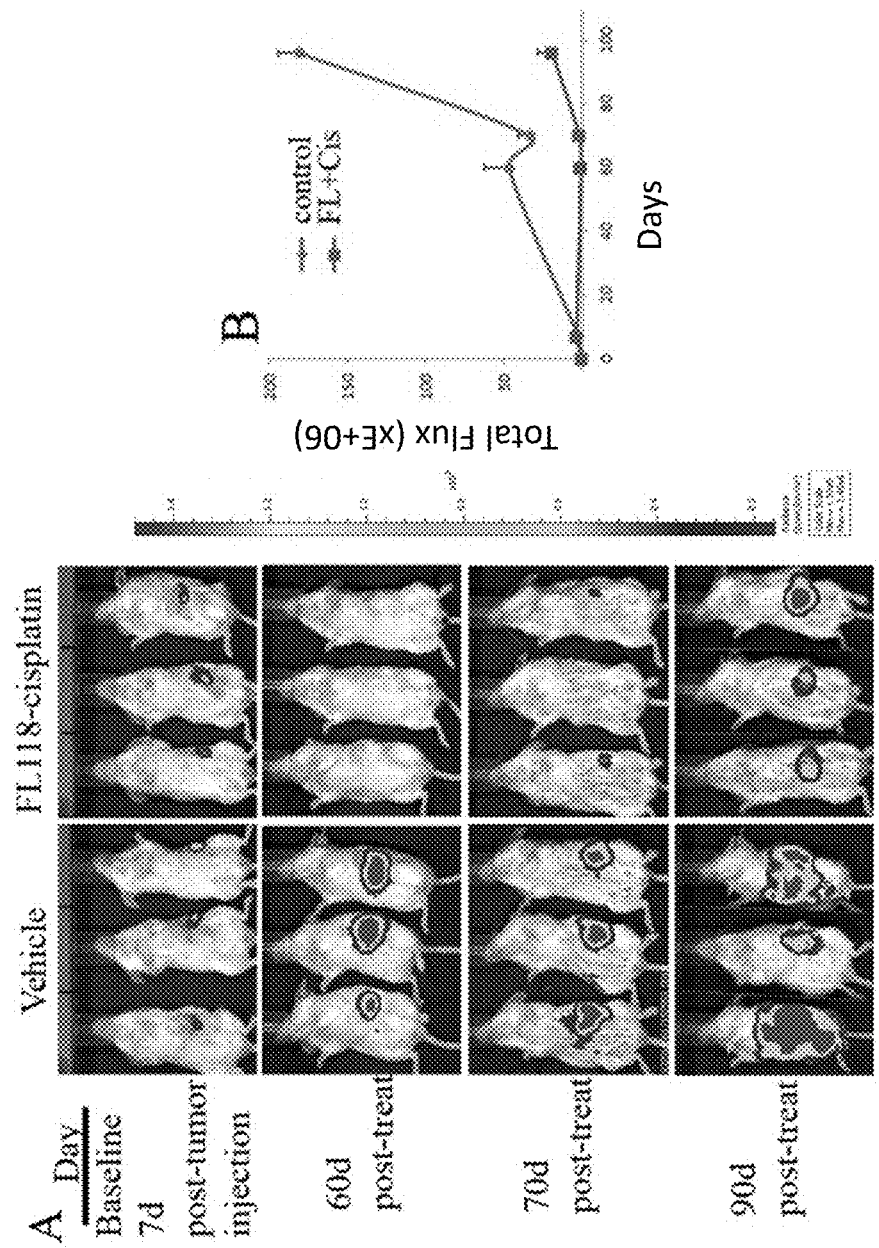
FIG. 6 shows the in vivo imaging to monitor pancreatic tumor growth and metastasis using an orthotopic LucPANC1 model with and without FL118 platform in combination of cisplatin: Model setting up was described in Methods. Several days after orthotopic implantation of LucPANA1 cells, mice were treated with and without FL118 and cisplatin as show via qw×4 schedules. A, Bioluminescent images of whole mouse bodies treated with and without FL118 and cisplatin overtime (shown on days 7, 60, 70 and 90). B, Tumor growth curve of bioluminescent image (BLI) was shown as total flux overtime. d, day/days. FL118 as a new drug platform in combination with cisplatin inhibits both pancreatic cancer cell growth and tumor metastasis.

Combination of the FL118 platform and cisplatin inhibits both pancreatic tumor growth and metastasis. PDAC resistance to treatment paves the way to cancer cell metastasis. Metastasis is a challenging concern since pancreatic cancer patients often present with metastatic disease. To test whether the FL118 platform could inhibit both PDAC tumor growth and metastasis to other sites, we used an orthotopic PANC1 model. In order to use bioluminescence in vivo imaging (BLI) to monitor tumor growth and metastasis in living mice, we generated luciferase expressing PANC1 cells (LucPANC1) and injected a million LucPANC1 cells in 20-microliter volumes into the pancreas of SCID mice. These mice were treated either with vehicle (FIG. 6A, left panel, n=3) or with FL118-cisplatin combination (FIG. 6A, right panel). These mice were treated with vehicle or FL118 at 0.75 mg/kg (⅙ maximum tolerate doses: ⅙MTD) in combination with cisplatin (5 mg/kg, ½MTD) via intraperitoneal (ip) injection from day 7, weekly for 4 times (qw×4). BLI was performed every 1-3 week with 7d as the baseline (FIG. 6A, top panel). Our studies indicated that the radiance intensities of individual tumors fell in a very narrow range, suggesting a small variation of tumor implantation in our procedure (FIG. 6A). FL118-cisplatin treatment considerably inhibits PANC1 tumor growth and metastasis to other sites in the LucPANC1 orthotopic model in a relatively low dosing level. For example, on day 60 (60d) after LucPANC1 cell implantation, tumors in all treated mice were regressed to an undetectable level (FIG. 6A, second row). Of note, on day 90, after finishing treatment on day 28, BLI detected local metastasis in two of the three mice in the control group (4 red tumor centers and 2 red tumor centers, respectively), but no local metastasis were detected in the FL118-cisplatin-treated group (FIG. 6, 90d, forth row/bottom panel). Necropsy from the animals at the end of the study indicated the tumor not only on the pancreas (primary tumors), but also on the liver (one mouse with two sites and the other with one site) and small intestine (only the former mouse with one site), indicating tumor metastasis. In contrast, only significantly smaller tumors grew in the original tumor site (pancreas) of the FL118-cisplatin treated mice. Importantly, this was only one cycle/course treatment. These results indicate that our model system could precisely measure the onset of metastasis to other organ sites. The overall BLI intensity quantified from the total tumor of each group over time were presented in FIG. 6B.

These observations indicate that the FL118 platform is a unique and promising platform and a core structural drug for generating new drugs with even better and/or differential antitumor efficacy in different types of human cancers. The study also suggests that FL118 platform kills both proliferative cancer cells and drug resistant/latent CSC-like cells, which will be further confirmed in the next exemplar experiment described below.

Figure 7:
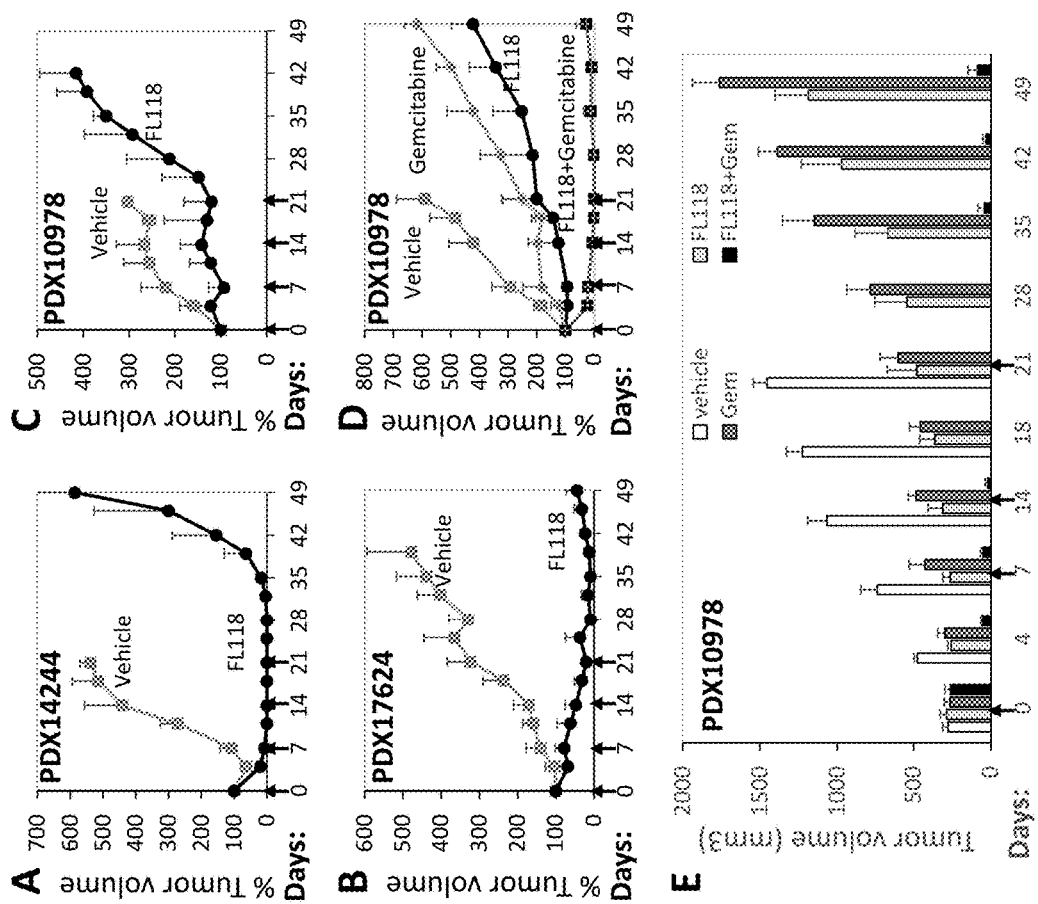
FIG. 7 shows the high efficacy of FL118 platform inhibition of pancreatic cancer PDX alone or in combination of gemcitabine: PDX tumors were originally established from pancreatic cancer patient tumor tissues obtained from metastatic sites of the disease in the clinic. Mouse models of human pancreatic cancer PDX tumors were set up by subcutaneously inoculating 30-40 mg tumor tissue on the flank of SCID mice. The FL118 platform drug was formulated in an organic solvent-free with HPβCD (2-hydroxy-propyl-β-cyclodextrin) as drug carriers in 2% HPMC (hydroxypropyl methylcellulose) and 1% PG (propylene glycol) in saline (a thick aqueous suspension) for oral administration. Pancreatic cancer PDX tumors were maintained on severe Combined Immunodeficiency (SCID) mice. Experimental SCID mice were subcutaneously implanted with individual pancreatic cancer PDX tumors at the flank area of mice. Seven to 14 days after the implanted tumors grew to 100-300 mm³ (designated as day 0), FL118 was administered via intraperitoneal injection (ip/IP) with a dose of about half maximum tolerated dose (½MTD, 5 mg/kg) (A, B, C) or with a dose of 0.75 mg/kg in combination with gemcitabine at 60 mg/kg (~½MTD) (D) weekly for 4 times (qw×4) as shown (arrows). A, Pancreatic cancer PDX14244 tumors. B, Results from pancreatic cancer PDX17624 tumors. C and D, Results from pancreatic cancer PDX10978 tumors. Each curve represents mean±SD derived from five mice (5 mice per group). E, The same data shown in the FIG. 7D were presented in the tumor volume format to show the really size of the tumor during the experiments. FL118 as a new drug platform effectively eliminates human pancreatic ductal ademocarcinoma adenocarcinoma (PDAC) tumors alone or in combination with gemcitabine in animal models (Oral).

The FL118 platform alone or in combination with gemcitabine eliminates human PDAC PDXs in animal models. Next, we used human pancreatic cancer patient-derived xenograft (PDX) tumor models for alternative in vivo studies, since the PDX model is the most clinically relevant animal model and can present many of the histological features and heterogeneous treatment sensitivity/response of tumors found in patients. It has been recently documented that pancreatic cancer PDXs retain active paracrine/Hedgehog signaling, and desmoplasia is active in PDX tumor mouse models. Our studies demonstrated that FL118 is not a substrate of ABCG2 and Pgp, and exhibits a favorable PK (see below). Based on these characteristics of the FL118 platform, we reasoned that desmoplasia-mediated drug resistance might not be a barrier preventing FL118 from reaching therapeutic levels in cancer cells. Therefore, we tested the FL118 efficacy alone and in combination with gemcitabine (a typical pancreatic cancer drug) in human PDAC PDX tumor models. Among eight PDAC PDX tumor models tested, we found that four of them exhibited high sensitivity to FL118 treatment. As shown in FIGS. 7A and 7B, PDX14244 and PDX17624 showed high sensitivity to FL118, and FL118 was able to eliminate these PDX tumors after one cycle of treatment (qw×4, FIG. 7A, 7B, only one cycle/course treatment). However, the other 4 exhibited less sensitivity in various degrees to FL118. For example, the PDX10978 shown in FIG. 7C, FL118 was only able to delay PDX10978 tumor growth. Next, we tested whether FL118 in combination with commonly used pancreatic cancer drugs such as gemcitabine could solve the FL118 insensitivity issue. We performed a FL118 and gemcitabine combination treatment on the FL118 less sensitive PDAC PDX10978 used above. In this study, we used FL118 at 0.75 mg/kg (~⅙MTD) and gemcitabine at 60 mg/kg (~½MTD) alone or in combination via ip with the qw×4 schedule (one cycle/course treatment). We found that either FL118 or gemcitabine alone only delayed tumor growth. In contrast, a combination of FL118 with gemcitabine was able to eliminate PDX10978 tumors in all 5 treated animals for 21 days with only one cycle of treatment (FIG. 7D, from days 14-35). Alternatively, we used tumor absolute size histogram format to show the synergy of the combination treatment (FIG. 7E). Our studies suggest that a large percentage of PDAC tumors could exhibit high sensitivity to the FL118 platform, while some other PDAC tumors may show less sensitivity to FL118 treatment. However, PDAC tumors with less sensitivity to FL118 could be sensitized by FL118 in combination with a pancreatic cancer cytotoxic drug such as gemcitabine, used here to eliminate such PDAC tumors.

Figure 8:
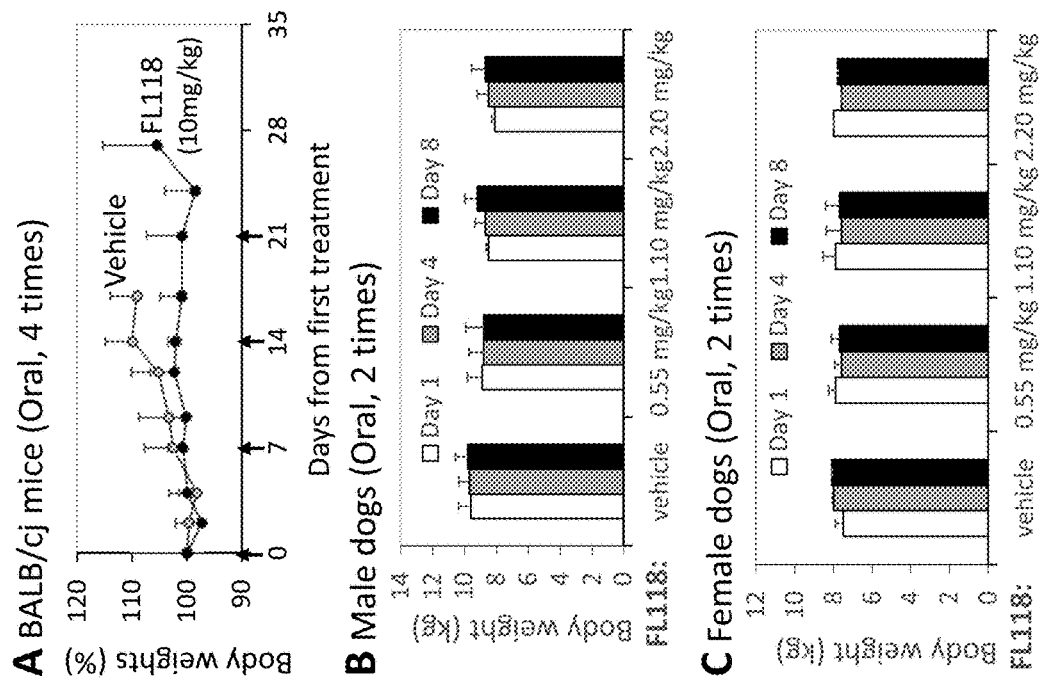
FIG. 8 shows the favorable effects of FL118 platform on animal body weight changes during treatment in both murine and canine animals: Model setting up was described in Methods. A, Effects of FL118 on the body weight change of BALB/cj mice. Results from vehicle and FL118 MTD dosing level (10 mg/kg) were shown with oral route via qw×4 (arrowed). The body weigh curves were derived from the mean±SD derived from 6 independent BALB/cj mice. B and C, Effects of FL118 on the body weight change of beagle dogs. Results from vehicle and FL118 at 0.55 mg/kg (¼MTD), 1.1 mg/kg (½MTD) and 2.2 mg/kg (MTD) dosing levels were shown with oral administration of FL118 on Days 1 and 8. The body weigh histograms were derived from the mean±SD derived from 2 male or 2 female beagle dogs. FL118 as a new drug platform induces minimal toxicity during treatment in both murine and canine animal models.

The FL118 platform exhibits favorable toxicology profile in both murine and canine animals. Our studies indicated that FL118 in its oral formulation has a maximum tolerated dose (MTD) at 10 mg/kg in human tumor-bearing SCID mice in the weekly for 4-time administration (qw×4). Since SCID mice have deficient immune systems, it is very important to determine whether FL118 has a similar MTD in immune competent mice at the same route and schedule. We found that the use of 12.5 mg/kg oral qw×4 resulted in >20% body weight loss including some mice with moribund states. However, the use of 10 mg/kg was well tolerated by BALB/cj mice and the mouse body weight loss is within normal variation range (FIG. 8A). Consistently, the result from the evaluation of 17 hematological parameters indicated that only the white blood cells (WBC) and lymphocytes (LYMPH) decreased to the edge of normal range, low side (Table 1). After FL118 treatment, all others are similar to vehicle-treated samples, and within the normal range variation (Table 1). Similarly, among the 12 clinical biochemistry parameters, the outcome from FL118-treated samples is very similar to the outcome from the vehicle-treated samples, which are close to or within the normal variation range (Table 2).

a. For the dog toxicology studies, all animals survived in good condition to the end of experiment. No significant FL118-related clinical observations were noted. Certain observed fecal abnormalities were infrequent, transient, and noted for some animals during the predose phase; therefore, they were not FL118-related. No, or only minimal body weight changes within the variation of normal animal weight changes were observed for all FL118-treated groups (FIG. 8B, C). These observations are consistent with the outcomes from hematological analysis of the collected samples, most of which have a change within the pre-dosing variation. The results from vehicle and highest FL118 dose-treated dogs are shown in Table 3. As shown, in this FL118 MTD dose level, FL118 only exhibits very minor effects on a few hematological parameters such as decreased platelets and monocytes, but none of these are considered serious (Table 3). Similarly, in clinical biochemistry studies, very few differences were present between control and FL118 test article-treated animals or between pre-dose and dosing phase test results for individual dogs, and all were consistent with normal variation and considered incidental (Table 4). The observed differences were characterized by most or all of the following: small magnitude, no relationship to dose, inconsistent between sexes, absence of correlative findings, and/or similarity to differences present before initiation of dosing. Thus, overall the FL118 platform toxicology profiles in dogs are highly favorable, which is crucial since the physiology of dogs is much closer to human than to the mice.

TABLE 3

| | RBC (M/µl) | HGB (g/dL) | HCT (%) | MCV (fL) | MCH (pg) | MCHC (g/dL) | RDW (%) | RET (K/µl) | PLT (K/µl) | WBC (K/µl) |
|---|---|---|---|---|---|---|---|---|---|---|
| Effects of FL118 on beagle dogs' hematological parameters | | | | | | | | | | |
| Vehicle TX pre-dosing) | 5.4-7.2 | 12.5-16.1 | 37.6-48.3 | 67-69.4 | 22-23.1 | 32.7-33.3 | 12.7-13.4 | 18.4-30.7 | 321-389 | 9.2-10.9 |
| Vehicle TX post-dosing) | 6.0-6.7 | 13-14 | 39.4-44.3 | 66.3-68.7 | 21.7-23 | 32.8-34 | 12.6-13.3 | 14.1-34.5 | 256-283 | 9.8-14.1 |

TABLE 3-continued

Effects of FL118 on beagle dogs' hematological parameters

| | | | | | | | | | | |
|---|---|---|---|---|---|---|---|---|---|---|
| FL118 (MTD) pre-dosing) | 5.1-5.9 | 11.8-13.2 | 35.4-40.2 | 67.4-69.3 | 22-23.2 | 33-33.5 | 13.4-13.4 | 11.6-45.3 | 318-386 | 7.1-8.7 |
| FL118 (MTD) post-dosing) | 5.2-6.0 | 12-13.8 | 35.4-40 | 66-68.2 | 22.5-23 | 33.7-34.7 | 12.4-13.5 | 3.7-25.9 | 219-267 | 5.2-9.9 |

| | NEUT (K/μl) | LYM (K/μl) | MONO (K/μl) | EOS (K/μl) | BASO (K/μl) | LUC (K/μl) | PT (sec) | APTT (sec) | FIB (mg/dL) |
|---|---|---|---|---|---|---|---|---|---|
| Vehicle TX pre-dosing) | 5.0-6.4 | 2.3-3.5 | 0.6-0.9 | 0.23-0.5 | 0.05-0.1 | 0.01-0.03 | 6.1-7.7 | 10.9-11.1 | 194-234 |
| Vehicle TX post-dosing) | 5.9-9.0 | 3.1-3.9 | 0.5-1.0 | 0.13-0.5 | 0.05-0.15 | 0.02-0.05 | 5.8-6.9 | 10.4-12 | 202-236 |
| FL118 (MTD) pre-dosing) | 3.7-5.2 | 2.4-3.7 | 0.5-0.6 | 0.18-0.26 | 0.05-0.1 | 0.02-0.05 | 6.1-6.9 | 10.5-11.7 | 209-313 |
| FL118 (MTD) post-dosing) | 3.2-9.0 | 1.6-3.0 | 0.1-0.41 | 0.06-0.28 | 0.01-0.03 | 0.00-0.01 | 5.6-6.4 | 10.1-11.2 | 210-364 |

LUC, large unstained cells; PT, prothrombin time; APTT, activated partial thromboplastin time; FIB, Fibrinogen.

TABLE 4

Effects of FL118 on beagle dogs' serum biochemical parameters

| | GLU (mg/dL) | BUN (mg/dL) | CREA (mg/dL) | TP (g/dL) | ALB (g/dL) | GLOB (g/dL) | A:G (mg/dL) | CHOL (mg/dL) | TRIG (mg/dL) | TBIL (mg/dL) |
|---|---|---|---|---|---|---|---|---|---|---|
| Vehicle TX pre-dosing) | 68-91 | 9-13 | 0.2-0.4 | 4.7-5.2 | 3.2-3.6 | 1.5-1.7 | 1.9-2.3 | 133-160 | 37-48 | ≤0.1 |
| Vehicle TX post-dosing) | 84-98 | 11-17 | 0.4 | 5.0-5.3 | 3.0-3.3 | 2.0-2.1 | 1.5-1.7 | 116-171 | 40-55 | ≤0.1 |
| FL118 (MTD) pre-dosing) | 72-93 | 9-13 | 0.3-0.4 | 4.8-5.2 | 3.3-3.4 | 1.5-1.9 | 1.7-2.2 | 112-206 | 34-45 | ≤0.1 |
| FL118 (MTD) post-dosing) | 87-105 | 12-20 | 0.4 | 4.7-5.2 | 2.8-3.2 | 1.8-2.1 | 1.5-1.8 | 119-195 | 18-46 | ≤0.1 |

| | AST (U/L) | ALT (U/L) | ALP (U/L) | GGT (U/L) | CK (U/L) | Ca (mg/dL) | PHOS (mg/dL) | Na (mmol/L) | K (mmol/L) | Cl (mmol/L) |
|---|---|---|---|---|---|---|---|---|---|---|
| Vehicle TX pre-dosing) | 29-36 | 33-49 | 87-132 | <3 | 302-524 | 10.8-11.1 | 6.7-8.0 | 143-148 | 4.6-5.0 | 104-106 |
| Vehicle TX post-dosing) | 34-88 | 41-46 | 96-129 | <3 | 387-4171 | 10.4-10.8 | 6.4-7.7 | 146-147 | 4.7-5.1 | 105-108 |
| FL118 (MTD) pre-dosing) | 31-39 | 29-41 | 103-116 | <3 | 339-457 | 11-11.5 | 7.1-8.1 | 145-148 | 4.9-5.3 | 105-109 |
| FL118 (MTD) post-dosing) | 40-48 | 23-51 | 81-106 | <3 | 410-794 | 10.2-10.7 | 6.1-7.0 | 146-148 | 4.5-4.9 | 108-112 |

GLOB, globulin; A:G, albumin:globulin; TRIG, triglyceride; AST, aspartate aminotransferase; GGT, gamma glutamyl transferase; CK, creatine kinase; Ca, calcium; Na, sodium; K, potassium; Cl, chloride.

A newly developed formulation for oral administration of FL118 obtained favorable pharmacokinetics (PK) profiles. Our previous studies reveal that FL118 intravenous (i.v.) injection is rapidly accumulated in tumor but quickly cleared from blood stream, while FL118 can be maintained in tumor for a long half-life (Ling, et al.: FL118, a novel camptothecin analogue, overcomes irinotecan and topotecan resistance in human tumor xenograft models, American Journal of Translational Research 2015, 7:1765-1781). However, i.v. injection is not convenient; administration of drug needs nurse help. So for commercialization of an anticancer drug, when possible, oral administration is always the first choice. In this regard, we took advantage of the newly developed formulation for oral administration of the FL118 platform as a formulation testing article; then we determined the PK profile of FL118 after oral administration. The PK studies in this way revealed that similar to i.v. administration of FL118, oral administration of FL118 in a organic solvent-free HPβCD as drug carrier aqueous/saline suspension obtained favorable PK profile.

Figure 9:
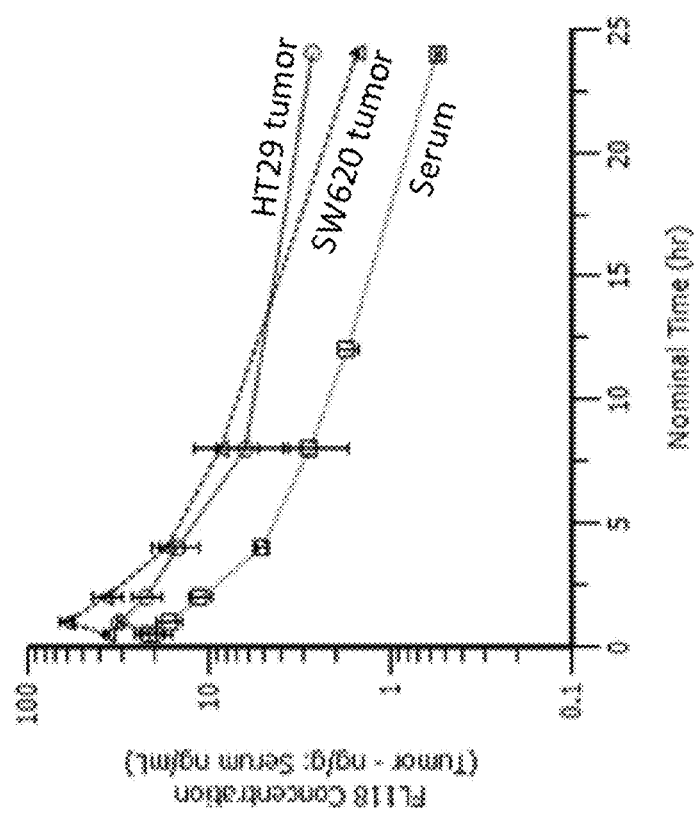
FIG. 9 shows the pharmacokinetics (PK) results of the oral administration of FL118 platform. SCID mice were subcutaneously implanted with human colon SW620 and HT-29 tumors. After the implanted tumor grew to 600-1000 mm³, FL118 was orally administrated at 1.5 mg/kg. Then, blood and tumor tissues were collected at 30 min, 1 h, 4 h, 8 h, 12 h and 24 h. Three SCID mice at each time point were used. Sample analyses were described in Methods. Each curve is the mean drug concentration±SD from 3 mice that were analyzed using Excel software. Oral administration of FL118 also shows favorable pharmacokinetics.

Specifically, after oral administration, FL118 quickly accumulated into tumor and the concentration of FL118 in tumor is many folds higher than those in serum (FIG. 9).

Figure 10:
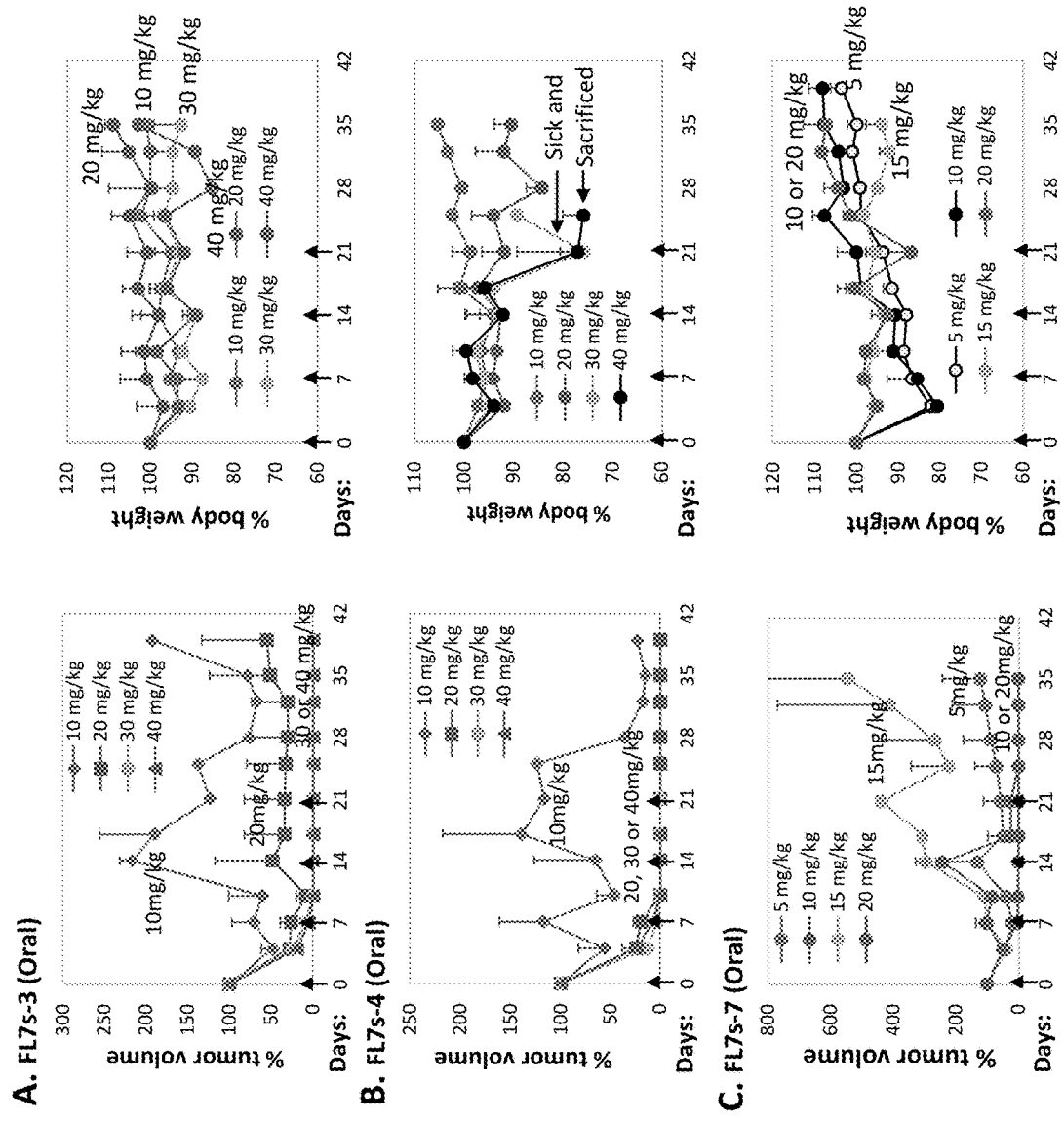
FIG. 10 shows the confirmative re-testing of the antitumor efficacy and toxicity of the FL118 analogues of FL7s-3, FL7s-4 and FL7s-7 in HT-3 retinoblastoma xenograft tumors. Human HT-3 retinoblastoma xenograft tumors were initially established by subcutaneously injection of $2-5\times10^6$ HT-3 cells in a volume of 100-200 μL medium. Mouse models of HT-3 xenografts were set up by subcutaneously inoculating 30-40 mg tumor tissue on the flank of SCID mice. Treatment with individual compounds was initiated 7-14 days after the transplanted tumors reached 100-200 mm³ (designated day 0). The treatment schedule is the weekly for four-times via oral drug administration (q7d×4) as arrowed. The individual compounds were formulated in an organic solvent-free with HPβCD as drug carriers in 2% HPMC (hydroxypropyl methylcellulose) and 1% PG (propylene glycol) in saline (a thick aqueous suspension) for oral administration. The vehicle is the same thick aqueous suspension without drug. A. FL7s-3-treated xenograft tumor curve profile (left panel) and body weight profile (right panel) over the experimental period. B. FL7s-4-treated xenograft tumor curve profile (left panel) and body weight profile (right panel) over the experimental period. C. FL7s-7-treated xenograft tumor curve profile (left panel) and body weight profile (right panel) over the experimental period. Of note, SCID mice bearing HT-3 retinoblastoma tumors treated with vehicles were euthanized with in 3 weeks due to over size tumors.
Figure 11:
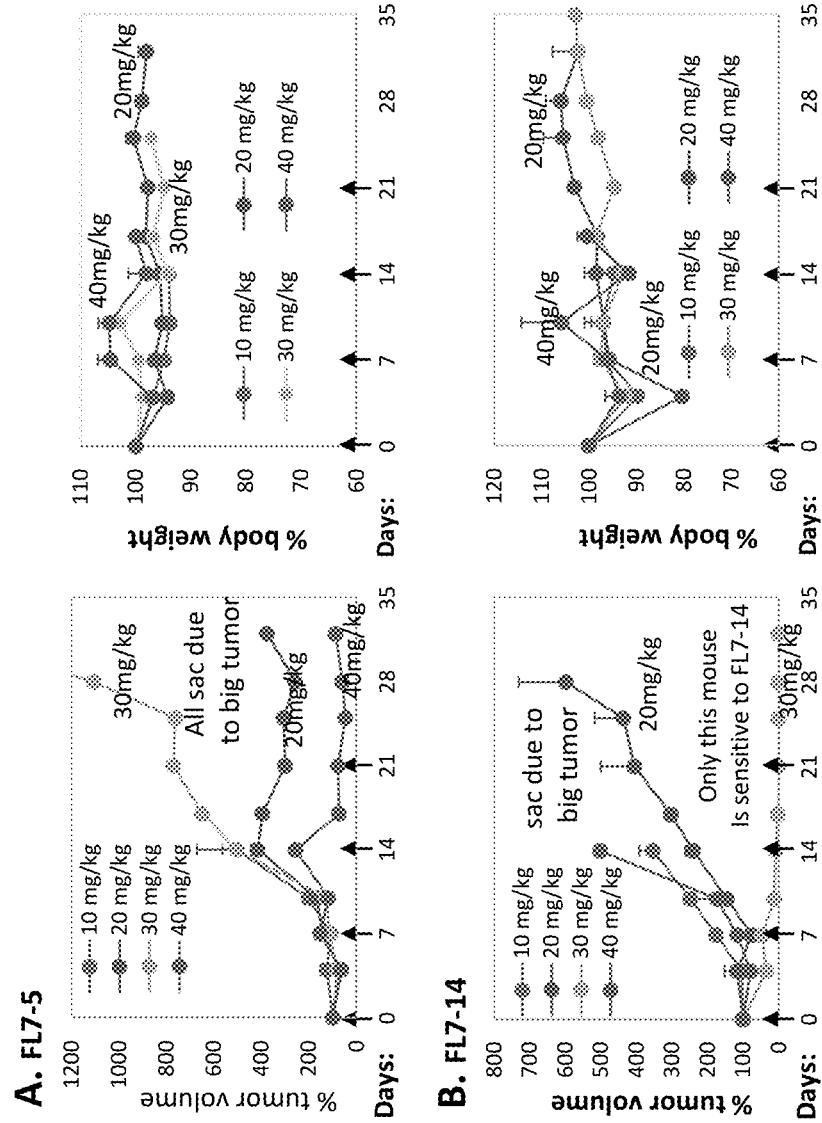
FIG. 11 shows the confirmation testing of the antitumor efficacy and toxicity of the FL118 analogues of FL7-5, and FL7-15 in HT-3 retinoblastoma xenograft tumors. Mouse models of human HT-3 retinoblastoma tumors were established as described in FIG. 10. Treatment with individual compounds was initiated 7-14 days after the transplanted tumors reached 100-150 mm³ (designated day 0). The treatment schedule is the weekly for four time oral administration (q7d×4) as shown with arrows using the organic solvent-free HPβCD thick soup containing 2% HPMC (hydroxylpropyl methylcellulase) and 1% PG (propylene glycol) in saline as vehicle. A. FL7-5-treated xenograft tumor curve profile (left panel) and body weight profile (right panel) over the experimental period. B. FL7-14-treated xenograft tumor curve profile (left panel) and body weight profile (right panel) over the experimental period. Of note, sac: sacrificed.

Several times of in vivo testing of a group of FL118 platform-derived analogues (FL7s-3, FL7s-4, FL7s-7, FL7-5, FL7-14, FL7-15, FL7-17) revealed that FL7s-3 and FL7s-7 are the top two promising candidate molecules for potentially moving on. Based on the initial finding from the oral administration of the FL118 analogues of FL7s-3, FL7s-4, FL7s-7, FL7-5, FL7-14, FL7-15 and FL7-17, we re-tested the antitumor activity and toxicity (body weight loss) profile in multiple doses for oral administration of the FL118 platform-derived analogues of FL7s-3, FL7s-4, FL7s-7, FL7-5, FL7-14. We did not include FL7-15 and FL7-17, because other in vivo data suggested that FL7-15 and FL7-17 is not as good as FL7-5 and FL7-14, in terms of overall antitumor activity versus toxicity profiles. By use of multiple doses of oral administration for the individual drugs of FL7s-3, FL7s-4, FL7s-7, FL7-5, FL7-14 with a weekly×4 schedule (FIGS. 10, 11), our in vivo animal model-of-human retinoblastoma xenograft studies indicated that FL7s-3 and FL7s-7 appear to be the top two candidates that need to be considered for moving on.

Figure 12:
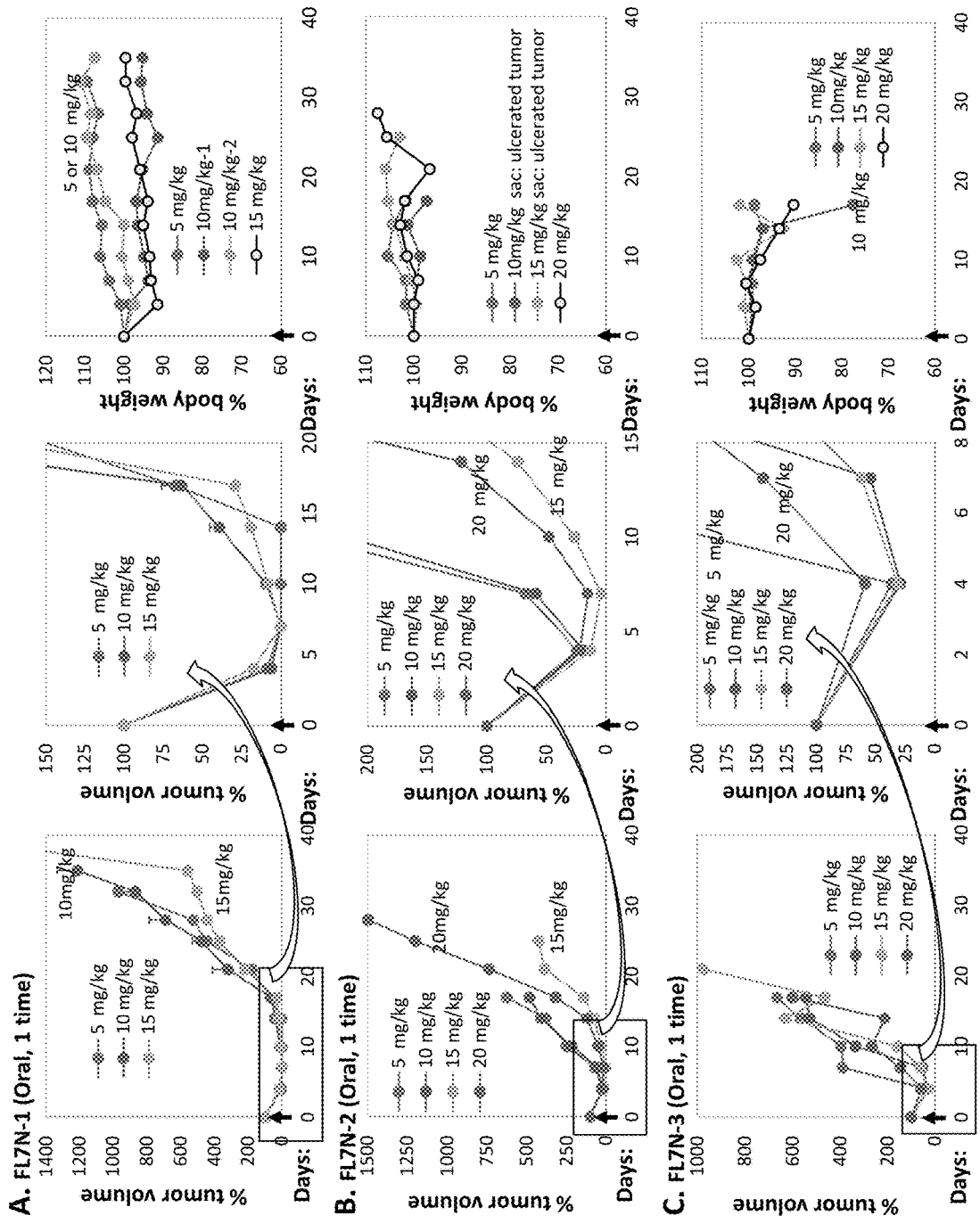
FIG. 12 shows the antitumor efficacy and toxicity of the FL118 platform-derived analogues, FL7N-1, FL7N-2 and FL7N-3, in HT-3 retinoblastoma xenograft tumor models. Mouse models of human HT-3 retinoblastoma tumors and drug formulation are the same as described in FIG. 10. Treatment with individual compounds was initiated 7 days after the transplanted tumors reached 100-200 mm$^3$ (designated day 0). The animal model of human HT-3 retinoblastoma xenograft tumors was only treated for once as shown by a black arrow via oral administration. A. FL7N-1 xenograft tumor curve profile for the entire experiment period (left panel) and for the first 20 days (middle panel) after treatment. The animal body weight profile was shown in the right panel over the experimental period. B. FL7N-2 xenograft tumor curve profile for the entire experiment period (left panel) and for the first 15 days (middle panel) after treatment. The animal body weight profile was shown in the right panel over the experimental period. C. FL7N-3 xenograft tumor curve profile for the entire experiment period (left panel) and for the first 8 days (middle panel) after treatment. The animal body weight profile was shown in the right panel over the experimental period. Of note, all mice were euthanized when tumor reached 1500 mm$^3$. So, individual mice were euthanized at on different days at different percentage of tumor size due to the tumor size was different at the time when treatment was given.

Another group of 3 FL118 platform-based analogues was synthesized: While all of the three new compounds are promising, one of the three candidates showed exceptional anti-retinoblastoma tumor activity without showing toxicity tested in all the three doses used. To these three novel compounds, we performed in vivo animal model studies to evaluate their antitumor activity and toxicity using the HT-3 retinoblastoma xenograft tumor models. In this experiment, we still took advantage of the newly developed formulation for oral administration of compounds. Due to the limited amount of compounds then, we were only able to orally administrate each drug for one time at 3-4 doses based on the drug availability as shown (FIG. 12). The in vivo animal model studies with oral administration revealed that all of the 3 new compounds, FL7N-1, FL7N-2 and FL7N-3 exhibited great antitumor activity and favorable toxicity profiles (FIG. 12). Moreover, the FL7N-1 exhibited exceptional antitumor activity in all three doses used (5 mg/kg, 10 mg/kg and 15 mg/kg) without showing toxicity (mouse body weight loss) at any of these three doses (FIG. 12A), suggesting a characteristic of a highly targeted in terms of mechanism of action (MOA).

Figure 13:
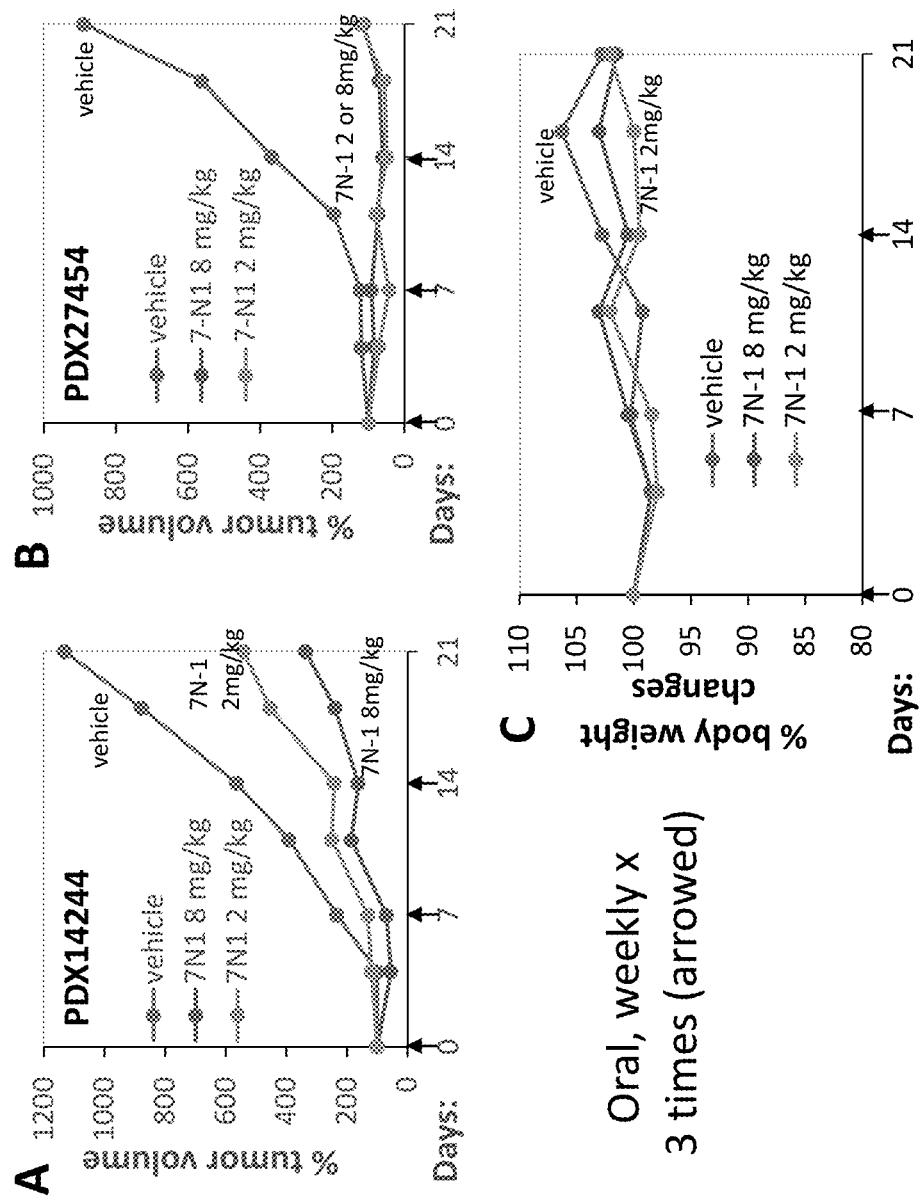
FIG. 13 shows the antitumor efficacy and toxicity (body weight changes) of the FL118 platform-derived analogue FL7N-1 in pancreatic cancer (14244) and colorectal cancer (27454) patient-derived xenograft (PDX) tumor in animal models. PDX tumors were originally established on severe Combined Immunodeficiency (SCID) mice from pancreatic and colorectal cancer patient tumor tissues obtained from metastatic sites of the disease in the clinic. The FL118 platform drug was formulated in an organic solvent-free with HPβCD (2-hydroxypropyl-β-cyclodextrin) as drug carriers in 2% HPMC (hydroxypropyl methylcellulose) and 1% PG (propylene glycol) in saline (a thick aqueous suspension) for oral administration. The vehicle is the same think aqueous suspension without drug. Experimental SCID mice were subcutaneously implanted with 30-40 mg individual PDX tumors (isolated from maintenance mice) at the flank area (left side for PDX14244, and right side for PDX27454) of SCID mice. Treatment with vehicle or drug was initiated 7-14 days after the transplanted tumors reached 100-200 mm$^3$ (designated day 0). The animal model of PDX tumors was orally treated weekly for 3 times as shown with black arrows. A. Pancreatic cancer PDX14244 tumor curve profile obtained after with vehicle or with FL7N1 treatment. B. Colorectal cancer PDX27454 tumor curve profile obtained after with vehicle or with FL7N1 treatment. C. The animal body weight change profile after with vehicle or with FL7N-1 treatment was shown over the experimental period.

FL7N-1 appears to be a great drug for treatment of children rare disease of retinoblastoma, although FL7N-1 exhibits good antitumor activity in pancreatic cancer patient-derived xenograft (PDX) tumor models (14244) and in colorectal cancer PDX models (27454). Based on the anti-retinoblastoma tumor activity of FL7N-1 obtained in FIG. 12 by using one time drug administration, we next tested the FL7N-1 antitumor efficacy and toxicity (body weight changes) in pancreatic cancer (14244) and colorectal cancer (27454) PDX tumor in animal models. PDX tumors were originally established on SCID mice from pancreatic and colorectal cancer patient tumor tissues obtained from metastatic sites of the disease in the clinic. The FL7N-1 was formulated in an organic solvent-free with HPβCD (2-hydroxypropyl-β-cyclodextrin) in 2% HPMC (hydroxypropyl methylcellulose) and 1% PG (propylene glycol) in saline (a thick aqueous suspension) for oral administration. The vehicle is the same aqueous suspension without FL7N-1. Experimental SCID mice were subcutaneously implanted with 30-40 mg individual PDX tumors (isolated from maintenance mice) at the flank area (left side for PDX14244, and right side for PDX27454) of SCID mice. Treatment with vehicle or FL7N-1 was initiated 7-14 days after the transplanted tumors reached 100-200 mm$^3$ (designated day 0). The animal model of PDX tumors was orally treated weekly for 3 times as shown with black arrows. Our studies indicated that while FL7N-1 exhibited very good anti-pancreatic cancer PDX14244 tumor (FIG. 13A) and anti-colorectal cancer PDX27454 tumor (FIG. 13B), it appears that FL7N-1 exhibited exceptional anti-retinoblastoma activity (FIG. 12A). Thus, FL7N-1 may be a priority candidate to be developed for treatment of children rare disease retinoblastoma.

Anti-tumor activity of FL118 platform-derived Wb series of drugs (W-b1, W-b2, W-b3, W-b4, W-b5, W-b6, W-b7, W-b9, W-b10/Hx7) in colorectal cancer SW620 cell-established xenograft tumors. We have also tested a new group of FL118 platform-derived compounds (W-b1, W-b2, W-b3, W-b4, W-b5, W-b6, W-b7, W-b9, W-b10/Hx7) using the SW620 cell-established xenograft tumors in SCID mice. Human SW620 xenograft tumors were initially established by subcutaneously injection of 2-5×10$^6$ SW620 cells in a volume of 100-150 μL medium. Mouse models of SW620 xenografts were set up by subcutaneously inoculating 30-40 mg tumor tissue (isolated from tumor maintenance SCID mice) on the flank of SCID mice. Treatment with individual compounds was initiated 7-14 days after the transplanted tumors reached 100-200 mm$^3$ (designated day 0). The treatment schedule is weekly for 1-2 times in a series of dose levels based on the available drug amounts then. The individual compounds were formulated in an organic solvent-free with HPβCD in 2% HPMC (hydroxypropyl methylcellulose) and 1% PG (propylene glycol) in saline (a thick aqueous suspension) for oral administration. The vehicle is the same thick aqueous suspension without drug.

Figure 14:
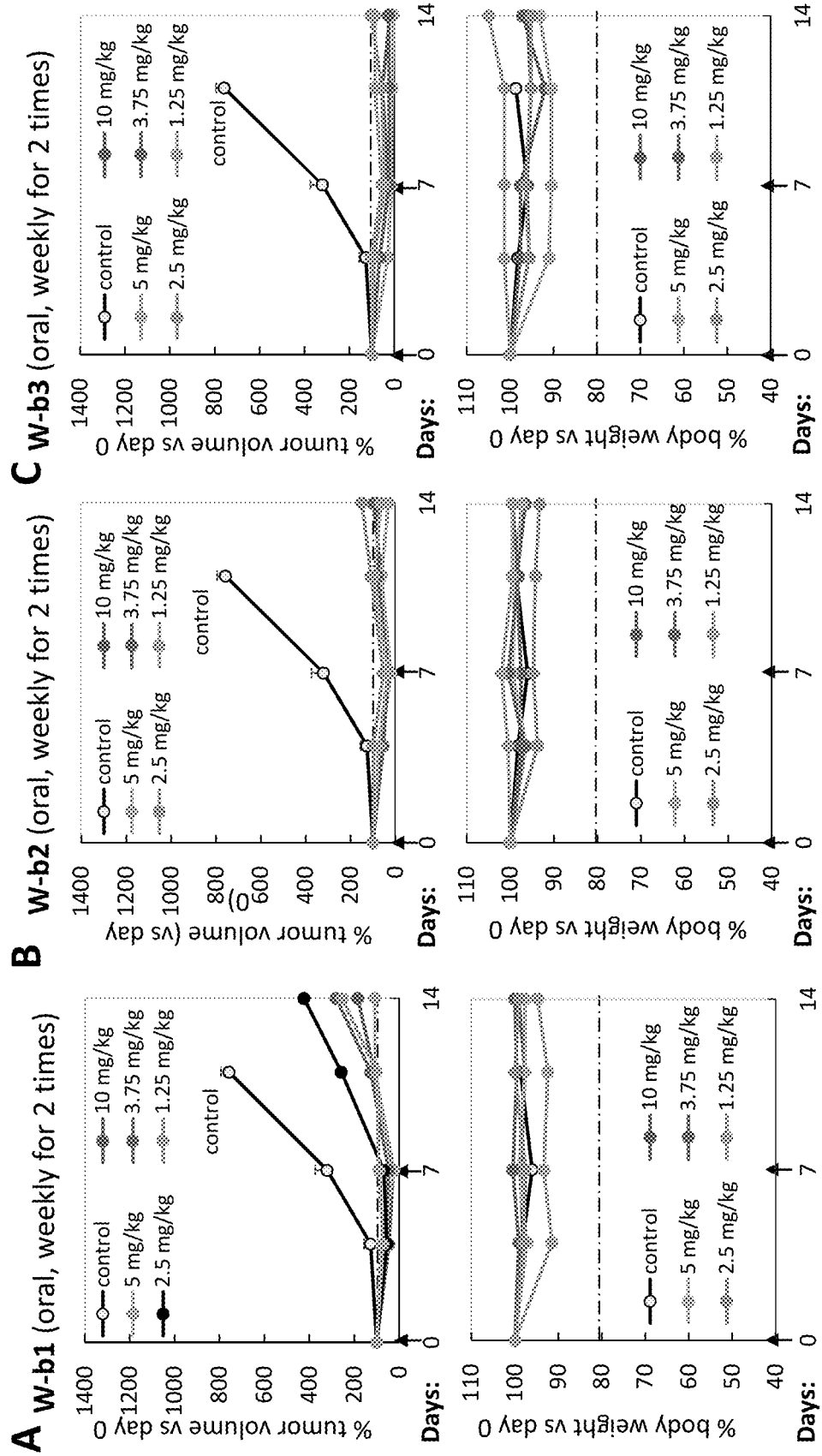
FIG. 14 shows the antitumor efficacy and toxicity of the FL118 platform-derived analogues, W-b1, W-b2 and W-b3, in SW620 colorectal cancer xenograft tumor models. Mouse models of human SW620 xenograft tumors and drug formulation are the same as described in FIG. 10. Treatment with individual compounds was initiated 7 days after the transplanted tumors reached 100-200 mm$^3$ (designated day 0). The animal model of human SW620 xenograft tumors was treated weekly for 2 times as shown with black arrows via oral administration. A. W-b1 xenograft tumor curve profile during the experiment period (upper panel). The animal body weight change profile was shown in the lower panel over the experimental period. B. W-b2 xenograft tumor curve profile during the experiment period (upper panel). The animal body weight change profile was shown in the lower panel over the experimental period. C. W-b3 xenograft tumor curve profile during the experiment period (upper panel). The animal body weight change profile was shown in the lower panel over the experimental period.
Figure 15:
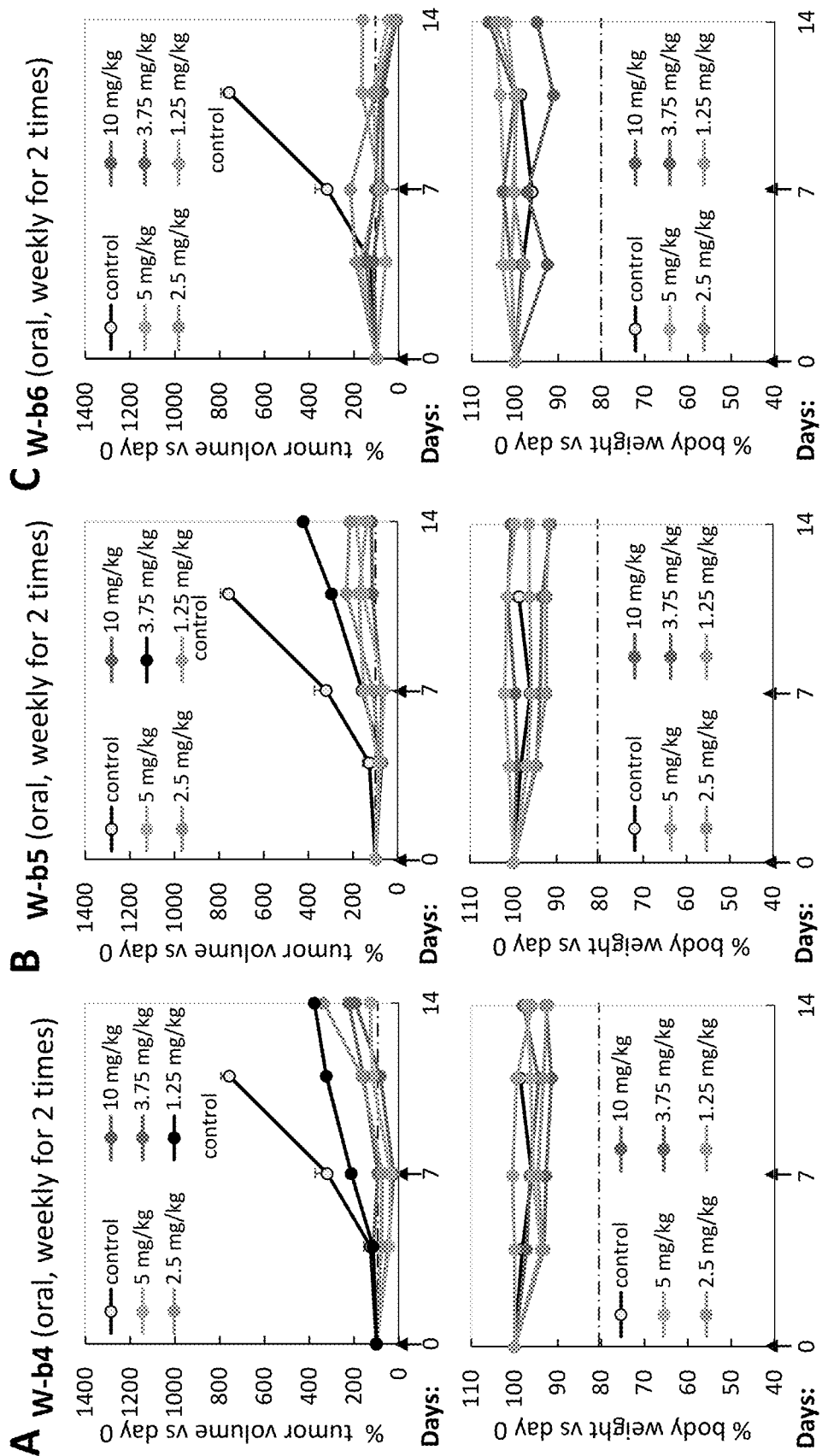
FIG. 15 shows the antitumor efficacy and toxicity of the FL118 platform-derived analogues, W-b4, W-b5 and W-b6, in SW620 colorectal cancer xenograft tumor models. Mouse models of human SW620 xenograft tumors and drug formulation are the same as described in FIG. 10. Treatment with individual compounds was initiated 7 days after the transplanted tumors reached 100-200 mm$^3$ (designated day 0). The animal model of human SW620 xenograft tumors was treated weekly for 2 times as shown with black arrows via oral administration. A. W-b4 xenograft tumor curve profile during the experiment period (upper panel). The animal body weight change profile was shown in the lower panel over the experimental period. B. W-b5 xenograft tumor curve profile during the experiment period (upper panel). The animal body weight change profile was shown in the lower panel over the experimental period. C. W-b6 xenograft tumor curve profile during the experiment period (upper panel). The animal body weight change profile was shown in the lower panel over the experimental period.
Figure 16:
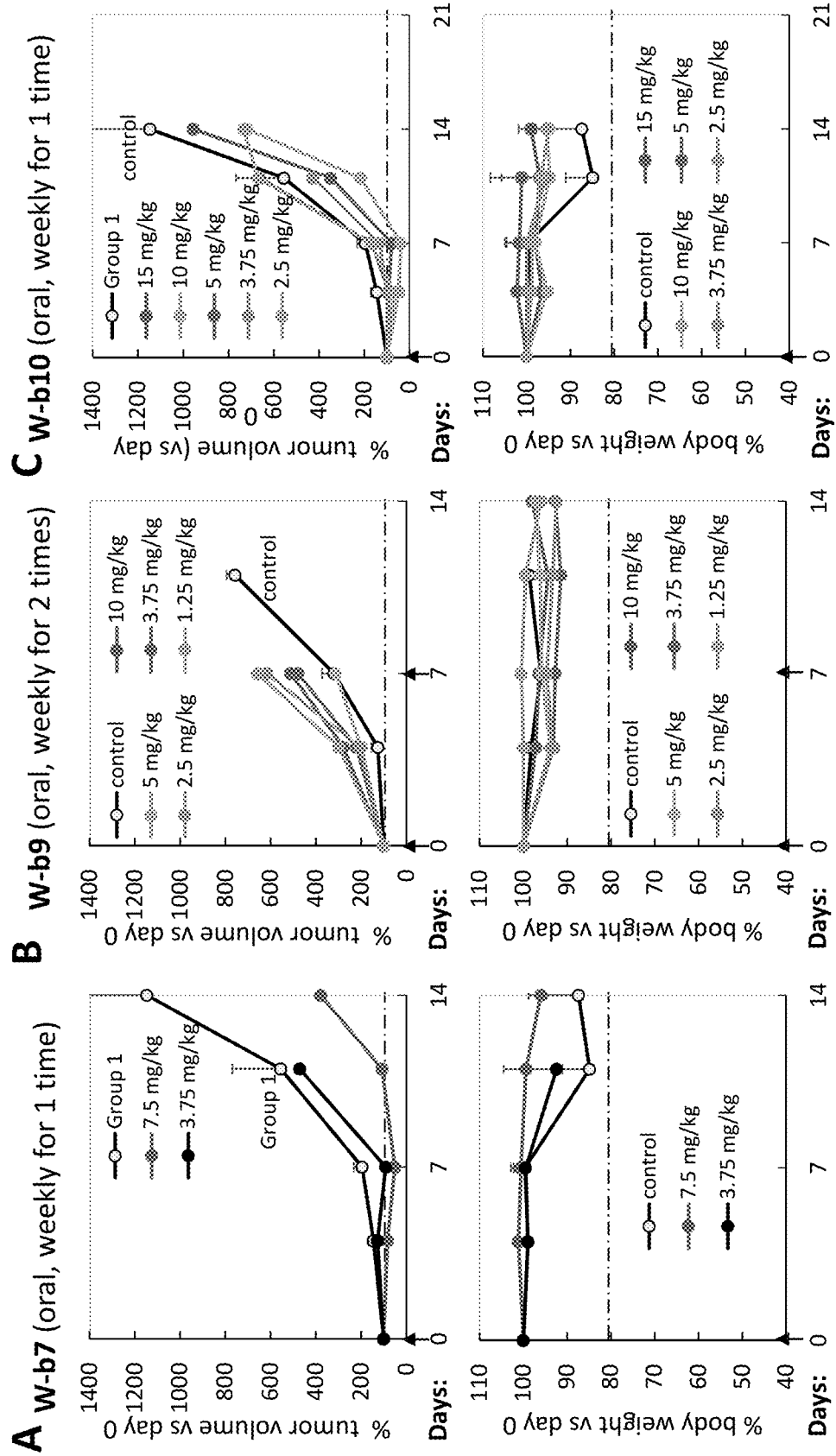
FIG. 16 shows the antitumor efficacy and toxicity of the FL118 platform-derived analogues, W-b7, W-b9 and W-b10, in SW620 colorectal cancer xenograft tumor models. Mouse models of human SW620 xenograft tumors and drug formulation are the same as described in FIG. 10. Treatment with individual compounds was initiated 7 days after the transplanted tumors reached 100-200 mm$^3$ (designated day 0). The animal model of human SW620 xenograft tumors was treated weekly for 1-2 times as shown with black arrows via oral administration. A. W-b1 xenograft tumor curve profile during the experiment period (upper panel). The animal body weight change profile was shown in the lower panel over the experimental period. B. W-b2 xenograft tumor curve profile during the experiment period (upper panel). The animal body weight change profile was shown in the lower panel over the experimental period. C. W-b3 xenograft tumor curve profile during the experiment period (upper panel). The animal body weight change profile was shown in the lower panel over the experimental period.
Figure 17:
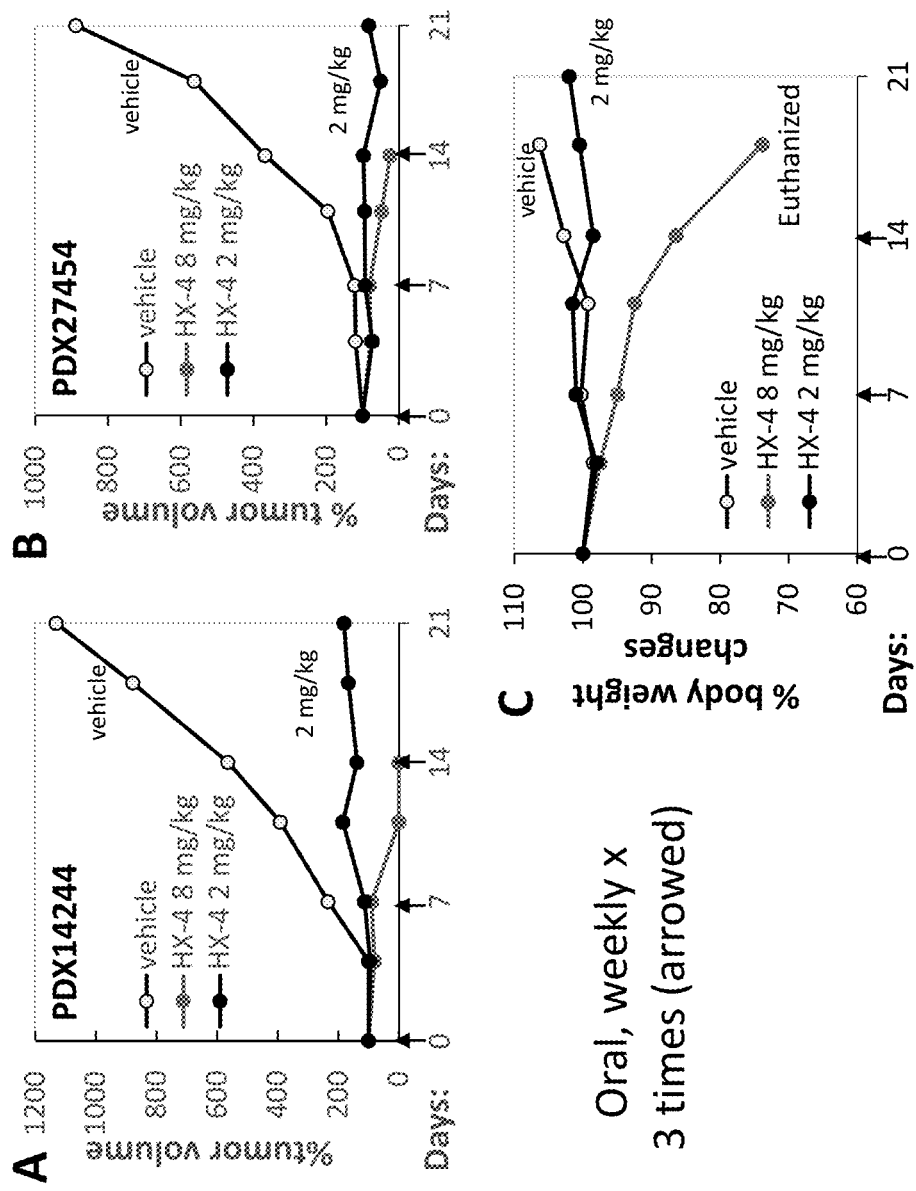
FIG. 17 shows the antitumor efficacy and toxicity (body weight changes) of the FL118 platform-derived analogue Hx-4 in pancreatic cancer (14244) and colorectal cancer (27454) patient-derived xenograft (PDX) tumor in animal models. PDX tumor establishment, drug formulation for oral administration, vehicle composition and experimental SCID mice of PDX tumors preparation were the same as described in FIGS. 7 and 13. PDX tumor SCID mice treatment with vehicle or with Hx-4 was initiated 7-14 days after the transplanted tumors reached 100-200 mm$^3$ (designated day 0). The animal model of PDX tumors was orally treated weekly for 3 times as shown with black arrows. A. Pancreatic cancer PDX14244 tumor curve profile obtained after with vehicle or with Hx-4 treatment. B. Colorectal cancer PDX27454 tumor curve profile obtained after with vehicle or with Hx-4 treatment. C. The animal body weight change profile after with vehicle or with Hx-4 treatment was shown over the experimental period.
Figure 18:
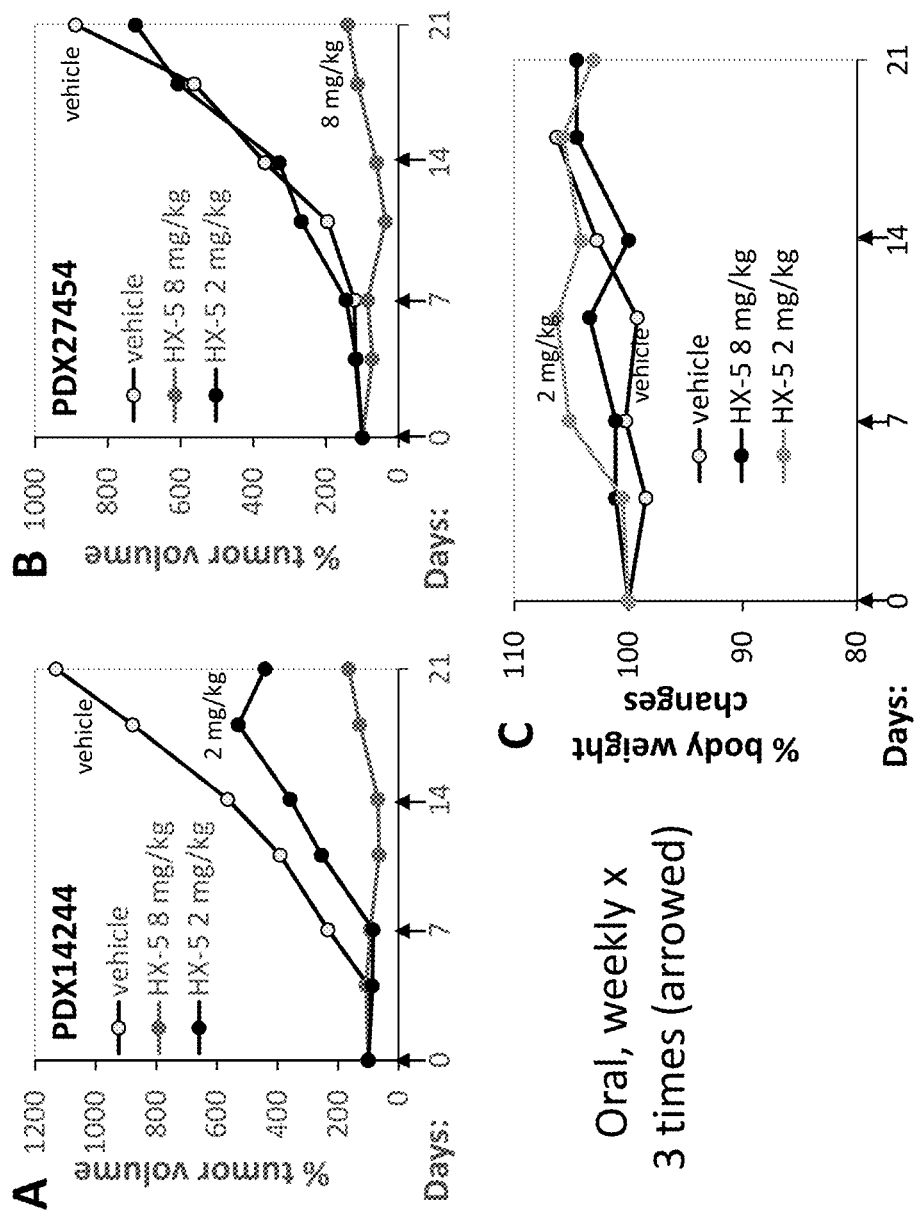
FIG. 18 shows the antitumor efficacy and toxicity (body weight changes) of the FL118 platform-derived analogue Hx-5 in pancreatic cancer (14244) and colorectal cancer (27454) patient-derived xenograft (PDX) tumor in animal models. PDX tumor establishment, drug formulation for oral administration, vehicle composition and experimental SCID mice of PDX tumors preparation were the same as described in FIGS. 7 and 13. PDX tumor SCID mice treatment with vehicle and Hx-5, respectively, was initiated 7-14 days after the transplanted tumors reached 100-200 mm$^3$ (designated day 0). The animal model of PDX tumors was orally treated weekly for 3 times as shown with black arrows. A. Pancreatic cancer PDX14244 tumor curve profile obtained after with vehicle or with Hx-5 treatment. B. Colorectal cancer PDX27454 tumor curve profile obtained after with vehicle or with Hx-5 treatment. C. The animal body weight change profile after with vehicle or with Hx-5 treatment was shown over the experimental period.
Figure 19:
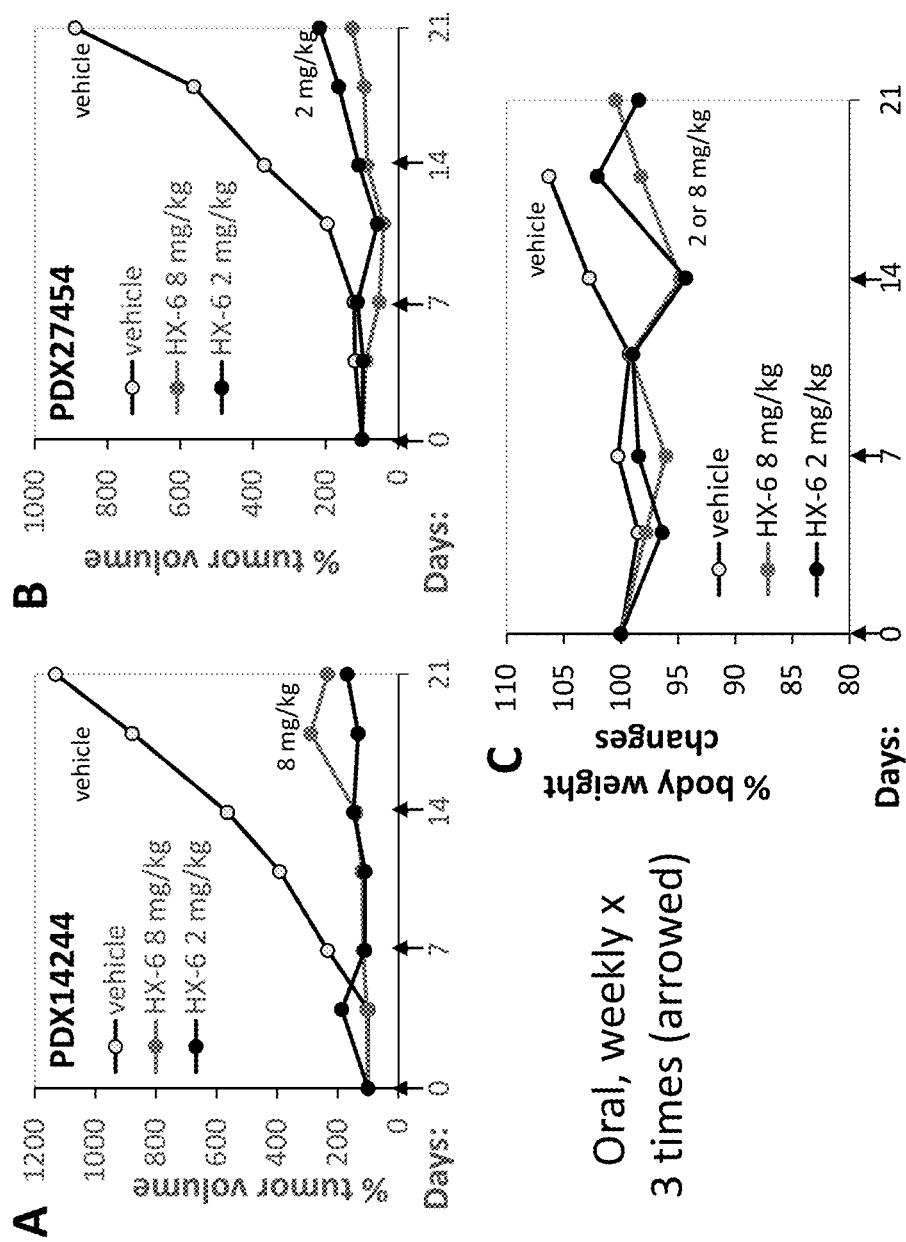
FIG. 19 shows the antitumor efficacy and toxicity (body weight changes) of the FL118 platform-derived analogue Hx-6 in pancreatic cancer (14244) and colorectal cancer (27454) patient-derived xenograft (PDX) tumor in animal models. PDX tumor establishment, drug formulation for oral administration, vehicle composition and experimental SCID mice of PDX tumors preparation were the same as described in FIGS. 7 and 13. PDX tumor SCID mice treatment with vehicle and Hx-6, respectively, was initiated 7-14 days after the transplanted tumors reached 100-200 mm$^3$ (designated day 0). The animal model of PDX tumors was orally treated weekly for 3 times as shown with black arrows. A. Pancreatic cancer PDX14244 tumor curve profile obtained after with vehicle or with Hx-6 treatment. B. Colorectal cancer PDX27454 tumor curve profile obtained after with vehicle or with Hx-6 treatment. C. The animal body weight change profile after with vehicle or with Hx-6 treatment was shown over the experimental period.
Figure 20:
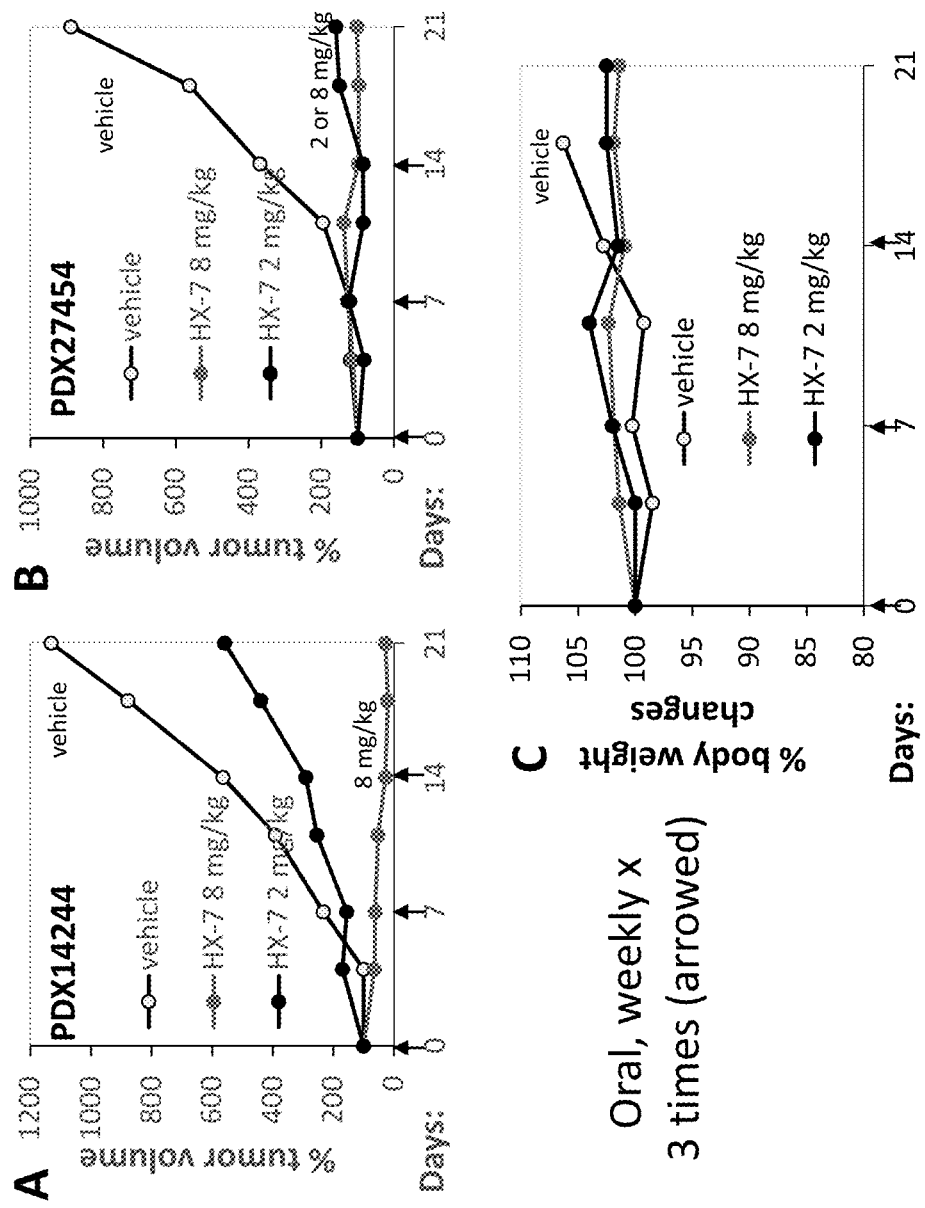
FIG. 20 shows the antitumor efficacy and toxicity (body weight changes) of the FL118 platform-derived analogue Hx-6 in pancreatic cancer (14244) and colorectal cancer (27454) patient-derived xenograft (PDX) tumor in animal models. PDX tumor establishment, drug formulation for oral administration, vehicle composition and experimental SCID mice of PDX tumors preparation were the same as described in FIGS. 7 and 13. PDX tumor SCID mice treatment with vehicle and Hx-7, respectively, was initiated 7-14 days after the transplanted tumors reached 100-200 mm$^3$ (designated day 0). The animal model of PDX tumors was orally treated weekly for 3 times as shown with black arrows. A. Pancreatic cancer PDX14244 tumor curve profile obtained after with vehicle or with Hx-7 treatment. B. Colorectal cancer PDX27454 tumor curve profile obtained after with vehicle or with Hx-7 treatment. C. The animal body weight change profile after with vehicle or with Hx-7 treatment was shown over the experimental period.

Our in vivo testing of these individual drugs revealed that while most of these compounds exhibited great antitumor activity, the compounds of W-b2, W-b3 and W-b6 possess much higher antitumor activity than the other compounds in this Wb-series (FIGS. 14-16).

Anti-tumor activity of FL118 platform-derived Hx-series of drugs (Hx4, Hx5, Hx6 and Hx7/W-b10) in pancreatic cancer patient-derived xenograft (PDX) tumor models (14244) and in colorectal cancer PDX models (27454). We have also tested another new group of FL118 platform-derived compounds (Hx4, Hx5, Hx6 and Hx7/W-b10) in pancreatic cancer (14244) and colorectal cancer (27454) patient-derived xenograft (PDX) tumor in animal models. PDX tumors were originally established on severe Combined Immunodeficiency (SCID) mice from pancreatic and colorectal cancer patient tumor tissues obtained from metastatic sites of the disease in the clinic. The FL118 platform drug was formulated in an organic solvent-free with HPβCD (2-hydroxypropyl-β-cyclodextrin) in 2% HPMC (hydroxypropyl methylcellulose) and 1% PG (propylene glycol) in saline (a thick aqueous suspension) for oral administration. The vehicle is the same think aqueous suspension without drug. Experimental SCID mice were subcutaneously implanted with 30-40 mg individual PDX tumors (isolated from maintenance mice) at the flank area (left side for PDX14244, and right side for PDX27454) of SCID mice. Treatment with vehicle or a drug (Hx4, Hx5, Hx6 and Hx7/W-b10) was initiated 7-14 days after the transplanted tumors reached 100-200 mm$^3$ (designated day 0). The animal model of PDX tumors was orally treated weekly for 3 times as shown with black arrows. Our in vivo testing of these individual drugs revealed that while each of these compounds exhibited great antitumor activity, the compounds of Hx6 and Hx7/W-b10 possess much higher antitumor activity with favorable toxicity (both weight changes) profiles than the other two compounds in this Hx-series (FIGS. 17-20).

Figures 1, 21:
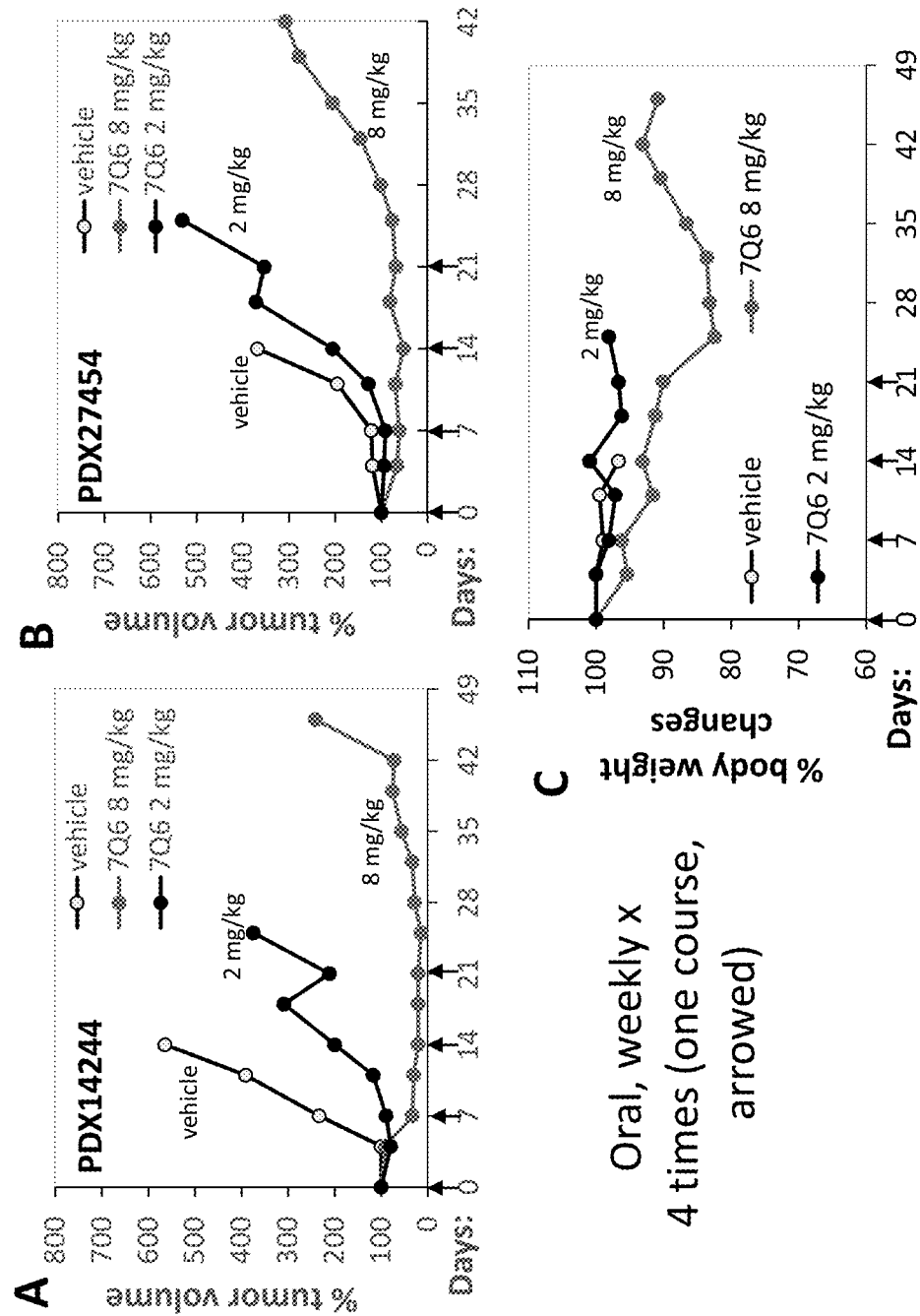
Figures 2, 21:
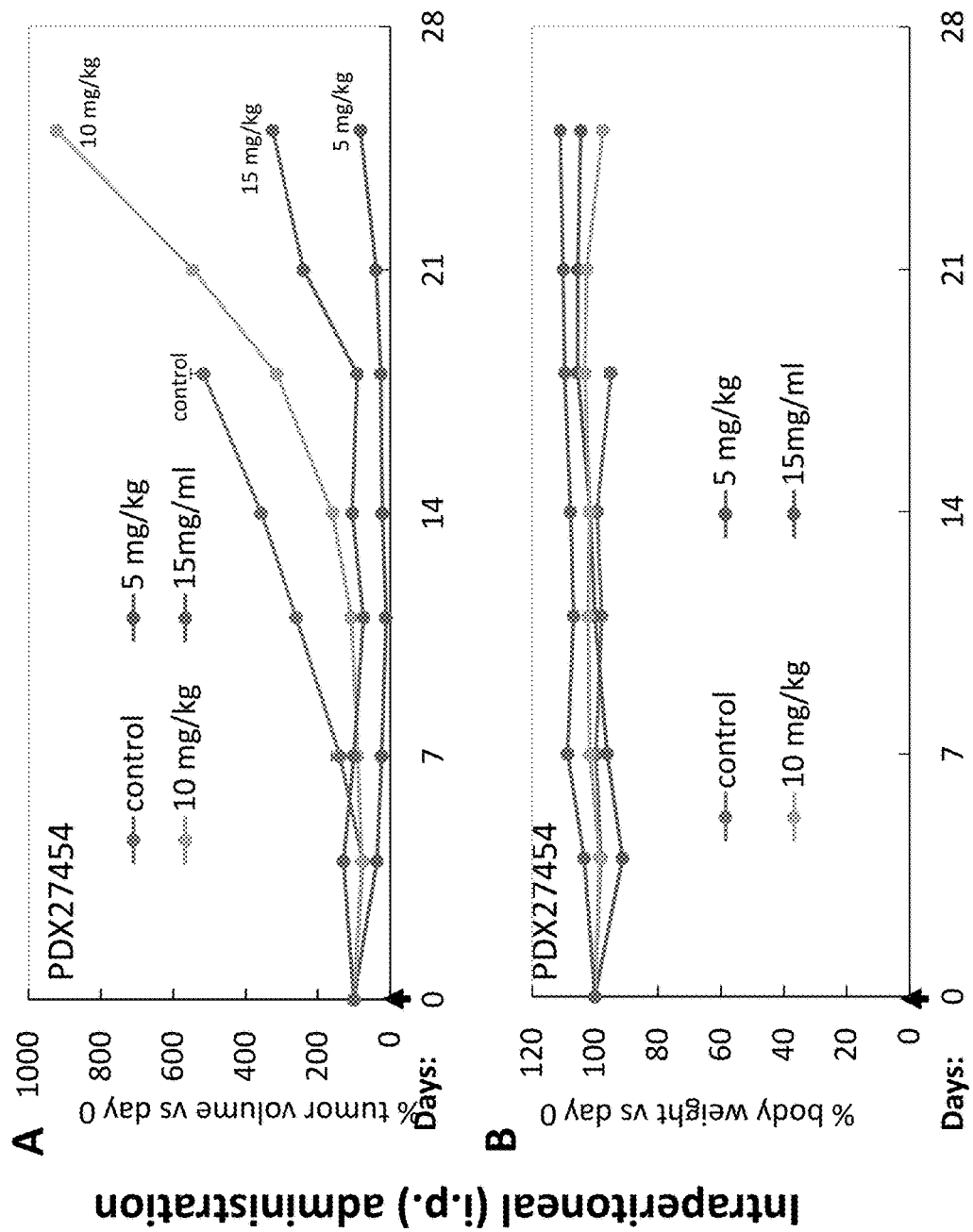
Figure 22:
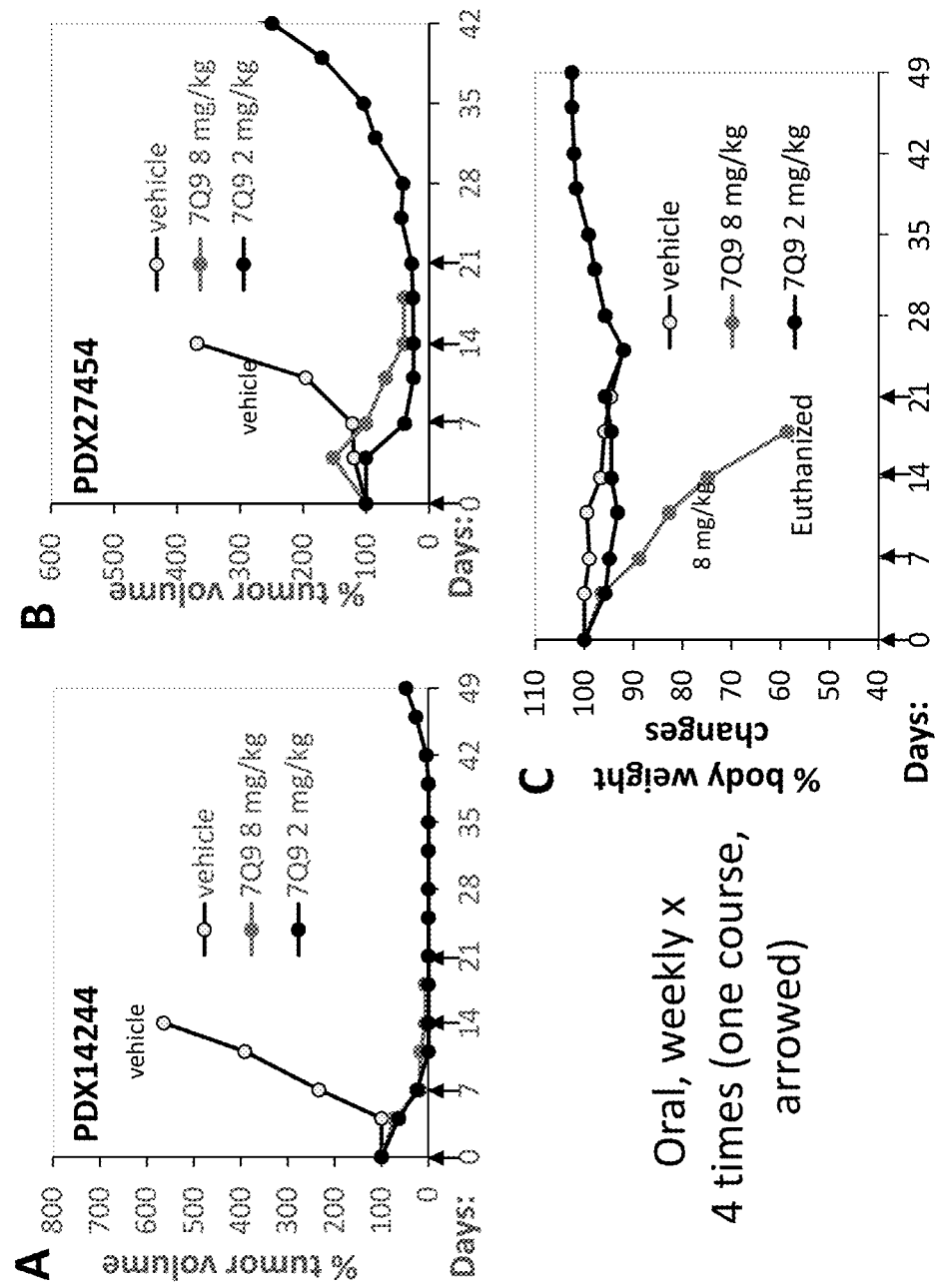
FIG. 22 shows the antitumor efficacy and toxicity (body weight changes) of the FL118 platform-derived analogue 7Q9 in pancreatic cancer (14244) and colorectal cancer (27454) patient-derived xenograft (PDX) tumor in animal models. PDX tumor establishment, drug formulation for oral administration, vehicle composition and experimental SCID mice of PDX tumors preparation were the same as described in FIGS. 7 and 13. PDX tumor SCID mice treatment with vehicle and 7Q9, respectively, was initiated 7-14 days after the transplanted tumors reached 100-200 mm$^3$ (designated day 0). The animal model of PDX tumors was orally treated weekly for 4 times as shown with black arrows (one course/cycle). A. Pancreatic cancer PDX14244 tumor curve profile obtained after with vehicle or with 7Q9 treatment. B. Colorectal cancer PDX27454 tumor curve profile obtained after with vehicle or with 7Q9 treatment. C. The animal body weight change profile after with vehicle or with 7Q9 treatment was shown over the experimental period.
Figure 23:
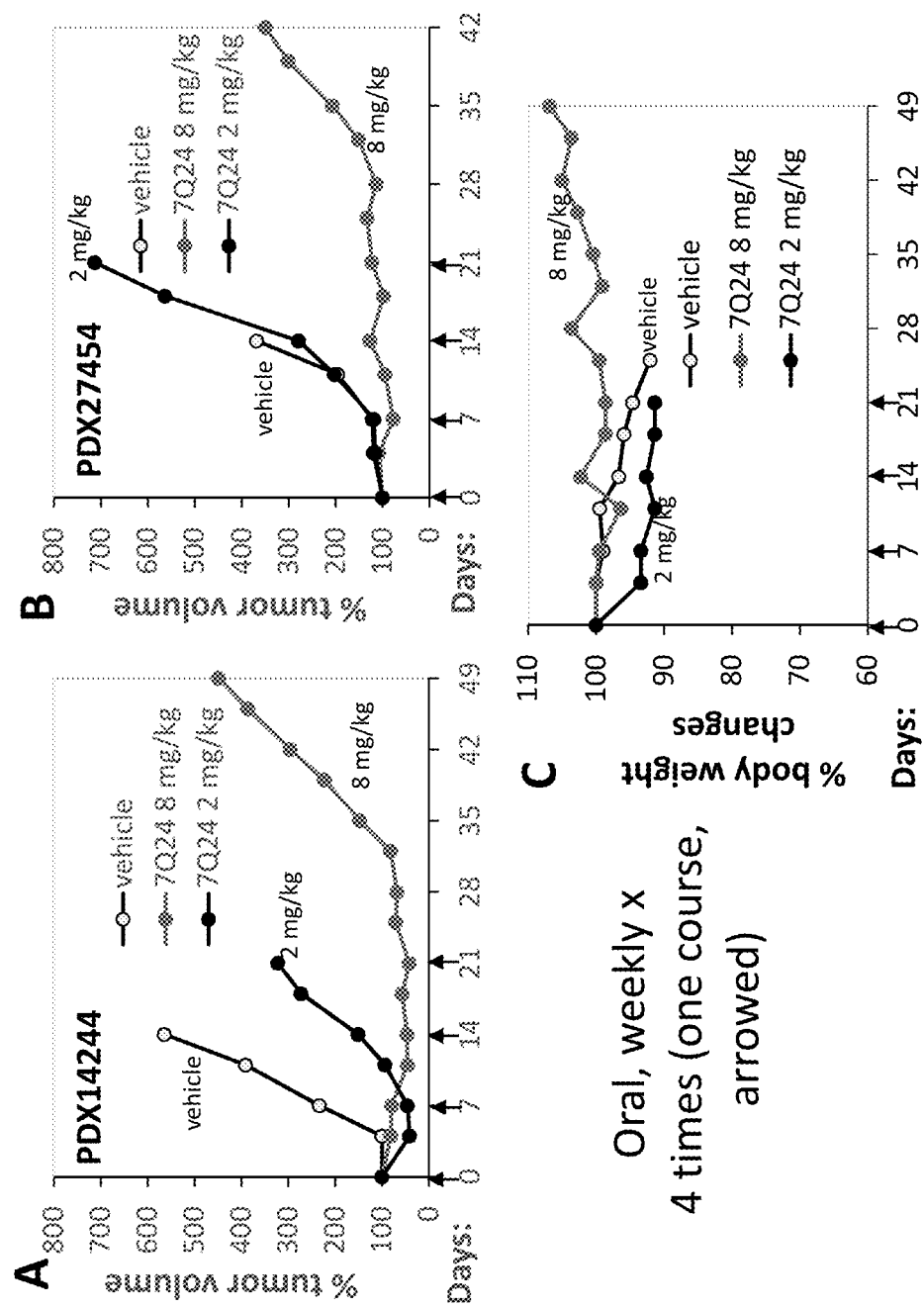
FIG. 23 shows the antitumor efficacy and toxicity (body weight changes) of the FL118 platform-derived analogue 7Q24 in pancreatic cancer (14244) and colorectal cancer (27454) patient-derived xenograft (PDX) tumor in animal models. PDX tumor establishment, drug formulation for oral administration, vehicle composition and experimental SCID mice of PDX tumors preparation were the same as described in FIGS. 7 and 13. PDX tumor SCID mice treatment with vehicle and 7Q24, respectively, was initiated 7-14 days after the transplanted tumors reached 100-200 mm$^3$ (designated day 0). The animal model of PDX tumors was orally treated weekly for 4 times as shown with black arrows (one course/cycle). A. Pancreatic cancer PDX14244 tumor curve profile obtained after with vehicle or with 7Q24 treatment. B. Colorectal cancer PDX27454 tumor curve profile obtained after with vehicle or with 7Q24 treatment. C. The animal body weight change profile after with vehicle or with 7Q24 treatment was shown over the experimental period.
Figure 24:
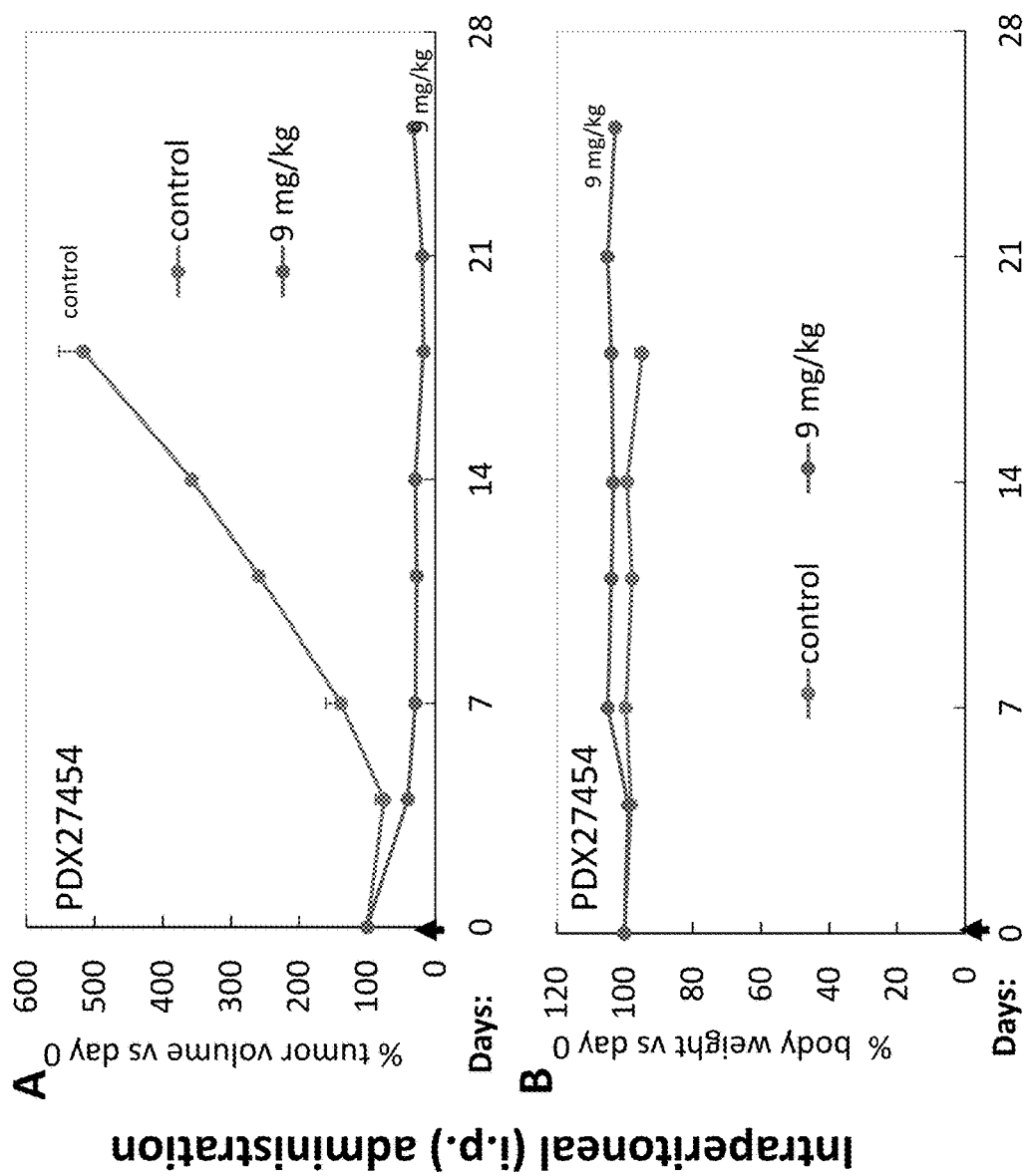
FIG. 24 shows the antitumor efficacy and toxicity (body weight changes) of the FL118 platform-derived analogue 7Q28 in colorectal cancer (27454) patient-derived xenograft (PDX) tumor in animal models. PDX tumor establishment, drug formulation for intra-peritoneal (i.p.) administration, vehicle composition and experimental SCID mice of PDX tumors preparation were the same as described in FIGS. 7 and 13. PDX tumor SCID mice treatment with vehicle and 7Q28 via i.p. for only one time as shown by an arrow, respectively, was initiated 7-14 days after the transplanted tumors reached 100-200 mm³ (designated day 0). A. Colorectal cancer PDX27454 tumor curve profile obtained after with vehicle or with 7Q28 treatment. B. The animal body weight change profile after with vehicle or with 7Q28 treatment was shown. Of note, oral administration of 7Q28 decreases 7Q28 antitumor efficacy (data note shown).
Figure 25:
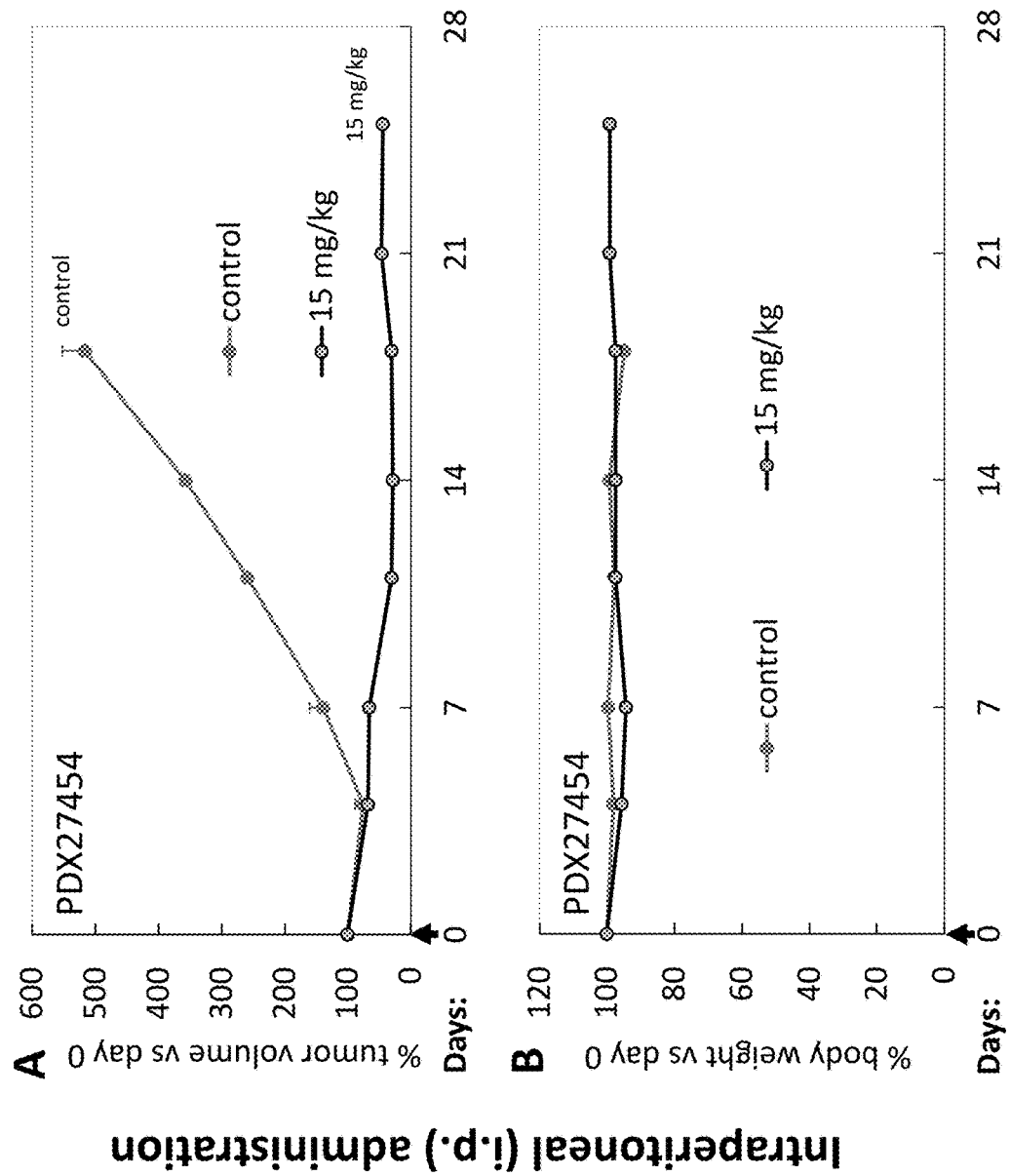
FIG. 25 shows the antitumor efficacy and toxicity (body weight changes) of the FL118 platform-derived analogue 7Q31 in colorectal cancer (27454) patient-derived xenograft (PDX) tumor in animal models. PDX tumor establishment, drug formulation for intra-peritoneal (i.p.) administration, vehicle composition and experimental SCID mice of PDX tumors preparation were the same as described in FIGS. 7 and 13. PDX tumor SCID mice treatment with vehicle and 7Q31 via i.p. for only one time as shown by an arrow, respectively, was initiated 7-14 days after the transplanted tumors reached 100-200 mm³ (designated day 0). A. Colorectal cancer PDX27454 tumor curve profile obtained after with vehicle or with 7Q31 treatment. B. The animal body weight change profile after with vehicle or with 7Q31 treatment was shown. Of note, oral administration of 7Q31 decreases 7Q28 antitumor efficacy (data note shown).
Figure 26:
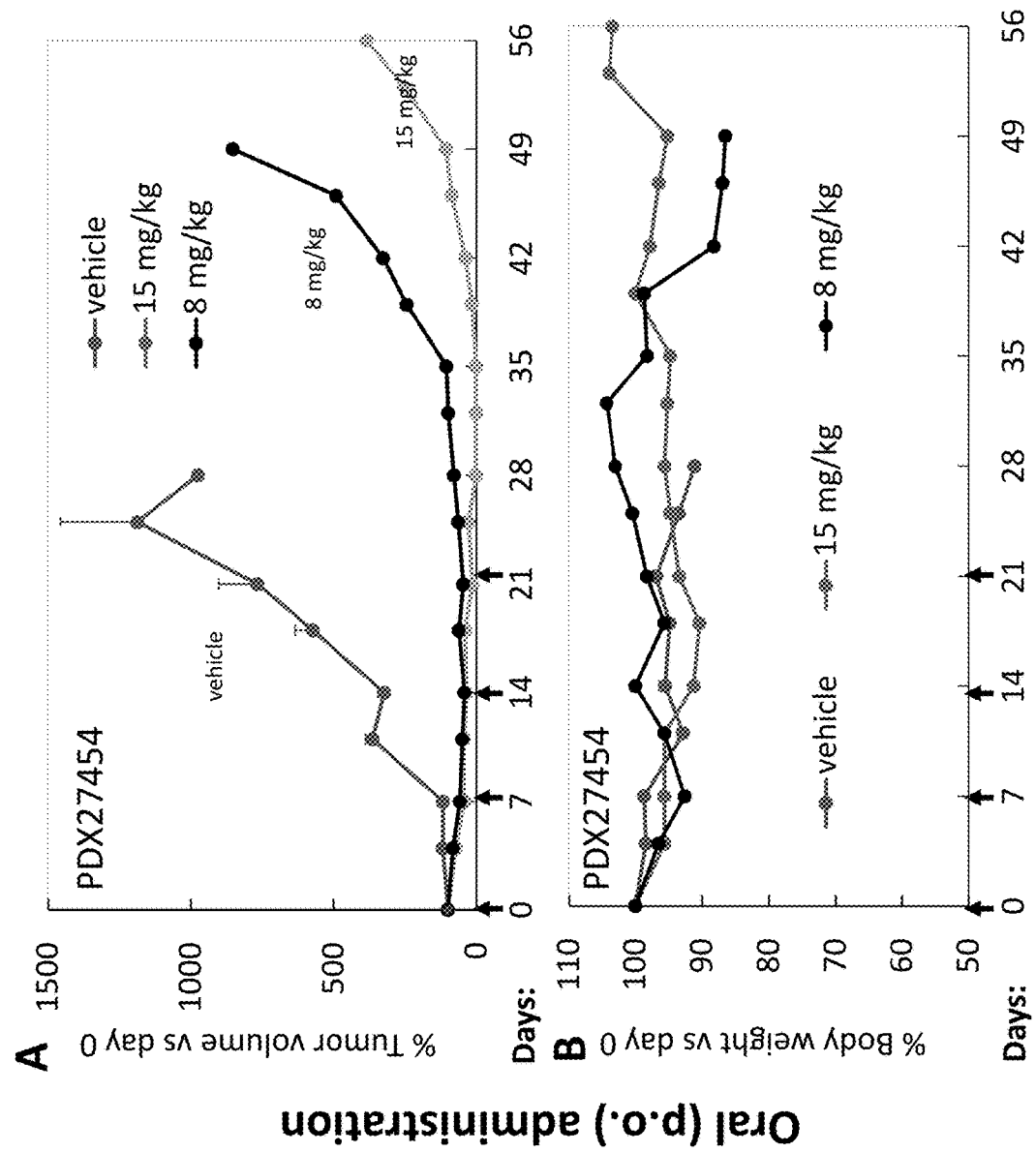
FIG. 26 shows the antitumor efficacy and toxicity (body weight changes) of the FL118 platform-derived analogue 7Q32 in colorectal cancer (27454) patient-derived xenograft (PDX) tumor in animal models. PDX tumor establishment, drug formulation for oral (p.o.) administration, vehicle composition and experimental SCID mice of PDX tumors preparation were the same as described in FIGS. 7 and 13. PDX tumor SCID mice treatment with vehicle and 7Q32 via p.o. for weekly×4 as shown by arrows (one cycle/course), respectively, was initiated 7-14 days after the transplanted tumors reached 100-200 mm³ (designated day 0). A. Colorectal cancer PDX27454 tumor curve profile obtained after with vehicle or with 7Q32 treatment. B. The animal body weight change profile after with vehicle or with 7Q32 treatment was shown. Of note, i.p. administration of 7Q32 increases 7Q32 toxicity to animals in comparison with oral administration of 7Q32 (data note shown).
Figure 27:
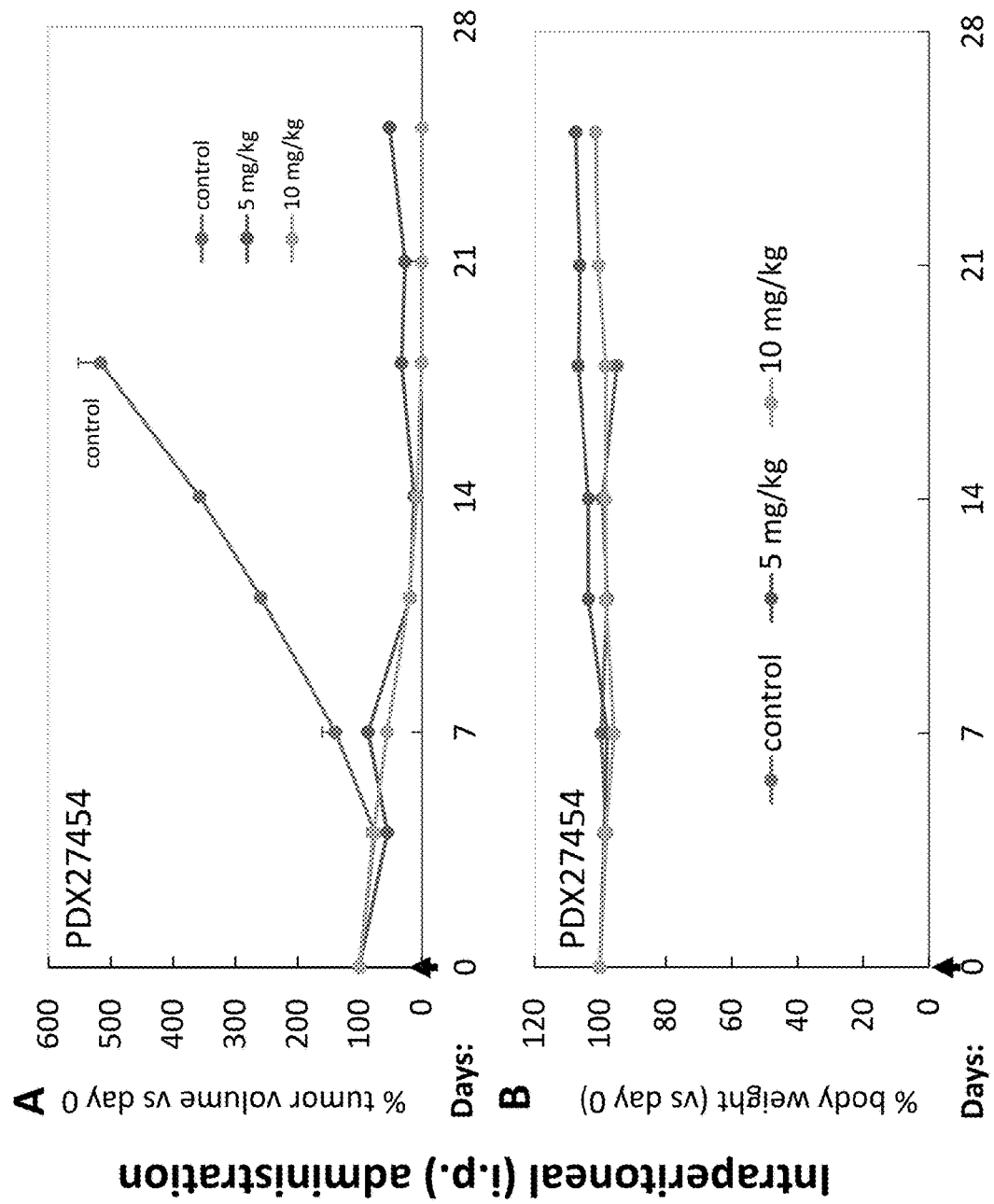
FIG. 27 shows the antitumor efficacy and toxicity (body weight changes) of the FL118 platform-derived analogue 7Q35 in colorectal cancer (27454) patient-derived xenograft (PDX) tumor in animal models. PDX tumor establishment, drug formulation for intra-peritoneal (i.p.) administration, vehicle composition and experimental SCID mice of PDX tumors preparation were the same as described in FIGS. 7 and 13. PDX tumor SCID mice treatment with vehicle and 7Q35 via i.p. for only one time as shown by an arrow, respectively, was initiated 7-14 days after the transplanted tumors reached 100-200 mm³ (designated day 0). A. Colorectal cancer PDX27454 tumor curve profile obtained after with vehicle or with 7Q35 treatment. B. The animal body weight change profile after with vehicle or with 7Q35 treatment was shown. Of note, oral administration of 7Q35 decreases 7Q35 antitumor efficacy (data note shown).
Figure 28:
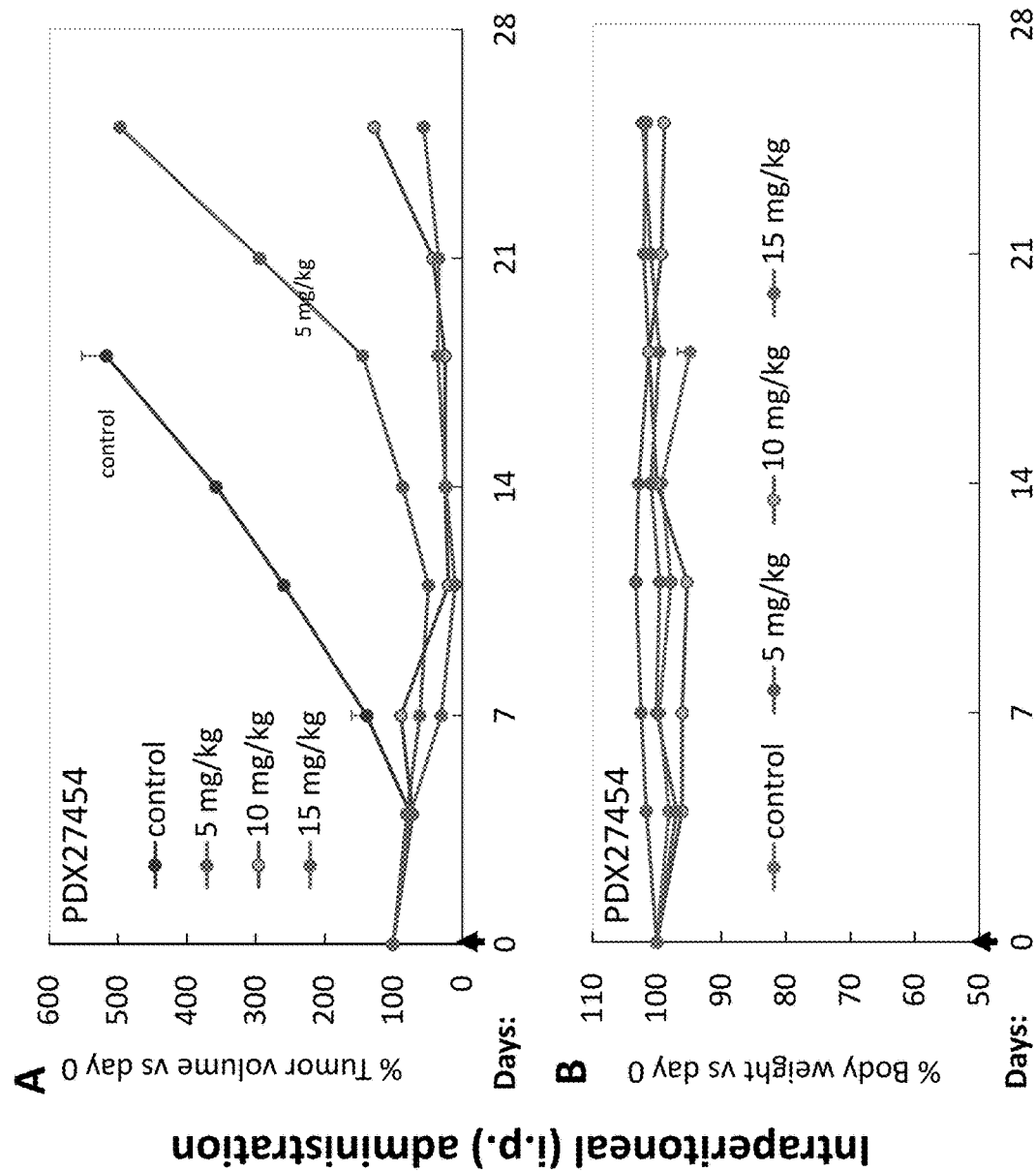
FIG. 28 shows the antitumor efficacy and toxicity (body weight changes) of the FL118 platform-derived analogue 7Q36 in colorectal cancer (27454) patient-derived xenograft (PDX) tumor in animal models. PDX tumor establishment, drug formulation for intra-peritoneal (i.p.) administration, vehicle composition and experimental SCID mice of PDX tumors preparation were the same as described in FIGS. 7 and 13. PDX tumor SCID mice treatment with vehicle and 7Q36 via i.p. for only one time as shown by an arrow, respectively, was initiated 7-14 days after the transplanted tumors reached 100-200 mm³ (designated day 0). A. Colorectal cancer PDX27454 tumor curve profile obtained after with vehicle or with 7Q36 treatment. B. The animal body weight change profile after with vehicle or with 7Q36 treatment was shown. Of note, oral administration of 7Q36 loses >80% 7Q35 antitumor efficacy (data note shown).

Anti-tumor activity of FL118 platform-derived 7Q-series (1: 7Q1-7Q24) of drugs in pancreatic cancer patient-derived xenograft (PDX) tumor models (14244) and in colorectal cancer PDX models (27454). We have also tested another new group of FL118 platform-derived 7Q-series (1) compounds in pancreatic cancer (14244) and colorectal cancer (27454) patient-derived xenograft (PDX) tumor in animal models and identified 7Q6, 7Q9, and 7Q24 as the top 3 compounds in these tumor models among the compounds of this series (1). Specifically, PDX tumors were originally established on severe Combined Immunodeficiency (SCID) mice from pancreatic and colorectal cancer patient tumor tissues obtained from metastatic sites of the disease in the clinic. The FL118 platform drug was formulated in an organic solvent-free with HPβCD (2-hydroxypropyl-β-cyclodextrin) in 2% HPMC (hydroxypropyl methylcellulose) and 1% PG (propylene glycol) in saline (a thick aqueous suspension) for oral administration. The vehicle is the same think aqueous suspension without drug. Experimental SCID mice were subcutaneously implanted with 30-40 mg individual PDX tumors (isolated from maintenance mice) at the flank area (left side for PDX14244, and right side for PDX27454) of SCID mice. Treatment with vehicle or a drug of 7Q-series (1) was initiated 7-14 days after the transplanted tumors reached 100-200 mm$^3$ (designated day 0). The animal model of PDX tumors was orally treated weekly for 4 times (one cycle/course, as shown with black arrows). Our in vivo testing of these individual drugs revealed that while each of these compounds exhibited good antitumor activity, the compounds of 7Q6, 7Q9, and 7Q24 possess much higher antitumor activity than the other compounds in this 7Q-series (1) (FIGS. 21-23).

Anti-tumor activity of FL118 platform-derived 7Q-series (2: 7Q24-7Q48)) of drugs in in colorectal cancer PDX models (27454). We have also tested a group of the 7Q-series (2) compounds in colorectal cancer (27454) patient-derived xenograft (PDX) tumor in animal models and identified 7Q28, 7Q31, 7Q32, 7Q35 and 7Q36 being highly promising in this tumor models among the compounds of this 7Q-series (2). Specifically, PDX tumors were originally established on severe Combined Immunodeficiency (SCID) mice from pancreatic and colorectal cancer patient tumor tissues obtained from metastatic sites of the disease in the clinic. The FL118 platform drug was formulated in an organic solvent-free with HPβCD (2-hydroxypropyl-β-cyclodextrin) in 2% HPMC (hydroxypropyl methylcellulose) and 1% PG (propylene glycol) in saline (a thick aqueous suspension) for oral administration or intra-peritoneal administration. The vehicle is the same think aqueous suspension without drug. Experimental SCID mice were subcutaneously implanted with 30-40 mg individual PDX tumors (isolated from maintenance mice) at the flank area for PDX27454 of SCID mice. Treatment with vehicle or a drug of 7Q-series (2) was initiated 7-14 days after the transplanted tumors reached 100-200 mm$^3$ (designated day 0). The animal model of PDX tumors was orally treated weekly for 4 times (one cycle/course, as shown with black arrows) or only one time drug administration. Our in vivo testing revealed that the compounds of 7Q28, 7Q31, 7Q32, 7Q35 and 7Q36 possess much higher antitumor activity than the other compounds in this 7Q-series (2) (FIGS. 24-28).

Figure 29:
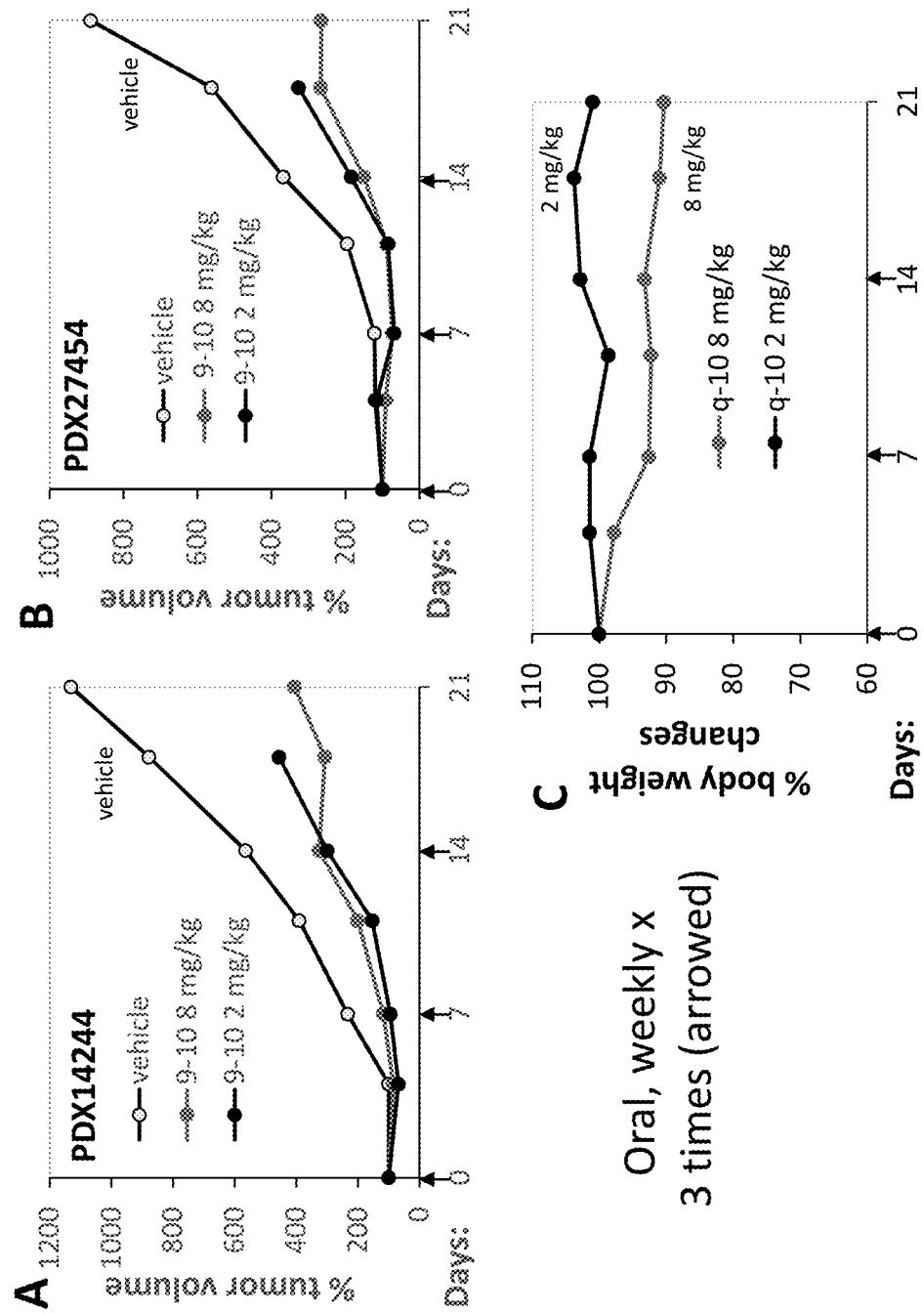
FIG. 29 shows the antitumor efficacy and toxicity (body weight changes) of the FL118 platform-derived analogue 9Q10 (9-10) in pancreatic cancer (14244) and colorectal cancer (27454) patient-derived xenograft (PDX) tumor in animal models. PDX tumor establishment, drug formulation for oral administration, vehicle composition and experimental SCID mice of PDX tumors preparation were the same as described in FIGS. 7 and 13. PDX tumor SCID mice treatment with vehicle and 9Q10 (9-10), respectively, was initiated 7-14 days after the transplanted tumors reached 100-200 mm³ (designated day 0). The animal model of PDX tumors was orally treated weekly for 3 times as shown with black arrows. A. Pancreatic cancer PDX14244 tumor curve profile obtained after with vehicle or with 9Q10 (9-10) treatment. B. Colorectal cancer PDX27454 tumor curve profile obtained after with vehicle or with 9Q10 (9-10) treatment. C. The animal body weight change profile after with vehicle or with 9Q10 (9-10) treatment was shown over the experimental period. Of note, vehicle mouse body weight changes were within 10%.
Figure 30:
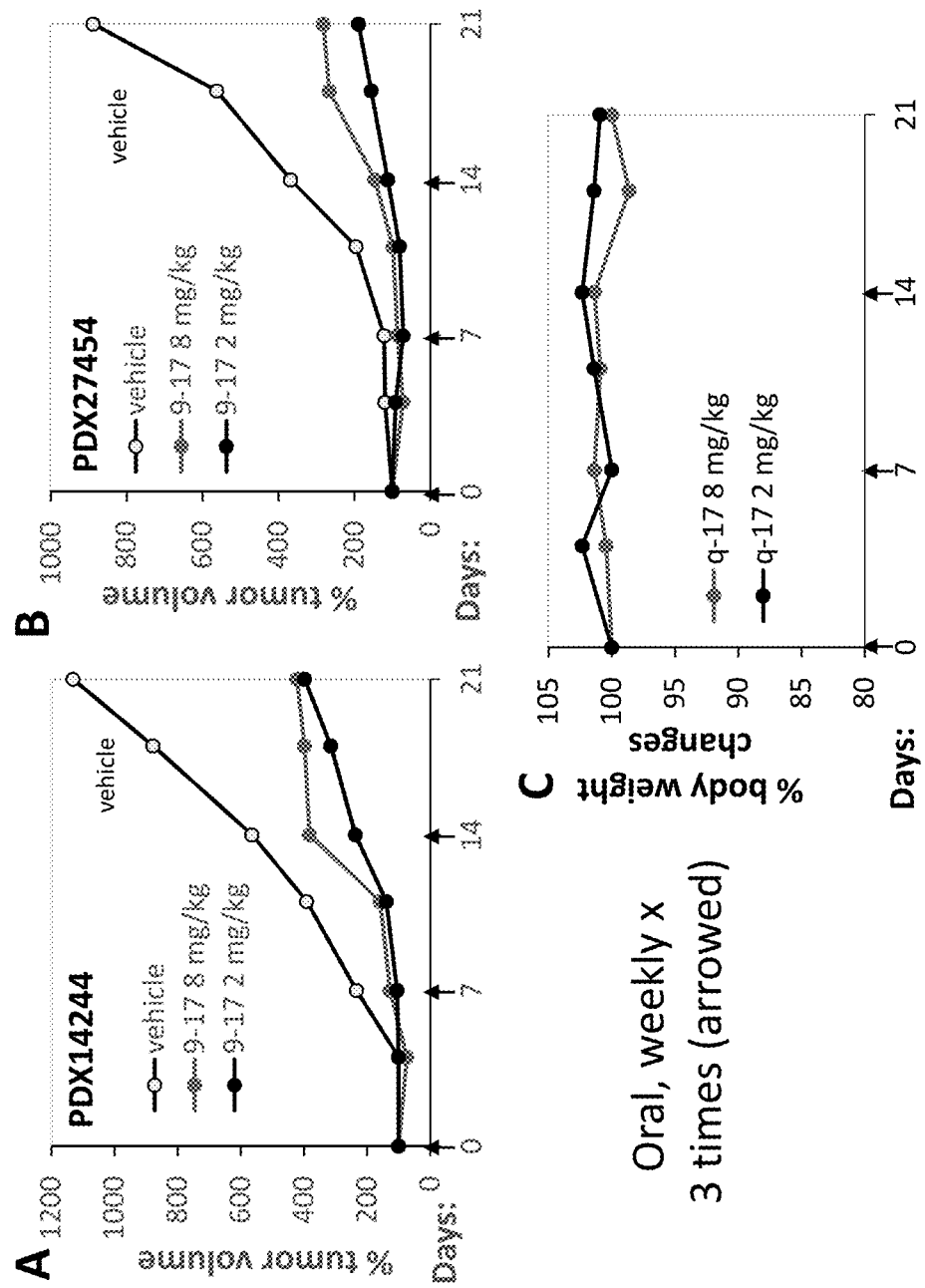
FIG. 30 shows the antitumor efficacy and toxicity (body weight changes) of the FL118 platform-derived analogue 9Q17 (9-17) in pancreatic cancer (14244) and colorectal cancer (27454) patient-derived xenograft (PDX) tumor in animal models. PDX tumor establishment, drug formulation for oral administration, vehicle composition and experimental SCID mice of PDX tumors preparation were the same as described in FIGS. 7 and 13. PDX tumor SCID mice treatment with vehicle and 9Q17 (9-17), respectively, was initiated 7-14 days after the transplanted tumors reached 100-200 mm³ (designated day 0). The animal model of PDX tumors was orally treated weekly for 3 times as shown with black arrows. A. Pancreatic cancer PDX14244 tumor curve profile obtained after with vehicle or with 9Q17 (9-17) treatment. B. Colorectal cancer PDX27454 tumor curve profile obtained after with vehicle or with 9Q17 (9-17) treatment. C. The animal body weight change profile after with vehicle or with 9Q17 (9-17) treatment was shown over the experimental period. Of note, vehicle mouse body weight changes were within 10%.
Figure 31:
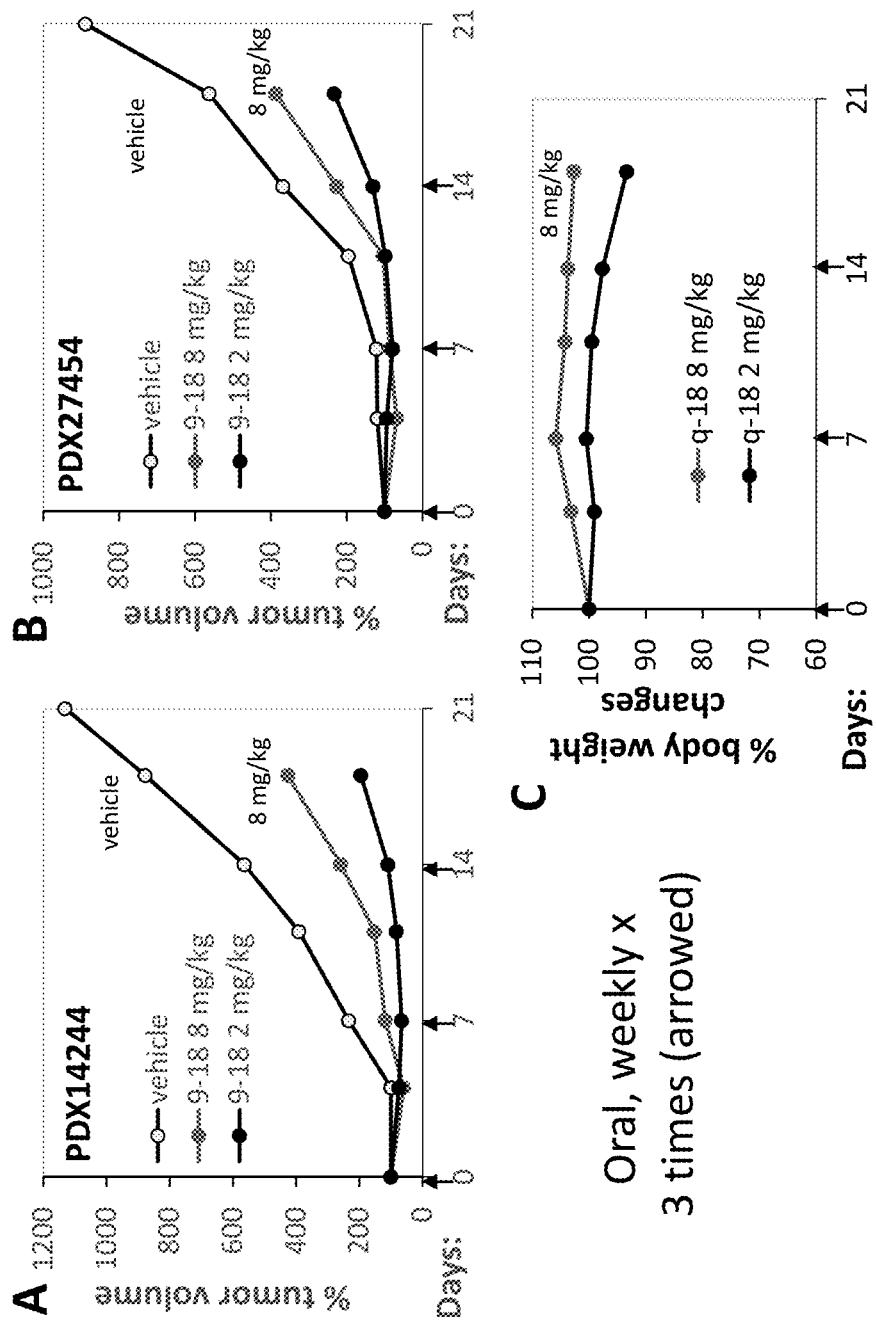
FIG. 31 shows the antitumor efficacy and toxicity (body weight changes) of the FL118 platform-derived analogue 9Q18 (9-18) in pancreatic cancer (14244) and colorectal cancer (27454) patient-derived xenograft (PDX) tumor in animal models. PDX tumor establishment, drug formulation for oral administration, vehicle composition and experimental SCID mice of PDX tumors preparation were the same as described in FIGS. 7 and 13. PDX tumor SCID mice treatment with vehicle and 9Q18 (9-18), respectively, was initiated 7-14 days after the transplanted tumors reached 100-200 mm³ (designated day 0). The animal model of PDX tumors was orally treated weekly for 3 times as shown with black arrows. A. Pancreatic cancer PDX14244 tumor curve profile obtained after with vehicle or with 9Q18 (9-18) treatment. B. Colorectal cancer PDX27454 tumor curve profile obtained after with vehicle or with 9Q18 (9-18) treatment. C. The animal body weight change profile after with vehicle or with 9Q18 (9-18) treatment was shown over the experimental period. Of note, vehicle mouse body weight changes were within 10%.

Anti-tumor activity of FL118 platform-derived 9Q-series of drugs in pancreatic cancer patient-derived xenograft (PDX) tumor models (14244) and in colorectal cancer PDX models (27454). We have also tested another new group of FL118 platform-derived 9Q-series compounds in pancreatic cancer (14244) and colorectal cancer (27454) patient-derived xenograft (PDX) tumor in animal models and identified 9Q10, 9Q17 and 9Q18 as the top 3 compounds in these tumor models among the compounds of this series. Specifically, PDX tumors were originally established on severe Combined Immunodeficiency (SCID) mice from pancreatic and colorectal cancer patient tumor tissues obtained from metastatic sites of the disease in the clinic. The FL118 platform drug was formulated in an organic solvent-free with HPβCD (2-hydroxypropyl-β-cyclodextrin) in 2% HPMC (hydroxypropyl methylcellulose) and 1% PG (propylene glycol) in saline (a thick aqueous suspension) for oral administration. The vehicle is the same think aqueous suspension without drug. Experimental SCID mice were subcutaneously implanted with 30-40 mg individual PDX tumors (isolated from maintenance mice) at the flank area (left side for PDX14244, and right side for PDX27454) of SCID mice. Treatment with vehicle or a drug of 9Q-series was initiated 7-14 days after the transplanted tumors reached 100-200 mm$^3$ (designated day 0). The animal model of PDX tumors was orally treated weekly for 3 times in two doses due to drug limitation then (as shown with black arrows). Our in vivo testing of these individual drugs revealed that while each of these compounds exhibited antitumor activity, the compounds of 9Q10, 9Q17 and 9Q18 possess higher antitumor activity than the other compounds in this 9Q-series (FIGS. 29-31). Here, we want to emphasize that while the 9Q-series compounds appear to have less antitumor activity than the 7Q-series compounds, 9Q-series compounds exhibited more favorable toxicity (body weight changes) profiles than the 7Q-series.

Figure 32:
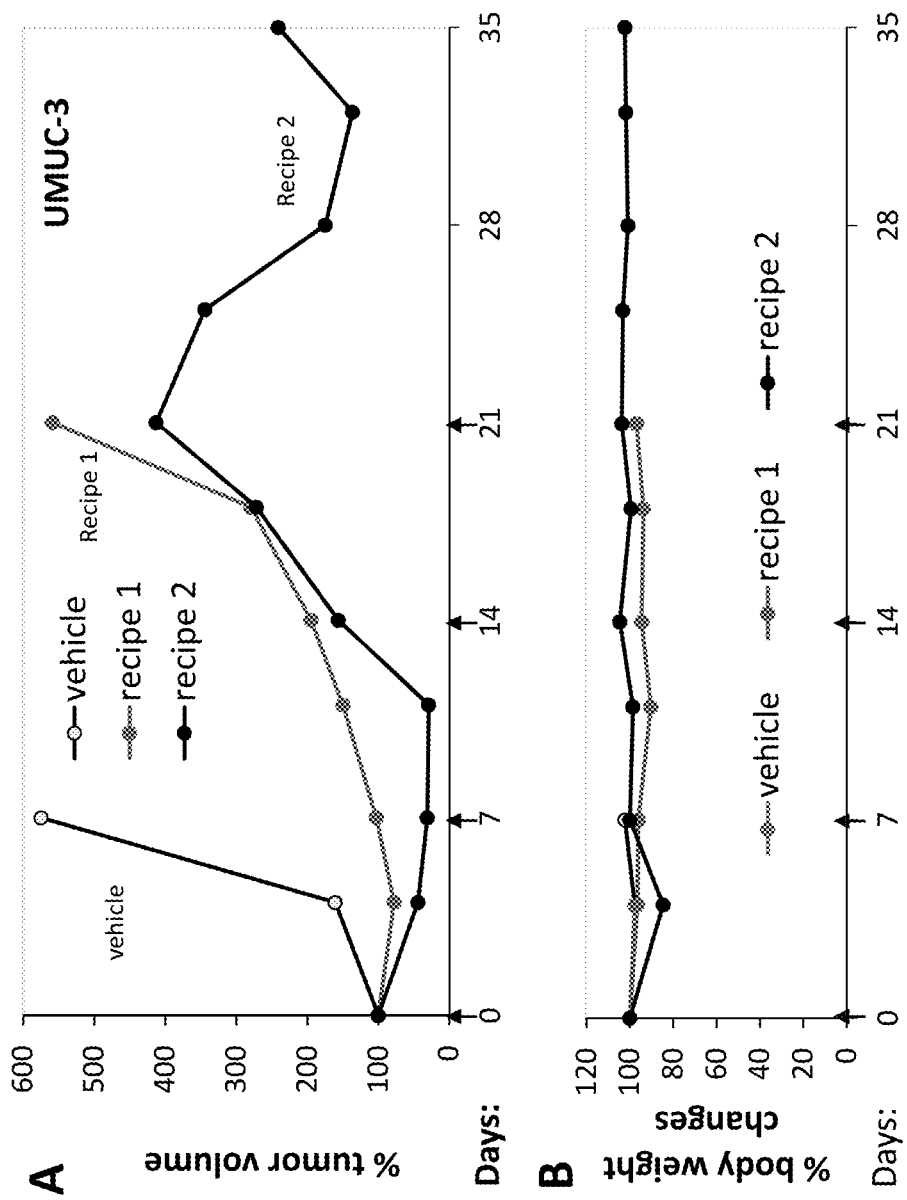
FIG. 32 shows the comparison of the antitumor efficacy and toxicity (body weight loss) of FL118 as an example in two distinct formulation recipes (Recipe 1: organic solvent-free aqueous suspension versus Recipe 2: ethanol-aqueous suspension) in human UMUC3 bladder cancer xenograft tumor of SCID mouse models: UMUC3 xenograft tumors were initially established by subcutaneously injection of 2-5×10$^6$ UMUC3 cells in a volume of 100-200 μL medium. Mouse models of UMUC3 xenografts were set up by subcutaneously inoculating 30-40 mg tumor tissue on the flank of SCID mice. Treatment with organic solvent-free aqueous FL118 suspension versus with ethanol-aqueous FL118 suspension was initiated 7-14 days after the transplanted tumors reached 100-200 mm$^3$ (designated day 0). The treatment schedule is the weekly for four-times via oral drug administration (q7d×4) as arrowed. A. Antitumor activity comparison of organic solvent-free aqueous FL118 suspension (Recipe 1) with ethanol-aqueous FL118 suspension (Recipe 2). B. Toxicity (body weight loss) comparison of organic solvent-free aqueous FL118 suspension (Recipe 1) with ethanol-aqueous FL118 suspension (Recipe 2).

Anti-tumor activity and toxicity comparison for oral administration of FL118 formulated in two different recipes: ethanol-HPβCD-FL118 complex suspension formulation (refer to [0139]) and organic solvent-free FL118 aqueous suspension formulation (refer to [0140]). We have performed comparison testing of two different inventive formulations to be used for FL118 or a compound of Formula 1 by using FL118 drug as an example. The detailed process of making the ethanol-HPβCD-FL118 complex suspension is described in [0139], and the detailed process of making the organic solvent-free drug aqueous suspension is described in [0140]. In this testing example, the ethanol-HPβCD-FL118 complex suspension (Recipe 2) contains 40 mg/mL drug (FL118 in this case), 40% HPβCD in non-aqueous 100% ethanol. This stock-state drug format was diluted for 80 times with saline to 0.5 mg/mL drug (FL118 in this case) before oral administration of the drug to mice. In contrast, the organic solvent-free drug aqueous suspension (Recipe 1) is a type of ready-to-use suspension that contains 0.5 mg/mL drug (FL118 in this case), 0.5% HPβCD, 2% HPMC and 1% PG in saline. We used human bladder cancer cell line UMUC3-established xenograft tumor models for the studies. Our studies demonstrated that while FL118 in the two different formulations exhibited antitumor activity with similar toxicity (body weight changes), it appears that the ethanol-HPβCD-FL118 complex (Recipe 2) exhibited better antitumor efficacy than those of the organic solvent-free FL118 aqueous suspension (Recipe 1) (FIG. 32).

Figure 33:
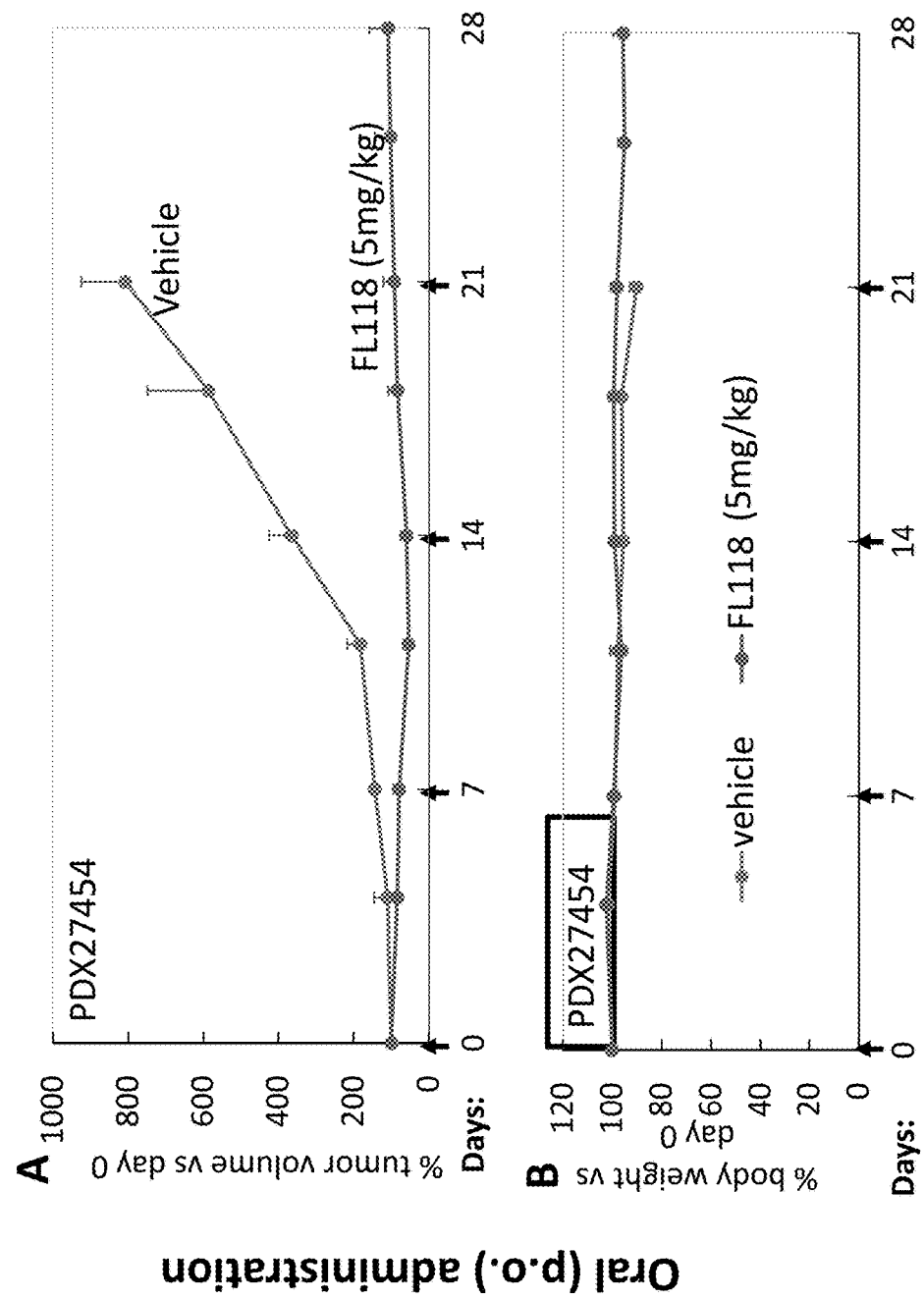
FIG. 33 shows the antitumor efficacy and toxicity (body weight loss) of FL118 in a convenient and clinical compatible formulation with spray-dry processes tested in human colorectal cancer (27454) patient-derived xenograft (PDX) tumors in animal models. FL118 was formulated into the ethanol solution with HPβCD (2-hydroxypropyl-β-cyclodextrin) and then use of spray-dry process to get an FL118-HPβCD formulated complex powder. The FL118-HPβCD complex powders were milled to a particle size≤400 mesh (37 microns), which was subsequently dissolved in saline with 5% PG (propylene glycol) to make a suspension before oral administration. The vehicle is the saline with 5% PG with equivalent HPβCD without FL118. PDX tumor establishment in experimental SCID mice was the same as described in FIGS. 7 and 13. PDX tumor SCID mice were treated with vehicle and FL118 via p.o. for weekly×4 as shown by arrows, after the transplanted tumors reached 100-200 mm$^3$ (designated day 0) in 7-14 days. A. Colorectal cancer PDX27454 tumor curve profile obtained after with vehicle or with FL118 treatment. B. The animal body weight change profile after with vehicle or with FL118 treatment was shown.

The antitumor efficacy and toxicity (body weight loss) of FL118 in a convenient and clinical compatible formulation the transplanted tumors reached 100-200 mm³ (designated day 0) in 7-14 days. As shown in the FIG. 33, FL118 at its half MTD exhibited great antitumor activity (FIG. 22A), while showing no toxicity at all (no mouse body weight changes, FIG. 22B).

The inhibition of cell growth and viability in various cancer cell types were tested using MTT assay for references. The $IC_{50}/EC_{50}$ results for the FL118 platform-derived 7Q-series drugs are shown in Table 5. The $IC_{50}/EC_{50}$ results for the FL118 platform-derived 9Q-series drugs are shown in Table 6. The $IC_{50}/EC_{50}$ results for the FL118 platform-derived FL7s- and FL7-series drugs are shown in Table 7. The $IC_{50}/EC_{50}$ results for the FL118 platform-derived FL7N-series drugs are shown in Table 8. The $IC_{50}/EC_{50}$ results for the FL118 platform-derived Wb-series drugs are shown in Table 9. The $IC_{50}/EC_{50}$ results for the FL118 platform-derived Hx-series drugs are shown in Table 10.

TABLE 5

In vitro antitumor activity of FL118 7Q-series derivatives (IC50/EC50 in μM)

| No. | HCT116 | HepG-2 | MCF-7 | A549 | Hela |
|---|---|---|---|---|---|
| 7Q 1 | 0.4000 | 0.8250 | 0.1219 | 0.0520 | 0.0614 |
| 7Q 2 | 0.5130 | >1.0000 | 0.0605 | 0.0549 | 0.1152 |
| 7Q 3 | 0.0913 | 0.3000 | 0.0725 | 0.0291 | 0.0958 |
| 7Q 4 | 0.2260 | >1.0000 | 0.0640 | 0.0612 | 0.0632 |
| 7Q 5 | 0.1180 | 0.8270 | 0.0640 | 0.0510 | 0.0594 |
| 7Q 6 | 0.0556 | 0.1600 | 0.0474 | 0.0572 | 0.0375 |
| 7Q 7 | 0.0559 | 0.2804 | 0.0478 | 0.0294 | 0.0522 |
| 7Q 8 | 0.0223 | 0.0640 | 0.0453 | 0.0221 | 0.3643 |
| 7Q 9 | 0.0177 | 0.0640 | 0.0458 | 0.0433 | 0.0483 |
| 7Q 10 | 0.0563 | 0.0740 | 0.8632 | 0.3210 | >1.0000 |
| 7Q 11 | 0.0832 | 0.1400 | 0.1600 | 0.0640 | >1.0000 |
| 7Q 12 | 0.0640 | 0.0454 | 0.0868 | 0.0360 | 0.0336 |
| 7Q 13 | 0.0618 | 0.0519 | 0.0534 | 0.0273 | 0.0587 |
| 7Q 14 | 0.0485 | 0.0148 | 0.0958 | 0.0214 | 0.0883 |
| 7Q 15 | 0.0461 | 0.0786 | 0.0346 | 0.1320 | 0.1251 |
| 7Q 16 | 0.0367 | 0.0611 | 0.0355 | 0.0846 | 0.4749 |
| 7Q 17 | 0.0218 | 0.1340 | 0.0386 | 0.1149 | 0.1444 |
| 7Q 18 | <0.0064 | 0.1600 | 0.0528 | 0.1419 | 0.5056 |
| 7Q 19 | 0.0396 | 0.7384 | 0.1011 | 0.1399 | 0.1999 |
| 7Q 21 | 0.2350 | >1.0000 | >1.0000 | 1.0000 | >1.0000 |
| 7Q 22 | 0.7930 | 1.0000 | 0.0641 | 0.4000 | 0.1431 |
| 7Q 23 | 0.5620 | 0.9930 | 0.0530 | 0.2253 | >1.0000 |
| 7Q 24 | 0.0994 | 0.1180 | <0.0064 | 0.0285 | <0.0064 |

| Drug/Cells | T24 | RT4 | H1376 | UMUC-3 | UOK151 | UOK262 | FaDu | A2008 | HT-3 |
|---|---|---|---|---|---|---|---|---|---|
| 7Q6 (nM) | 0.19 | 1.51 | 386 | 0.4 | | | 0.85 | 1.34 | 3.11 |
| 7Q9 (nM) | 0.32 | 3.37 | >500 | 0.35 | 50 | 32 | | | |
| 7Q24 (nM) | 0.08 | 1.44 | 246 | 0.21 | | | 0.68 | 1.95 | 3.59 |
| SN38 (nM) | 2.32 | 17.6 | >500 | 8.2 | >500 | 33.8 | | | |
| Topotecan (nM) | 37.2 | 96.4 | >500 | 52.8 | >200 | >200 | 26.63 | 46.1 | 83.42 |

Colorectal cancer cell lines: HCT116; liver cancer cell lines: HepG-2; breast cancer cell lines: MCF-7; lung cancer cell lines: A549; cervical cancer cell lines: Hela.
Bladder cancer cell lines: T24, RT4; bladder cancer cell lines: H1376, UMUC-3; kidney cancer cell lines: UOK151, UOK262; head-and-neck cancer cell lines: FaDu; Ovarian cancer cell lines: A2008; retinoblastoma cancer cell lines: HT-3.

with pray-dry processes tested in human colorectal cancer (27454) patient-derived xenograft (PDX) tumors in animal models. FL118 was formulated into the ethanol-HPβCD (2-hydroxypropyl-β-cyclodextrin) muster solution and then use of spray-dry process to get an FL118-HPβCD formulated complex powder. The FL118-HPβCD complex powders were milled to a particle size≤400 mesh (37 microns), which was subsequently dissolved in saline with 5% PG (propylene glycol) to make a suspension before oral administration. The vehicle is the saline with 5% PG with equivalent HPβCD without FL118. PDX tumor establishment in experimental SCID mice was the same as described in FIGS. 7 and 13. PDX tumor SCID mice were treated with vehicle and FL118 via p.o. for weekly×4 as shown by arrows, after

TABLE 6

In vitro antitumor activity of FL118 9Q-series derivatives (IC50/EC50 in μM)

| No. | HCT116 | HepG-2 | MCF-7 | A549 | Hela |
|---|---|---|---|---|---|
| 9Q 1 | >1 | >1 | 0.800 | 0.764 | >1 |
| 9Q 2 | 0.759 | >1 | >1 | 0.540 | >1 |
| 9Q 3 | 0.620 | 0.401 | >1 | 0.210 | >1 |
| 9Q 4 | 0.176 | >1 | >1 | 0.296 | >1 |
| 9Q 5 | 0.951 | >1 | >1 | 0.423 | >1 |
| 9Q 6 | 0.697 | >1 | >1 | 0.264 | >1 |
| 9Q 7 | 0.255 | 0.199 | 0.156 | 0.110 | >1 |
| 9Q 8 | 0.773 | >1 | >1 | 0.259 | >1 |
| 9Q 9 | 0.162 | 0.527 | 0.160 | 0.163 | >1 |

TABLE 6-continued

In vitro antitumor activity of FL118 9Q-series derivatives (IC50/EC50 in μM)

| No. | HCT116 | HepG-2 | MCF-7 | A549 | Hela |
|---|---|---|---|---|---|
| 9Q 10 | 0.253 | 0.176 | 0.104 | 0.085 | 0.160 |
| 9Q 11 | >1 | >1 | >1 | 0.910 | 0.673 |
| 9Q 12 | 0.709 | 0.292 | 0.160 | 0.106 | 0.115 |
| 9Q 13 | 0.581 | 0.303 | 0.157 | 0.220 | 0.160 |
| 9Q 14 | >1 | >1 | >1 | 0.990 | >1 |
| 9Q 15 | 0.133 | 0.189 | 0.098 | 0.133 | 0.032 |
| 9Q 16 | 0.059 | 0.350 | 0.032 | 0.110 | 0.032 |
| 9Q 17 | 0.478 | 0.200 | 0.131 | >1 | 0.032 |
| 9Q 18 | 0.947 | 0.909 | 0.600 | 0.141 | 0.151 |
| 9Q 19 | 0.136 | 0.951 | 0.756 | 1.000 | 0.140 |
| 9Q 20 | 0.933 | >1 | 0.785 | 0.803 | >1 |
| 9Q 21 | 0.782 | 0.569 | 0.343 | 0.616 | 0.592 |
| 9Q 22 | 0.183 | 0.161 | 0.148 | 0.148 | 0.160 |
| 9Q 23 | 0.563 | >1 | >1 | 1.000 | 0.531 |
| 9Q 24 | 0.022 | 0.028 | 0.029 | 0.433 | 0.032 |

Colorectal cancer cell lines: HCT116; liver cancer cell lines: HepG-2; breast cancer cell lines: MCF-7; lung cancer cell lines: A549; cervical cancer cell lines: Hela.

TABLE 7

FL7s- and FL7-series IC50/EC50 in cancer cells in nM

| Drug/Cells | HT-3 | Y79 | Wer 127 | HCT116 |
|---|---|---|---|---|
| SN38 (nM) | 18 | 5.25 | 6.85 | 619.8 |
| FL7s-1 (nM) | 11.9 | 4.16 | >500 | |
| FL7s-2 (nM) | 113.2 | 41.48 | >500 | |
| FL7s-3 (nM) | 1.68 | 0.61 | 40.69 | |
| FL7s-4 (nM) | 4.7 | 0.62 | 49.46 | |
| FL7s-5 (nM) | 3.58 | 1.11 | 381.2 | |
| FL7s-6 (nM) | 7.7 | 1.52 | 6.48 | |
| FL7s-7 nM) | 2.22 | 0.29 | 4.76 | |
| FL7s-8 (nM) | 4.88 | 1.56 | 28.99 | |
| FL7s-9 (nM) | 3.42 | 1 | 1.86 | |
| FL7s-10 (nM) | 3.44 | 1.15 | 12.26 | |
| FL7-5 (nM) | 5.89 | 2.51 | 5.13 | |
| FL7-14 (nM) | 36.9 | 8.39 | 4.1 | |
| FL7-15 (nM) | 45.81 | 12.59 | >500 | |
| FL7-17 (nM) | 6.48 | 1.57 | 2.48 | |

Retinoblastoma cancer cell lines: HT-3, Y79, Weil27; colorectal cancer cell lines: HCT116.

TABLE 8

FL7N-series IC50/EC50 in cancer cells in nM

| Drug/Cells | H1376 | UMUC-3 | UOK151 | UOK262 |
|---|---|---|---|---|
| SN38 (nM) | >500 | 8.2 | >500 | 33.8 |
| Topotecan (nM) | >500 | 52.8 | >200 | >200 |
| 7N1 (nM) | >500 | 2.05 | 42.8 | 38 |

| Drug/Cells | HCT116 |
|---|---|
| 7N1 (nM) | 11.6 |
| 7N2 (nM) | 25.62 |
| 7N3 (nM) | 171.9 |
| SN38 (nM) | 619.8 |

Bladder cancer cell lines: H1376, UMUC-3; kidney cancer lines UOK151, UOK262. Colorectal cancer cell lines: HCT116.

TABLE 9

Wb-series IC50/EC50 in cancer cells in nM

| Drug/Cells | A549 | A2008 |
|---|---|---|
| W-b1 (nM) | 73.4 | 24.4 |
| W-b2 (nM) | 2.24 | 4.6 |
| W-b3 (nM) | 0.92 | 16.15 |
| W-b4 (nM) | 1.99 | 31.9 |
| W-b5 (nM) | 2.29 | 17.5 |
| W-b6 (nM) | 1.2 | 11.1 |
| W-b7 (nM) | 0.39 | 0.19 |
| W-b9 (nM) | 1.28 | 3.49 |
| W-b10/Hx7 (nM) | 5.29 | 7.31 |

Lung cancer cell lines: A549; ovarian cancer cell lines: A2008.

TABLE 10

Hx-series IC50/EC50 in cancer cells in nM

| Drug/Cells | UOK151 | UOK262 |
|---|---|---|
| HX6 (nM) | 4.6 | 4.9 |
| HX7 (nM) | >500 | 33.4 |
| SN38 (nM) | >500 | 33.8 |
| Topotecan (nM) | >200 | >200 |

Kidney cancer cell lines: UOK151, UOK262.

Protein biomarkers and targets discovered from ligand (FL118 or an analogue) affinity purification and protein ProtoArray probing. Through the use of FL118 or an FL118 analogue as a ligand for affinity purification and/or use of tritium ($^3$H)-labeled ligand screening of the over 9,000 human protein on the ProtoArray (Invitrogen), we found many proteins that can bind to the ligand. The top candidates were shown in Table 12.

TABLE 12

Potential biochemical biomarkers and targets identified using ligands (FL118 and FL118 analogue) through ligand affinity purification and tritium (3H)-labeled ligand screening of protein ProtoArray

| Full names of the Protien markers and Targets | Protein short name (symbol) |
|---|---|
| heat shock protein 60 | (HSP60) |
| stress-70 protein | (GRP75) |
| ATP-dependent RNA helicase DDX5 | (DDX5 (p68) |
| nucleolar RNA helicase 2 | (DDX21) |
| elongation factor 2 | (EF2) |
| pre-mRNA-splicing factor ATP-dependent RNA helicase | (DHX15) |
| Transitional endoplasmic reticulum ATPase | (TERA) |
| Transferrin receptor protein | (TFR1) |
| MAP kinase-activated protein kinase 2 | (MAPK2) |
| Catenin beta-1 | (CTNB1) |
| Early endosome antigen 1 | (EEA1) |
| Guanine nucleotide-binding protein subunit beta-2-like 1 | (GBLP) |
| Electron transfer flavoprotein subunit alpha | (ETFA) |
| Proteasome activator complex subunit 3 | (PSME3) |
| UPF0368 protein Cxorf26 | (CX026) |
| Peroxiredoxin-2 | (PRDX2) |
| Peroxiredoxin-1 | (PRDX1) |
| Thioredoxin-dependent peroxide reductase | (PRDX3) |
| Serine/arginine-rich splicing factor 3 | (SRSF3) |
| Proteasome subunit beta type-2 | (PSB2) |
| Glutathione S-transferase P | (GSTP1) |
| MAP/microtubule affinity-regulating kinase 3 | (MARK3) |
| DNA-damage inducible 1 | (DDI1) |
| tumor protein D52-like 2 | (TPD52L2) |
| calcium channel, voltage-dependent, beta 1 subunit | (CACNB1) |
| Probable G-protein coupled receptor 1 | (PGPCR1) |
| ubiquitin specific peptidase 2a | (USP2a) |
| melanocortin 2 receptor | (MC2R) |
| Fibroblast growth factor 18 | (FGF18) |
| tumor protein p53 inducible protein 3 | (TP5313) |
| CCHC-type zinc finger nucleic acid binding protein | (CNBP) |
| WD repeat domain 22 | (WDR22) |

TABLE 12-continued

Potential biochemical biomarkers and targets identified using ligands (FL118 and FL118 analogue) through ligand affinity purification and tritium (3H)-labeled ligand screening of protein ProtoArray

| Full names of the Protien markers and Targets | Protein short name (symbol) |
|---|---|
| Potassium voltage-gated channel subfamily E member 1 | (PVGCSE-M1) |
| ubiquitin-conjugating enzyme E2T (putative) | (UBE2T) |
| Ubiquitin-like protein 7 | (ULP7) |
| RNA binding motif, single stranded interacting protein 2 | (RBMS2) |
| Cytoplasmic tyrosine-protein kinase | (BMX) |
| cyclin B1 interacting protein 1 | (CCNB1IP1) |

Pharmaceutical Formulation Process

The newly invented formulation is the further to the development of related inventions. See, e.g., PCT/US15/22095 (Use of the FL118 core chemical structure platform to generate FL118 derivatives for treatment of human disease), all of which are hereby incorporated by reference in their entirety.

The aqueous suspension formulation of the compound of Formula 1 for oral administration (in some cases, iv or ip is also compatible) was invented in two situations as described blow.

The aqueous suspension formulation (Recipe 1) of a compound of Formula 1 for oral administration is further invented to be prepared in the following steps:

Step 1: Dissolving a type of cyclodextrin (e.g. hydroxypropyl-β-cyclodextrin, HPβCD) into ethanol in some embodiments; or into dimethyl sulfoxide (DMSO) in some embodiments; or into dimethylacetamide (DMA) in some embodiments; or into dimethylformamide (DMF) in some embodiments; or into N-methyl-2-pyrrolidone (NMP) in some embodiments or into heptafluorobutyric acid/perfluorobutyric acid (HFBA/PFBA) in some embodiments; (but not into dichlormethane; chloroform; acetone; tetralydrofuran; 1,4-dioxone; trichloroethylene; 1,1, dichloro-1-fluoroethane; perfluoropolyether; perfluoohexane; trifluoroacetic acid; pentafluoropropionic anhydride; perchloroethylene; bis(trifluoromethane) sulfonamide; or perfluorooctane); to make an organic solvent-cyclodextrin master solution in an appropriate concentration, which depend on the amount of a compound of Formula 1 that will be dissolved in. Generally speaking, each compound molecule of Formula 1 should have 1.5 to 2.0 molecules of a type of cyclodextrin (e.g. HPβCD) in a test-demonstrated working organic solvents (i.e. ethanol, DMSO, DMA, DMF, NMP or HFBA/PFBA).

Step 2: Dissolving FL118 or a compound of Formula 1 into an organic solvent-cyclodextrin solution, by vigorous vortex for ≥1 hour or shaking for ≥24 hours to make sure the drug loading formulation completion (i.e. 100% drug/API loading into HPβCD). Then the resultant mixed polymer-state suspension goes into a process to get rig of these organic solvents. This can go through different approaches including, but not limited to, lyophilization, drum dryers, falling film evaporators, thin film evaporators, and little-ford reactors to get rid of the organic solvents. For some of these organic solvent suspension complex mixtures such as in the case of ethanol, it is also possible to use spry-drying approach by the use of a closed loop spray drying system with solvent recovery and an inert gas (e.g. nitrogen) to make an inert atmosphere during spray drying process.

Step 3: The remained Formula 1 compound-cyclodextrin complex powder in a dry state is then resuspended with an aqueous solution containing: hydroxypropyl methylcellulose (HPMC, e.g. HPMC with viscosity of 40-60 cps at 2-5%) and propylene glycol (PG, 1-5%) in saline (NaCl, 0.85% with pH5-6.5) with polyethylene glycol (PEG) 300 or PEG400 at a concentration of 0-4%. the formulation at a final concentration of a compound of Formula 1 may be at range from 0.1 to about 5 mg/ml for oral administration.

Preparation of 8% Stock Solution of HPMC with Viscosity of 40-60 Cps for 100-Ml as Example:

Weight 80g HPMC and add them into a 1000 ml thick glass bottle and then add ~900 ml 85-95° C. hot saline and put the bottle into a 95° C. water bath. Shaking every 15-30 min for 6 hours, then add hot saline to 1000 ml (8% HPMC in saline).

Then fix the 1000 ml bottom in a horizontal position on a shaker, and shaking overnight at RT at 200 rpm. It should be very thick transparent solution appears.

Preparation of 2% HPMC for 1000 ml containing 1% PG as example:

250 ml 8% HPMC+740 ml saline+10 ml PG=1000 ml 2% HPMC

The aqueous suspension formulation of a compound of Formula 1 in Recipe 2 for po, ip or iv administration is further invented to be prepared in the following steps:

Step 1: Dissolve a type of cyclodextrin such as 2-hydroxypropyl-β-cyclodextrin (HPβCD) into non-aqueous 100% ethanol (but neither DMSO; DMA; DMF; NMP or HFBA/PFBA); nor dichlormethane; chloroform; acetone; tetralydrofuran; 1,4-dioxone; trichloroethylene; 1,1, dichloro-1-fluoroethane; perfluoropolyether; perfluoohexane; trifluoroacetic acid; pentafluoropropionic anhydride; perchloroethylene; bis(trifluoromethane) sulfonamide; or perfluorooctane) to make an ethanol-HPβCD master solution.

Step 2: Dissolve FL118 or a compound of Formula 1 into the ethanol-HPβCD master solution to form an ethanol-HPβCD-drug complex.

Step 3: Spry-drying of the ethanol-HPβCD-drug complex suspension is then carried out by the use of a closed loop spray drying system with solvent recovery and an inert gas (e.g. nitrogen) to make an inert atmosphere during spray drying process. This process will result in an HPβCD-drug complex powder.

Step 4: The prepared HPβCD-drug complex powder will be further dried under vacuum at 30° C. overnight to get the HPβCD-drug complex powders drying enough for the next step jet milling.

Step 4: Use of a jet-milling system/machine to mill the HPβCD-drug complex powder into fine particles (≤37 microns).

Step 5: At the time before oral administration to a subject/patient, dilute the milled HPβCD-drug complex powder with saline in the presence of up to 5% PG by vigorous shaking before oral administration to the subject (patient).

A particular example is provided below:

1) Weight 20 g HPβCD to be dissolved in non-aqueous 100% ethanol to a total volume of 100 mL (of note, need about 87 mL non-aqueous ethanol in this case) to make a 20% HPβCD-ethanol master solution by shaking ≥1 hour to make sure dissolving completion.

2) Dissolve 2 g of FL118 or a compound of Formula 1 into the 100 mL 20% HPβCD-ethanol master solution (i.e. 20 mg drug per mL) through high-speed (such 1,000 rpm) mixture with a magnetic bar for ≥24 hours.

3) Spry-drying the ethanol-HPβCD-drug complex suspension by the use of a closed loop spray drying system with solvent recovery and an inert gas (e.g. nitrogen) to make an inert atmosphere during spray drying process. This process will result in an HPβCD-drug complex powder. Of note, the ethanol-HPβCD-drug complex suspension should be stirring during spray drying.

4) The prepared HPβCD-drug complex powders will be dried under vacuum at 30° C. overnight to get the HPβCD-drug complex powders drying enough for the next step jet milling.

5) Process of jet milling: The drying HPβCD-drug complex powders will be milled through a jet mill machine to get the HPβCD-drug complex powders in a fine size (≤37 microns/400 mesh).

6) At the time before oral administration to a patient, dissolve the milled HPβCD-drug complex powder into a concentration of drug/API at 0.1-10 mg/mL using saline in the presence of 0-5% PG by vigorous shaking. For ip or iv route API concentration should be 0.1-2 mg/mL and for po it can be 1-10 mg/mL.

The milled HPβCD-drug complex powders can be further formulated into the tablet product for oral administration. This can be prepared in the following steps:

Step 1: The milled HPβCD-drug complex powders (10-50%) will be mixture with microcrystalline cellulose (MCC, 30%-80%), corn starch (0%-40%), lactose (10%-25%), colloidal silicone dioxide (0%-3%), dibasic calcium phosphate (1%-10%), and magnesium stearate (0.2%-3%). The excipient mixture will be further milled to let every ingredient be evenly distributed in the powder.

Step 2: This smooth powder is then pressed into various sizes and forms of tablets by a dry compression process.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting. In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member.

While various aspects and illustrative embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein are incorporated by reference herein in their entireties and for all purposes to the same extent as if each individual publication, patent, or patent application is specifically and individually incorporated by reference in its entirety for all purposes.

The foregoing summary is illustrative only and is not intended to be in any way limiting. In addition to the illustrative aspects, embodiments, and features described above, further aspects, embodiments, and features will become apparent by reference to the drawings and examples presented in the detailed description in the current invention.

What is claimed is:

1. A composition comprising a compound selected from the group consisting of

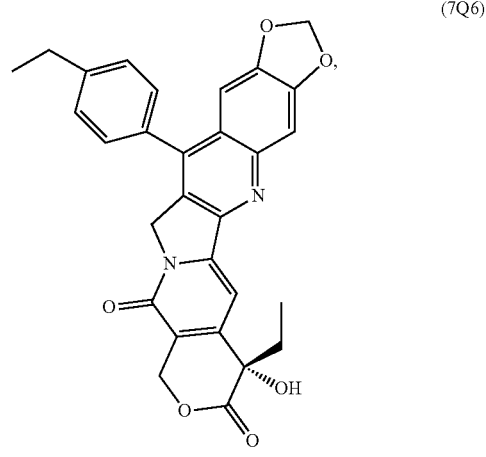

(7Q6)

FL776

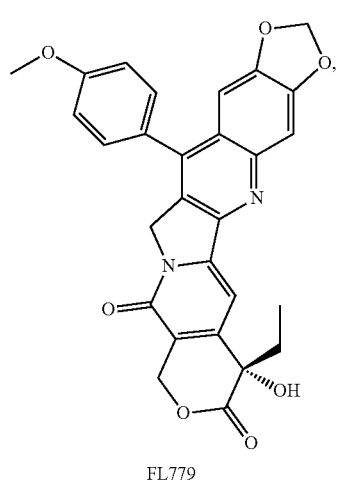

FL779 (7Q9)

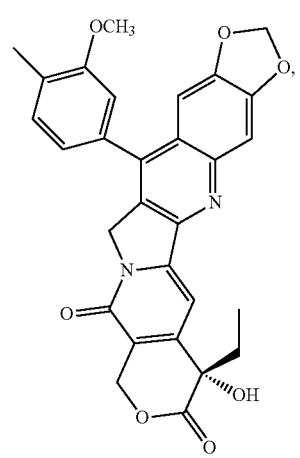

FL7732 (7q32)

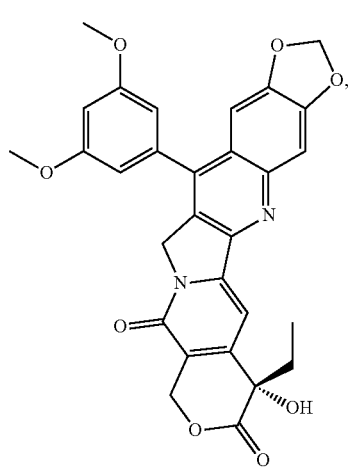

(7Q24)

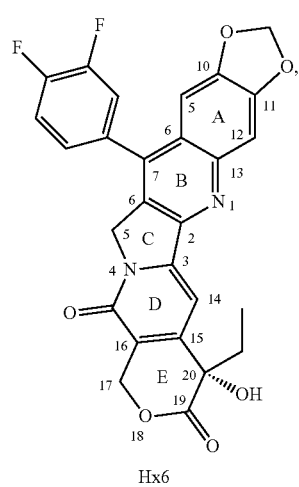

Hx6 (FL496)

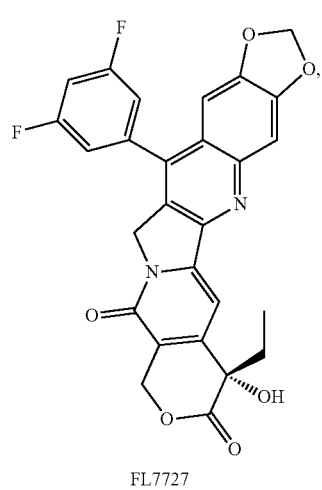

FL7727 (7Q27)

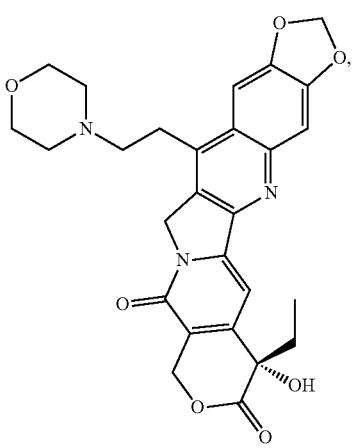

FL7N-1 or a pharmaceutically acceptable salt of the compound wherein the compound is formulated into a cyclodextrin-drug complex.

2. The composition of claim 1, wherein the pharmaceutically acceptable salt selected from the group consisting of chloride, phosphate, mesylate, bismesylate, tosylate, lactate, tartrate, malate, bis-acetate, and citrate salts.

3. The composition of claim 1, wherein the composition is formulated for oral administration, intravenous administration, subcutaneous administration, transdermal administration, intraperitoneal administration, or inhaled administration.

4. The composition of claim 1, wherein the cyclodextrin is selected from the group consisting of hydroxypropyl-β-cyclodextrin (HPβCD), β cyclodextrin (βCD), and sulfobutylether-β-cyclodextrin (SBβCD).

5. The composition of claim 3, wherein the formulation for oral administration is a tablet, a capsule, an oral powder, a solution, nanoparticles, or a suspension.

6. The composition of claim 5, wherein the formulation is an oral powder wherein when the oral powder is reconstituted it provides final concentration of the compound in a range from about 0.1 mg/mL to about 5 mg/mL.

7. The composition of claim 5, wherein the formulation is an oral powder, further wherein the oral powder may be pressed into a tablet.

8. The composition of claim 7, wherein the oral powder comprises:
    about 10-about 50% of the cyclodextrin-drug complex,
    about 30%-about 80% microcrystalline cellulose (MCC),
    about 0%-about 40% corn starch,
    about 10%-about 25% lactose,
    about 0%-about 3% colloidal silicone dioxide,
    about 1%-about 10% dibasic calcium phosphate, and
    about 0.2%-about 3% magnesium stearate.

9. The composition of claim 1, wherein the formulation is configured to be administered from about once a week to about five times a week.

10. The composition of claim 1, wherein the composition is co-administered separately, sequentially, or simultaneously to a subject in need thereof, with at least one agent selected from the group consisting of: chemotherapeutic agents, chemopreventive agents, anti-cancer agents derived from natural plants, anti-cancer agents derived from non-plants, selenium-containing compounds, *Amoora rohituka*-derived AMR analogs, Docosahexaenoic acid, Ciglitazone, HDAC inhibitors, prostanoids, endothelin antagonists, cytoplasmic kinase inhibitors, receptor kinase inhibitors, endothelin receptor antagonists, PDE5 (PDE-V) inhibitors, calcium channel blockers, cyclosporins, CTLA4-Ig, antibodies, CD40 fusion proteins, gp39 fusion proteins, nuclear translocation inhibitors of NF-kappa B function, cholesterol biosynthesis inhibitors, HMG CoA reductase inhibitors, non-steroidal anti-inflammatory drugs (NSAIDs), steroids, gold compounds, beta-agonists, leukotriene antagonists, antiproliferative agents, cytotoxic drugs, antimetabolites, methotrexate, topoisomerase inhibitors, DNA alkylators, kinase inhibitors, microtubule poisons, TNF-α inhibitors, anti-TNF antibodies, soluble TNF receptors, hydroxy urea, rapamycin, and combinations thereof.

11. The composition of claim 1 use in treating a disease, wherein the disease is selected from the group consisting of cancer, a neoplastic disease, an autoimmune disease, restenosis, and Tuberous Sclerosis Complex (TSC).

12. The composition of claim 1 use in the selective inhibition of a cancer molecular phenotype that expresses one or more biomarkers or targets selected from the group consisting of Survivin, Mcl-1, XIAP, cIAP2, Hdm2 (Mdm2), HdmX (MdmX/Mdm4), p53, (mutant) Kras, ATP-dependent RNA helicase DDX5 (p68), ubiquitin specific peptidase 2a (USP2a), ubiquitin-conjugating enzyme E2T (putative) (UBE2T) and Ubiquitin-like protein 7 (ULP7).

13. A compound selected from the group consisting of

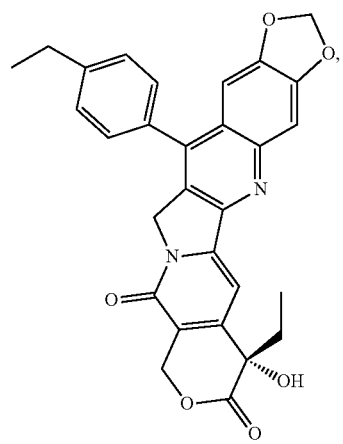

FL776 (7Q6)

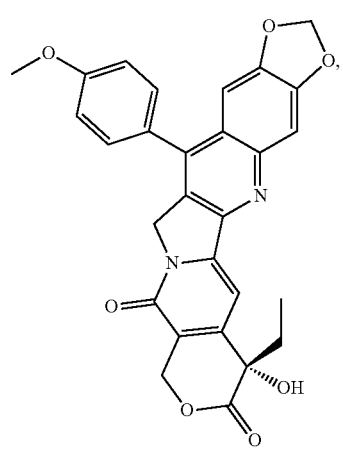

FL779 (7Q9)

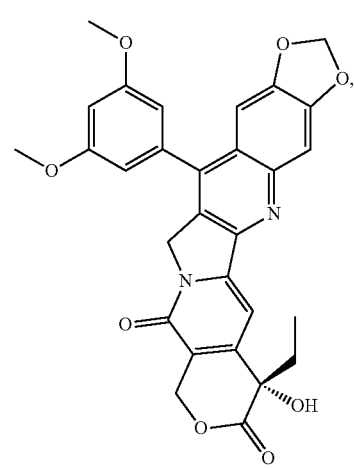

7Q24

113
-continued
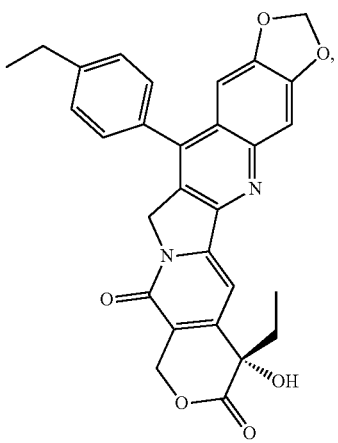
FL776 (7Q6)
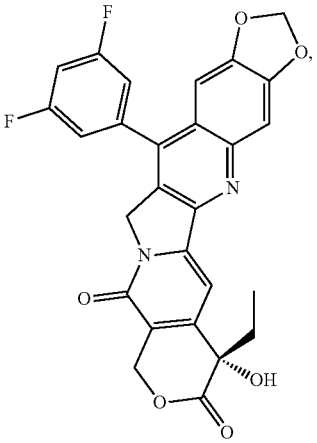
FL7727 (7Q27)
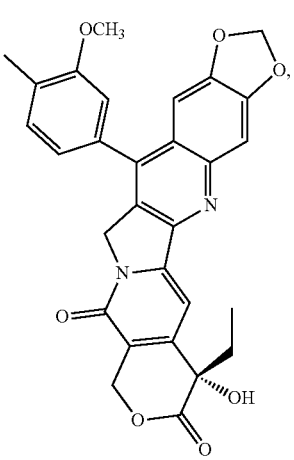
FL7732 (7q32)
FL779 (7Q9)
7Q24
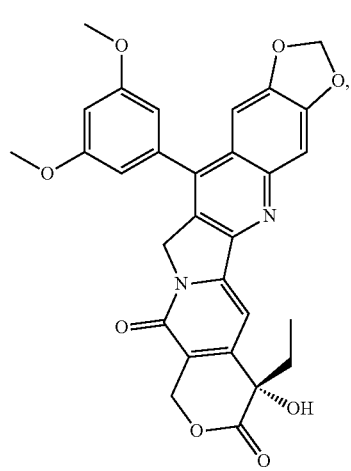
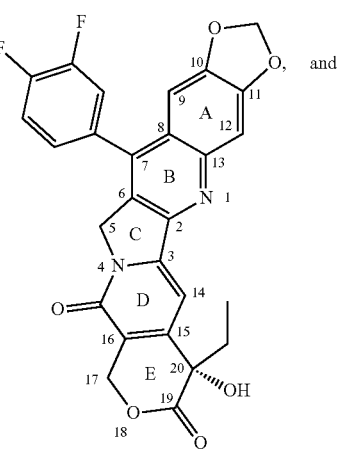
Hx6(FL496)
and
114
-continued FL7N-1
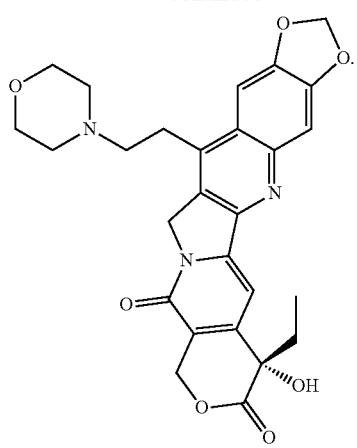
14. The composition of claim 3, wherein the composition further comprises at least one filler, binder, diluent, disintegratant, glidant, lubricant, antimicrobial, or preservative.
* * * * *